"""

US012258352B2

(12) United States Patent
Jung et al.

(10) Patent No.: US 12,258,352 B2
(45) Date of Patent: Mar. 25, 2025

(54) ORGANIC ELECTROLUMINESCENT COMPOUND, A PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: So-Young Jung, Gyeonggi-do (KR); Jin-Ri Hong, Gyeonggi-do (KR); Doo-Hyeon Moon, Gyeonggi-do (KR); Sang-Hee Cho, Gyeonggi-do (KR); Su-Hyun Lee, Gyeonggi-do (KR); Du-Yong Park, Gyeonggi-do (KR); Mi-Ja Lee, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 776 days.

(21) Appl. No.: 17/384,108

(22) Filed: Jul. 23, 2021

(65) Prior Publication Data
US 2022/0033414 A1  Feb. 3, 2022

(30) Foreign Application Priority Data

Jul. 24, 2020 (KR) .................. 10-2020-0092465
Jun. 25, 2021 (KR) .................. 10-2021-0082869

(51) Int. Cl.
| | |
|---|---|
| H01L 51/50 | (2006.01) |
| C07D 493/00 | (2006.01) |
| C07D 495/00 | (2006.01) |
| H10K 85/60 | (2023.01) |
| H10K 50/11 | (2023.01) |
| H10K 101/00 | (2023.01) |
| H10K 101/10 | (2023.01) |
| H10K 101/30 | (2023.01) |

(52) U.S. Cl.
CPC ......... *C07D 495/00* (2013.01); *C07D 493/00* (2013.01); *H10K 85/622* (2023.02); *H10K 85/623* (2023.02); *H10K 85/624* (2023.02); *H10K 85/626* (2023.02); *H10K 85/636* (2023.02); *H10K 85/654* (2023.02); *H10K 85/6572* (2023.02); *H10K 85/6574* (2023.02); *H10K 85/6576* (2023.02); *H10K 50/11* (2023.02); *H10K 2101/10* (2023.02); *H10K 2101/30* (2023.02); *H10K 2101/90* (2023.02)

(58) Field of Classification Search
None
See application file for complete search history.

(56) References Cited

U.S. PATENT DOCUMENTS

| | | |
|---|---|---|
| 2018/0208837 A1 | 7/2018 | Ahn |
| 2018/0323397 A1 | 11/2018 | Ahn et al. |
| 2019/0393427 A1 | 12/2019 | Moon et al. |
| 2020/0203623 A1 | 6/2020 | Lee et al. |
| 2021/0328154 A1 | 10/2021 | Kim et al. |
| 2022/0029104 A1* | 1/2022 | Lee ................... H10K 85/624 |
| 2022/0102646 A1 | 3/2022 | Kim et al. |

FOREIGN PATENT DOCUMENTS

| | | |
|---|---|---|
| CN | 109134443 A | 1/2019 |
| CN | 113195479 A | 7/2021 |
| KR | 20120104067 A | 9/2012 |
| KR | 2020079980 A | 7/2020 |
| WO | 2019083216 A1 | 5/2019 |
| WO | 2019231272 A1 | 12/2019 |

OTHER PUBLICATIONS

Search Report from China National Intellectual Property Administration for Chinese patent application No. 202110833828.5; Application Date: Jul. 22, 2021.

* cited by examiner

*Primary Examiner* — Gregory D Clark
(74) *Attorney, Agent, or Firm* — G. Creston Campbell

(57) ABSTRACT

The present disclosure relates to an organic electroluminescent compound represented by formula 2' or formula 2", a plurality of host materials comprising at least one first host compound and at least one second host compound, and an organic electroluminescent device comprising the same. An organic electroluminescent device having improved driving voltage, luminous efficiency, power efficiency and/or lifespan properties can be provided by including the organic electroluminescent compound or a specific combination of compounds according to the present disclosure as a host material(s).

8 Claims, No Drawings
"""

ORGANIC ELECTROLUMINESCENT COMPOUND, A PLURALITY OF HOST MATERIALS AND ORGANIC ELECTROLUMINESCENT DEVICE COMPRISING THE SAME

TECHNICAL FIELD

The present disclosure relates to an organic electroluminescent compound, a plurality of host materials, and an organic electroluminescent device comprising the same.

BACKGROUND ART

In 1987, Tang et al. of Eastman Kodak first developed a small molecule green organic electroluminescent device (OLED) of TPD/Alq$_3$ bilayer consisting of a light-emitting layer and a charge transport layer. Thereafter, the development of OLEDs was rapidly effected and OLEDs have been commercialized. Currently, the organic electroluminescent device mainly uses a phosphor having excellent luminous efficiency in realizing a panel. OLEDs having high luminous efficiency and/or long lifespan are required for long-term use and high resolution of the display.

In order to improve luminous efficiency, driving voltage, and/or lifespan, various materials or concepts for the organic layer of an organic electroluminescent device have been proposed, but they have not been satisfactory in practical use. Accordingly, there has been a continuous need to develop an organic electroluminescent device having improved performance, for example, improved driving voltage, luminous efficiency, power efficiency, and/or lifespan properties, compared to the conventional organic electroluminescent device.

Meanwhile, Korean Patent Appln. Laid-Open No. 2012-0104067 discloses a compound in which a nitrogen-containing heteroaryl is bonded to a benzonaphthothiophene moiety, but fails to specifically disclose a specific combination of host materials claimed herein.

DISCLOSURE OF INVENTION

Technical Problems

The objective of the present disclosure is to provide a compound having a novel structure suitable for use as an organic electroluminescent material. Another objective of the present disclosure is to provide an organic electroluminescent device having low driving voltage, high luminous efficiency, high power efficiency and/or excellent lifespan properties by including a plurality of host materials comprising a specific combination of compounds.

Solution to Problem

As a result of intensive research to solve the above technical problems, the present inventors found that the above objective can be achieved by an organic electroluminescent compound represented by the following formula 2' or formula 2". In addition, the present inventors found that the above objective can be achieved by a plurality of host materials comprising at least one first host compound and at least one second host compound achieve the above-described object, wherein the first host compound is represented by the following formula 1, and the second host compound is represented by the following formula 2.

$$Ar_{11}(L_{11}\text{-HAr})_e \qquad (2')$$

In formula 2',

HAr each independently represents a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted benzofuropyrimidinyl, or a substituted or unsubstituted benzothienopyrimidinyl;

$L_{11}$ each independently represents a single bond, a substituted or unsubstituted (C6-C30)arylene, or a substituted or unsubstituted (3- to 30-membered)heteroarylene;

$Ar_{11}$ each independently represents any one of the following formulas 3 to 5:

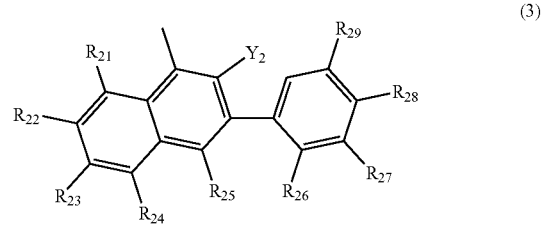

(3)

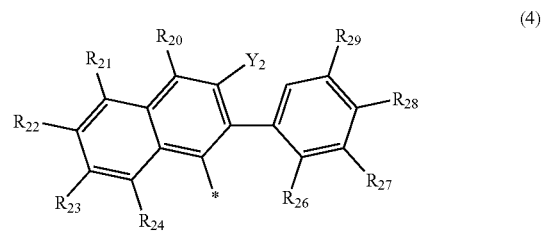

(4)

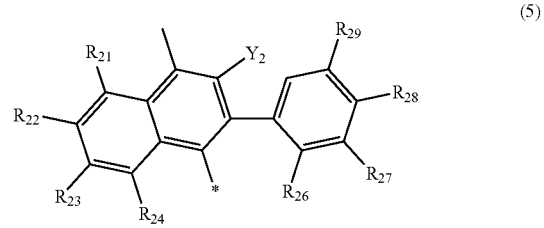

(5)

in formulas 3 to 5, $Y_2$ represents O or S;

$R_{20}$ to $R_{29}$ represent hydrogen or deuterium;

e represents 1 or 2, and when e is 2, each of ($L_{11}$-HAr) may be the same as or different from each other; and * represents a site linked to $L_{11}$;

with the proviso that when HAr is a substituted triazinyl, the substituents of the substituted triazinyl each independently are selected from deuterium, a phenyl, a naphthyl, a biphenyl, a terphenyl, a phenanthrenyl, a triphenylenyl, a dimethylfluorenyl, a fluoranthenyl, a chrysenyl, a carbazolyl, and combinations thereof, and when there are two substituents, they are the same as or different from each other.

$$Ar_{11}(L_{11}\text{-HAr})_e \qquad (2'')$$

In formula 2",

HAr each independently represents a substituted or unsubstituted triazinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted benzofuropyrimidinyl, or a substituted or unsubstituted benzothienopyrimidinyl;

$L_{11}$ each independently represents a single bond, a substituted or unsubstituted (C6-C30)arylene, or a substituted or unsubstituted (3- to 30-membered)heteroarylene;

$Ar_{11}$ each independently represents any one of the following formulas 3 to 5:

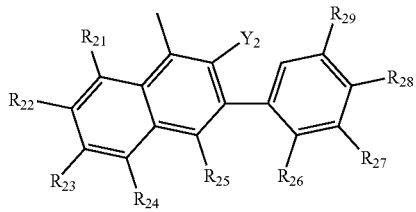
(3)

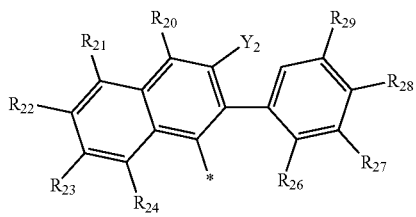
(4)

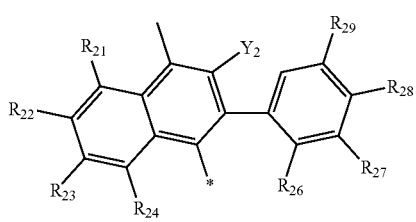
(5)

in formulas 3 to 5, $Y_2$ represents O or S;

$R_{21}$ to $R_{24}$ and $R_{26}$ to $R_{29}$ each independently represent hydrogen, deuterium, a substituted or unsubstituted (C6-C30)aryl, or a substituted or unsubstituted (3- to 30-membered)heteroaryl;

$R_{20}$ and $R_{25}$ each independently represent a substituted or unsubstituted (C6-C30)aryl, or a substituted or unsubstituted (3- to 30-membered)heteroaryl;

e represents 1 or 2, and when e is 2, each of ($L_{11}$-HAr) may be the same as or different from each other; and

* represents a site linked to $L_{11}$.

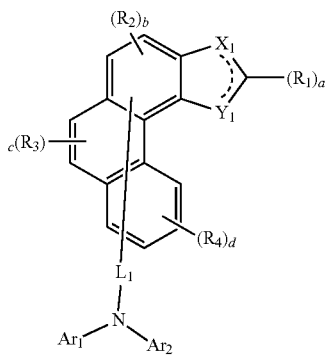
(1)

In formula 1, $X_1$ and $Y_1$ each independently represent —N═, —NR$_5$—, —O—, or —S—, with the proviso that any one of $X_1$ and $Y_1$ represents —N═, and the other one of $X_1$ and $Y_1$ represents —NR$_5$—, —O—, or —S—;

$R_1$ represents a substituted or unsubstituted (C6-C30)aryl, or a substituted or unsubstituted (3- to 30-membered) heteroaryl;

$L_1$ represents a single bond, a substituted or unsubstituted (C6-C30)arylene, or a substituted or unsubstituted (3- to 30-membered)heteroarylene;

$Ar_1$ and $Ar_2$ each independently represent a substituted or unsubstituted (C6-C30)aryl, or a substituted or unsubstituted (3- to 30-membered)heteroaryl;

$R_2$ to $R_5$ each independently represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring(s) and a (C6-C30)aromatic ring(s), or -$L_3$-N(Ar$_3$)(Ar$_4$); or may be linked to an adjacent substituent to form a ring;

a represents 1, b and c each independently represent 1 or 2, and d represents an integer of 1 to 4, where if b to d are an integer of 2 or more, each of $R_2$ to each of $R_4$ may be the same as or different from each other;

$$Ar_{11}(L_{11}\text{-}HAr)_e \qquad (2)$$

In formula 2,

HAr each independently represents a substituted or unsubstituted nitrogen-containing (3- to 20-membered) heteroaryl;

$L_{11}$ each independently represents a single bond, a substituted or unsubstituted (C6-C30)arylene, or a substituted or unsubstituted (3- to 30-membered)heteroarylene;

$Ar_{11}$ each independently represents any one of the following formulas 3 to 5:

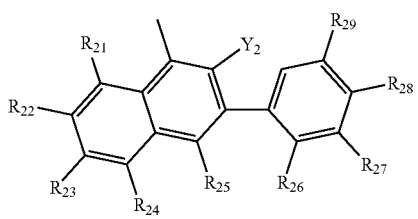
(3)

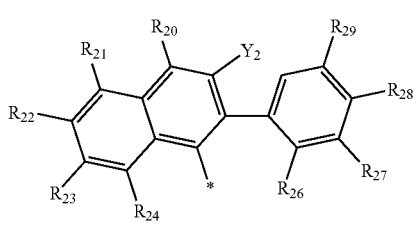
(4)

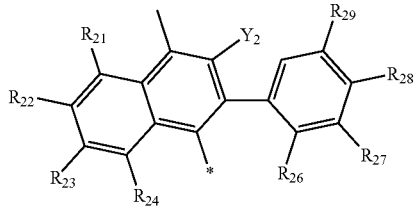

(5)

in formulas 3 to 5, $Y_2$ represents O or S;

$R_{20}$ to $R_{29}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring(s) and a (C6-C30)aromatic ring(s), or -$L_3$-N($Ar_3$)($Ar_4$);

e represents 1 or 2, where if e is 2, each of ($L_{11}$-HAr) may be the same as or different from each other;

* represents a site linked to $L_{11}$;

in formulas 1 and 3 to 5, $L_3$ each independently represents a single bond, a substituted or unsubstituted (C6-C30)arylene, or a substituted or unsubstituted (3- to 30-membered)heteroarylene; and $Ar_3$ and $Ar_4$ each independently represent hydrogen, a substituted or unsubstituted (C1-C30)alkyl, a substituted or unsubstituted (C2-C30)alkenyl, a substituted or unsubstituted fused ring of a (C3-C30)aliphatic ring(s) and a (C6-C30)aromatic ring(s), a substituted or unsubstituted (C6-C30)aryl, or a substituted or unsubstituted (3- to 30-membered)heteroaryl.

Advantageous Effects of Invention

The organic electroluminescent compound according to the present disclosure exhibits suitable performance for use in organic electroluminescent devices. In addition, an organic electroluminescent device having lower driving voltage, higher luminous efficiency, higher power efficiency and/or excellent lifespan properties compared to a conventional organic electroluminescent device is provided by including a plurality of host materials according to the present disclosure, and it is possible to manufacture a display device or a lighting device using the same.

MODE FOR THE INVENTION

Hereinafter, the present disclosure will be described in detail. However, the following description is intended to explain the present disclosure, and is not meant to restrict the scope of the present disclosure.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, or an electron injection material, etc.

The term "a plurality of organic electroluminescent material(s)" in the present disclosure means an organic electroluminescent material(s) comprising a combination of at least two compounds, which may be comprised in any layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of organic electroluminescent material(s) may be a combination of two or more compounds that may be included in at least one layer of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. Such two or more compounds may be included in the same layer or different layers, and may be mixture-evaporated or co-evaporated, or individually deposited.

The term "a plurality of host materials" in the present disclosure means an organic electroluminescent material in which at least two host materials are combined, which may mean both a material before being comprised in an organic electroluminescent device (for example, before vapor deposition) and a material after being comprised in an organic electroluminescent device (for example, after vapor deposition). A plurality of host materials of the present disclosure may be included in any light-emitting layer constituting an organic electroluminescent device, wherein the two or more compounds comprised in the plurality of host materials may be together included in one light-emitting layer or may be respectively included in different light-emitting layers. In case the two or more host materials are comprised in one layer, for example, they may be mixture-evaporated to form a layer, or may be individually and simultaneously co-evaporated to form a layer.

Herein, the term "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, sec-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-

C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. The term "(3- to 7-membered)heterocycloalkyl" is meant to be a cycloalkyl having 3 to 7, preferably 5 to 7 ring backbone atoms, and including at least one heteroatom selected from the group consisting of B, N, O, S, Si, and P, preferably the group consisting of O, S, and N. The above heterocycloalkyl may include tetrahydrofuran, pyrrolidine, thiolane, tetrahydropyran, etc. The term "(C6-C30)aryl(ene)" is meant to be a monocyclic or fused ring radical derived from an aromatic hydrocarbon having 6 to 30 ring backbone carbon atoms, which may be partially saturated. The number of ring backbone carbon atoms is preferably 6 to 25, and more preferably 6 to 18. The above aryl comprises those having a spiro structure. The above aryl may include phenyl, biphenyl, terphenyl, naphthyl, binaphthyl, phenylnaphthyl, naphthylphenyl, phenylterphenyl, fluorenyl, phenylfluorenyl, diphenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, azulenyl, tetramethyldihydrophenanthrenyl, etc. More specifically, the aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzo[a]fluorenyl, benzo[b]fluorenyl, benzo[c]fluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-tert-butylphenyl, p-(2-phenylpropyl)phenyl, 4'-methylbiphenylyl, 4"-tert-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc.

The term "(3- to 30-membered)heteroaryl(ene)" means an aryl group or arylene group having 3 to 30 ring backbone atoms and including at least one heteroatom(s) selected from the group consisting of B, N, O, S, Si, and P. The number of heteroatoms is preferably 1 to 4. The above heteroaryl(ene) may be a monocyclic ring or a fused ring condensed with at least one benzene ring, and may be partially saturated. In addition, the above heteroaryl(ene) comprises the form in which at least one heteroaryl or aryl group is linked to a heteroaryl group via a single bond(s), and also comprises those having a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, dibenzoselenophenyl, naphthobenzofuranyl, naphthobenzothiophenyl, benzofuroquinolyl, benzofuroquinazolinyl, benzofuronaphthyridinyl, benzofuropyrimidinyl, naphthofuropyrimidinyl, benzothienoquinolyl, benzothienoquinazolinyl, benzothienonaphthyridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, benzotriazolephenazinyl, imidazopyridyl, chromenoquinazolinyl, thiochromenoquinazolinyl, dimethylbenzoperimidinyl, indolocarbazolyl, indenocarbazolyl, etc. More specifically, the heteroaryl may include 1-pyrrolyl, 2-pyrrolyl, 3-pyrrolyl, pyrazinyl, 2-pyridyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridyl, 3-imidazopyridyl, 5-imidazopyridyl, 6-imidazopyridyl, 7-imidazopyridyl, 8-imidazopyridyl, 3-pyridyl, 4-pyridyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-tert-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl, 4-tert-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. In the present disclosure, "halogen" includes F, Cl, Br, and I.

In addition, "ortho (o-)," "meta (m-)," and "para (p-)" are prefixes, which represent the relative positions of substituents, respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

In addition, "substituted" in the expression "substituted or unsubstituted" means that a hydrogen atom in a certain functional group is replaced with another atom or another functional group (i.e., a substituent), and also comprises being substituted with a group in which two or more of the substituents are linked. For example, "a substituent in which two or more substituents are linked" may be pyridine-triazine. That is, pyridine-triazine may be interpreted as one heteroaryl substituent or the substituents in which two heteroaryl substituents are linked. In formulas of the present disclosure, the substituents of the substituted alkyl, the substituted alkenyl, the substituted aryl, the substituted arylene, the substituted heteroaryl, the substituted heteroarylene, the substituted nitrogen-containing heteroaryl, the substituted cycloalkyl, the substituted alkoxy, the substituted trialkylsilyl, the substituted dialkylarylsilyl, the substituted alkyldiarylsilyl, the substituted triarylsilyl, and the substituted fused ring of an aliphatic ring(s) and an aromatic ring(s) each independently are at least one selected from the group consisting of deuterium; a halogen; a cyano; a carboxyl; a nitro; a hydroxyl; a phosphine oxide; a (C1-C30)alkyl; a halo(C1-C30)alkyl; a (C2—C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with at least one of a (C1-C30)alkyl(s) and a (C6-C30)aryl(s); a (C6-C30)aryl unsubstituted or substituted with at least one of deuterium, a cyano, a (C1-C30)alkyl(s), a (C3-C30)cycloalkyl(s), a tri(C1-C30)alkylsilyl(s), a (C6-C30)aryl(s), and a (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; a fused ring of a (C3-C30)aliphatic ring(s) and a (C6-C30)aromatic ring(s); an amino; a mono- or di-(C1-C30)alkylamino; a mono- or di-(C2-C30)alkenylamino; a (C1-C30)alkyl(C2-C30)alkenylamino; a mono- or di-(C6-C30)arylamino(s); a (C1-C30)alkyl(C6-C30)arylamino; a mono- or di-(3- to 30-membered)heteroarylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30) arylcarbonyl; a (C6-C30)arylphosphine; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. According to one embodiment of the present disclosure, the substituents, each independently, are at least one selected from the group consisting of deuterium; a cyano; a (C1-C20)alkyl; a (C6-C25)cycloalkyl; a (5- to 25-membered)heteroaryl unsubstituted or substituted with at least one (C6-C25)aryl(s); a (C6-C25)aryl(s) unsubstituted or substituted with at least one of deuterium, a cyano, a (C1-C20)alkyl(s), a (C6-C25)cycloalkyl(s), a tri(C1-C20)alkylsilyl(s), a (C6-C25)aryl(s), and a (5- to 25-membered)heteroaryl(s); a mono- or di-(C6-C25)arylamino; a mono- or di-(5- to 25-membered)heteroarylamino; and a (C6-C25)aryl(5- to 25-membered)heteroarylamino. According to another embodiment of the present disclosure, the substituents, each independently, are at least one selected from the group consisting of deuterium; a cyano; a (C1-C10)alkyl; a (C6-C18)cycloalkyl; a (5- to 20-membered) heteroaryl unsubstituted or substituted with at least one (C6-C18)aryl(s); a (C6-C25)aryl(s) unsubstituted or substituted with at least one of deuterium, a cyano, a (C1-C10) alkyl(s), a (C6-C18)cycloalkyl(s), a tri(C1-C10) alkylsilyl(s), a (C6-C15)aryl(s), and a (5- to 20-membered) heteroaryl(s); a di-(C6-C18)arylamino; and a (C6-C18)aryl (5- to 20-membered)heteroarylamino. Specifically, the substituents, each independently, may be at least one of deuterium; a cyano; methyl; a cyclohexyl; a substituted or unsubstituted phenyl; a naphthyl; a phenylnaphthyl; a biphenyl; a methylfluorenyl; a dimethylfluorenyl; a diphenylfluorenyl; a phenanthrenyl; an anthracenyl; a fluoranthenyl; a terphenyl; a chrysenyl; a triphenylenyl; a spirobifluorenyl; a pyridyl substituted with a phenyl(s); a benzimidazolyl substituted with a phenyl(s); a triazinyl substituted with at least one selected from the group consisting of a phenyl(s) and a naphthyl(s); a benzothiophenyl; a dibenzothiophenyl; a dibenzofuranyl unsubstituted or substituted with a phenyl(s) and/or a biphenyl(s); a carbazolyl unsubstituted or substituted with a phenyl(s); a naphthooxazolyl substituted with a phenyl(s); a diphenylamino; a dibiphenylamino; a phenylbiphenylamino; a phenyldibenzothiofuranylamino; a phenyldibenzothiophenylamino, etc., and the substituents of the substituted phenyl may be at least one of deuterium, a cyano, a methyl, a tert-butyl, a naphthyl, a trimethylsilyl, a carbazolyl, and a cyclohexyl.

In the formulas of the present disclosure, in case a substituent is linked to an adjacent substituent to form a ring, the ring may be a substituted or unsubstituted mono- or polycyclic (3- to 30-membered) alicyclic or aromatic ring, or the combination thereof formed from at least two adjacent substituents being linked. In addition, the formed ring may contain at least one heteroatom selected from B, N, O, S, Si, and P, preferably at least one heteroatom selected from N, O, and S. According to one embodiment of the present disclosure, the number of ring backbone atoms is 5 to 20, and according to another embodiment of the present disclosure, the number of ring backbone atoms is 5 to 15.

In the formulas of the present disclosure, the heteroaryl, the heteroarylene, and the heterocycloalkyl, each independently, may contain at least one heteroatom selected from B, N, O, S, Si, and P. Also, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl (C6-C30)arylamino.

The present disclosure provides an organic electroluminescent device comprising an organic electroluminescent compound represented by the following formula 2' or formula 2″. Herein, the organic electroluminescent compound of formula 2' or formula 2″ may be included in a light-emitting layer or an electron transport layer.

Hereinafter, the compound represented by formula 2' will be described in more detail.

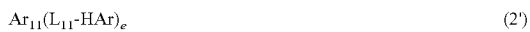

In formula 2',

HAr each independently represents a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted benzofuropyrimidinyl, or a substituted or unsubstituted benzothienopyrimidinyl;

$L_{11}$ each independently represents a single bond, a substituted or unsubstituted (C6-C30)arylene, or a substituted or unsubstituted (3- to 30-membered)heteroarylene;

$Ar_{11}$ each independently represents any one of the following formulas 3 to 5:

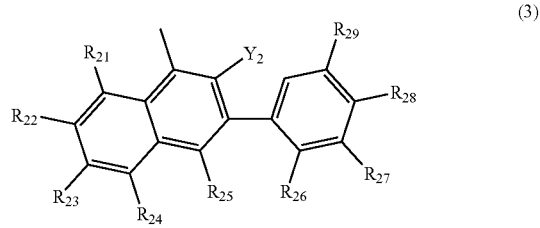

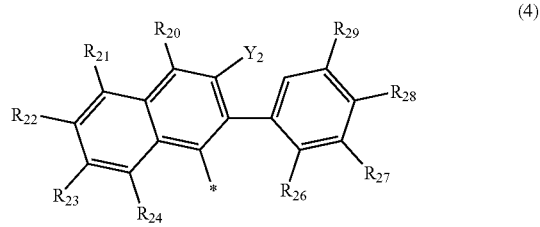

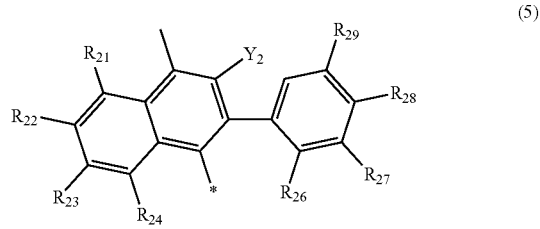

in formulas 3 to 5,
Y$_2$ represents O or S;
R$_{20}$ to R$_{29}$ represent hydrogen or deuterium;
e represents 1 or 2, where if e is 2, each of (L$_{11}$-HAr) may be the same as or different from each other; and
* represents a site linked to L$_{11}$;
with the proviso that when HAr is a substituted triazinyl, the substituents of the substituted triazinyl each independently are selected from deuterium, phenyl, naphthyl, biphenyl, terphenyl, phenanthrenyl, triphenylenyl, dimethylfluorenyl, fluoranthenyl, chrysenyl, carbazolyl, and combinations thereof, and when there are two substituents, they are the same as or different from each other.

The compound represented by formula 2' may be at least one selected from the following compounds, but is not limited thereto.

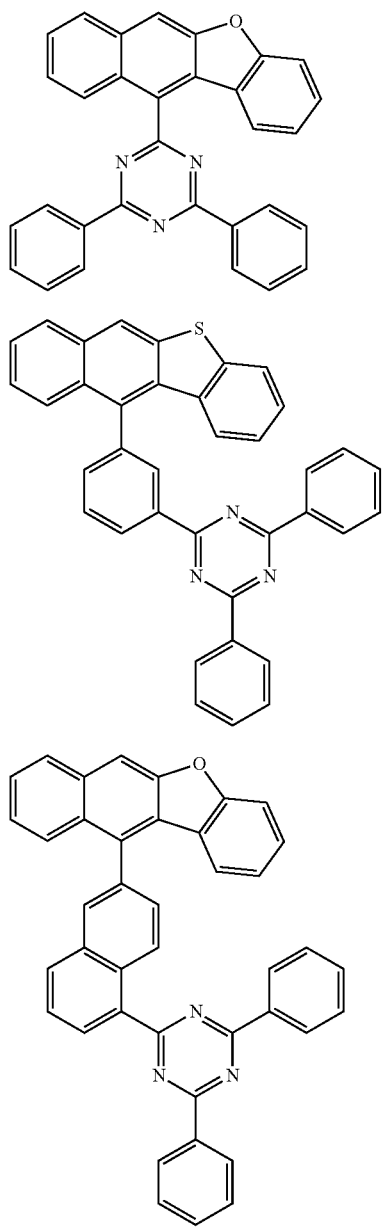

C-1

C-2

C-3

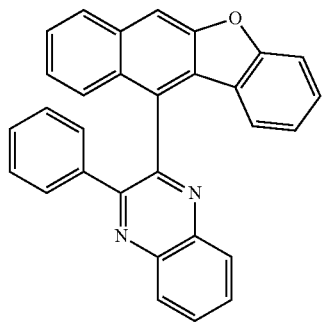

C-4

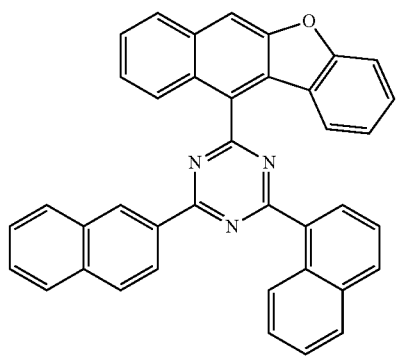

C-5

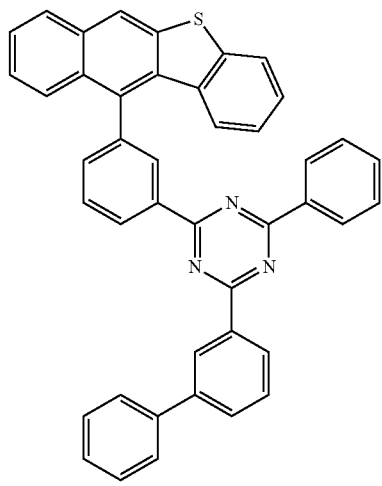

C-6

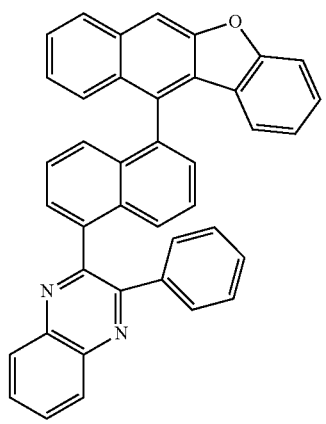

C-7

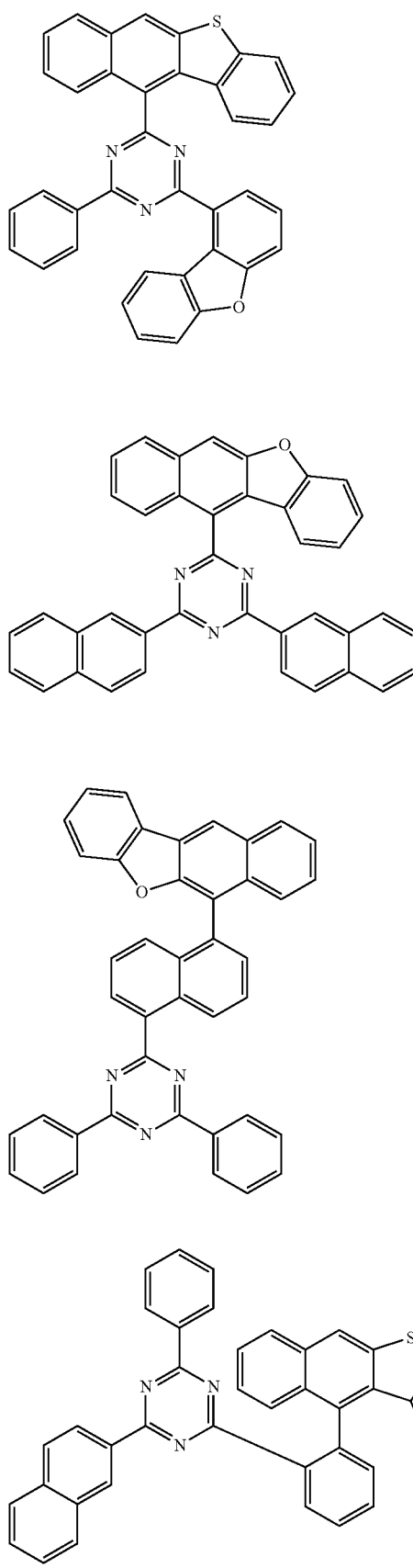
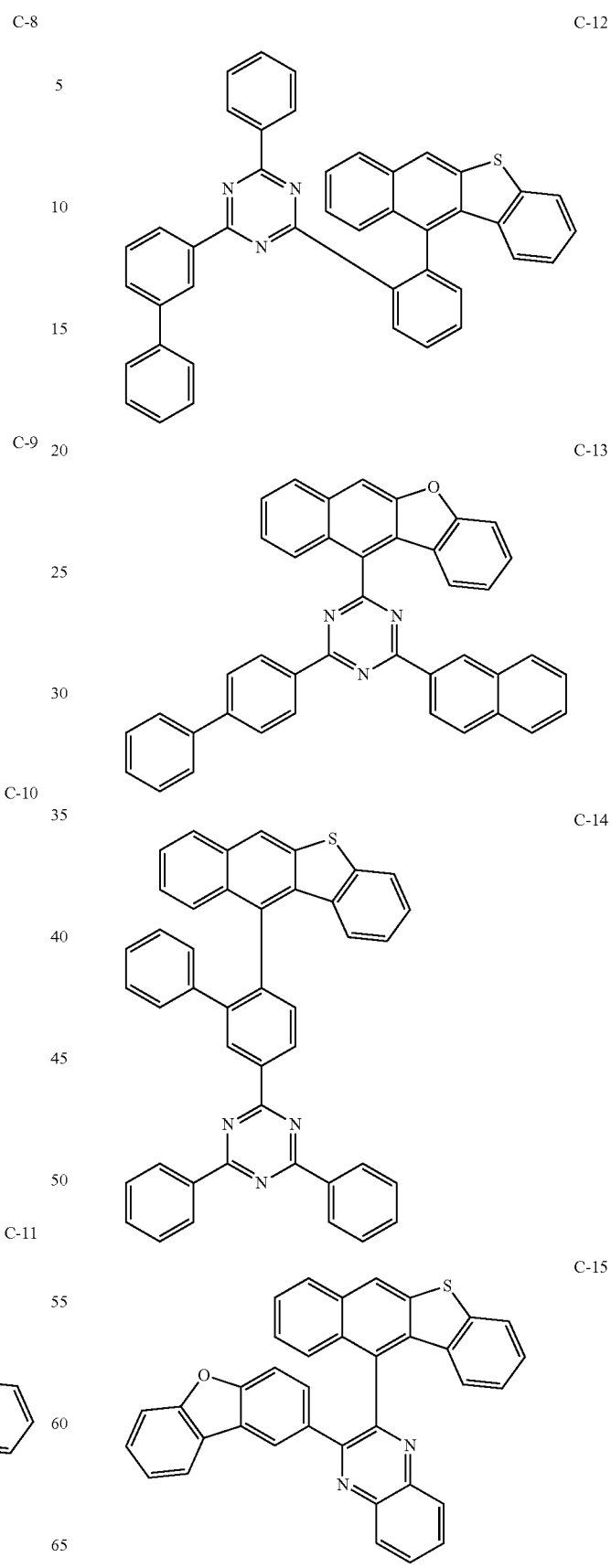

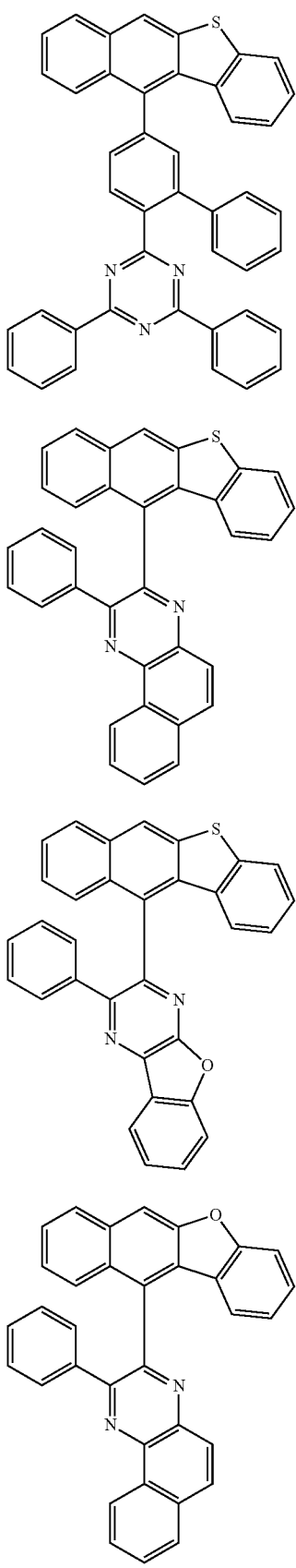
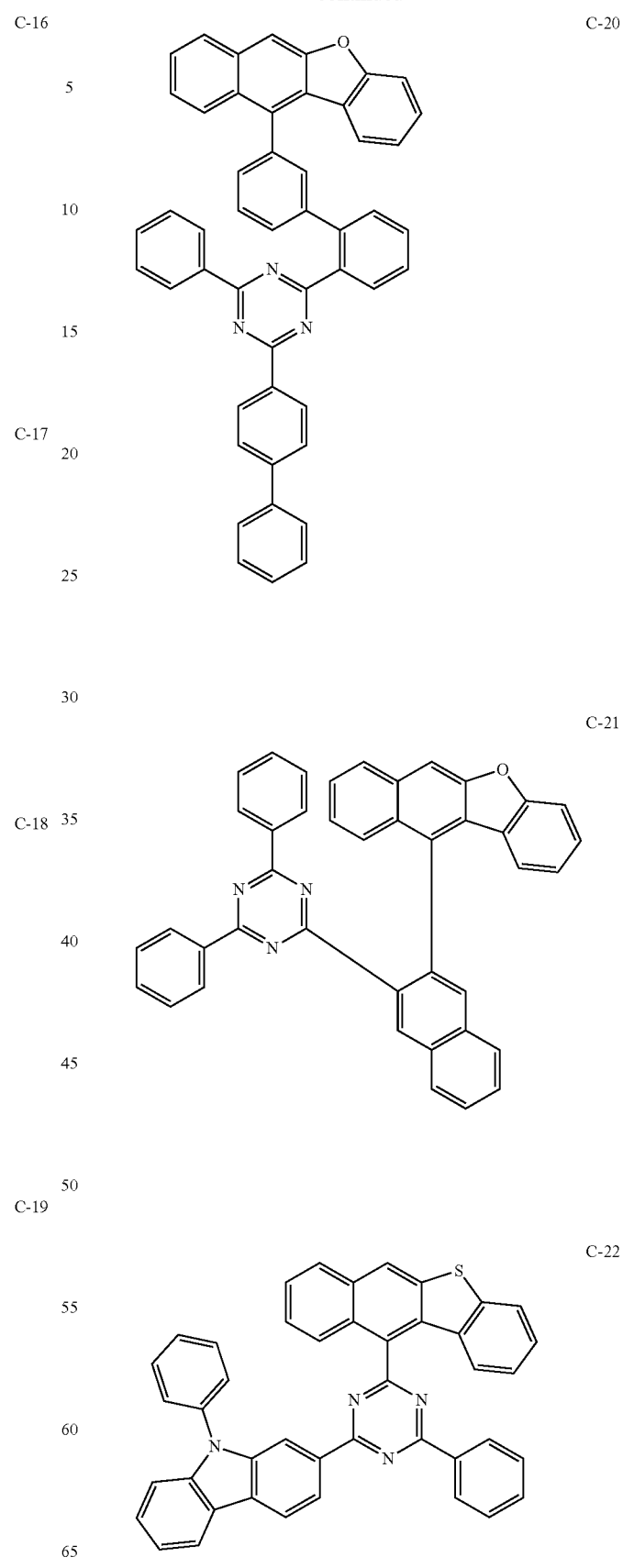

C-23
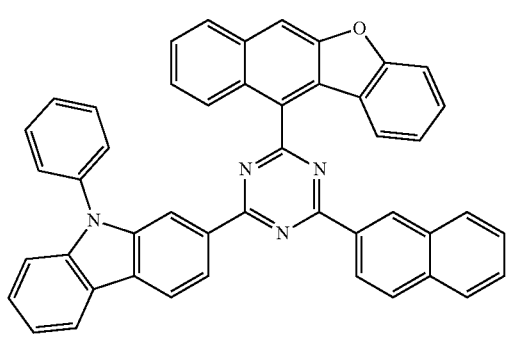
C-24
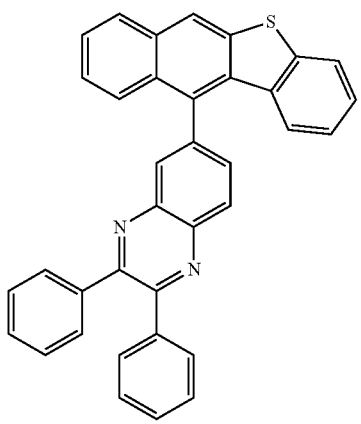
C-25
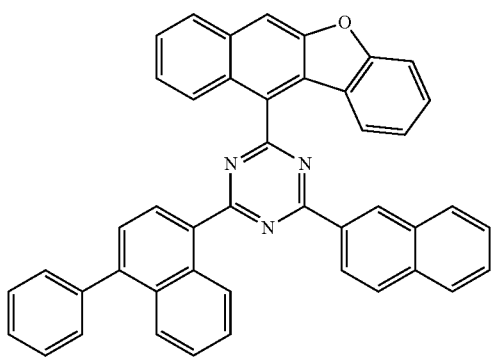
C-26
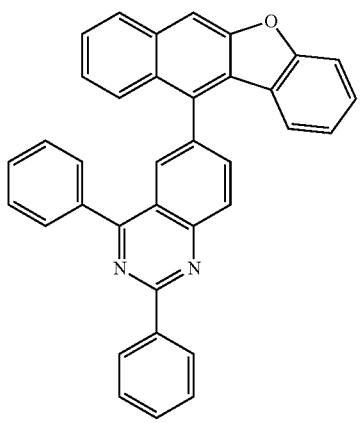
C-27
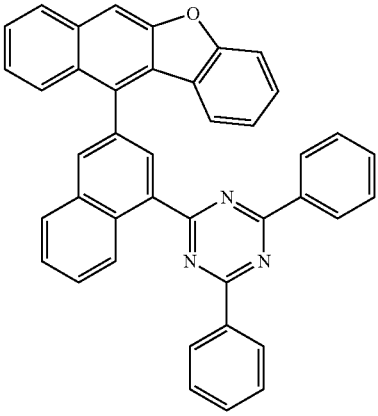
C-28
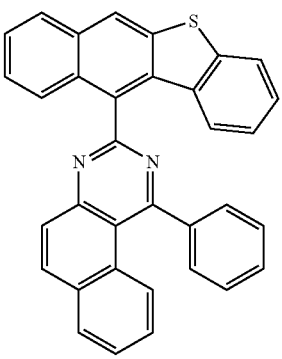
C-29
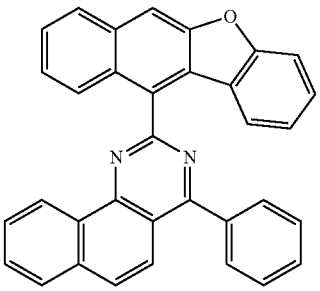
C-30
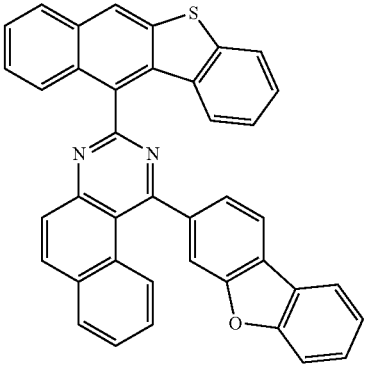

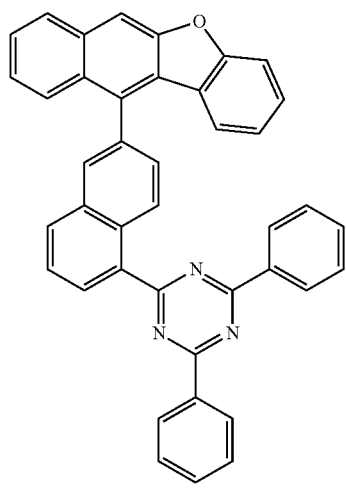
C-31
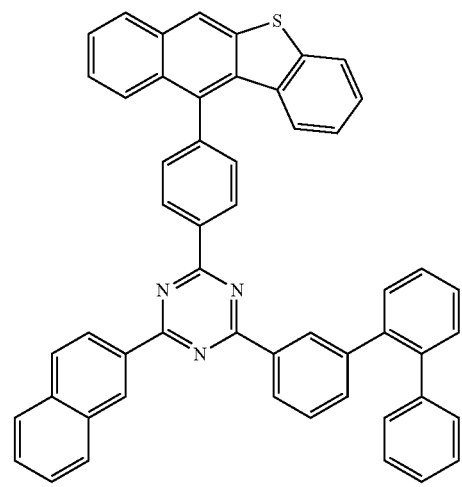
C-34
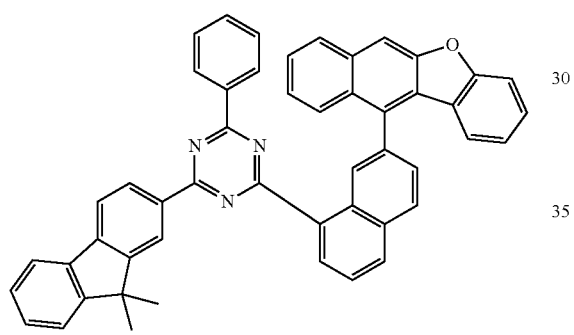
C-32
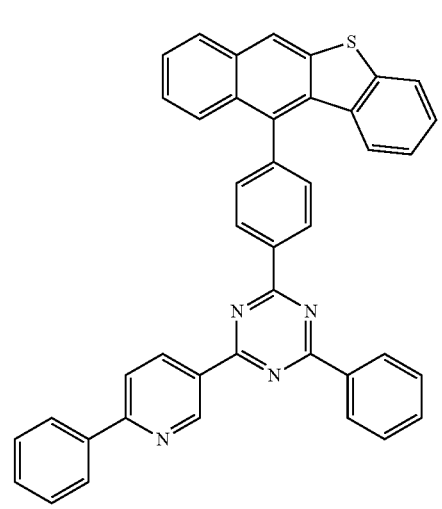
C-35
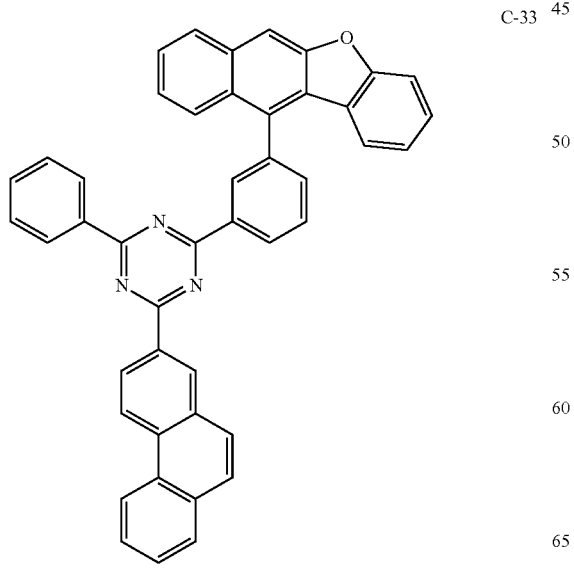
C-33
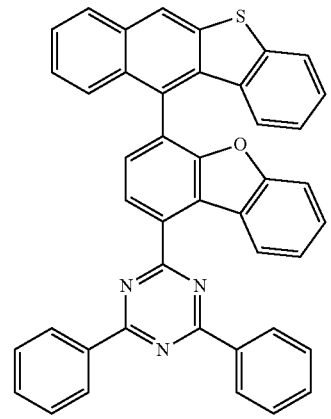
C-36

C-37
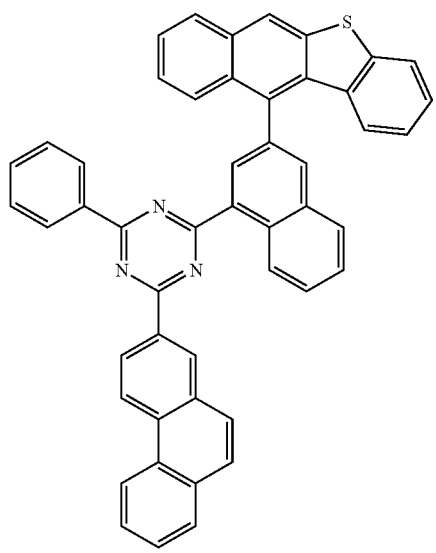
C-38
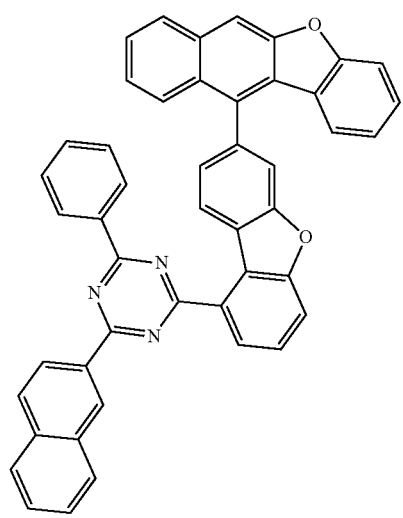
C-39
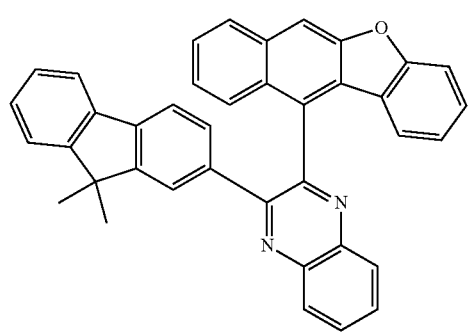
C-40
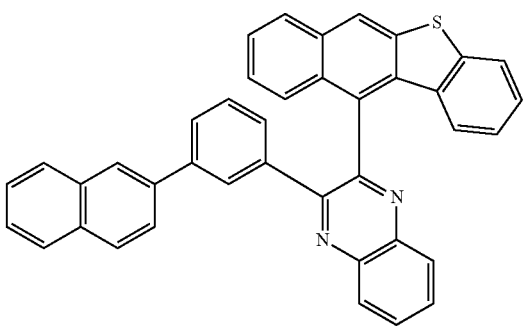
C-41
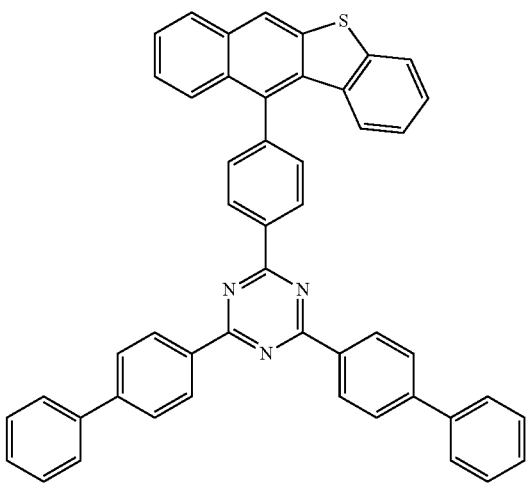
C-42
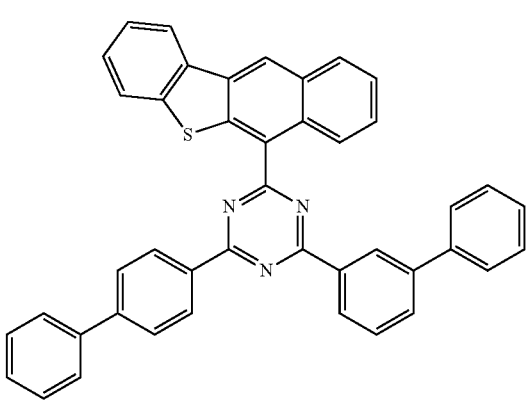
C-43
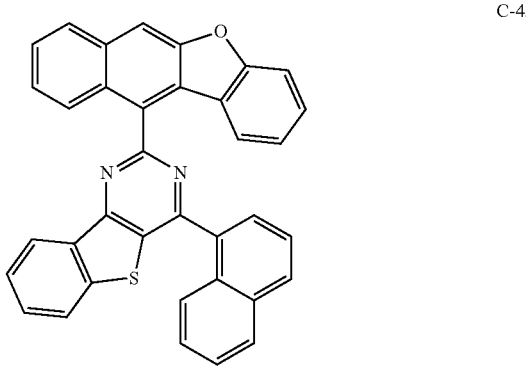

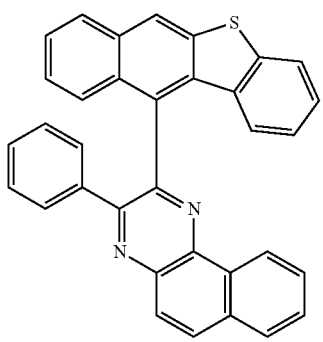
C-44
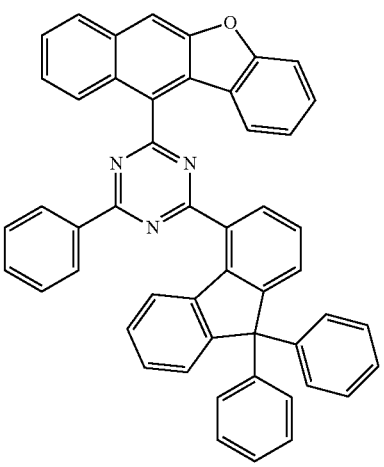
C-47
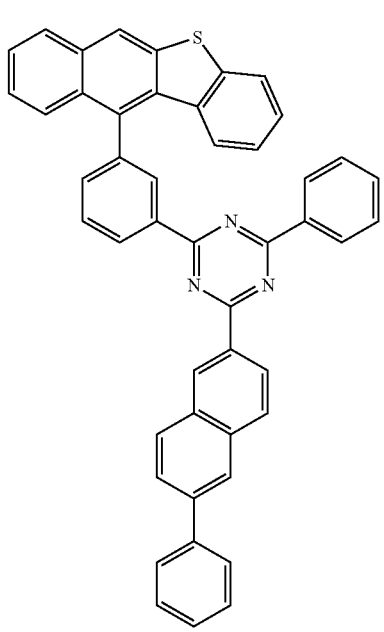
C-45
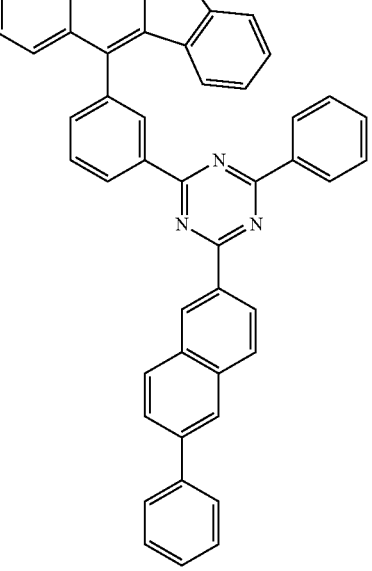
C-48
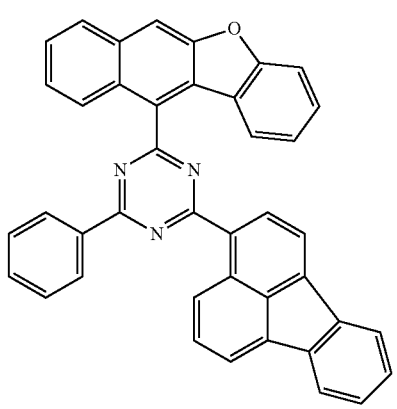
C-46
C-49

-continued
C-50
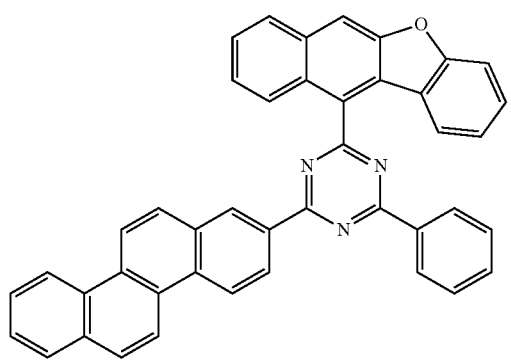
C-51
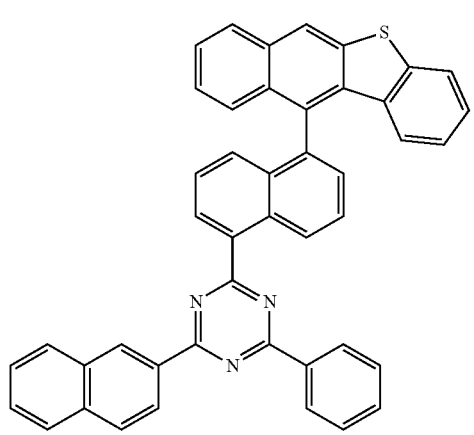
C-52
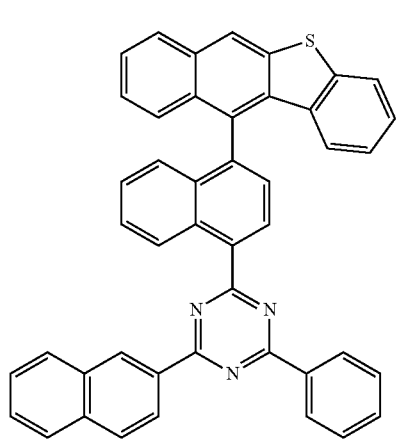
C-53
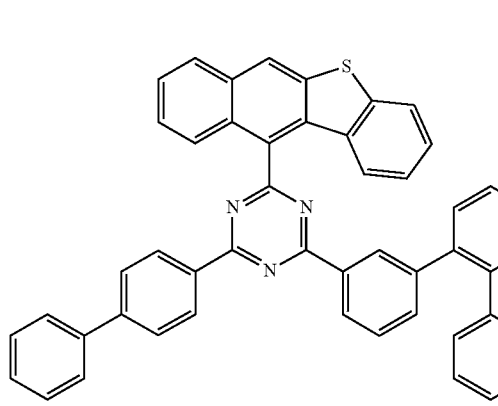
-continued
C-54
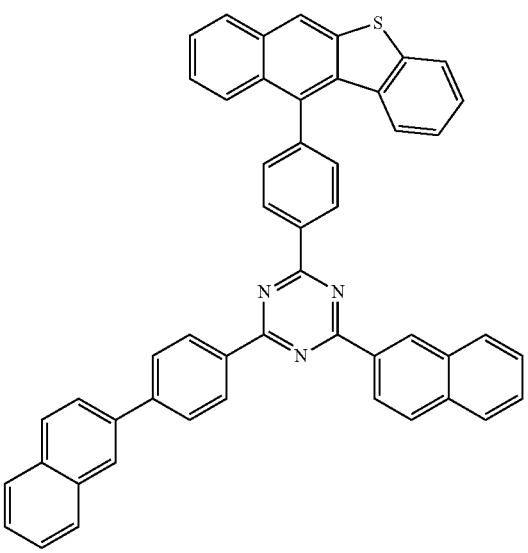
C-55
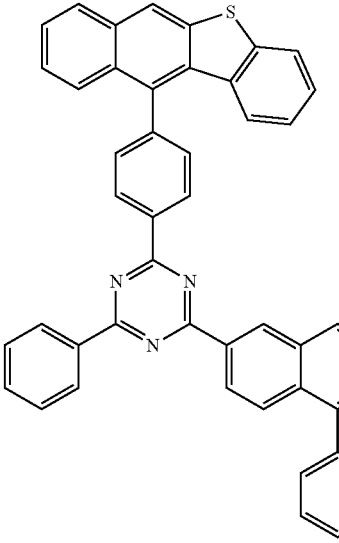
C-56
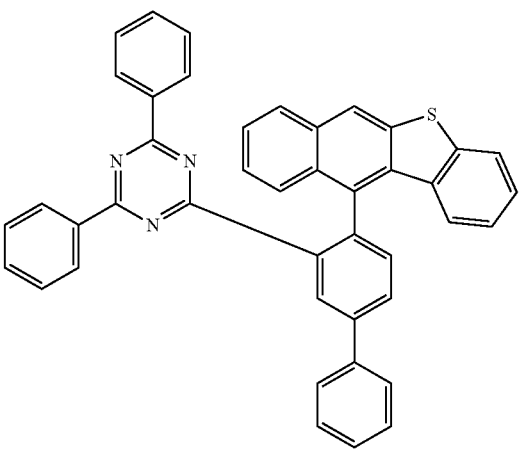

-continued

C-57
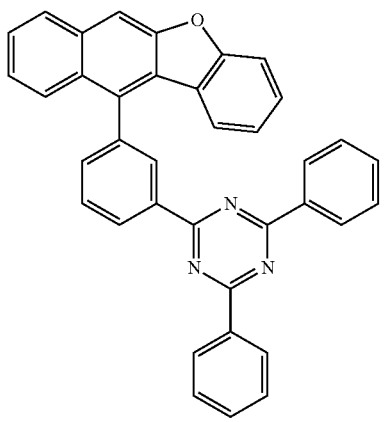

C-58
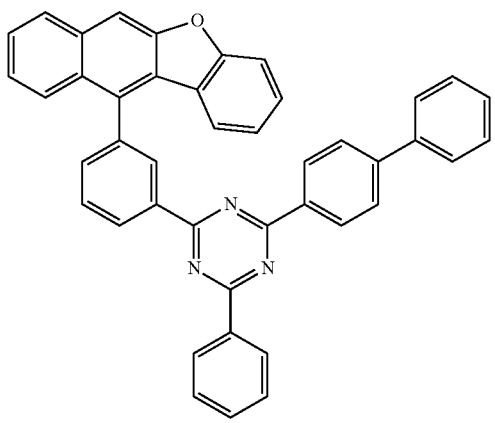

C-59
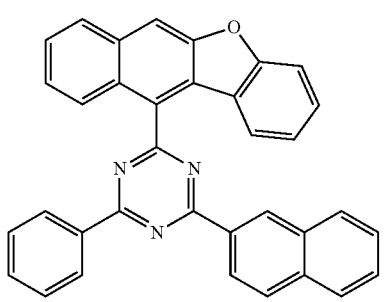

C-60
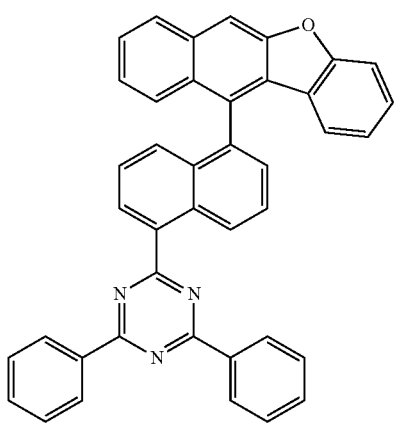

Hereinafter, the compound represented by formula 2″ will be described in more detail.

$$Ar_{11}(L_{11}\text{-}HAr)_e \tag{2″}$$

In formula 2″,

HAr each independently represents a substituted or unsubstituted triazinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted benzofuropyrimidinyl, or a substituted or unsubstituted benzothienopyrimidinyl;

$L_{11}$ each independently represents a single bond, a substituted or unsubstituted (C6-C30)arylene, or a substituted or unsubstituted (3- to 30-membered)heteroarylene;

$Ar_{11}$ each independently represents any one of the following formulas 3 to 5:

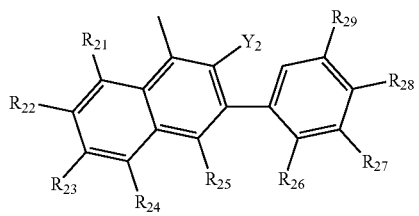
(3)

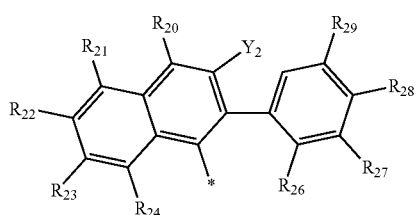
(4)

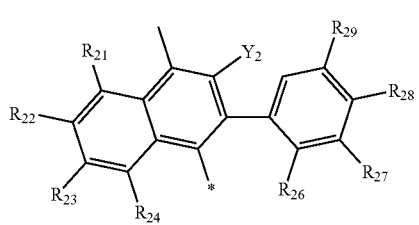
(5)

in formulas 3 to 5, $Y_2$ represents O or S;

$R_{21}$ to $R_{24}$ and $R_{26}$ to $R_{29}$ each independently represent hydrogen, deuterium, a substituted or unsubstituted (C6-C30)aryl, or a substituted or unsubstituted (3- to 30-membered)heteroaryl;

$R_{20}$ and $R_{25}$ each independently represent a substituted or unsubstituted (C6-C30)aryl, or a substituted or unsubstituted (3- to 30-membered)heteroaryl;

e represents 1 or 2, where if e is 2, each of ($L_{11}$-HAr) may be the same as or different from each other; and

* represents a site linked to $L_{11}$.

The compound represented by formula 2″ may be at least one selected from the following compounds, but is not limited thereto.

C-61 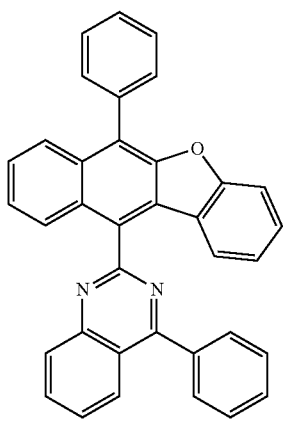
C-62 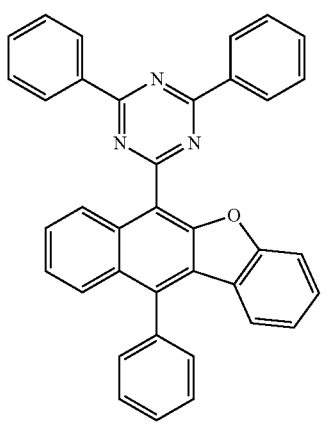
C-63 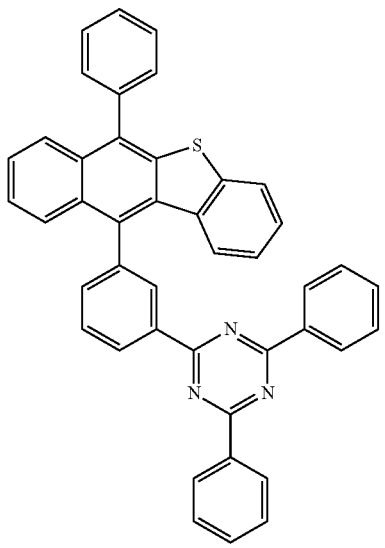
C-64 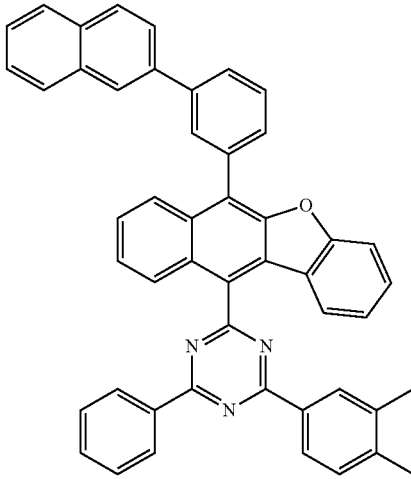
C-65 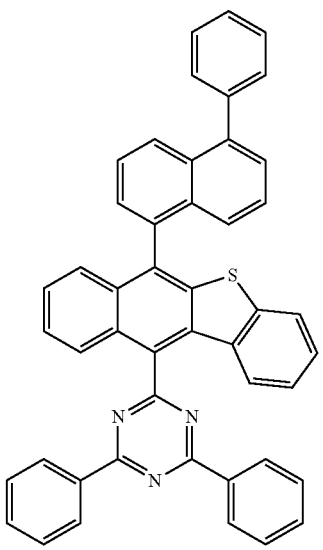
C-66 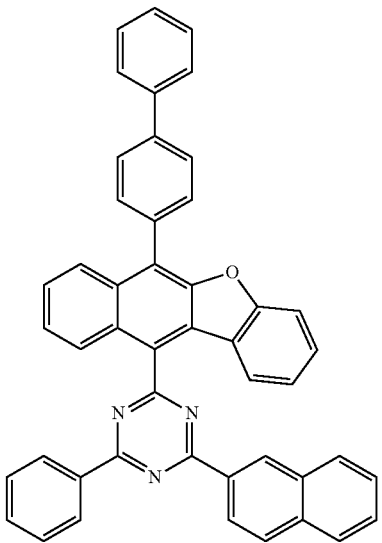

-continued
C-67
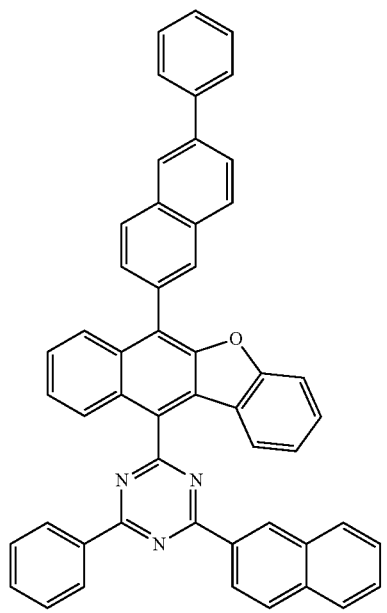
C-68
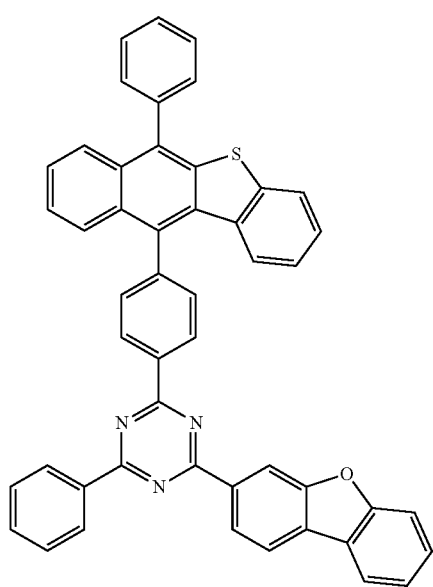
C-69
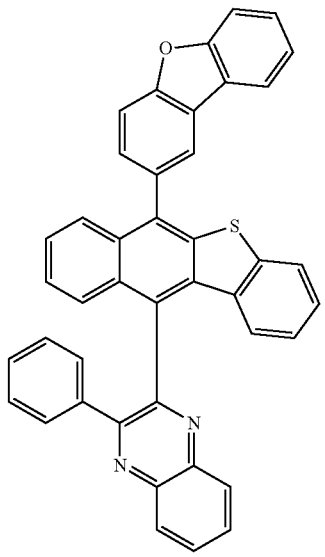
C-70
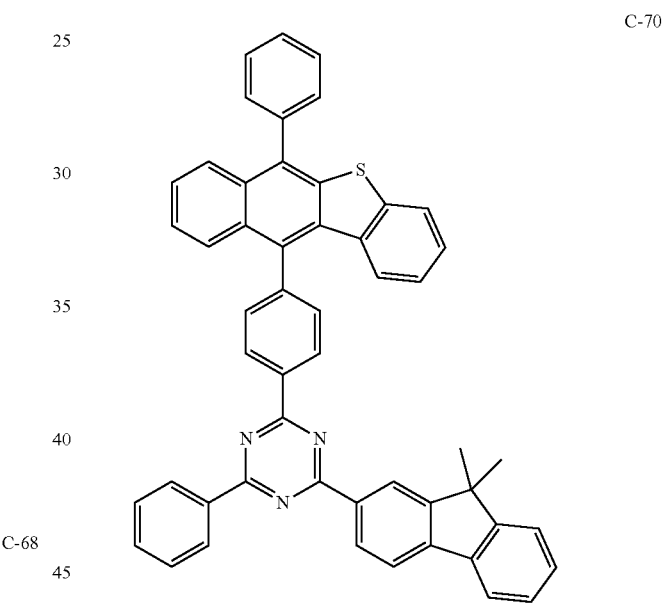
C-71
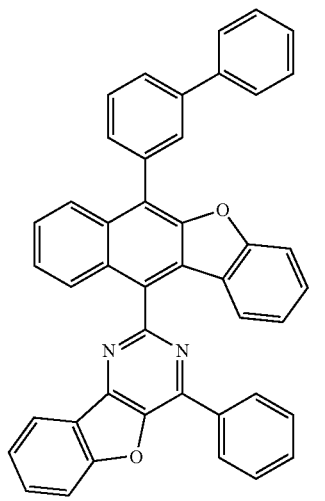

C-72
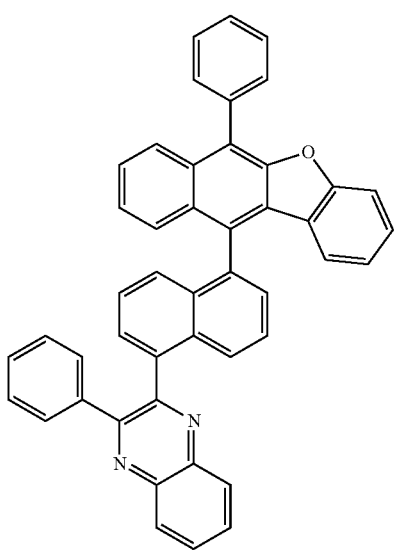
C-73
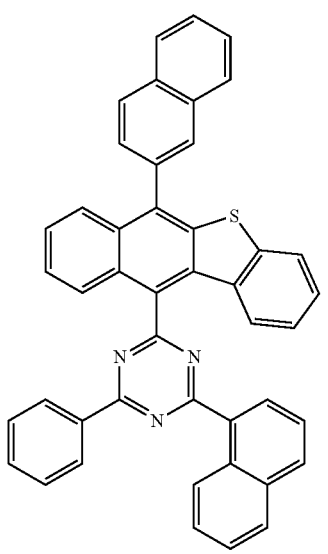
C-74
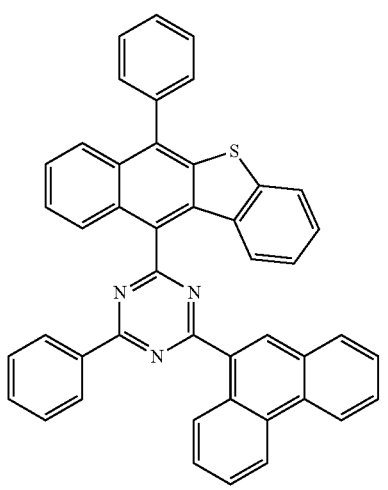
C-75
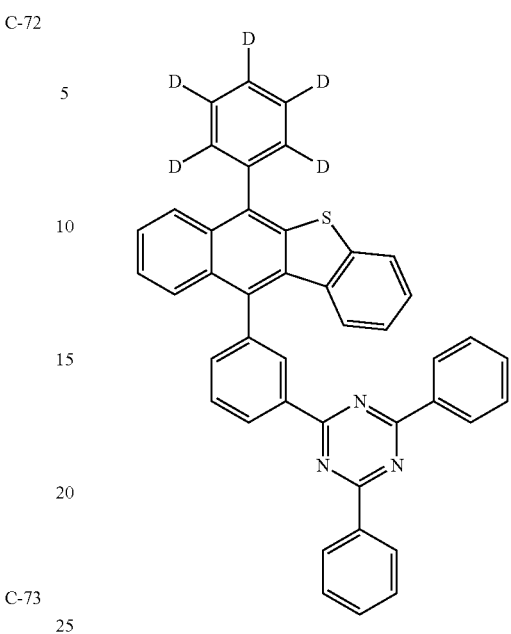
C-76

C-77
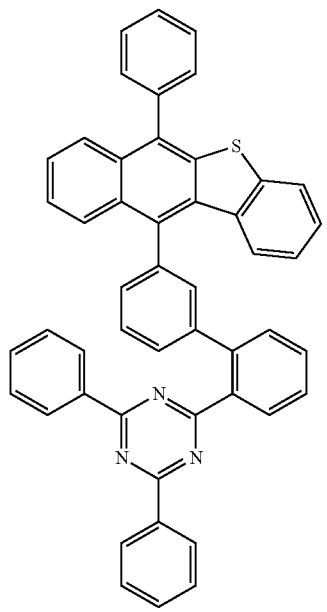
C-78
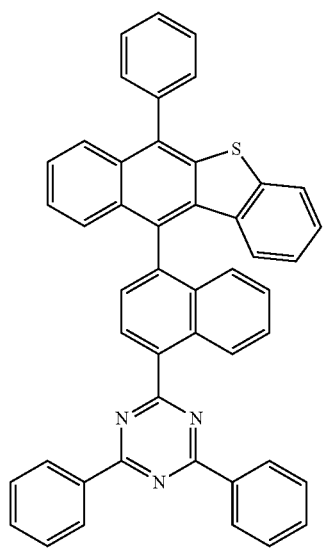
C-79
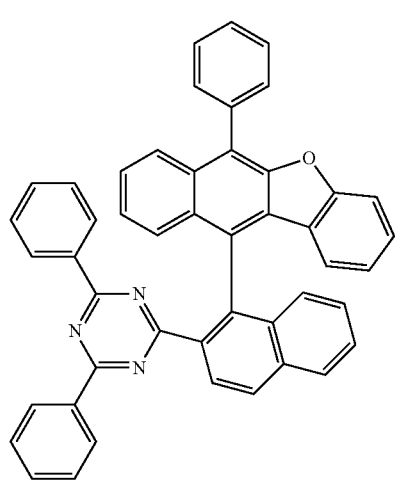
C-80
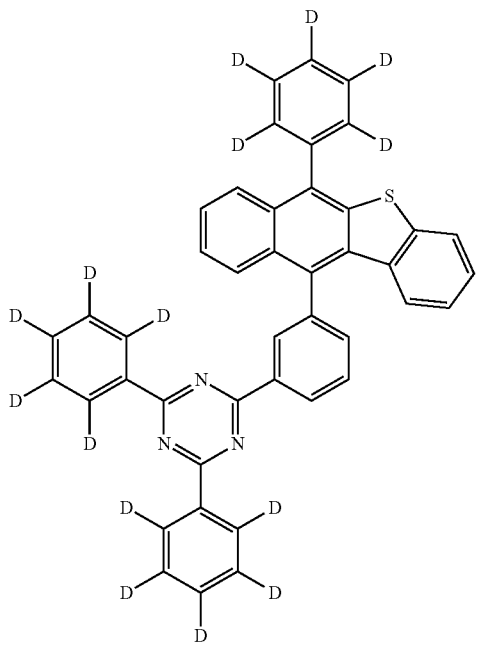
C-81
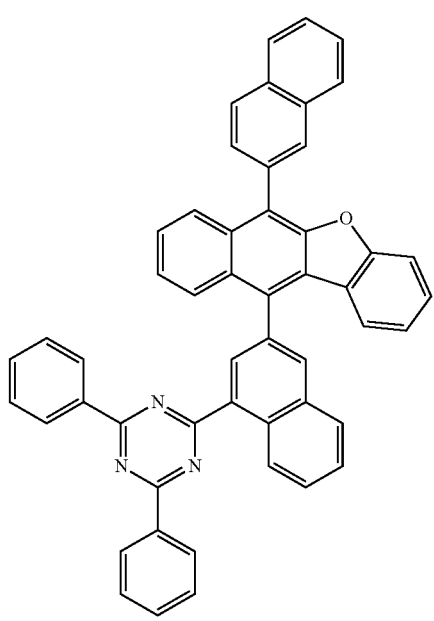

C-82
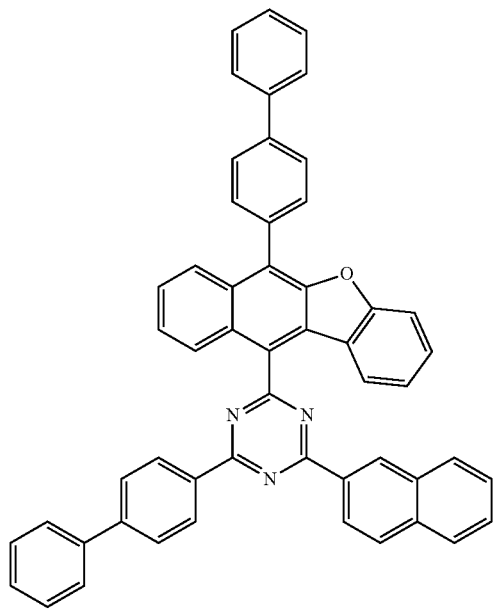
C-83
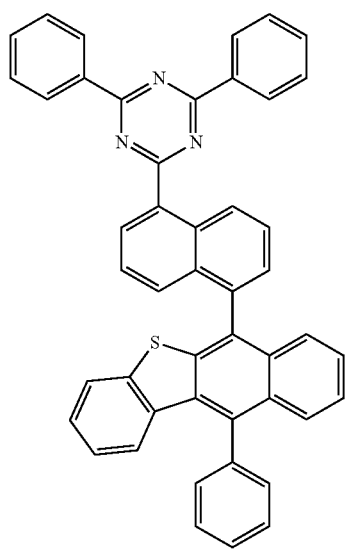
C-84
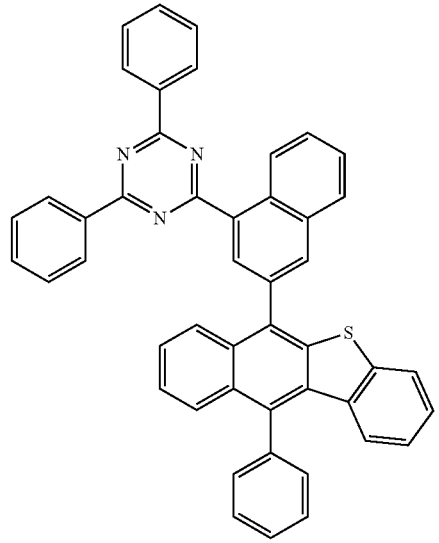
C-85
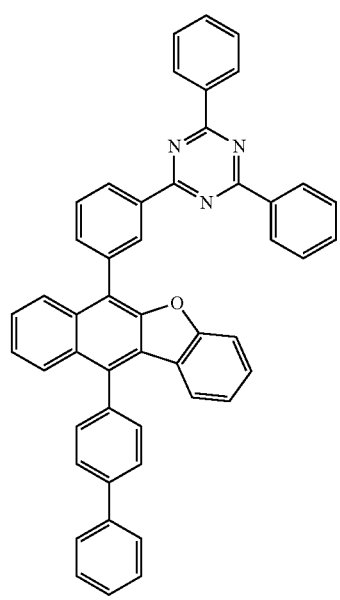
C86
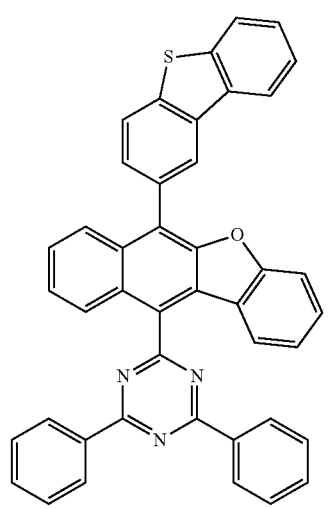

C-87
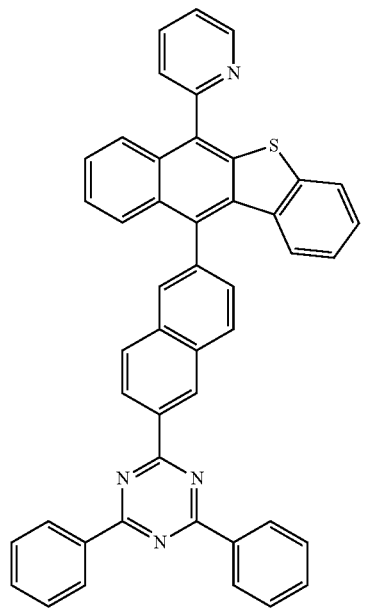
C-88
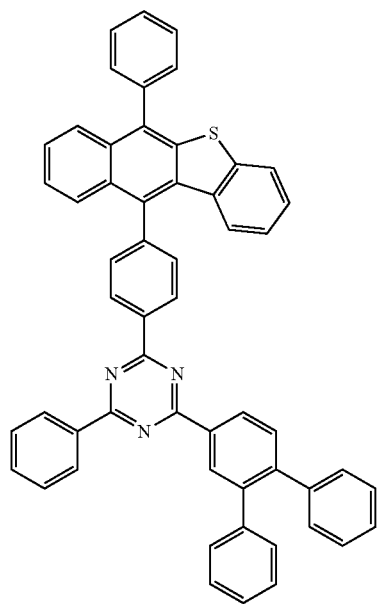
C-89
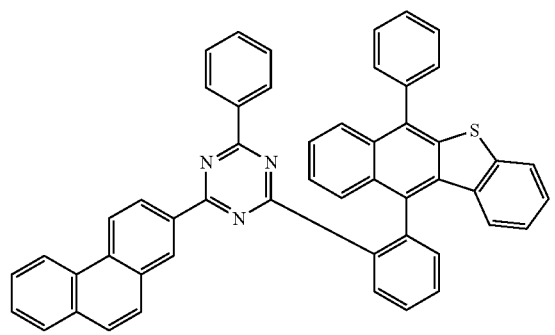
C-90
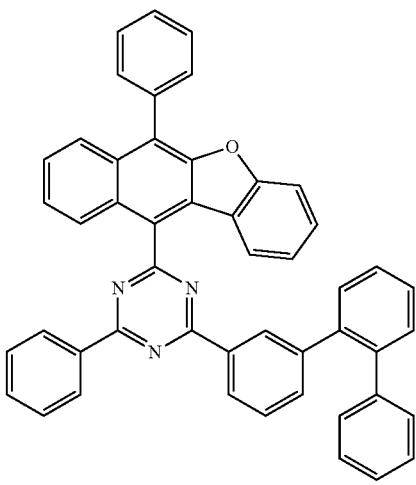
C-91
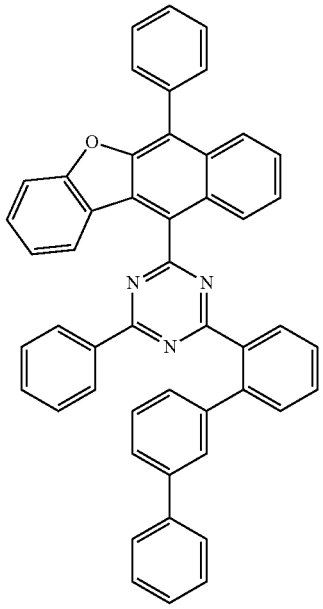

C-92
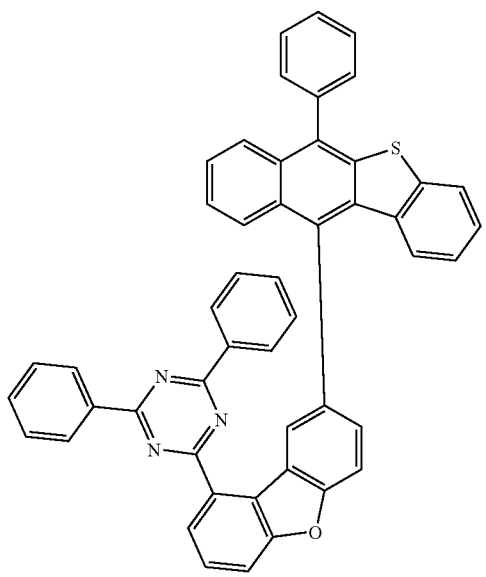
C-94
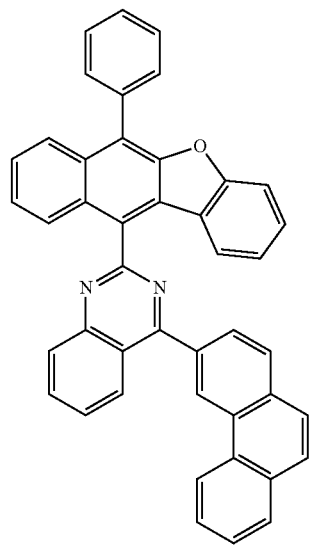
C-95
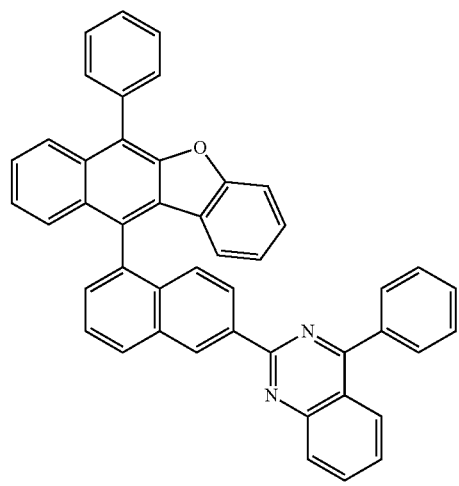
C-93
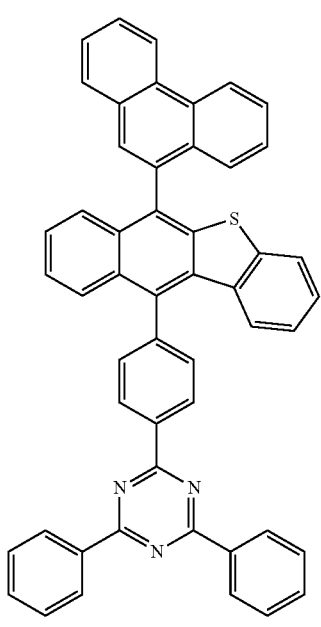
C-96
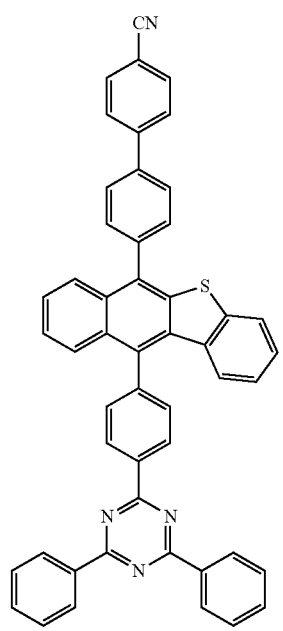

C-97
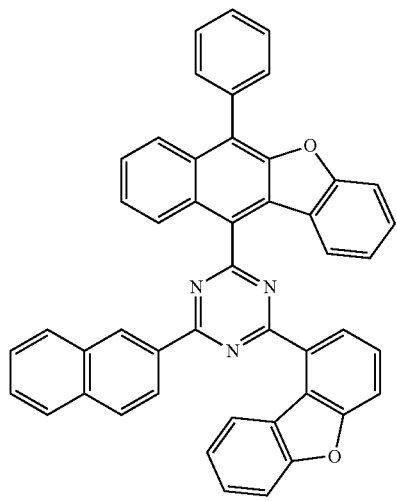
C-98
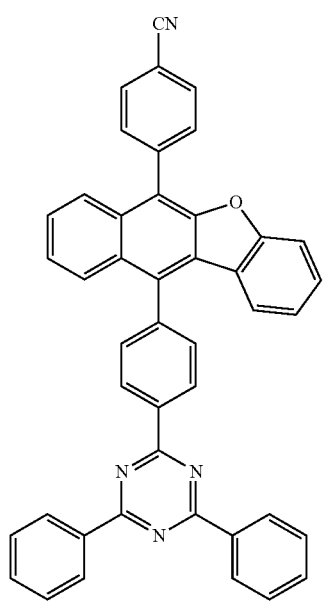
C-99
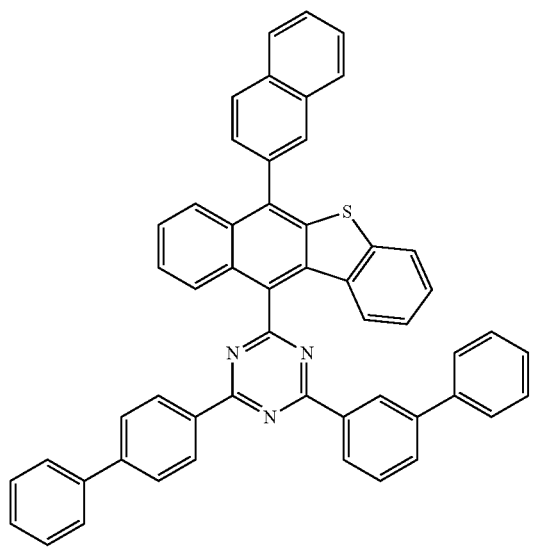
C-100
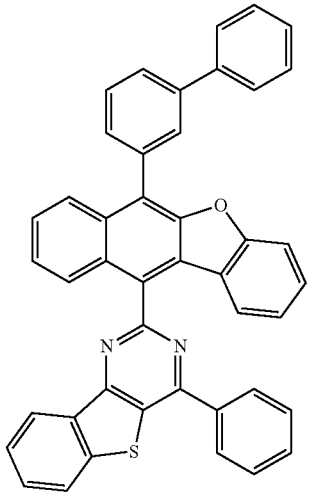
C-101
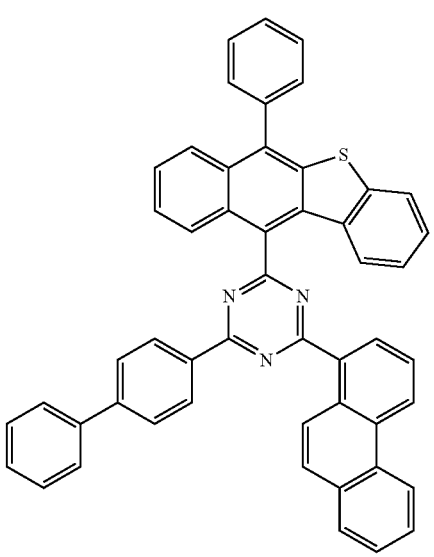
C-102
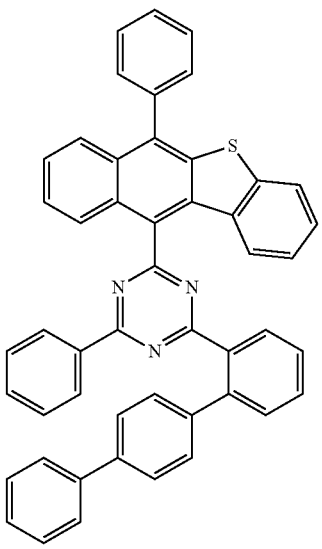

-continued
C-103
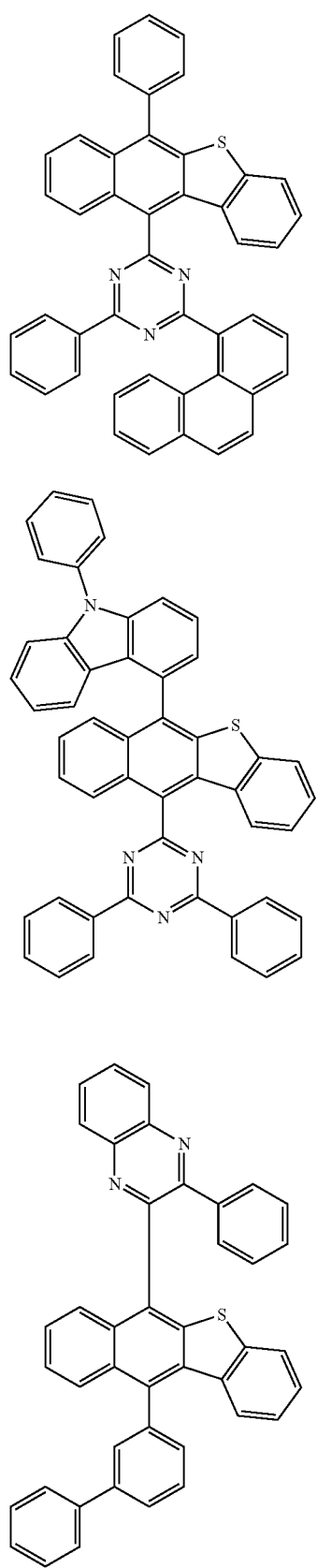
C-104
C-105
-continued
C-106
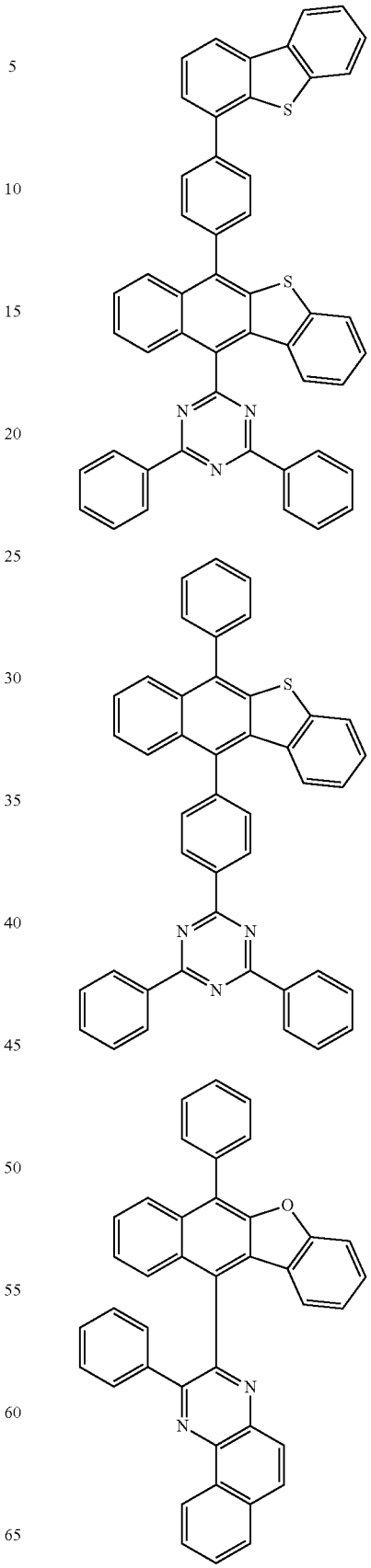
C-107
C-108

C-109
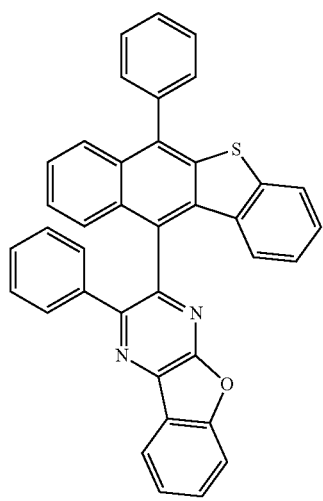
C-110
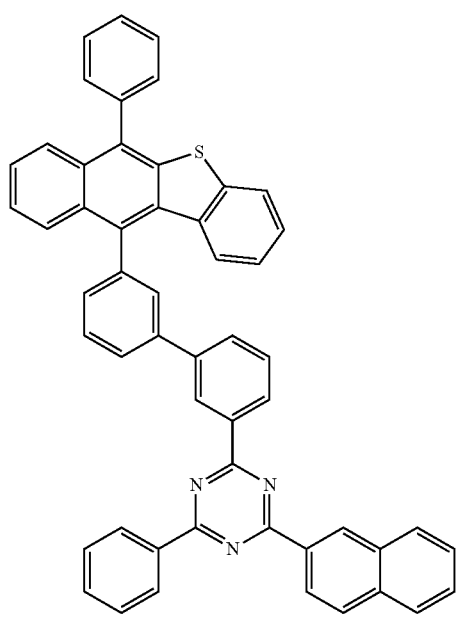
C-111
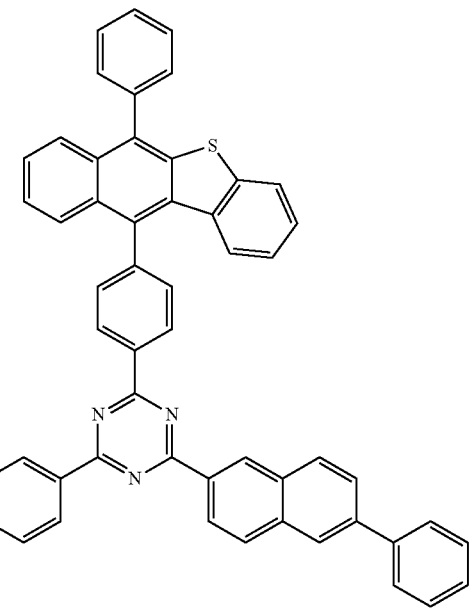
C-112
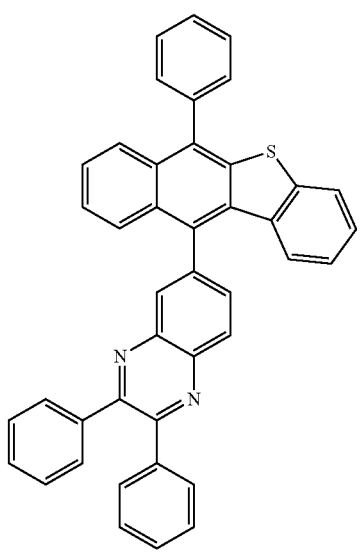

C-113
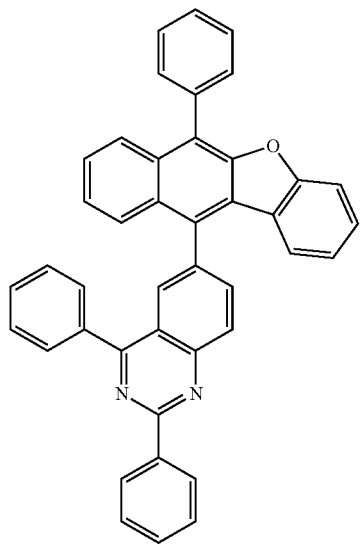
C-114
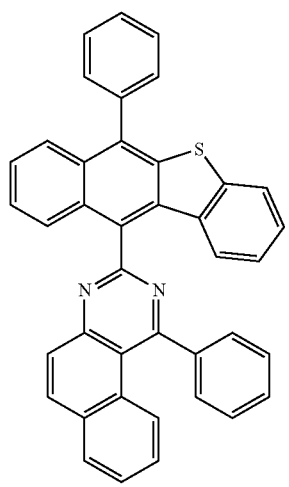
C-115
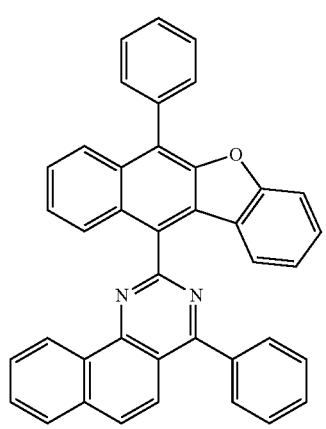
C-116
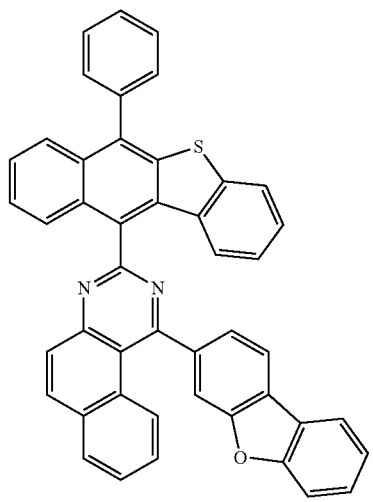
C-117
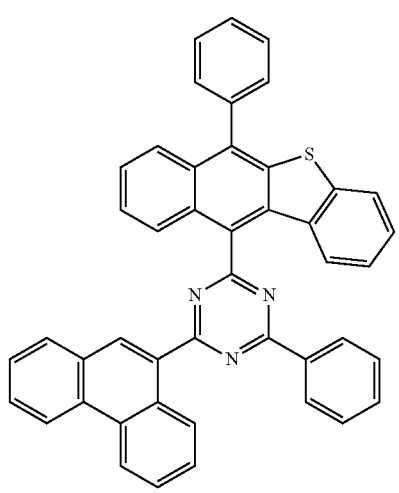
C-118
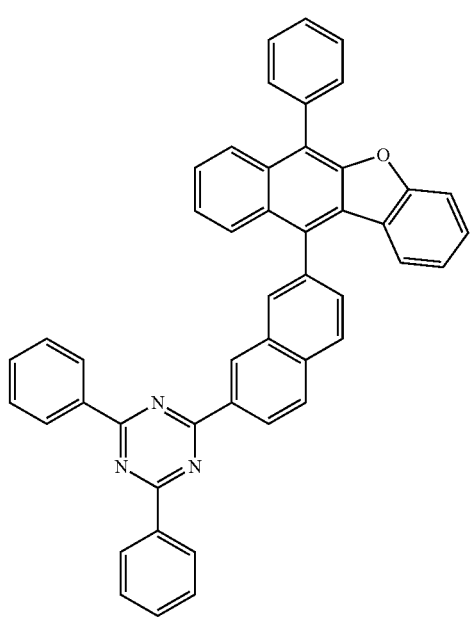

-continued

C-119

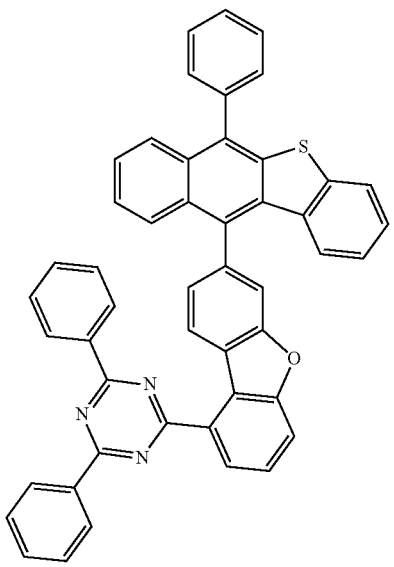

A plurality of host materials according to one embodiment of the present disclosure comprises a first host material comprising the compound represented by formula 1, and a second host material comprising the compound represented by formula 2, which may be comprised in a light-emitting layer of an organic electroluminescent device according to one embodiment of the present disclosure.

Hereinafter, the compound represented by formula 1 will be described in more detail.

In formula 1, $X_1$ and $Y_1$ each independently represent —N═, —NR$_5$—, —O—, or —S—, with the proviso that any one of $X_1$ and $Y_1$ represents —N═, and the other one of $X_1$ and $Y_1$ represents —NR$_5$—, —O—, or —S—. According to one embodiment of the present disclosure, any one of $X_1$ and $Y_1$ represents —N═, and the other one of $X_1$ and $Y_1$ represents —O— or —S—. That is, it may be that $X_1$ is —N═, and $Y_1$ is —O—; $X_1$ is —N═, and $Y_1$ is —S—; $X_1$ is —O—, and $Y_1$ is —N═; or $X_1$ is —S— and $Y_1$ is —N═.

In formula 1, $R_1$ represents a substituted or unsubstituted (C6-C30)aryl, or a substituted or unsubstituted (3- to 30-membered)heteroaryl. According to one embodiment of the present disclosure, $R_1$ represents a substituted or unsubstituted (C6-C30)aryl, or a substituted or unsubstituted (5- to 25-membered)heteroaryl. According to another embodiment of the present disclosure, $R_1$ represents a substituted or unsubstituted (C6-C30)aryl, or a substituted (5- to 20-membered)heteroaryl. For example, $R_1$ may be an unsubstituted phenyl, an unsubstituted biphenyl, an unsubstituted naphthyl, a fluorenyl substituted with a methyl(s), a benzofluorenyl substituted with a methyl(s), an unsubstituted dibenzofuranyl, an unsubstituted dibenzothiophenyl, a spiro[fluorene-fluoren]yl, a spiro[fluorene-benzofluoren]yl, an unsubstituted pyridyl, etc.

In formula 1, $L_1$ represents a single bond, a substituted or unsubstituted (C6-C30)arylene, or a substituted or unsubstituted (3- to 30-membered)heteroarylene. According to one embodiment of the present disclosure, $L_1$ represents a single bond, or a substituted or unsubstituted (C6-C18) arylene. According to another embodiment of the present disclosure, $L_1$ represents a single bond, or an unsubstituted (C6-C12)arylene. For example, $L_1$ may be a single bond, an unsubstituted phenylene, an unsubstituted naphthylene, etc.

In formula 1, $Ar_1$ and $Ar_2$ each independently represent a substituted or unsubstituted (C6-C30)aryl, or a substituted or unsubstituted (3- to 30-membered)heteroaryl. According to one embodiment of the present disclosure, $Ar_1$ and $Ar_2$ each independently represent a substituted or unsubstituted (C6-C25)aryl, or a substituted or unsubstituted (3-20 membered) heteroaryl. According to another embodiment of the present disclosure, $Ar_1$ and $Ar_2$ each independently represent a (C6-C25)aryl unsubstituted or substituted with at least one of deuterium, a (C1-C6)alkyl(s), a (C6-C25)aryl(s), a (3- to 20-membered)heteroaryl(s), a (C3-C7)cycloalkyl(s), and a (C1-C6)alkyl(C6-C12)aryl(s); or a (3- to 20-membered) heteroaryl unsubstituted or substituted with at least one of a (C6-C12)aryl(s) and a (5- to 15-membered)heteroaryl(s). For example, $Ar_1$ and $Ar_2$ may each independently be at least one of a substituted phenyl, a naphthyl, a biphenyl, a phenanthrenyl, a dimethylfluorenyl, a diphenylfluorenyl, a naphthylphenyl, a phenylnaphthyl, a dimethylbenzofluorenyl, a terphenyl, a spirobifluorenyl, a benzofuranyl, a benzothiophenyl, a dibenzothiophenyl unsubstituted or substituted with a phenyl(s), a dibenzofuranyl unsubstituted or substituted with a phenyl(s) or a pyridyl(s), a carbazolyl substituted with a phenyl(s), a benzonaphthofuranyl, a benzonaphthothiophenyl, a benzofuropyridyl, etc.; wherein the substituents of the substituted phenyl may be at least one of a phenyl substituted with at least one of deuterium, a methyl(s), and a tert-butyl(s); an anthracenyl; a fluoranthenyl; a phenylfluorenyl; a cyclohexyl; a pyridyl substituted with a phenyl(s); a phenoxazinyl; and a benzimidazolyl substituted with a phenyl(s).

In formula 1, $R_2$ to $R_5$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring(s) and a (C6-C30)aromatic ring(s), or -L$_3$-N(Ar$_3$) (Ar$_4$); or may be linked to an adjacent substituent to form a ring. According to one embodiment of the present disclosure, $R_2$ to $R_5$ each independently represent hydrogen, or a substituted or unsubstituted (C6-C12)aryl. According to another embodiment of the present disclosure, $R_2$ to $R_5$ each independently represent hydrogen or an unsubstituted (C6-C12)aryl. For example, $R_2$ and $R_3$ may be hydrogen, and $R_4$ may be hydrogen, phenyl, etc.

In formula 1, a represents 1; b and c each independently represent 1 or 2, preferably 1; d represents an integer of 1 to 4, preferably 1 or 2; and when b to d are an integer of 2 or more, each of $R_2$ to each of $R_4$ may be the same as or different from each other.

According to one embodiment of the present disclosure, formula 1 may be represented by at least one of the following formulas 1-1 to 1-4:

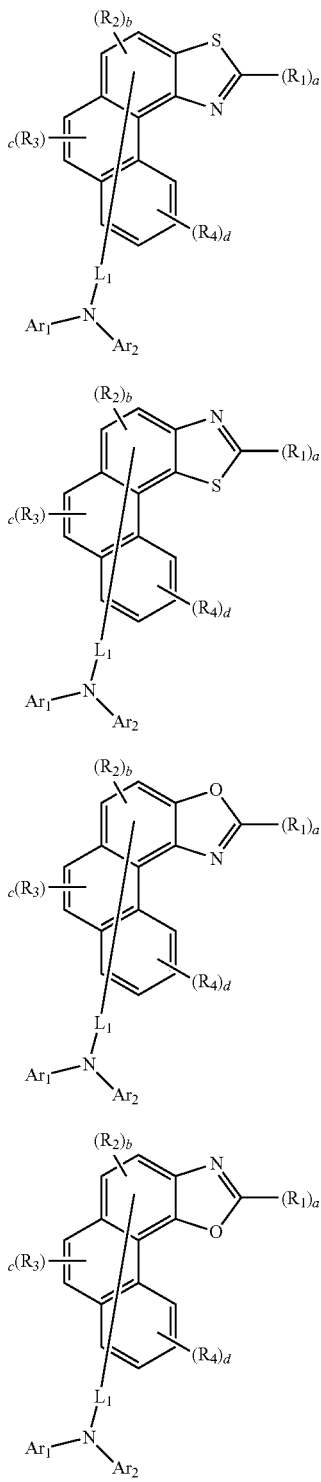

(1-1)

(1-2)

(1-3)

(1-4)

In formulas 1-1 to 1-4, $R_1$ to $R_4$, $Ar_1$, $Ar_2$, $L_1$, and a to d are as defined in formula 1.

Hereinafter, the compound represented by formula 2 will be described in more detail.

In formula 2, HAr each independently represents a substituted or unsubstituted nitrogen-containing (3- to 20-membered)heteroaryl. According to one embodiment of the present disclosure, HAr each independently represents a substituted or unsubstituted nitrogen-containing (5- to 15-membered)heteroaryl. According to another embodiment of the present disclosure, HAr each independently represents a nitrogen-containing (5- to 15-membered)heteroaryl unsubstituted or substituted with at least one of deuterium; a (C1-C6)alkyl; a (C6-C20)aryl unsubstituted or substituted with at least one of deuterium, a (C1-C6)alkyl(s), and a (C6-C12)aryl(s); a (5- to 15-membered)heteroaryl unsubstituted or substituted with a (C6-C12)aryl(s); and a (C1-C6) alkyl(C6-C20)aryl. For example, HAr may each independently be a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted carbazolyl, a substituted or unsubstituted triazolyl, a substituted or unsubstituted pyrazolyl, a substituted or unsubstituted naphthyridinyl, a substituted or unsubstituted triazanaphthyl, a substituted or unsubstituted benzofuropyrimidinyl, or a substituted or unsubstituted benzothienopyrimidinyl, etc, wherein the substituent may be at least one of deuterium, a methyl, a phenyl, a phenyl substituted with at least one deuterium, a naphthylphenyl, a naphthyl, a phenylnaphthyl, a biphenyl, a dimethylfluorenyl, a diphenylfluorenyl, a phenanthrenyl, a fluoranthenyl, a terphenyl, a chrysenyl, a triphenylenyl, a phenylpyridyl, a dibenzofuranyl, a dibenzothiophenyl, and a phenylcarbazolyl.

In formula 2, $L_{11}$ each independently represents a single bond, a substituted or unsubstituted (C6-C30)arylene, or a substituted or unsubstituted (3- to 30-membered)heteroarylene. According to one embodiment of the present disclosure, $L_{11}$ each independently represents a single bond, a substituted or unsubstituted (C6-C15)arylene, or a substituted or unsubstituted (5- to 15-membered)heteroarylene. According to another embodiment of the present disclosure, $L_{11}$ each independently represents a single bond, (C6-C15) arylene unsubstituted or substituted with a (C6-C12)aryl(s), or an unsubstituted (5- to 15-membered)heteroarylene. For example, $L_{11}$ may each independently be a single bond, a phenylene, a naphthylene, a biphenylene, a phenylene substituted with a phenyl(s), a dibenzofuranylene, etc.

In formula 2, $Ar_{11}$ each independently represents any one of the following formulas 3 to 5.

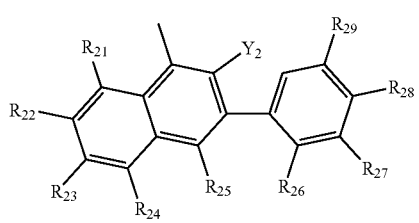

(3)

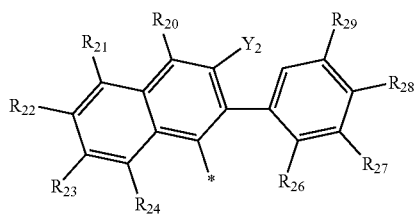

(4)

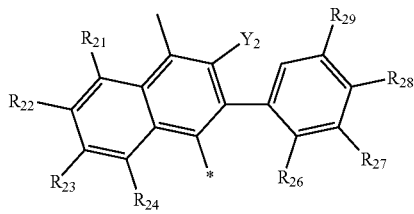

(5)

In formulas 3 to 5, $Y_2$ represents O or S.

In formulas 3 to 5, $R_{20}$ to $R_{29}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring(s) and a (C6-C30)aromatic ring(s), or -$L_3$-N($Ar_3$)($Ar_4$). According to one embodiment of the present disclosure, $R_{20}$ to $R_{29}$ each independently represent hydrogen, a substituted or unsubstituted (C6-C20)aryl, or a substituted or unsubstituted (5- to 15-membered)heteroaryl. According to another embodiment of the present disclosure, $R_{20}$ to $R_{29}$ each independently represent hydrogen; a (C6-C20)aryl unsubstituted or substituted with at least one of deuterium, a cyano(s), a (C6-C12)aryl(s), and a (5- to 15-membered)heteroaryl(s); or a (5- to 15-membered)heteroaryl unsubstituted or substituted with a (C6-C12)aryl(s). For example, $R_{20}$ to $R_{29}$ may each independently be hydrogen, a phenyl, a phenyl substituted with at least one deuterium, a phenyl substituted with a cyano(s), a naphthylphenyl, a phenyl substituted with a dibenzothiophenyl(s), a naphthyl, a phenylnaphthyl, a biphenyl, a biphenyl substituted with at least one cyano, a phenanthrenyl, a pyridyl, a pyridyl substituted with a phenyl(s), an isoquinolyl, a carbazolyl substituted with a phenyl(s), a dibenzofuranyl, a dibenzothiophenyl, etc.

In formula 2, e represents 1 or 2, and when e is 2, each of ($L_{11}$-HAr) may be the same as or different from each other.

In formulas 3 to 5, * represents a site linked to $L_{11}$.

In formulas 1 and 3 to 5, $L_3$ each independently represents a single bond, a substituted or unsubstituted (C6-C30) arylene, or a substituted or unsubstituted (3- to 30-membered)heteroarylene.

In formulas 1 and 3 to 5, $Ar_3$ and $Ar_4$ each independently represent hydrogen, a substituted or unsubstituted (C1-C30) alkyl, a substituted or unsubstituted (C2-C30)alkenyl, a substituted or unsubstituted fused ring of a (C3-C30)aliphatic ring(s) and a (C6-C30)aromatic ring(s), a substituted or unsubstituted (C6-C30)aryl, or a substituted or unsubstituted (3- to 30-membered)heteroaryl.

The compound represented by formula 1 may be at least one selected from the following compounds, but is not limited thereto.

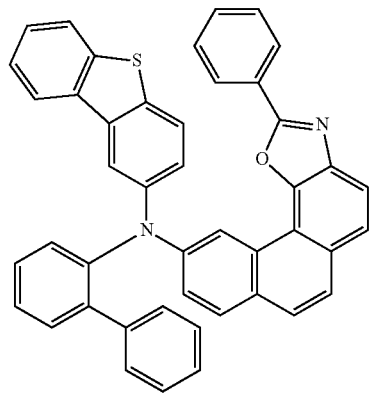

H1-1

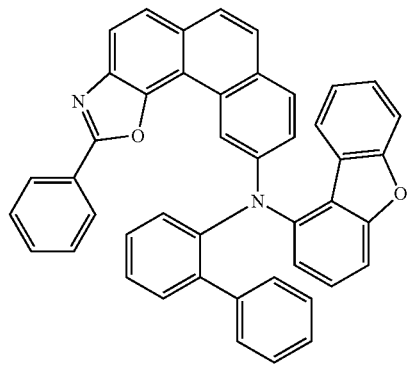

H1-2

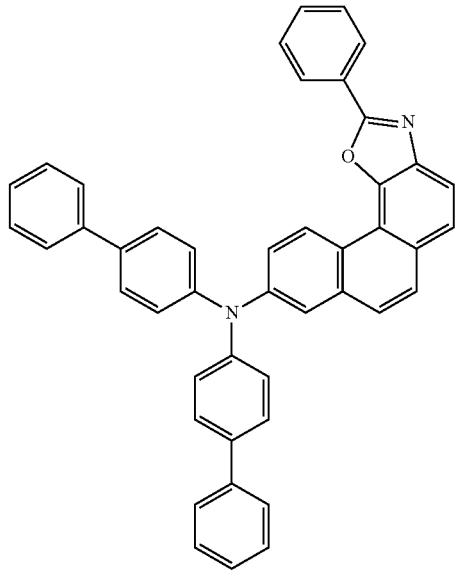

H1-3

H1-4
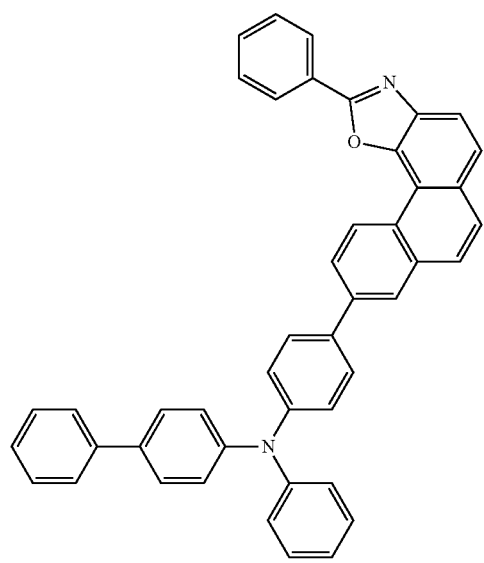
H1-5
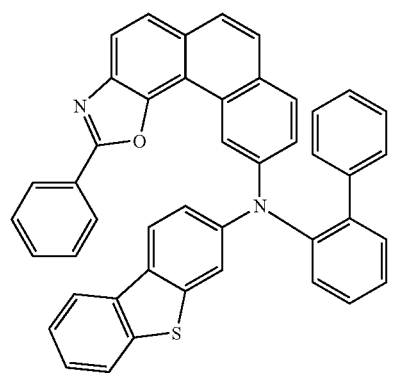
H1-6
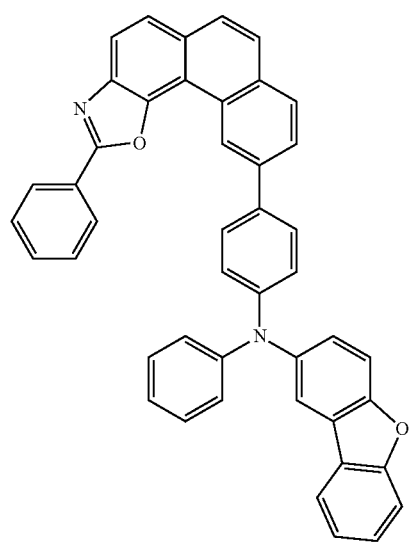
H1-7
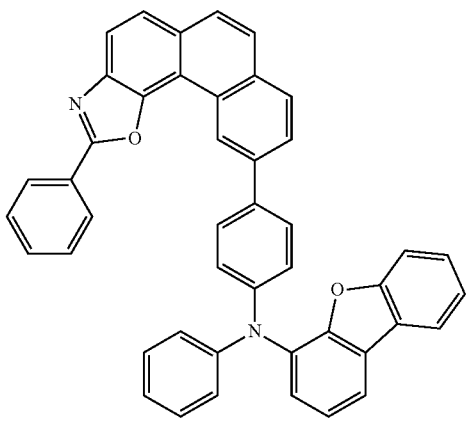
H1-8
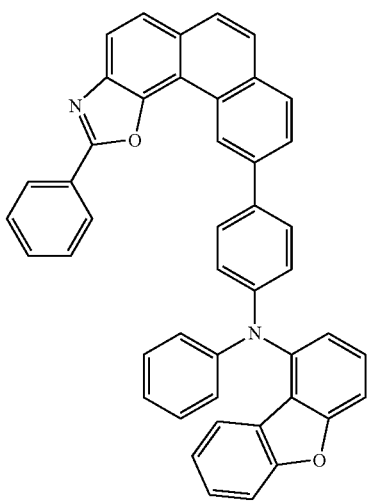
H1-9
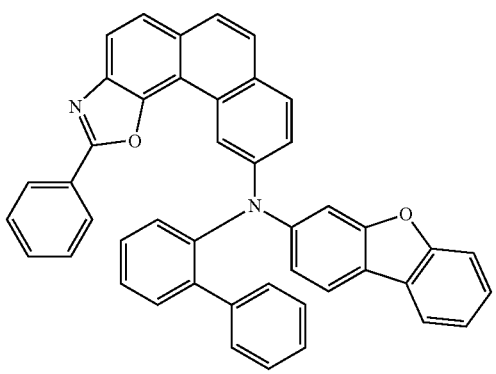

H1-10
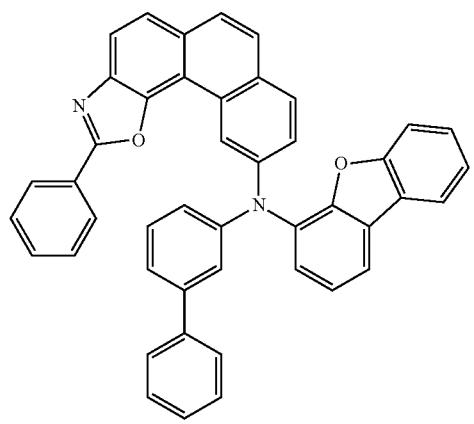
H1-11
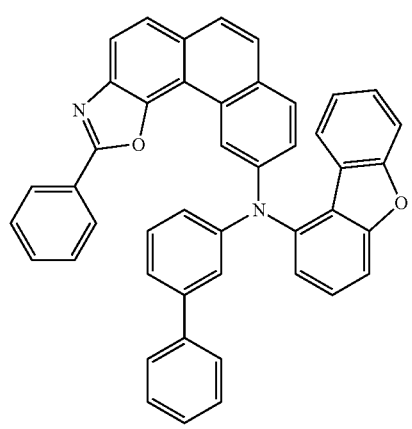
H1-12
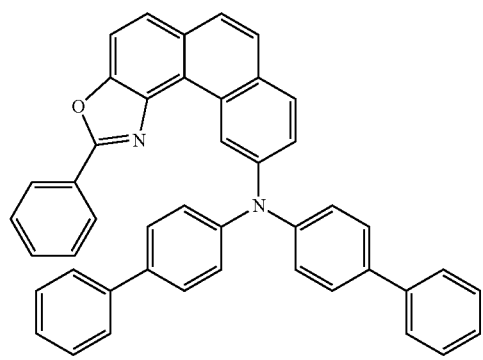
H1-13
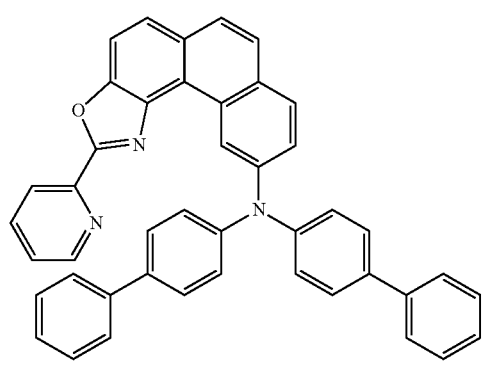
H1-14
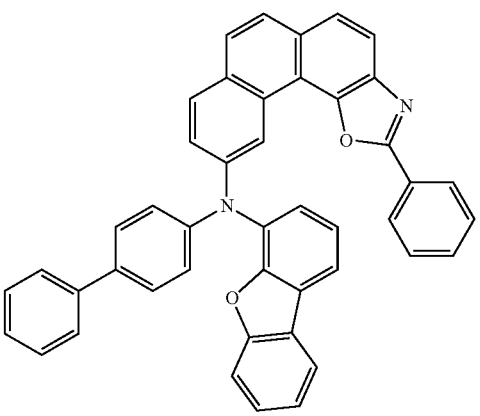
H1-15
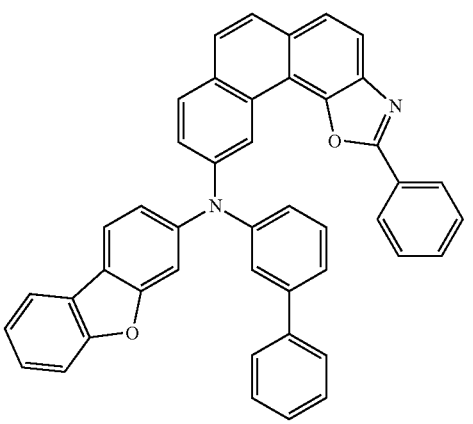
H1-16
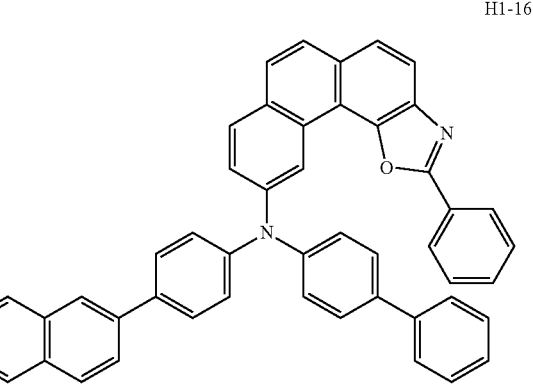
H1-17
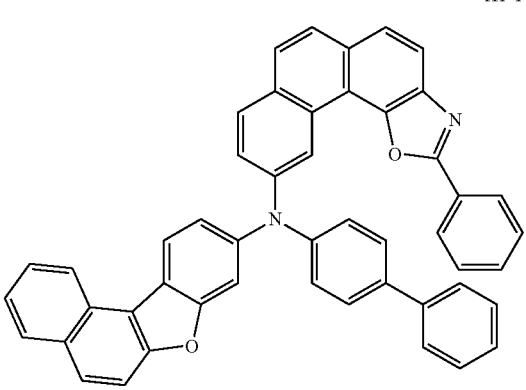

H1-18
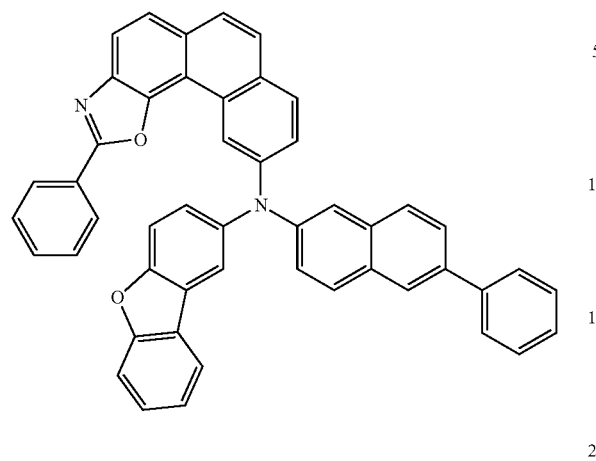
H1-19
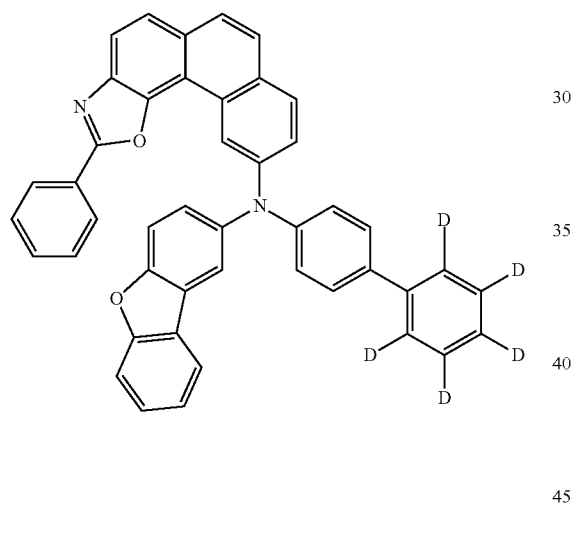
H1-20
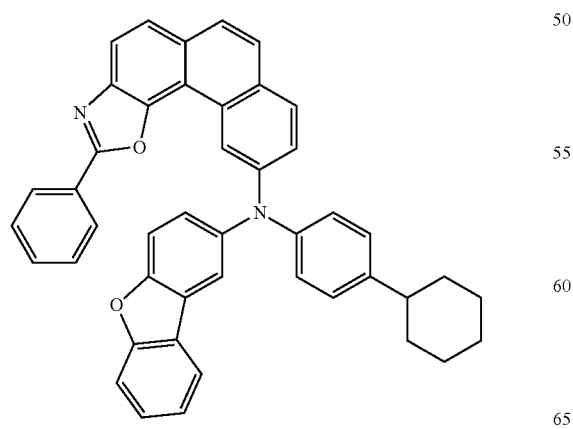
H1-21
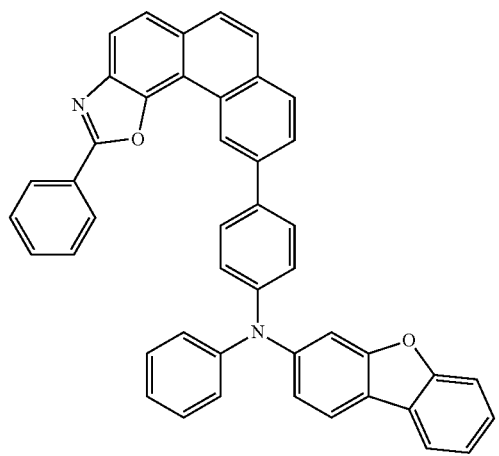
H1-22
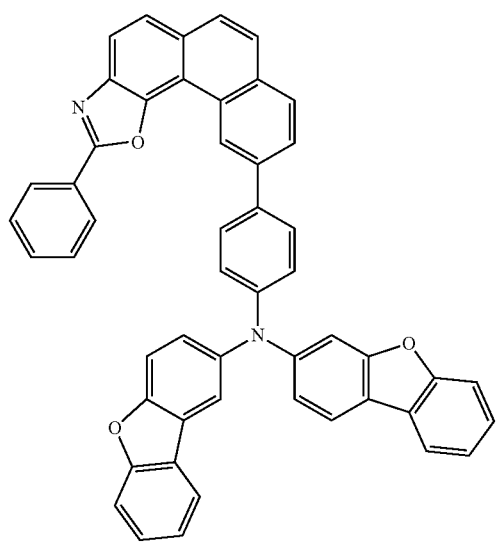
H1-23
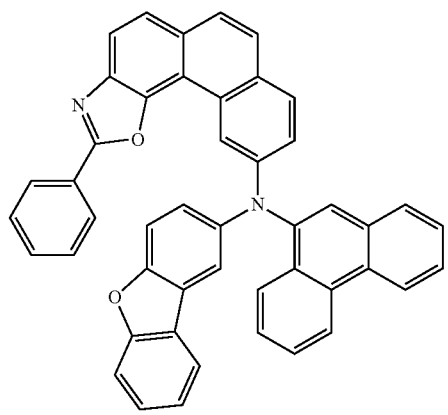

H1-24
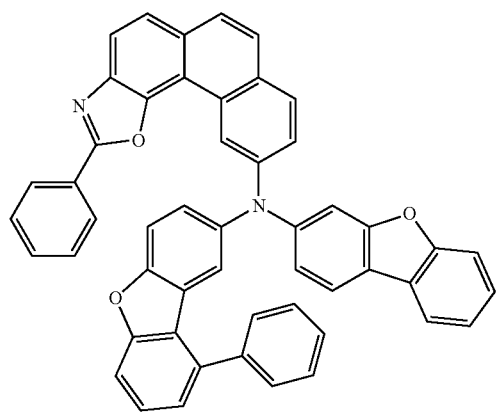
H1-27
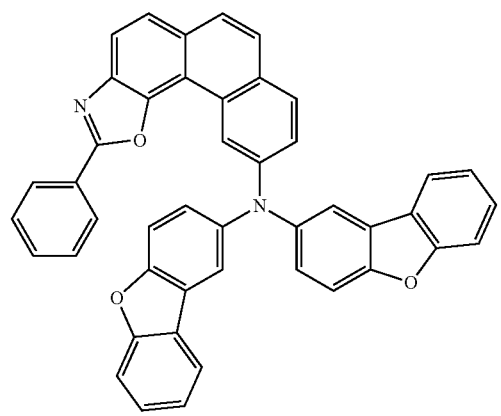
H1-25
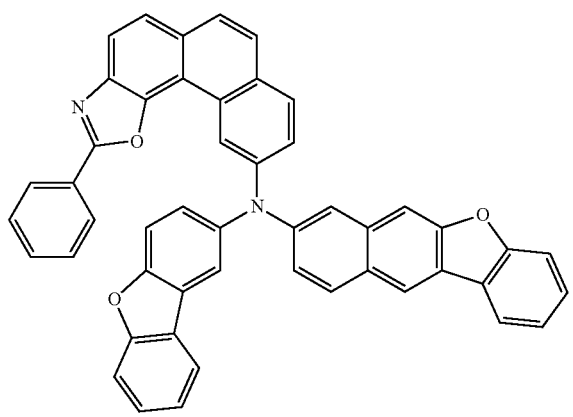
H1-28
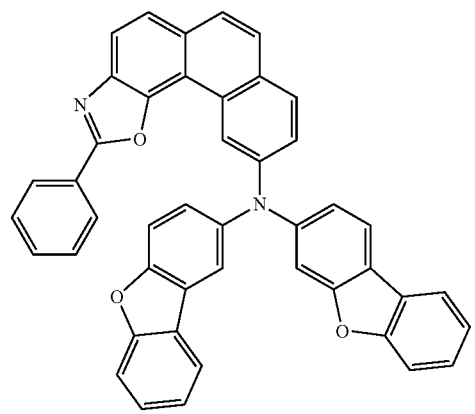
H1-26
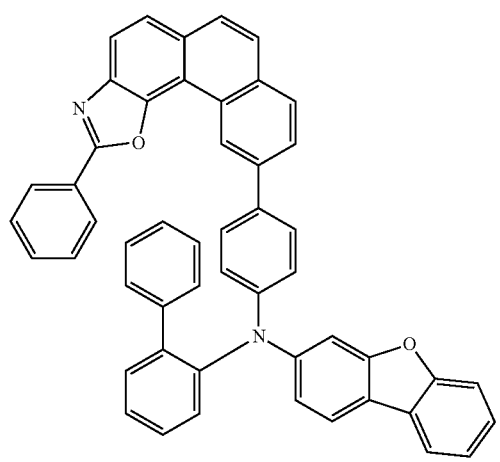
H1-29
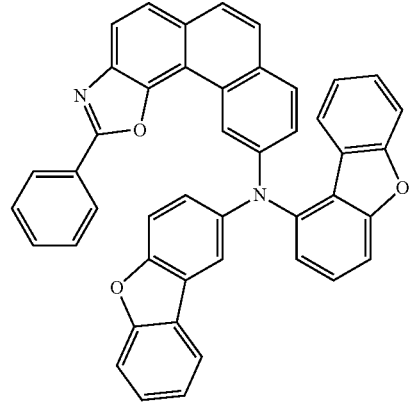

H1-30
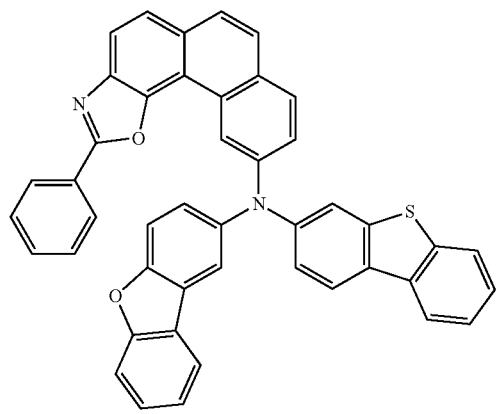
H1-31
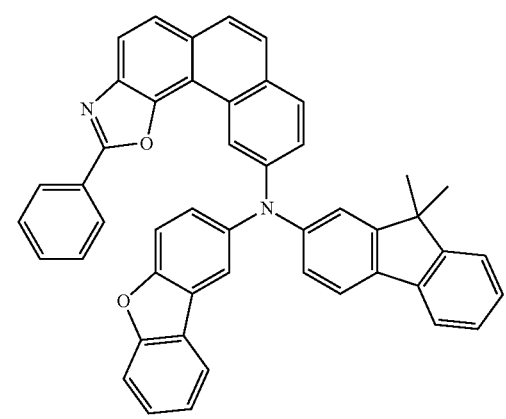
H1-32
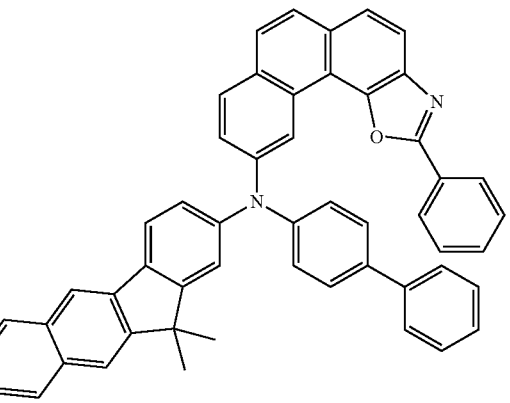
H1-33
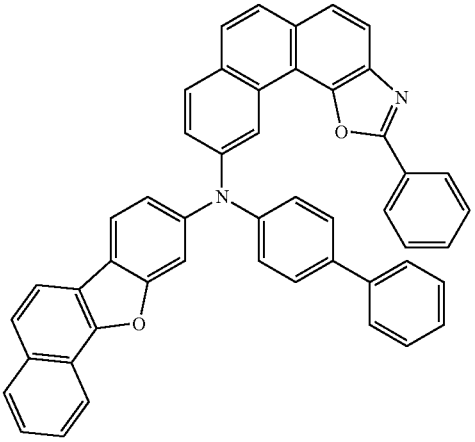
H1-34
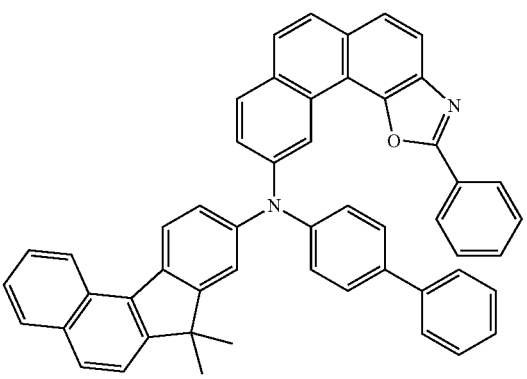
H1-35
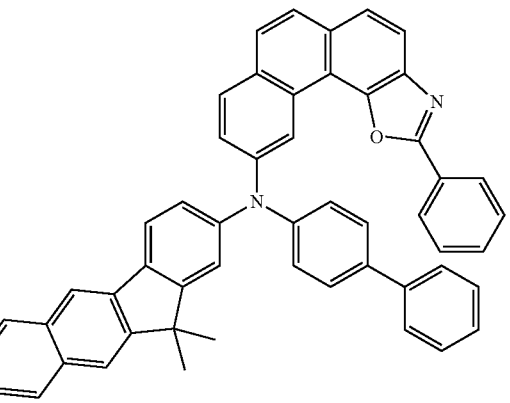
H1-36
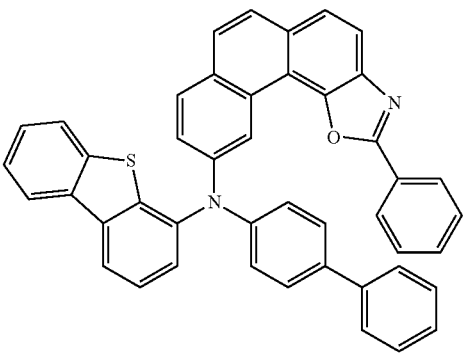

H1-37
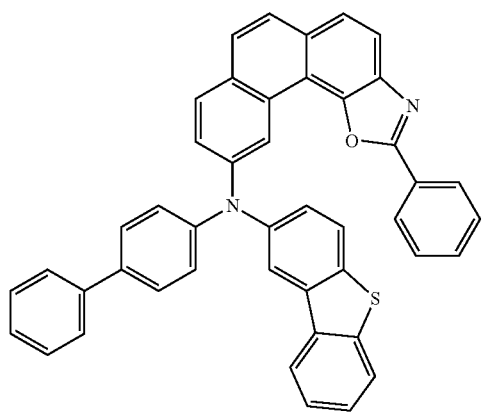
H1-38
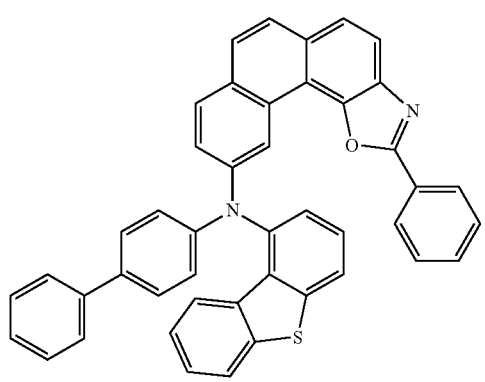
H1-39
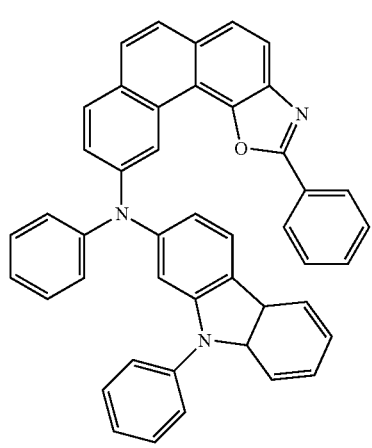
H1-40
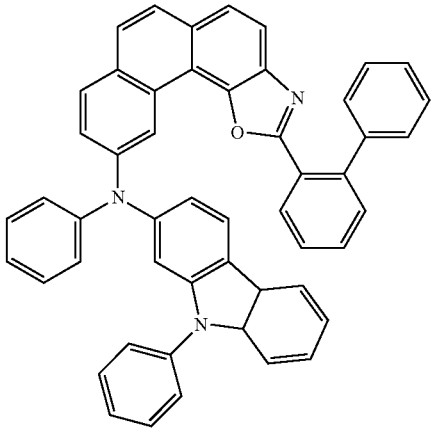
H1-41
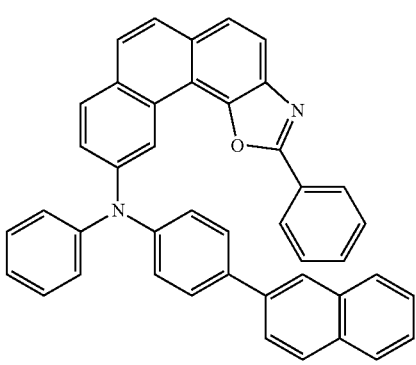
H1-42
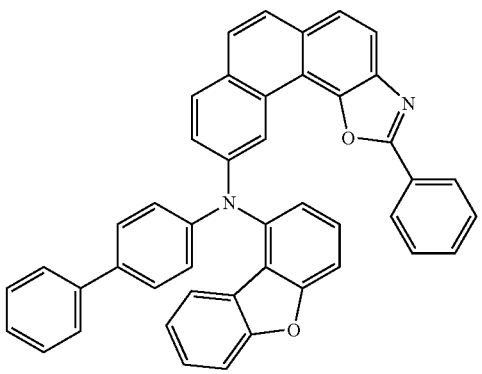
H1-43
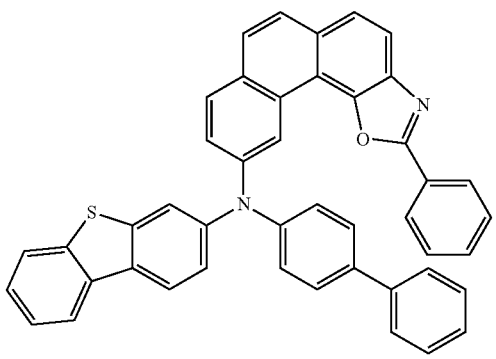

H1-44
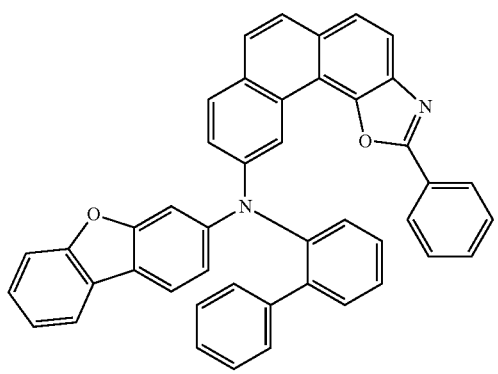
H1-45
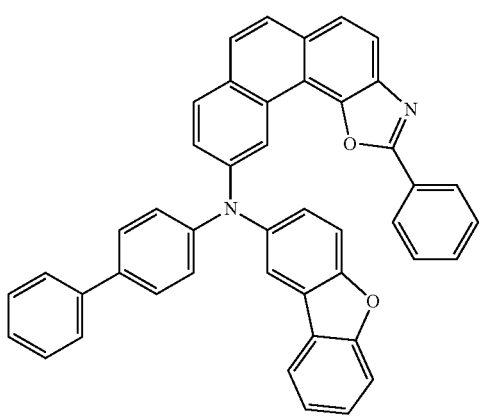
H1-46
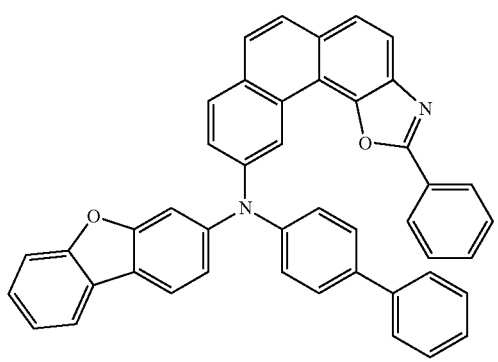
H1-47
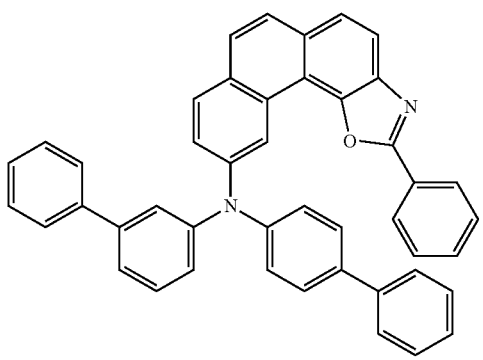
H1-48
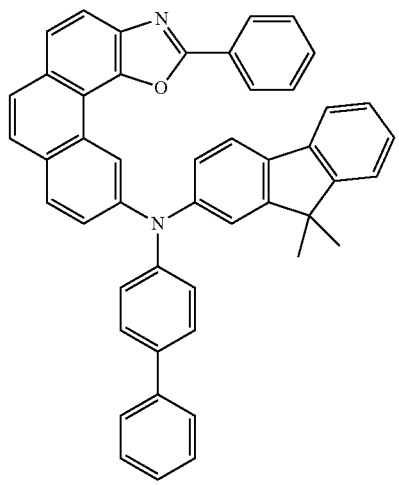
H1-49
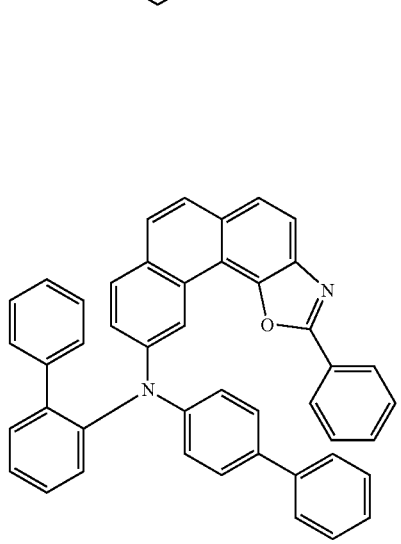
H1-50
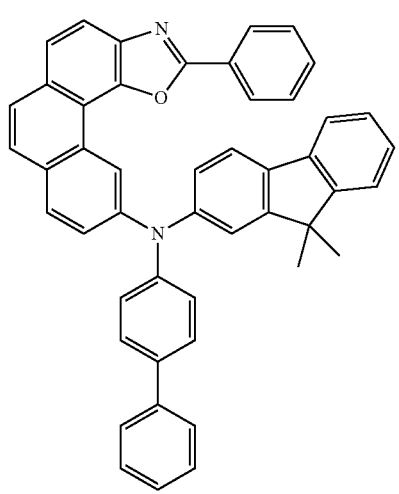

H1-51
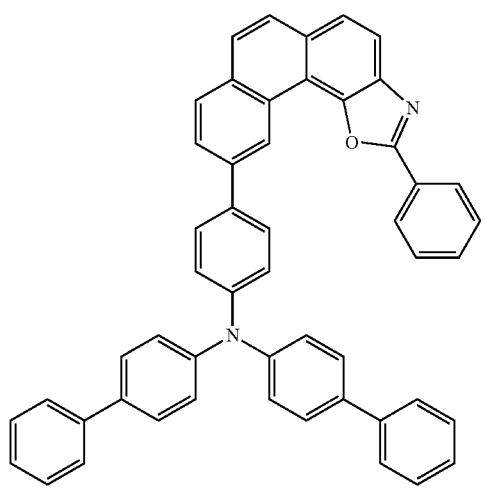
H1-52
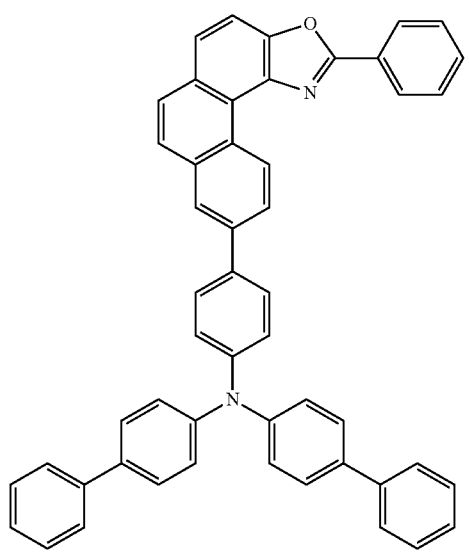
H1-53
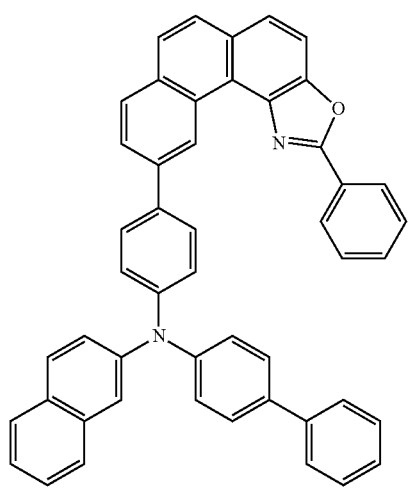
H1-54
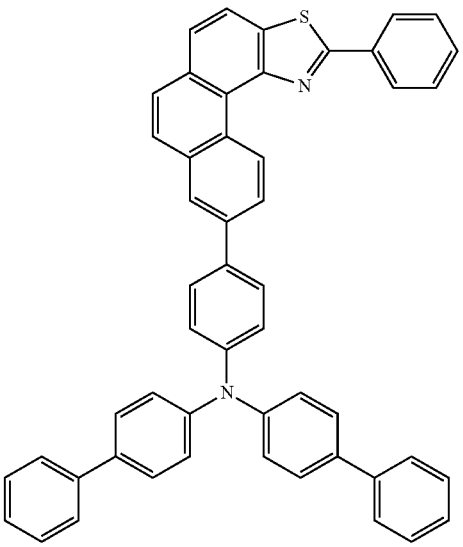
H1-55
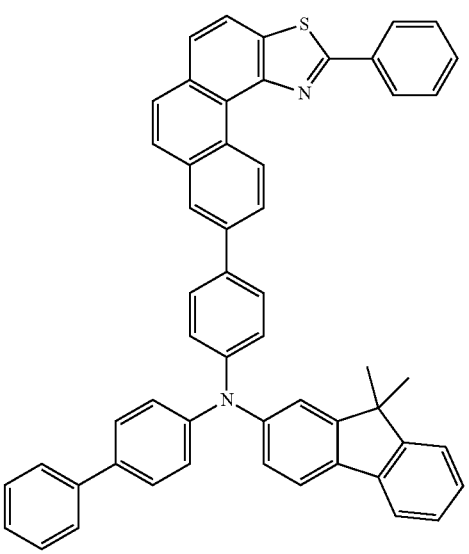
H1-56
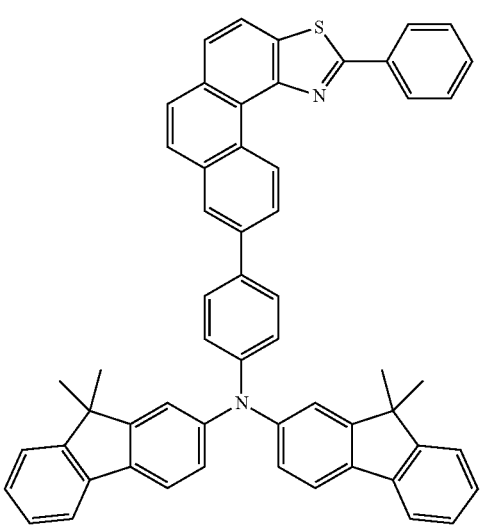

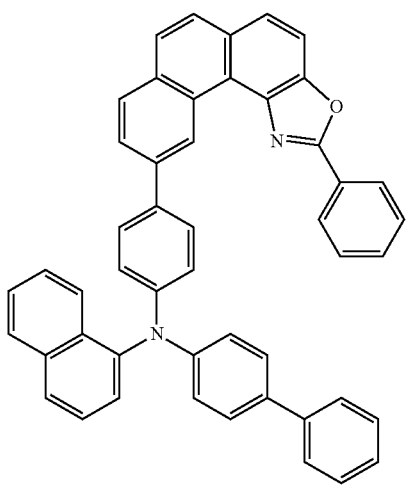
H1-57
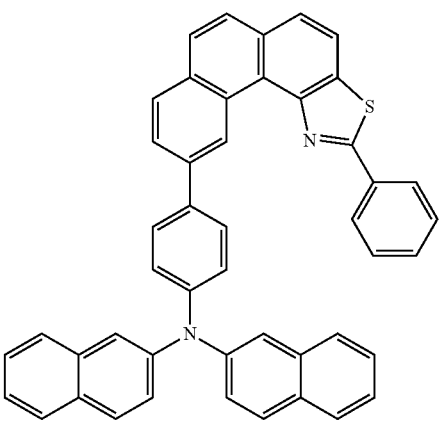
H1-60
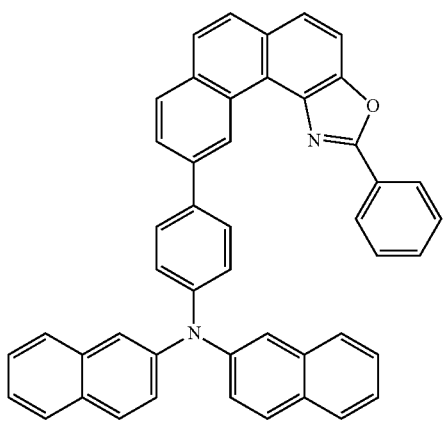
H1-58
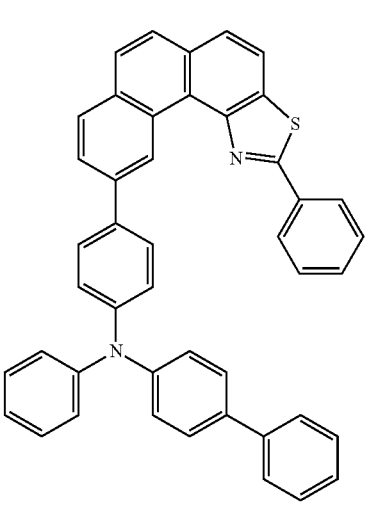
H1-61
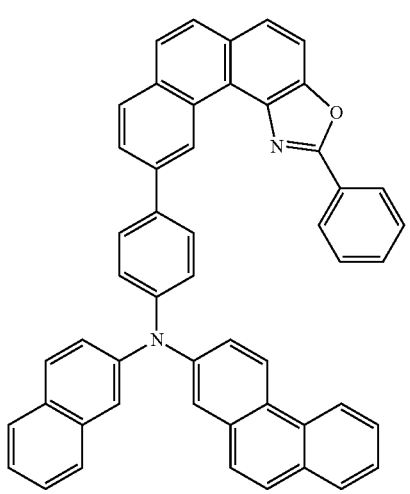
H1-59
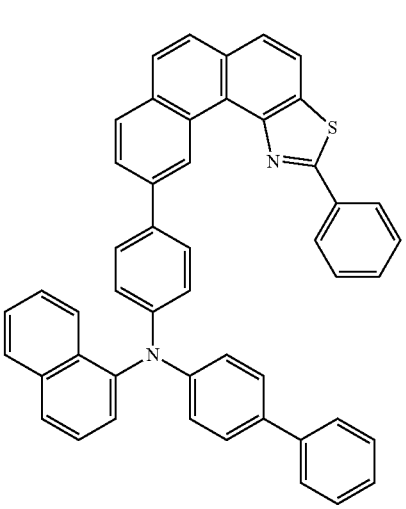
H1-62

-continued
H1-63
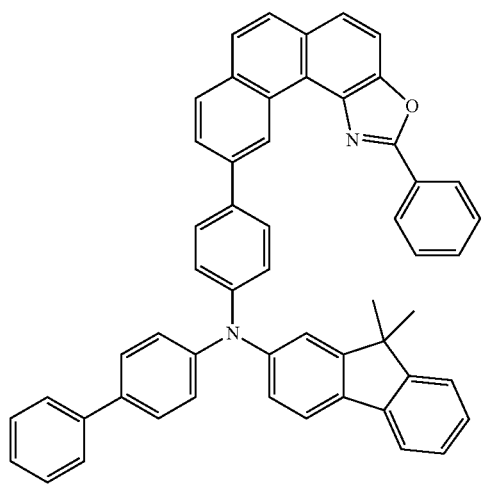
H1-64
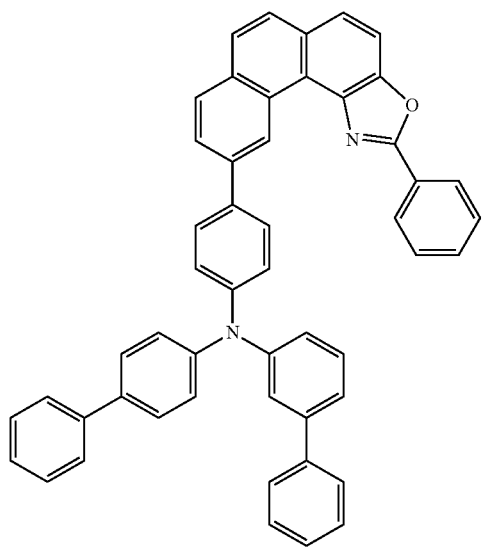
H1-65
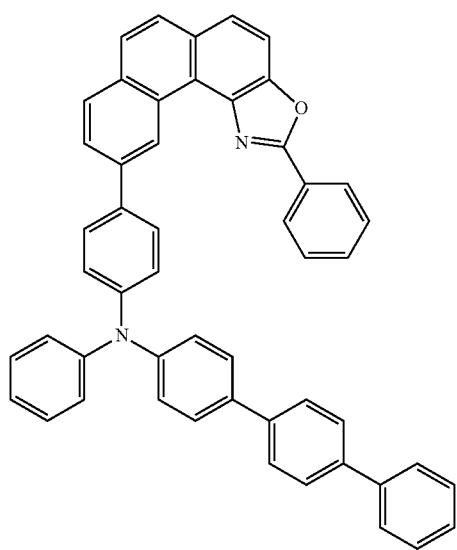
-continued
H1-66
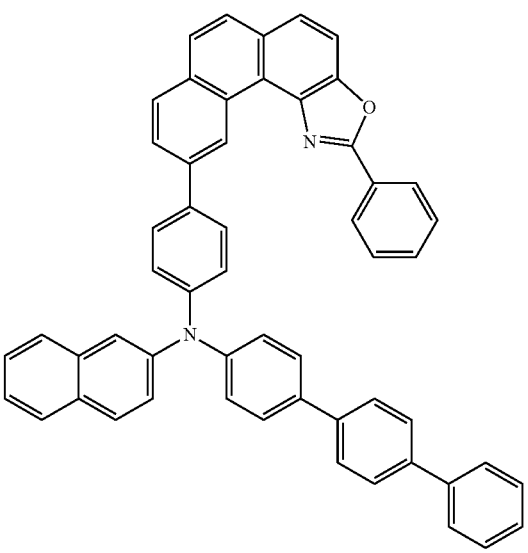
H1-67
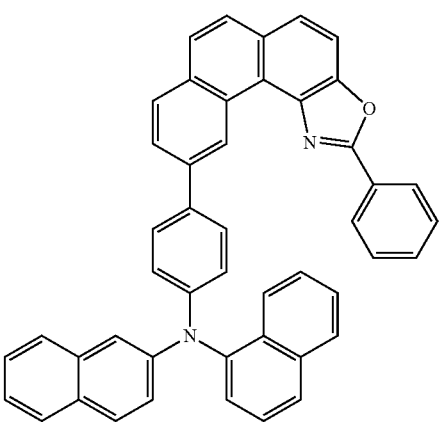
H1-68
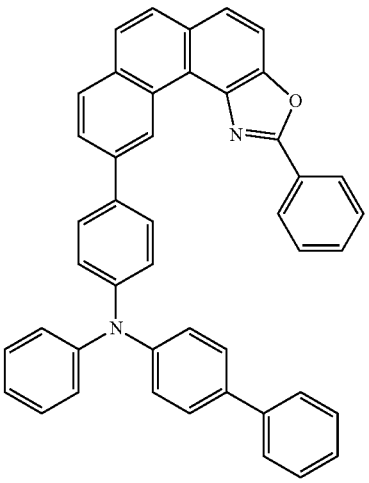

-continued
H1-69
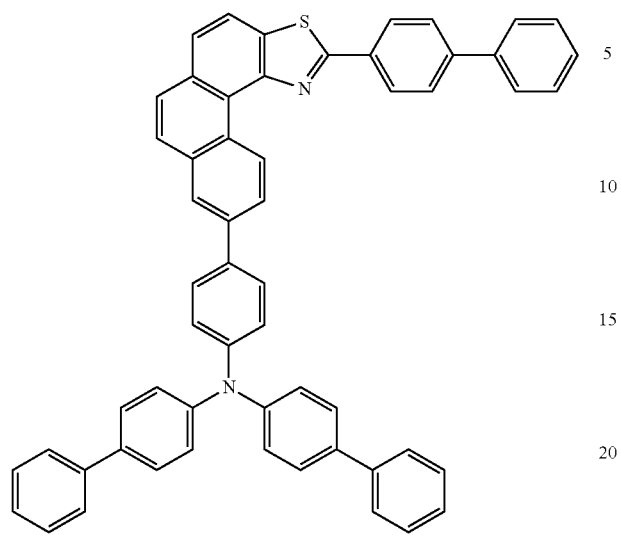
H1-72
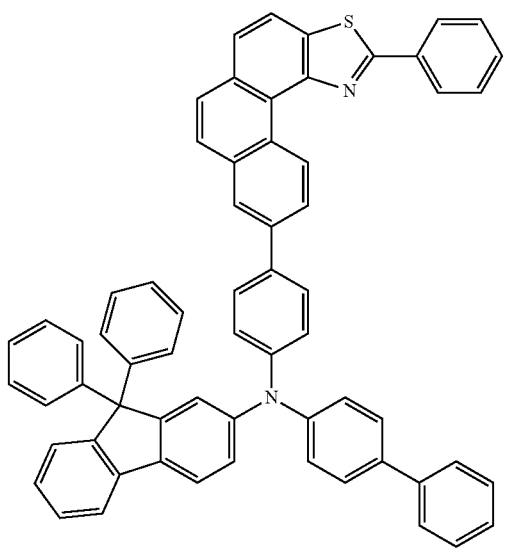
H1-70
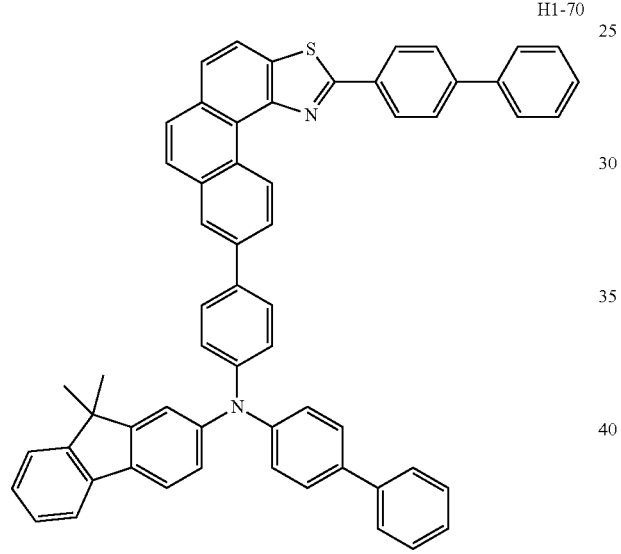
H1-73
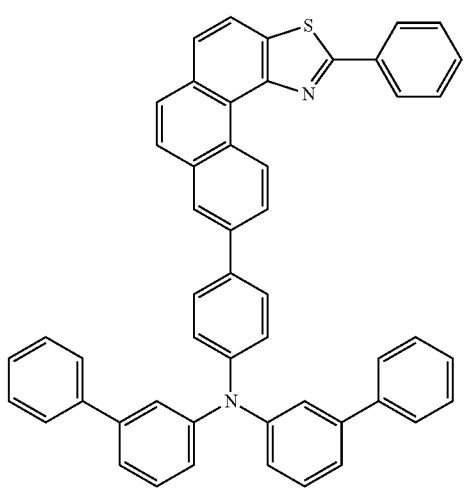
H1-71
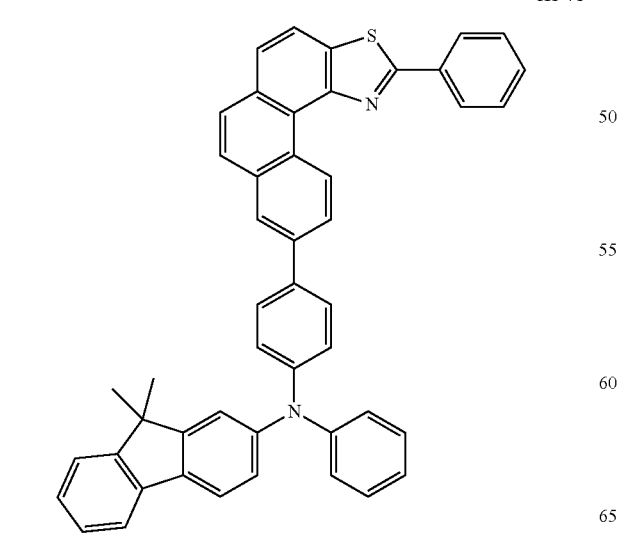
H1-74
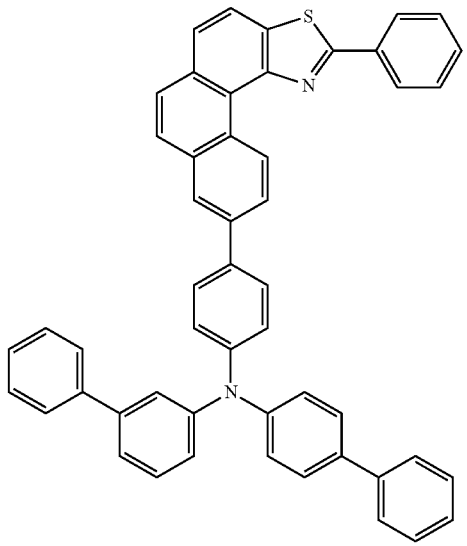

H1-75
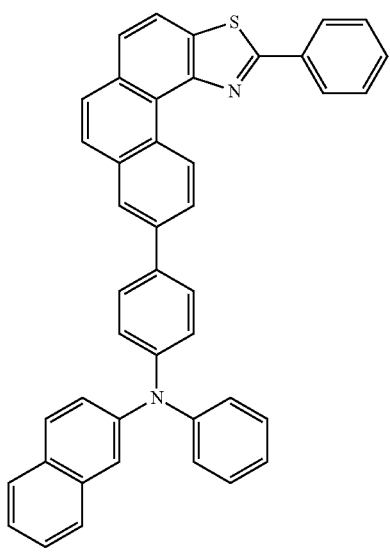
H1-76
H1-77
H1-78
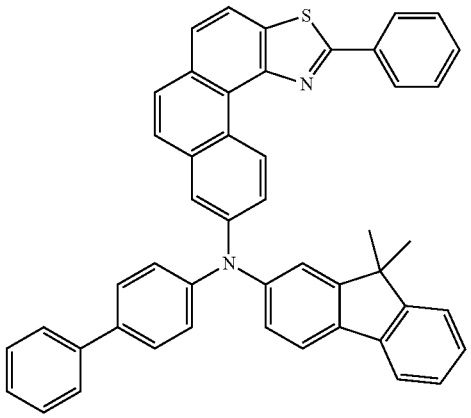
H1-79
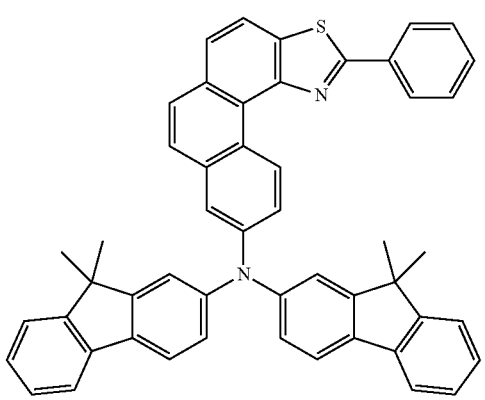
H1-80
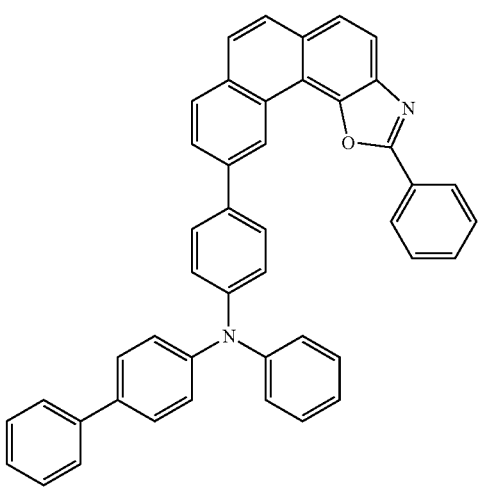

-continued
H1-81
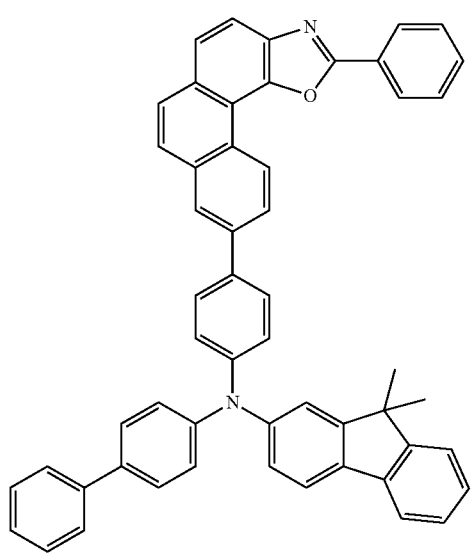
H1-82
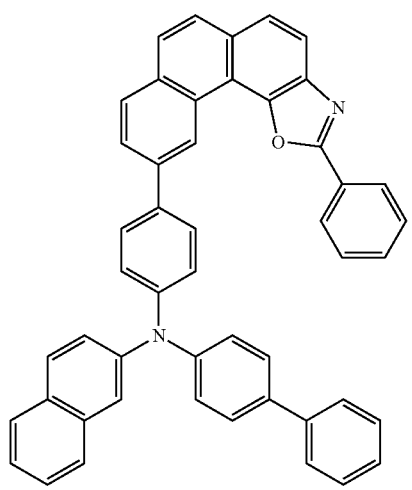
H1-83
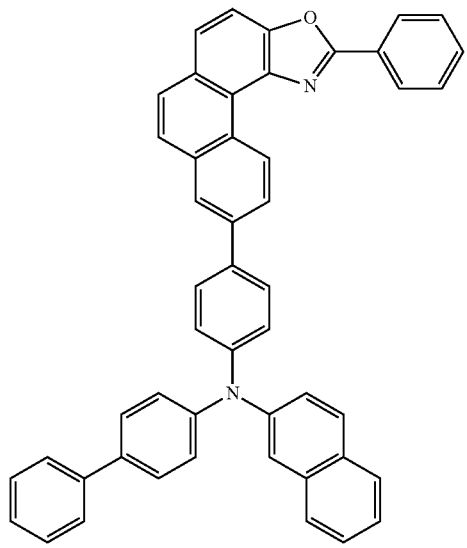
H1-84
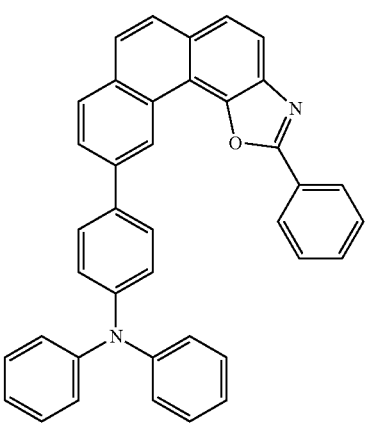
H1-85
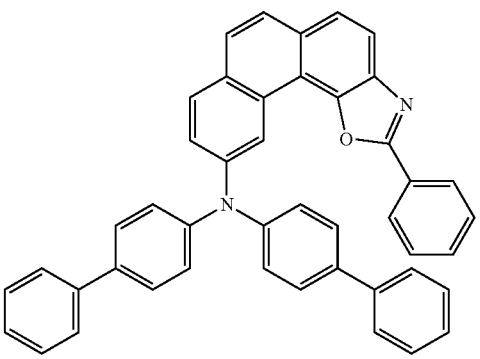
H1-86
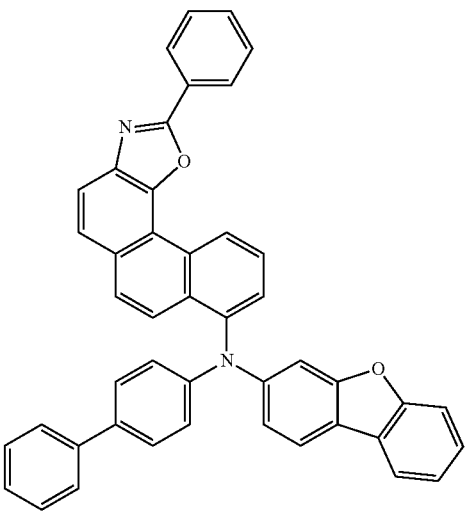

H1-87
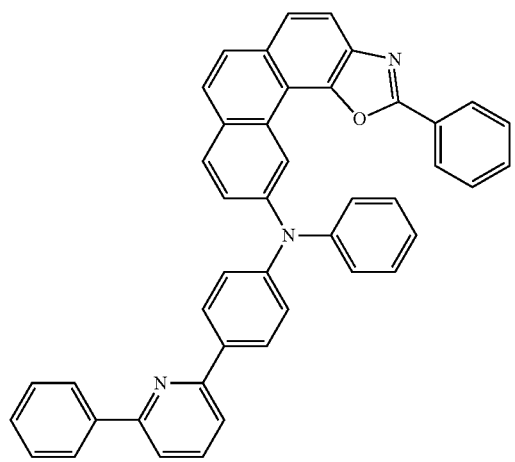
H1-90
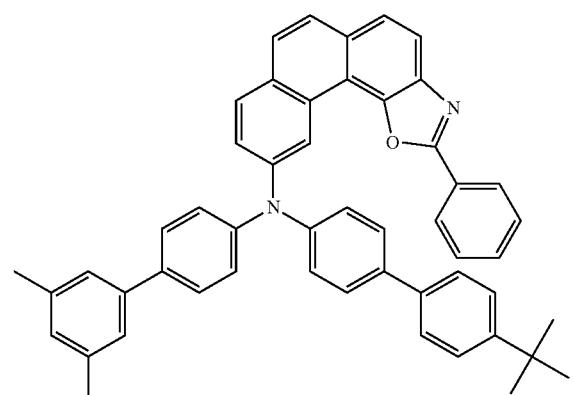
H1-88
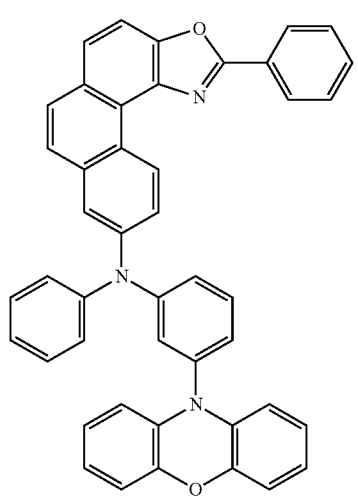
H1-91
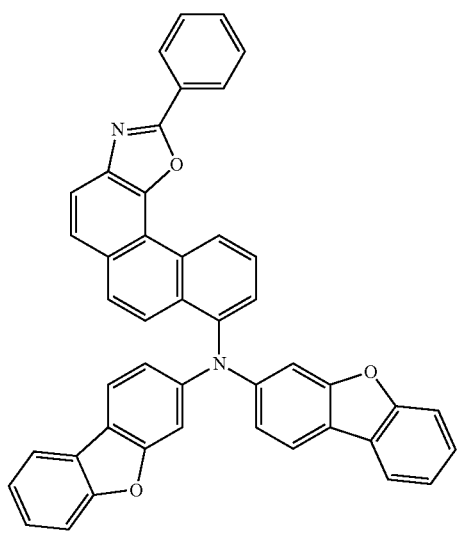
H1-89
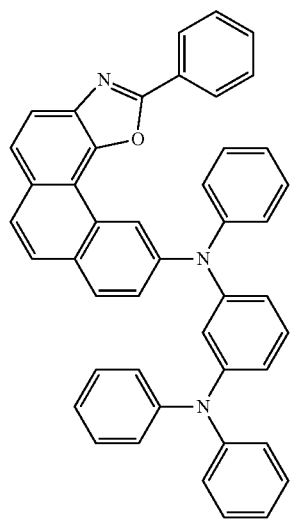
H1-92
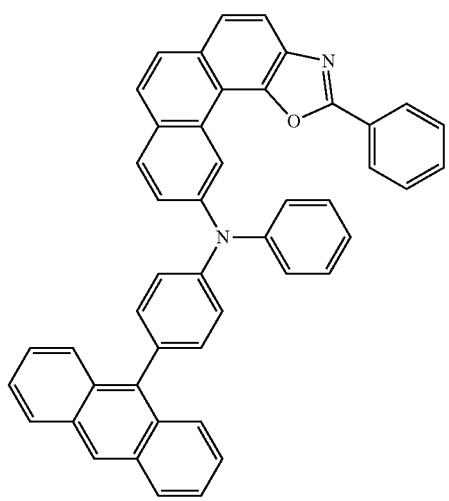

H1-93
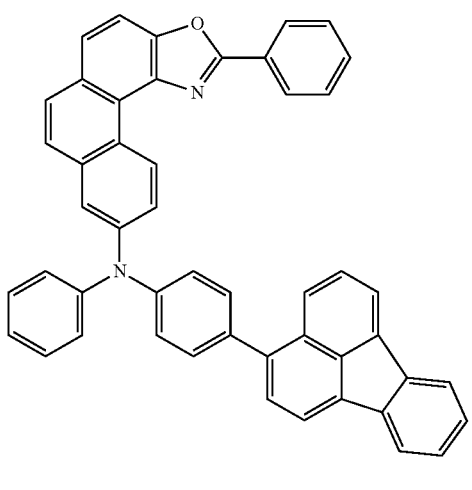
H1-94
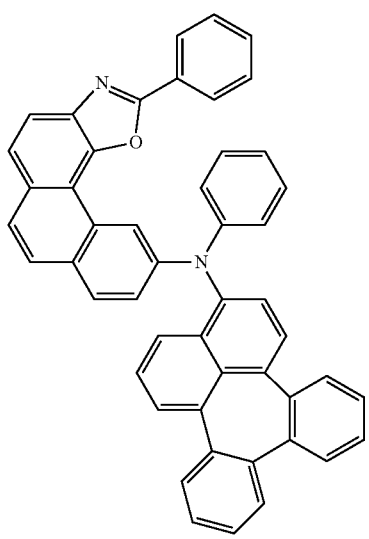
H1-95
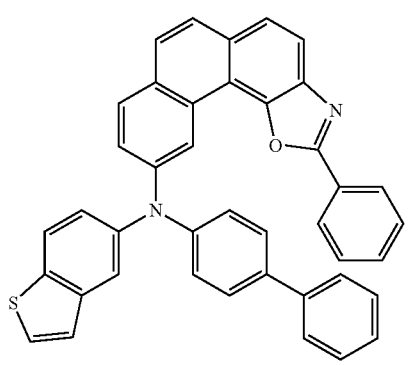
H1-96
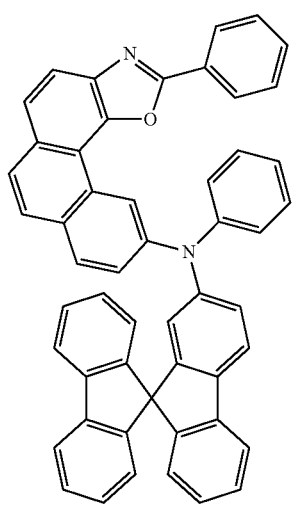
H1-97
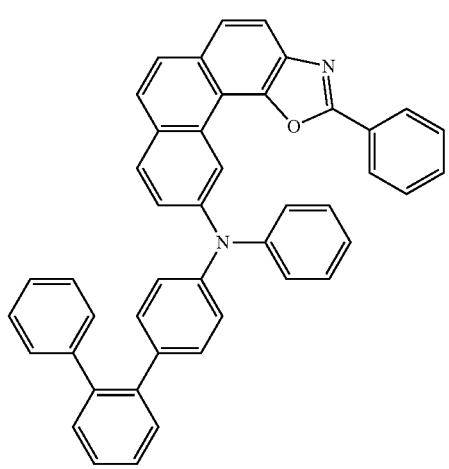
H1-98
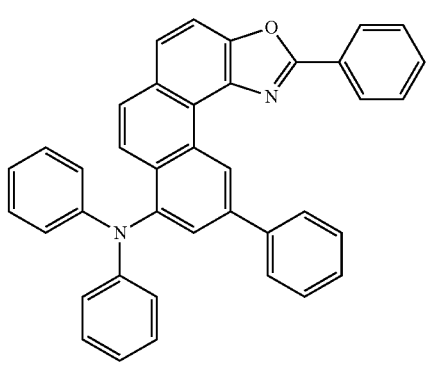

H1-99
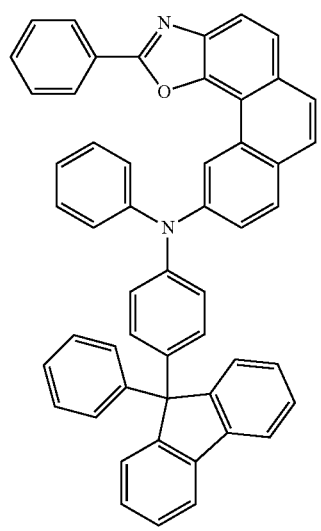
H1-100
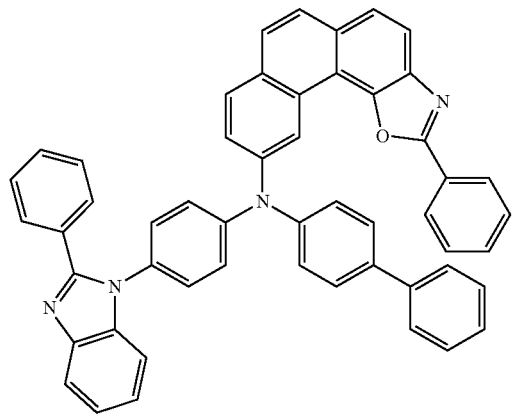
H1-101
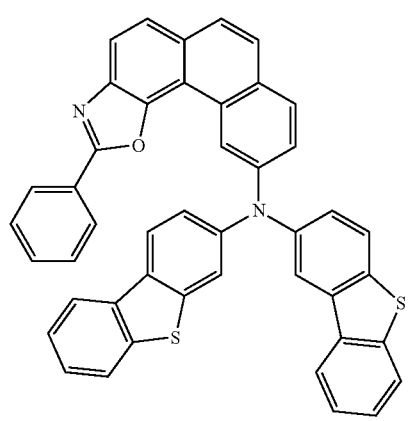
H1-102
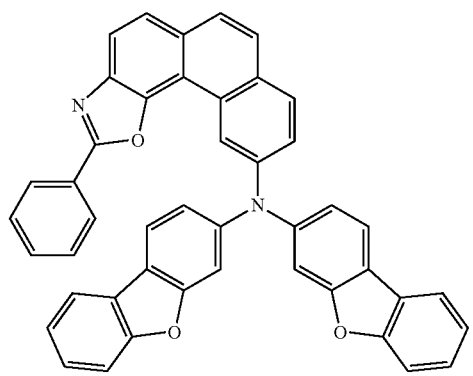
H1-103
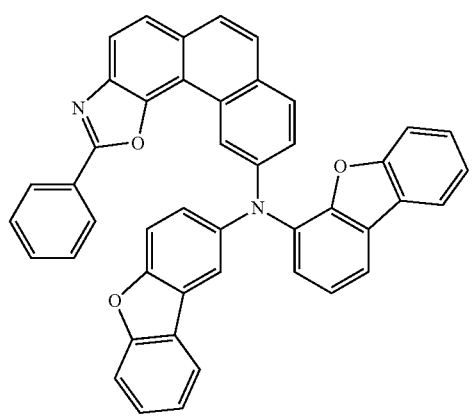
H1-104
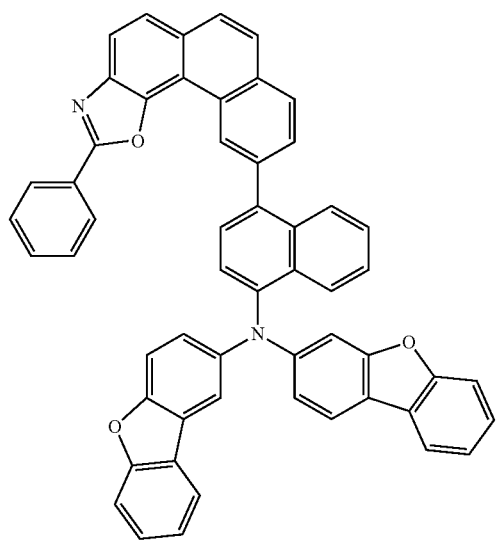

H1-105
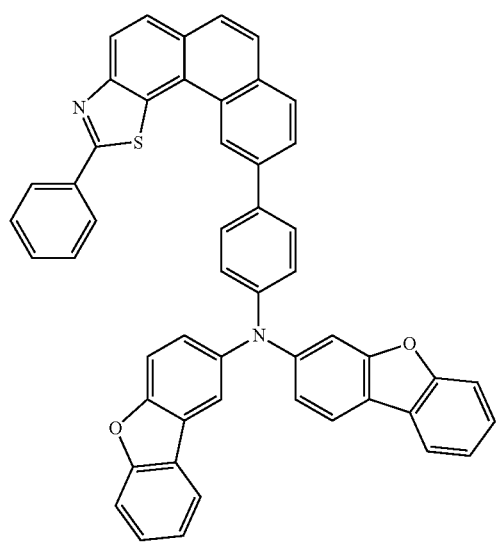
H1-106
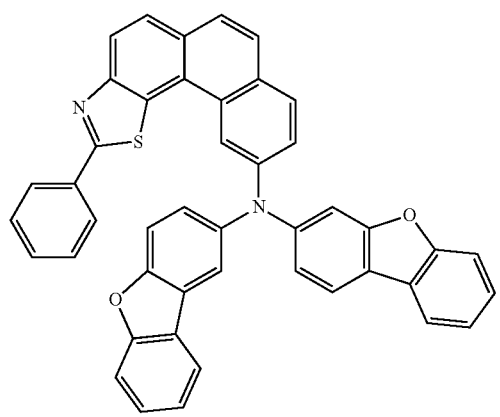
H1-107
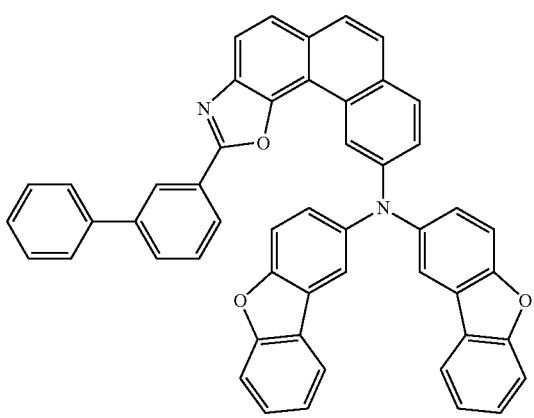
H1-108
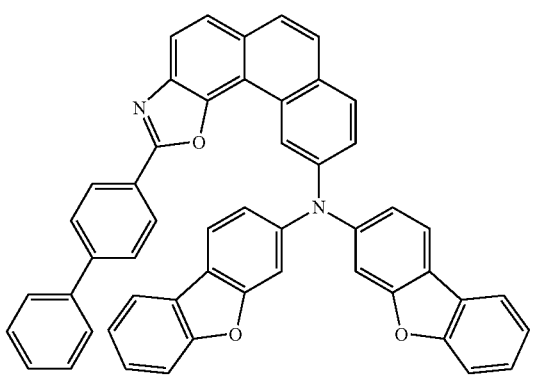
H1-109
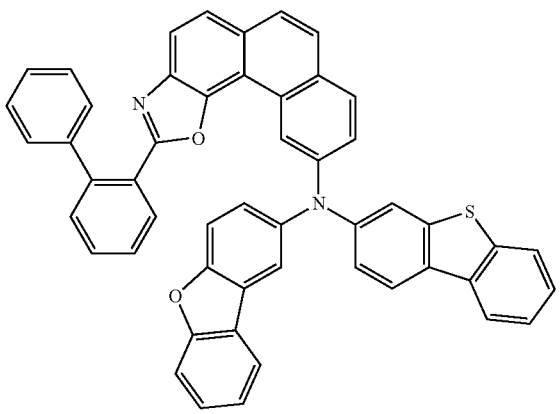
H1-110
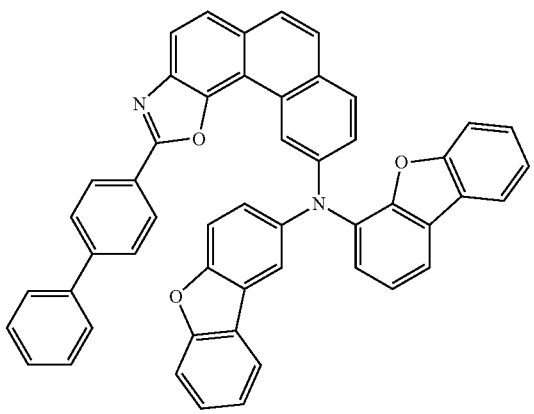

93
-continued
H1-111
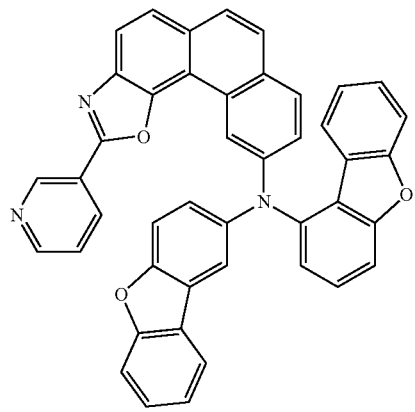
H1-112
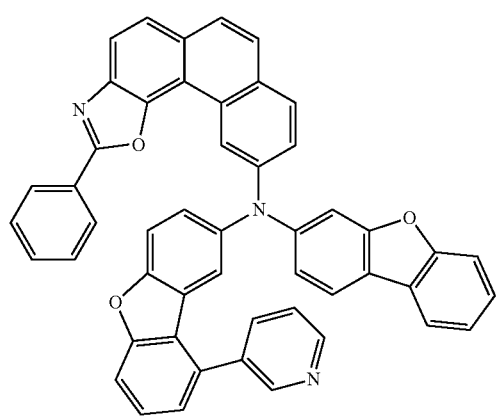
H1-113
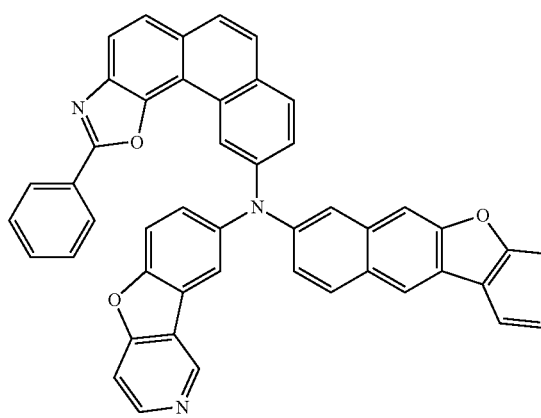
94
-continued
H1-114
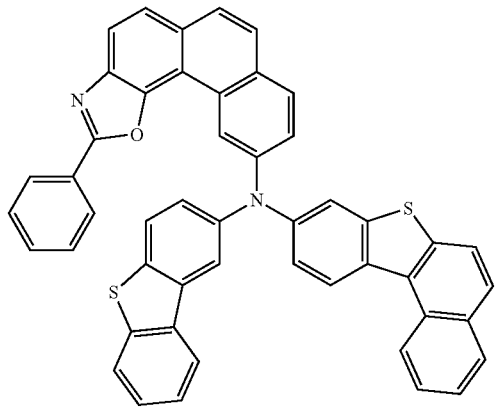
H1-115
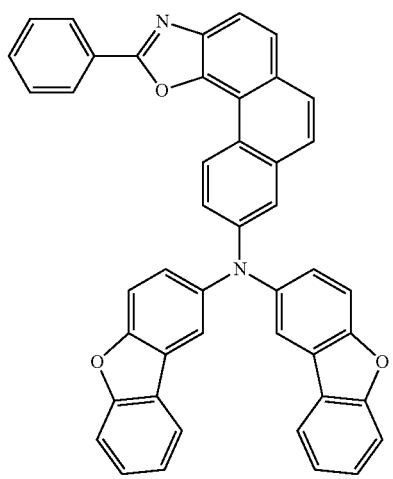
H1-116
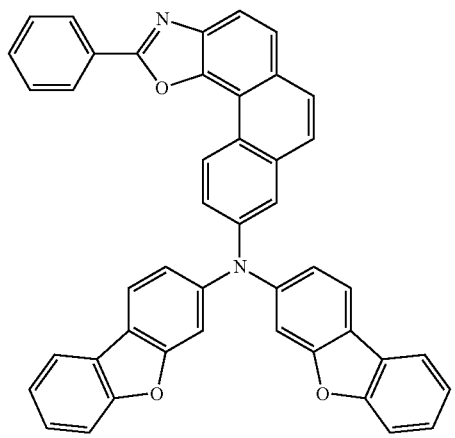

H1-117
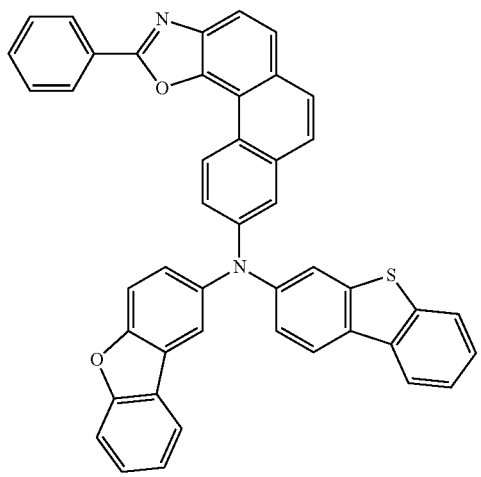
H1-118
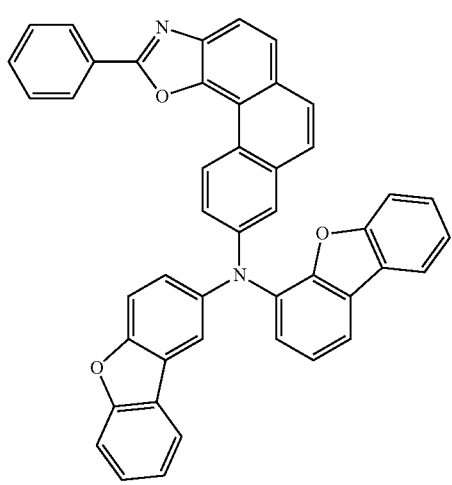
H1-119
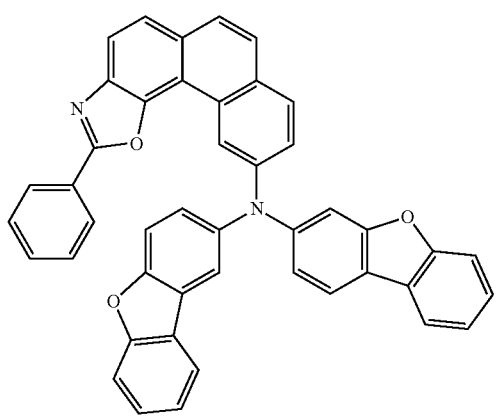
H1-120
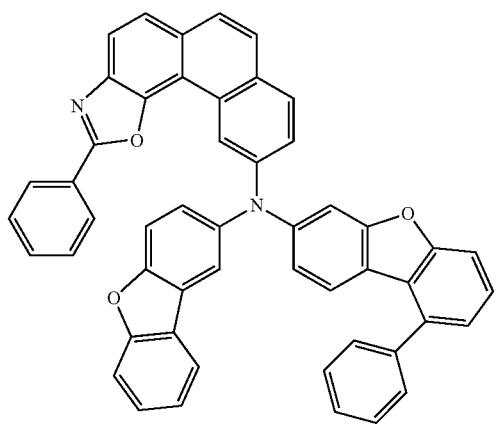
H1-121
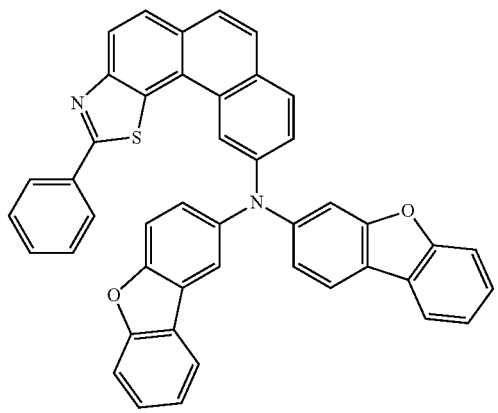
H1-122
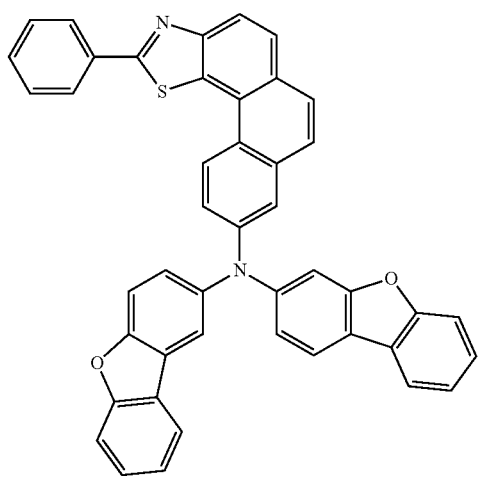

H1-123
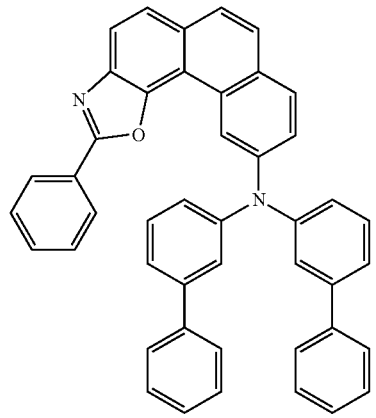
H1-124
H1-125
H1-126
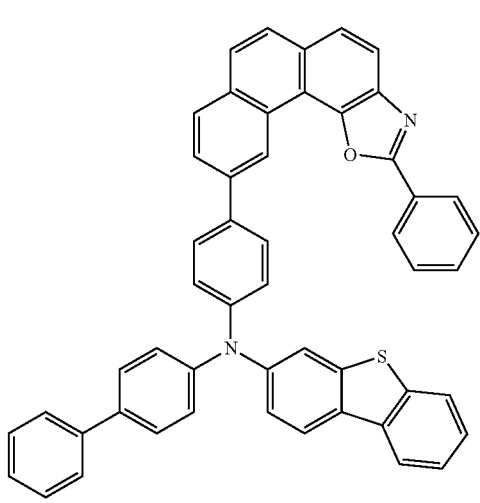
H1-127
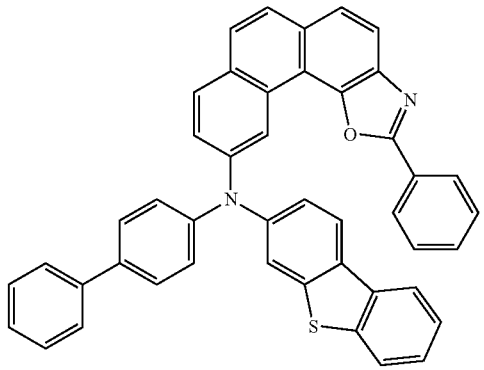
H1-128
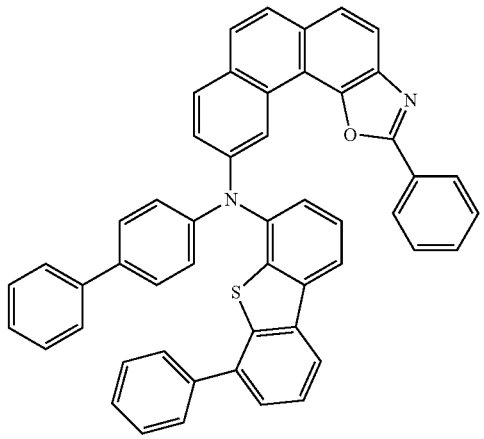

H1-129
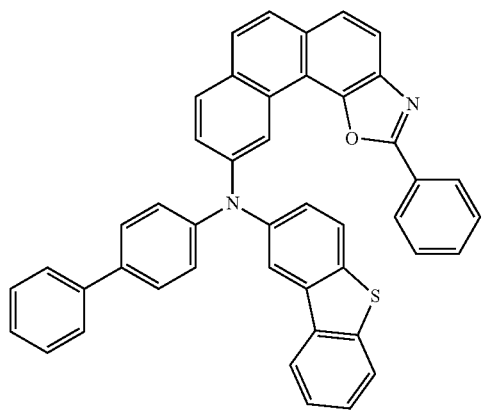
H1-132
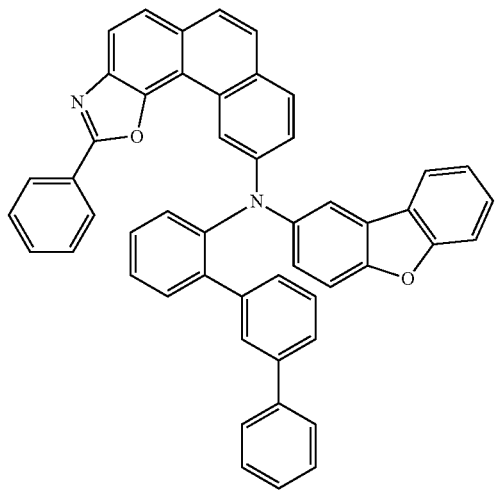
H1-130
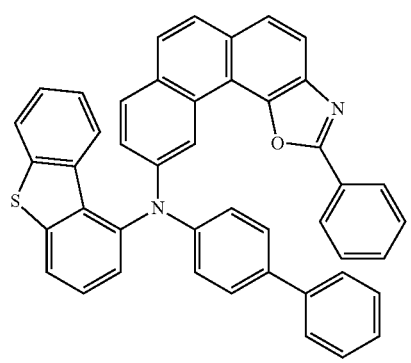
H1-133
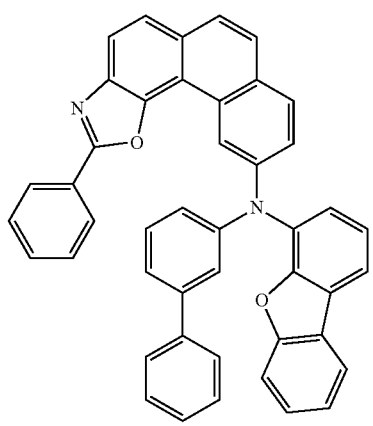
H1-131
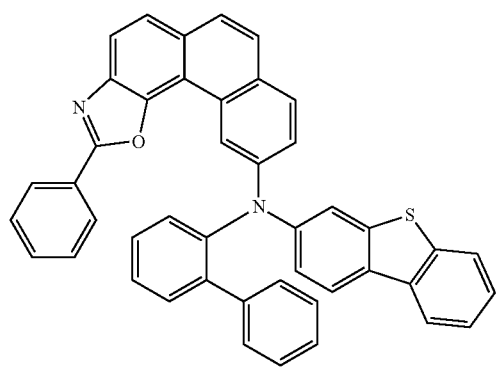
H1-134
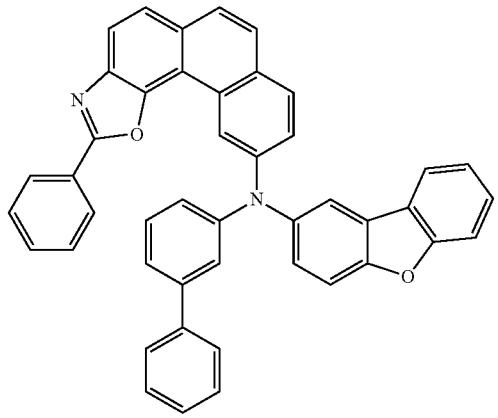

H1-135
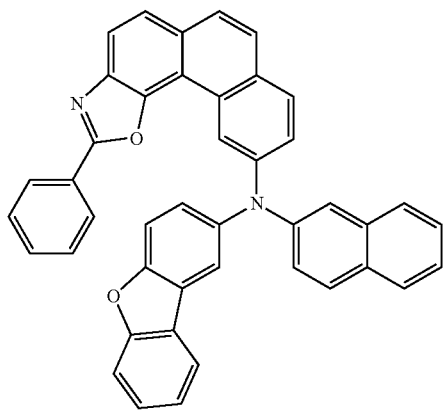
H1-136
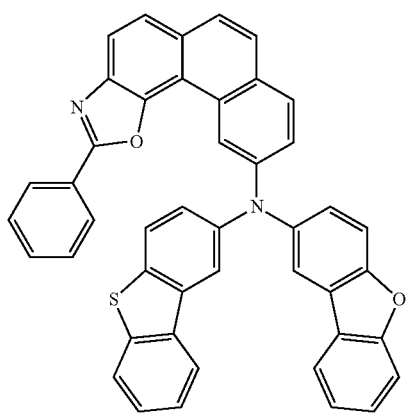
The compound represented by formula 2 may be at least one selected from the following compounds, but is not limited thereto.
C-1
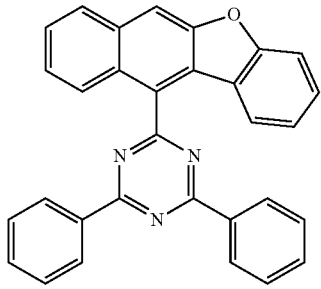
C-2
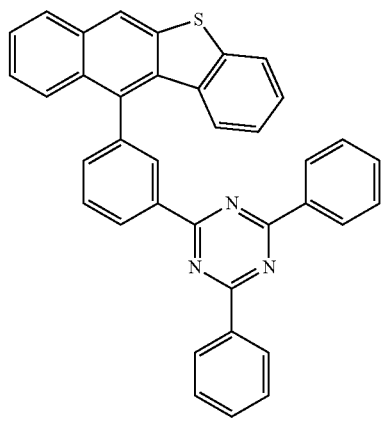
C-3
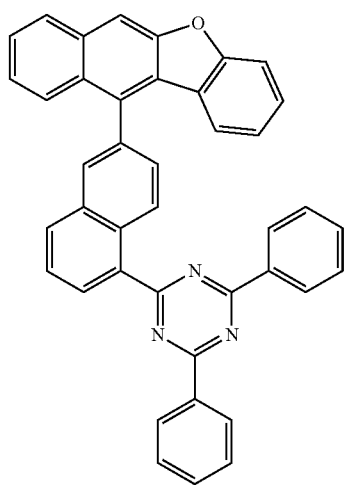
C-4
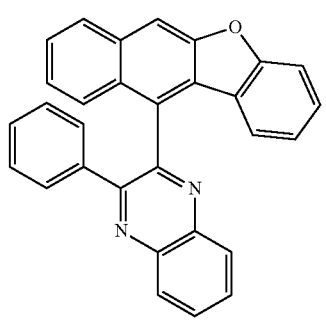
C-5
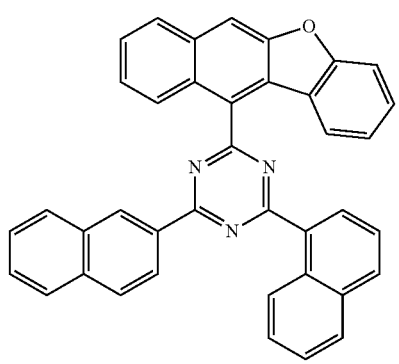

C-6
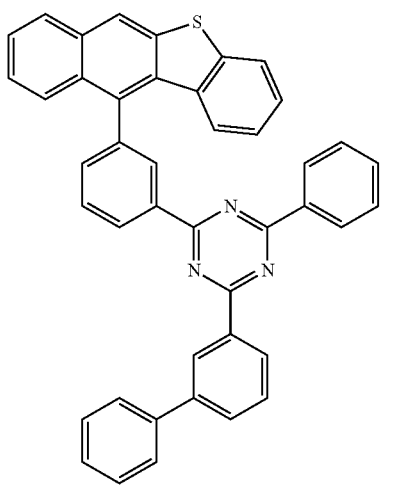
C-7
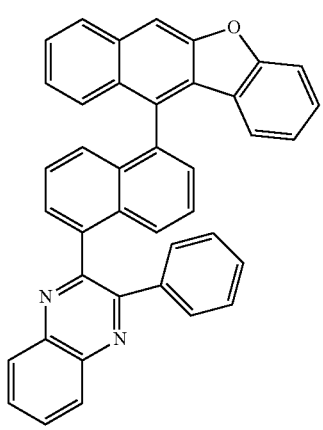
C-8
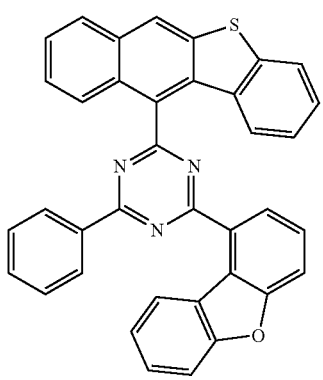
C-9
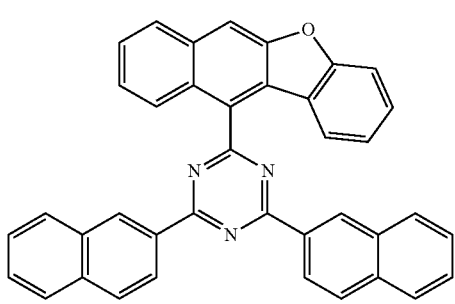
C-10
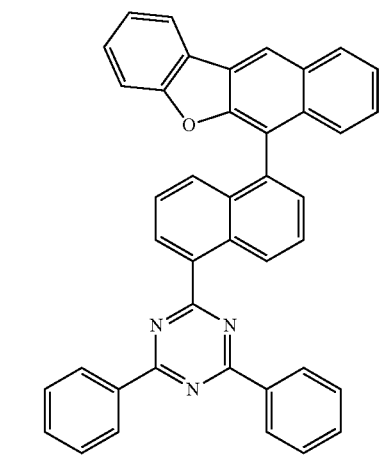
C-11
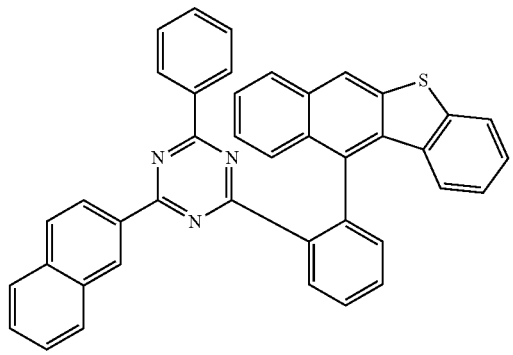
C-12
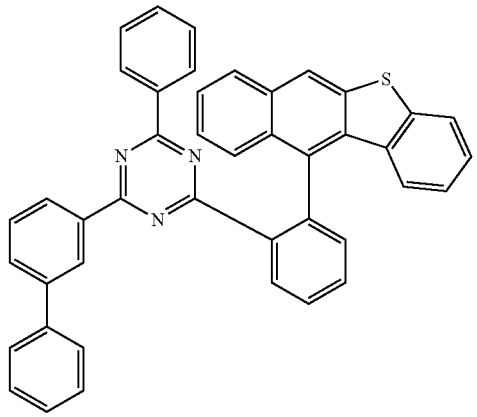
C-13
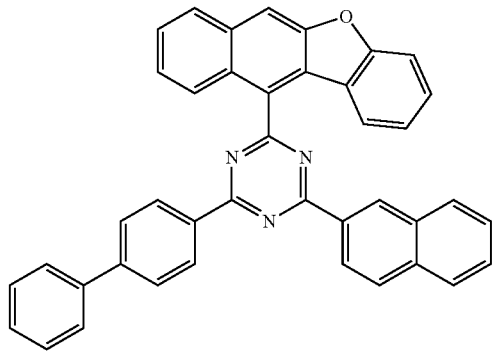

C-14 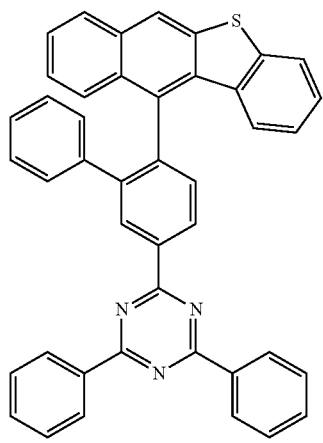
C-15 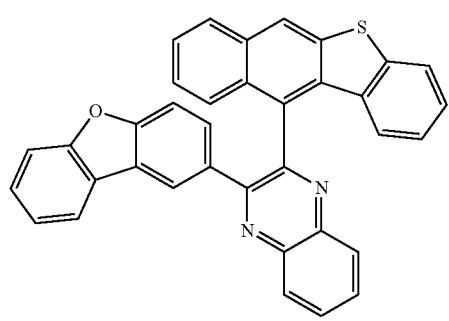
C-16 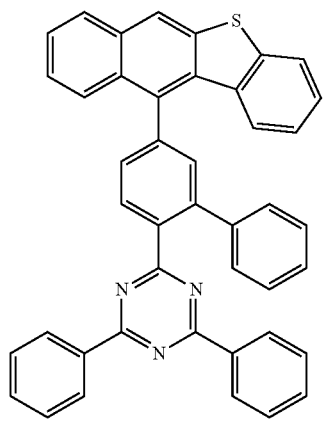
C-17 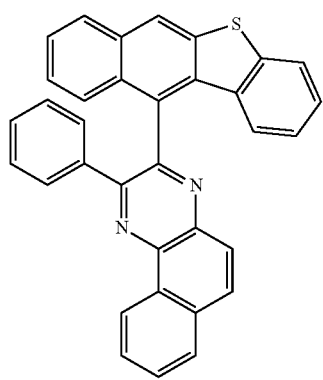
C-18 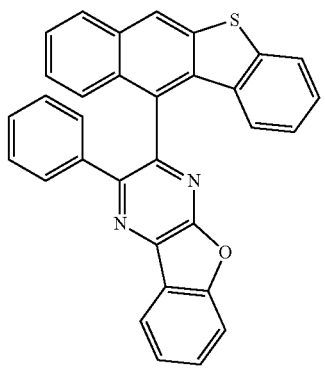
C-19 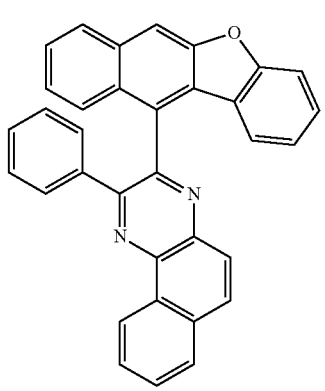
C-20 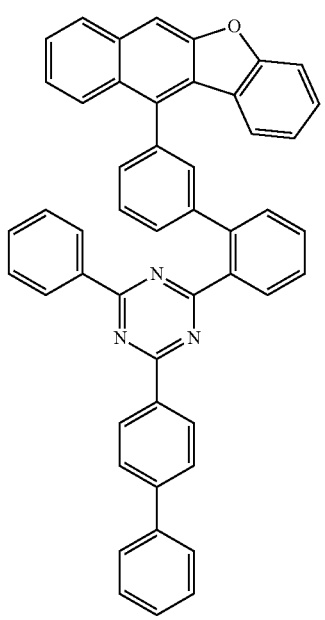

-continued
C-21
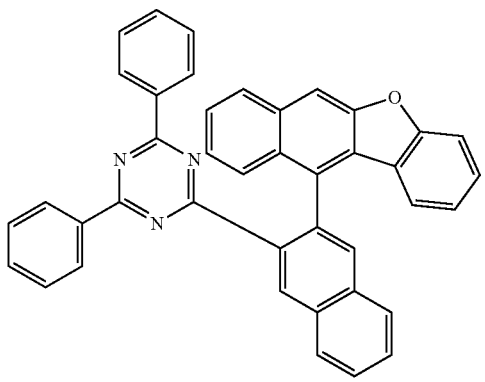
C-22
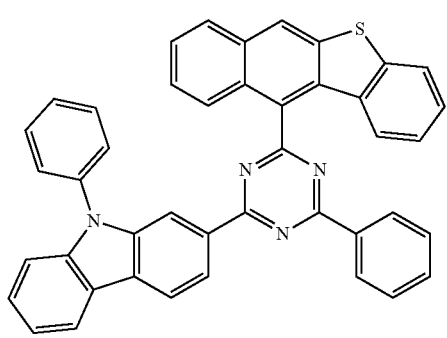
C-23
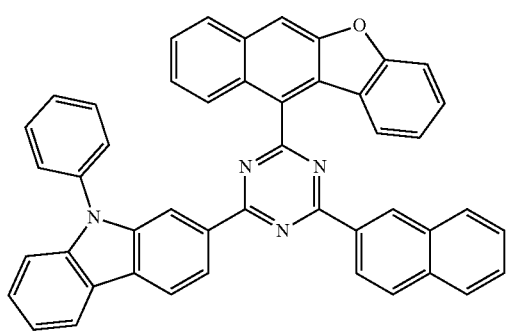
C-24
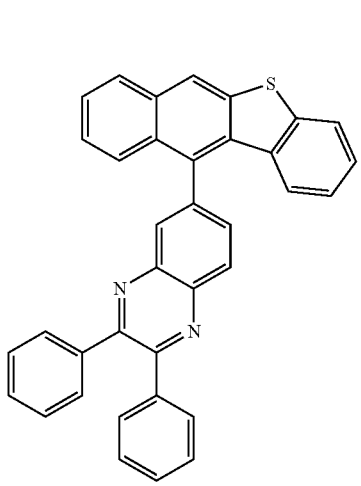
-continued
C-25
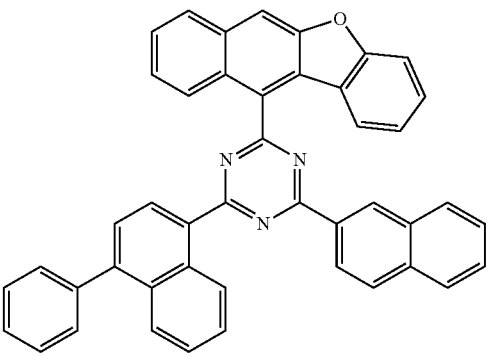
C-26
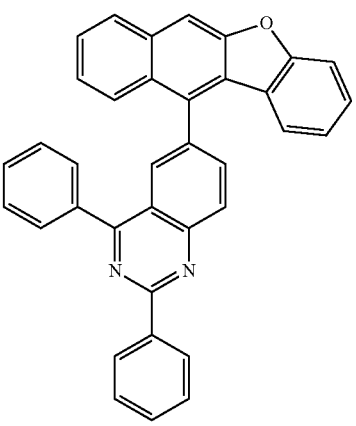
C-27
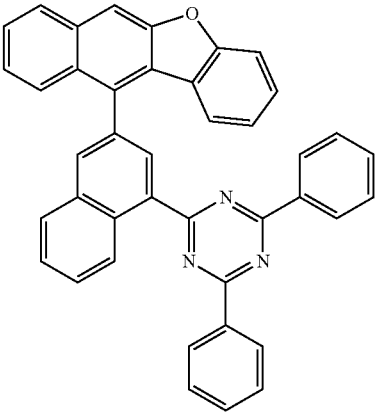
C-28
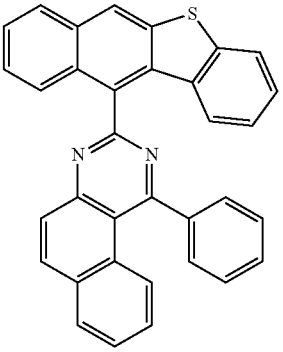

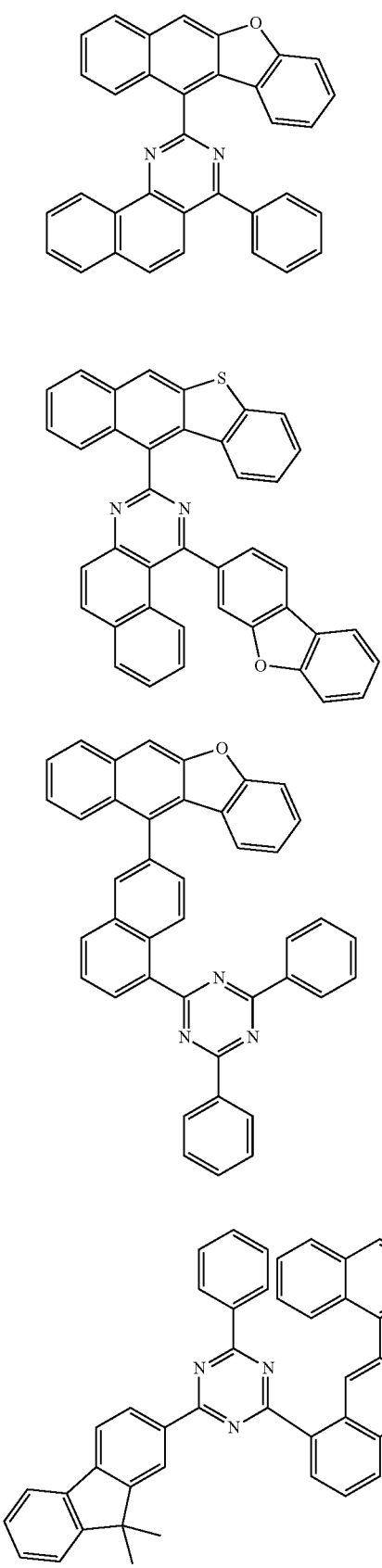
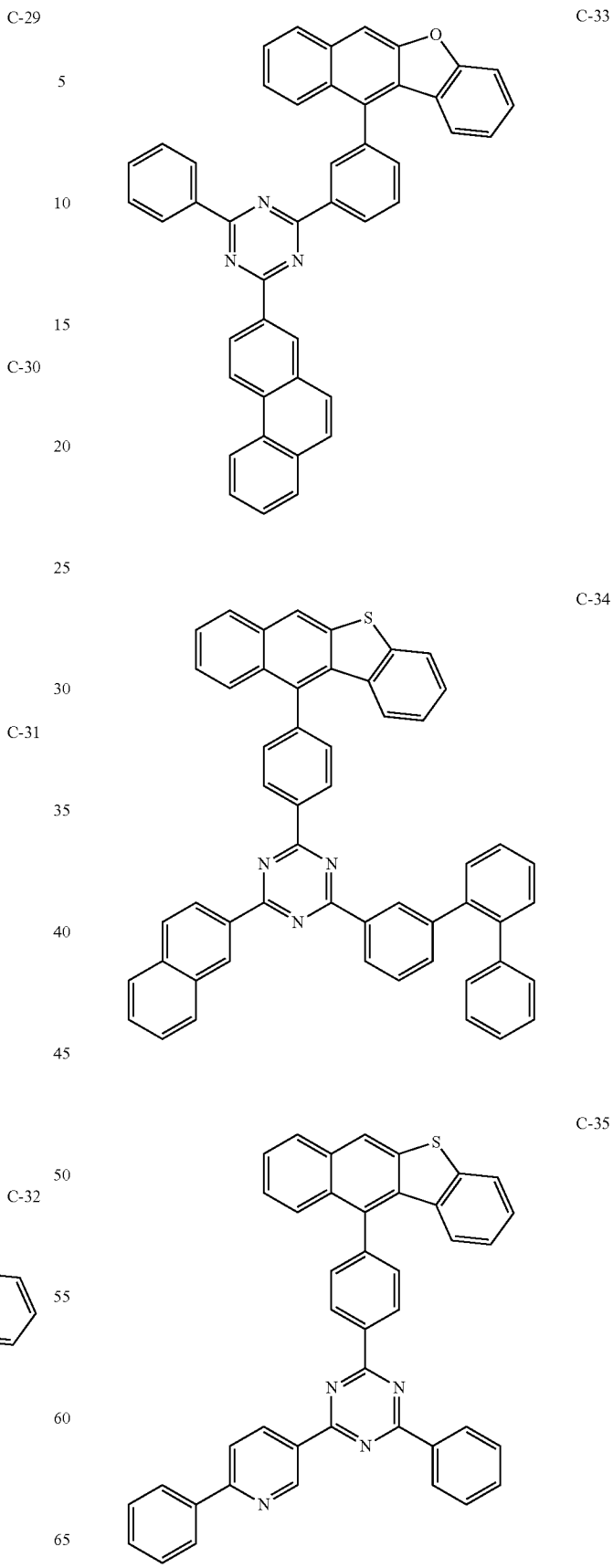

C-36
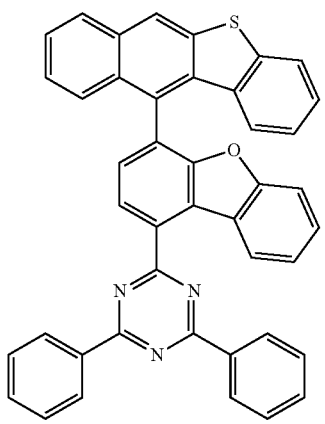
C-37
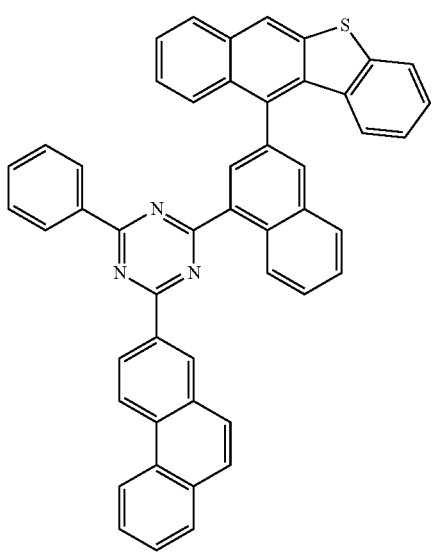
C-38
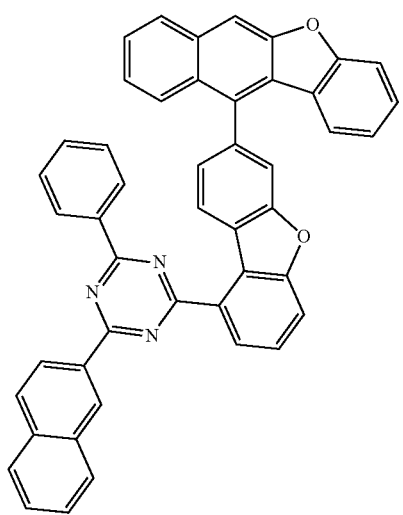
C-39
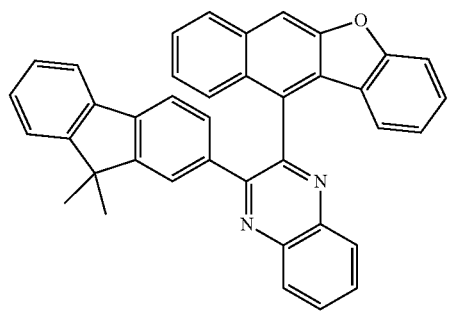
C-40
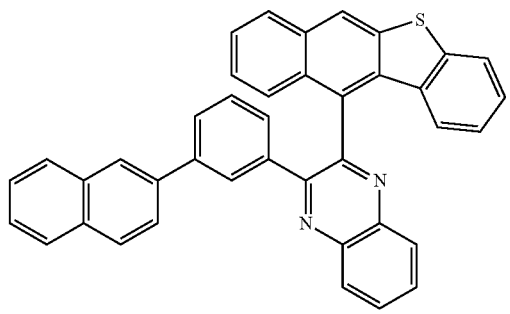
C-41
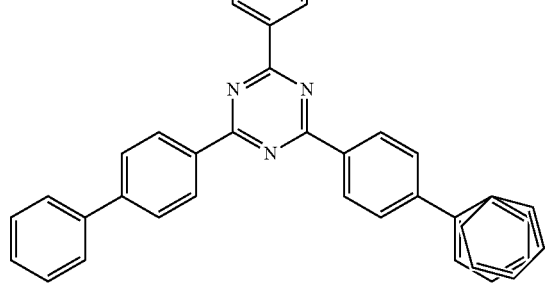
C-42
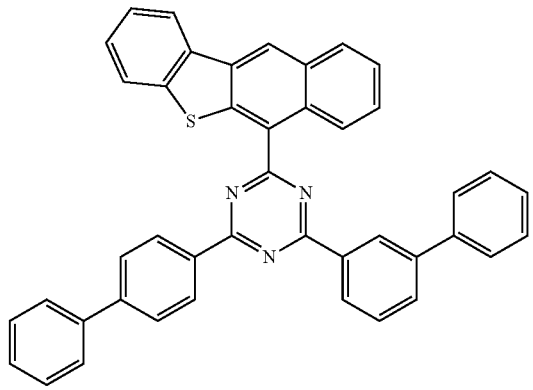

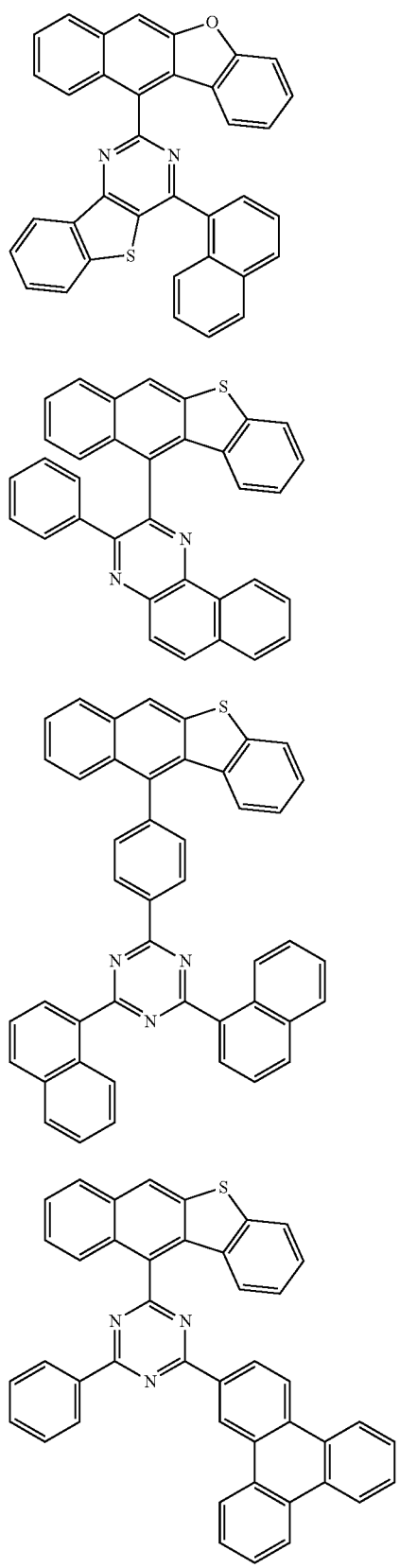
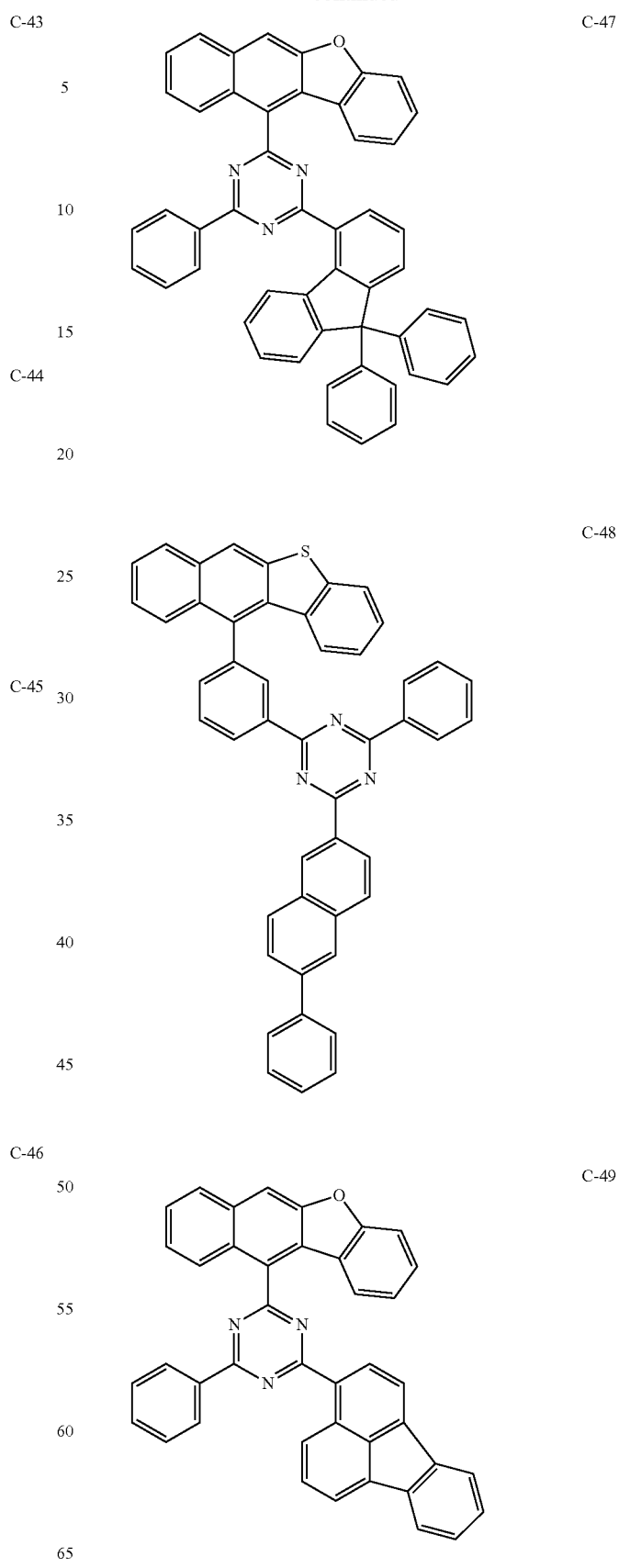

C-50
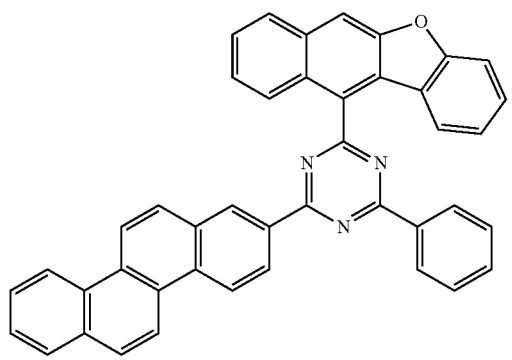
C-51
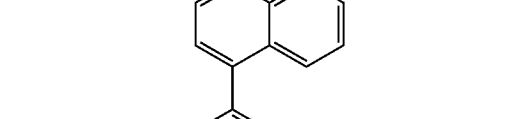
C-52
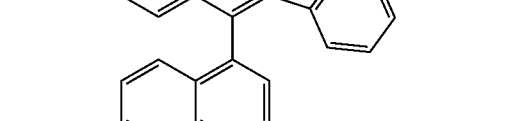
C-53
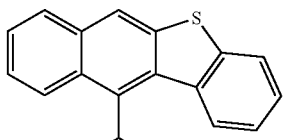
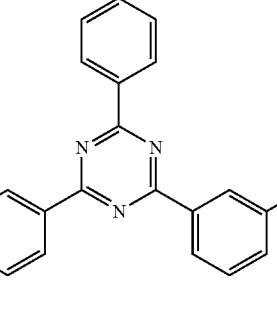
C-54
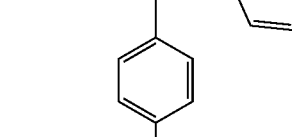
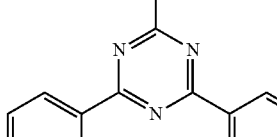
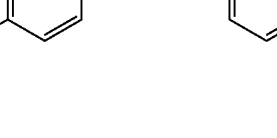
C-55
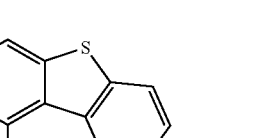
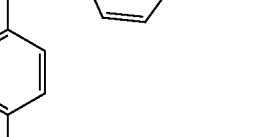
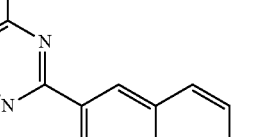

C-56
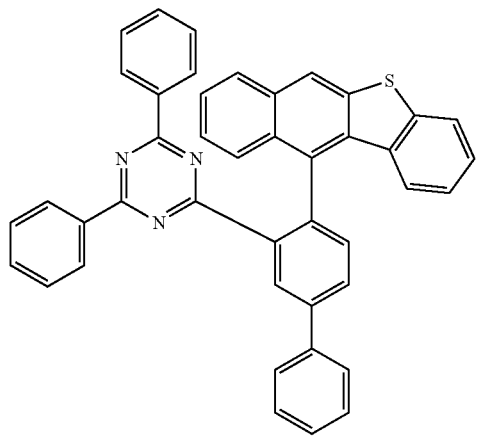
C-57
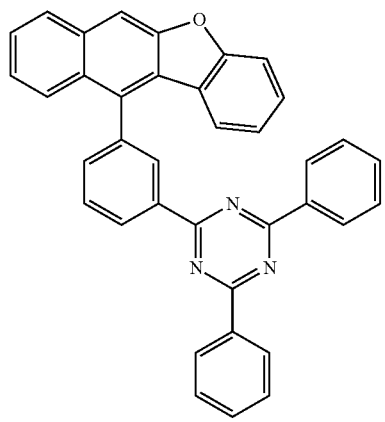
C-58
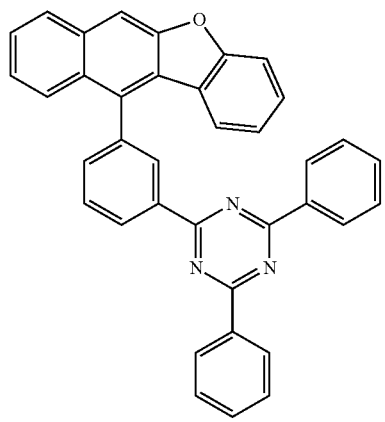
C-59
C-60
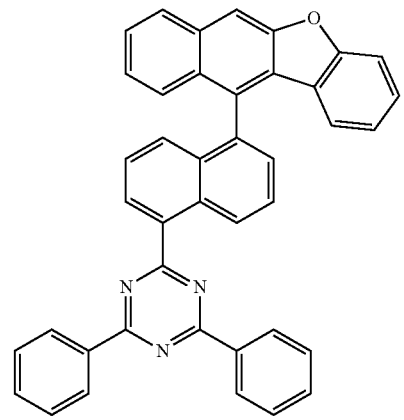
C-61
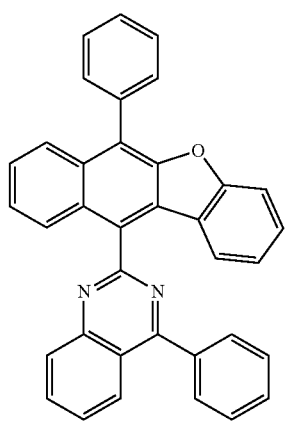
C-62
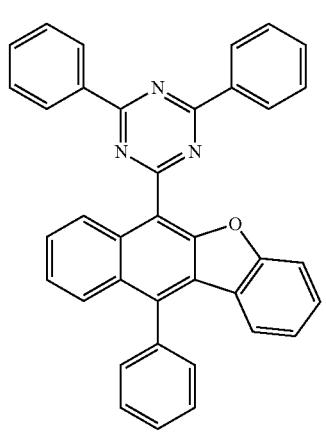

C-63
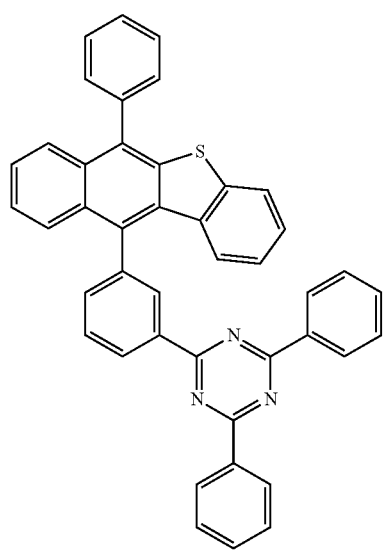
C-64
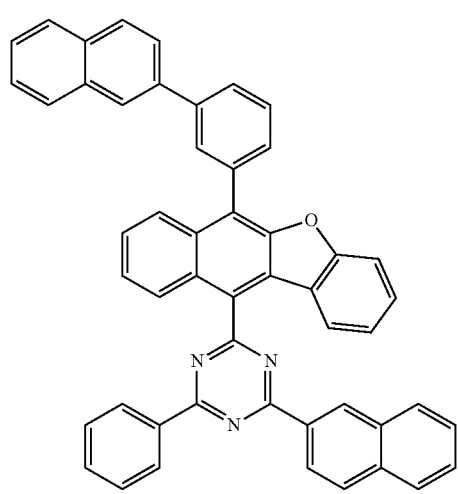
C-65
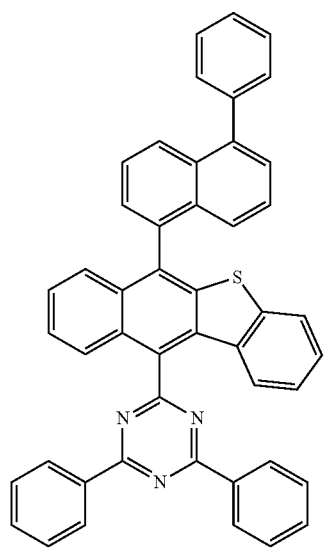
C-66
C-67
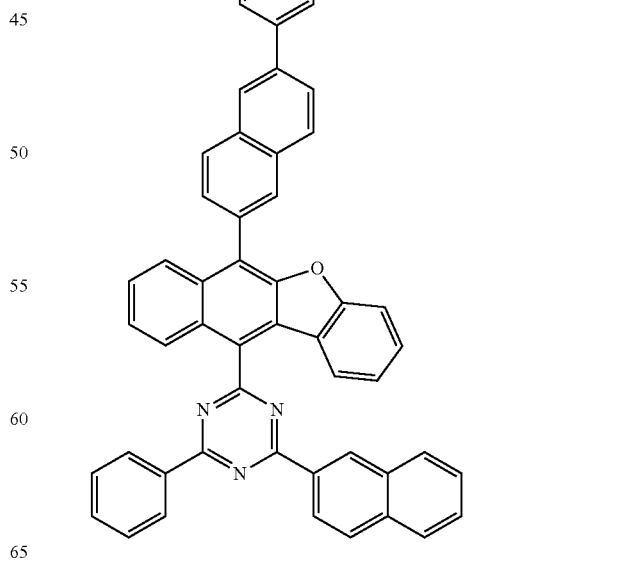

C-68
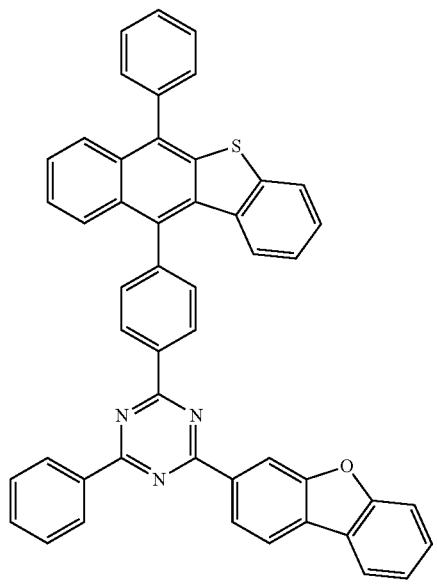
C-69
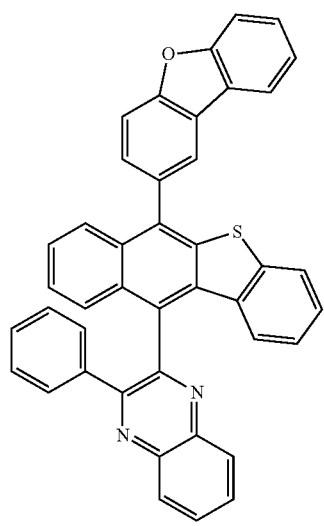
C-70
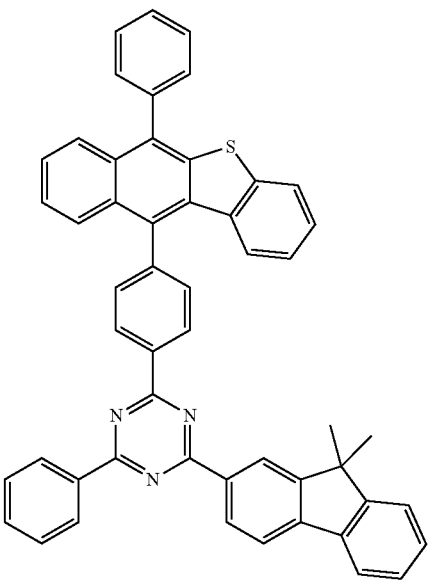
C-71
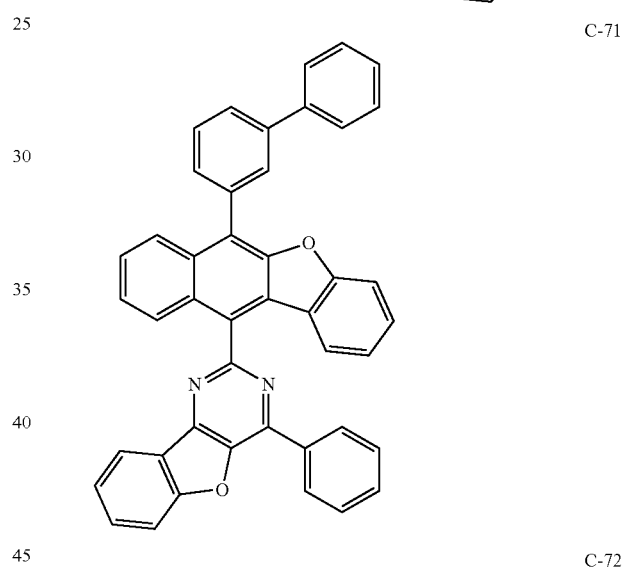
C-72
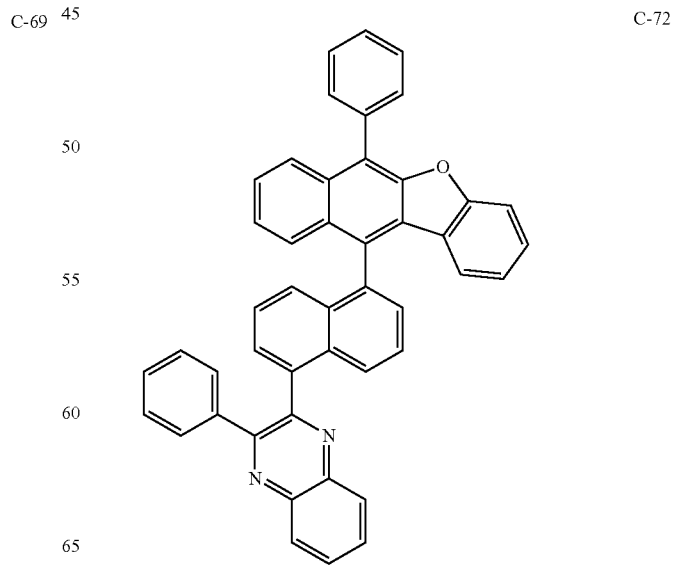

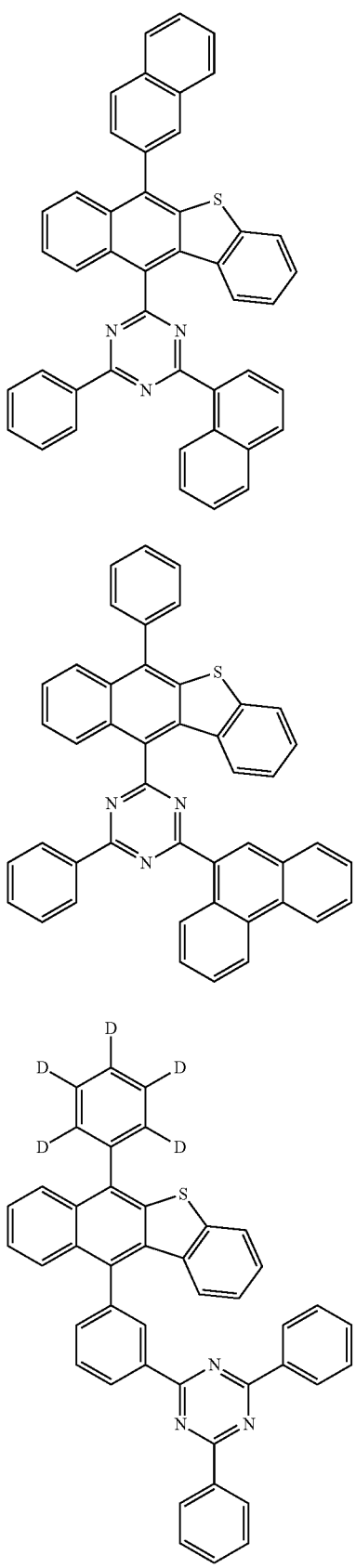
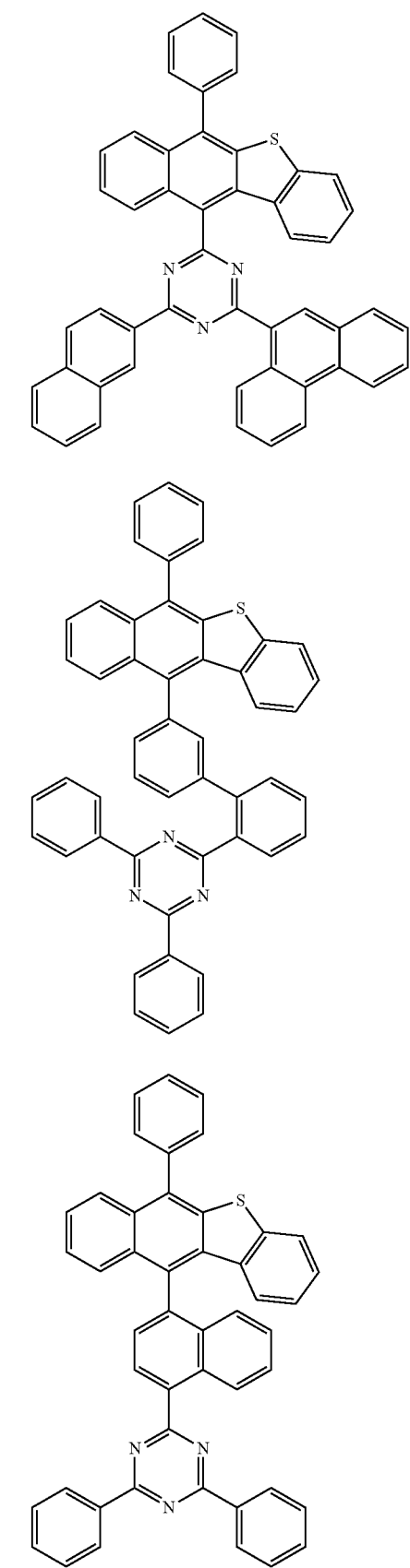

C-79
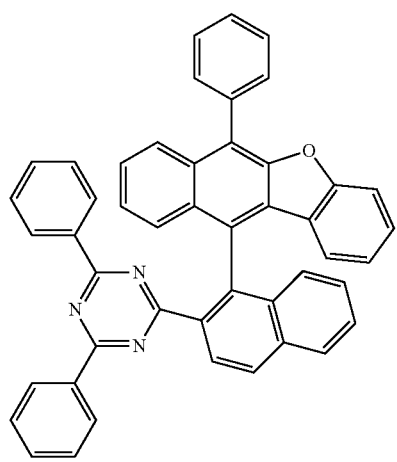
C-80
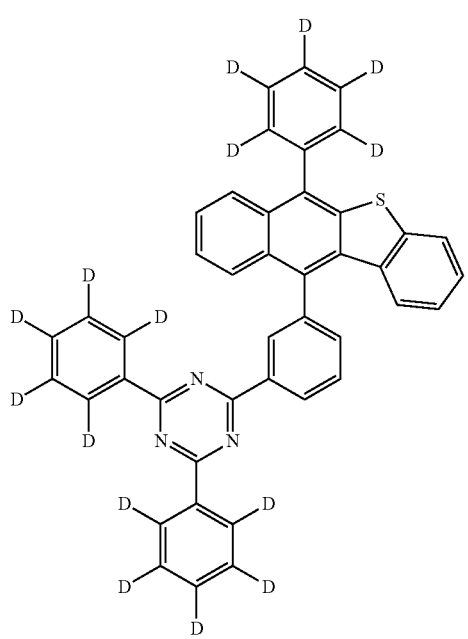
C-81
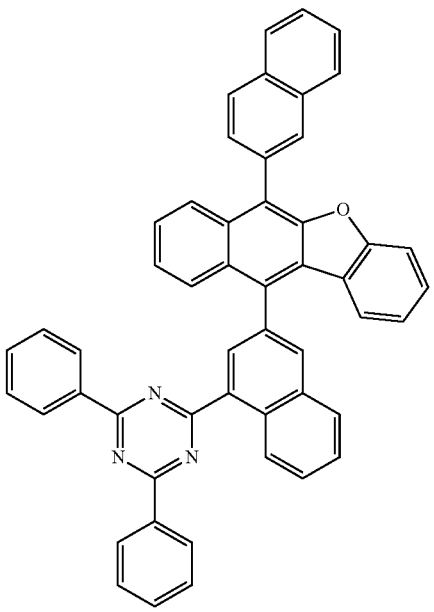
C-82
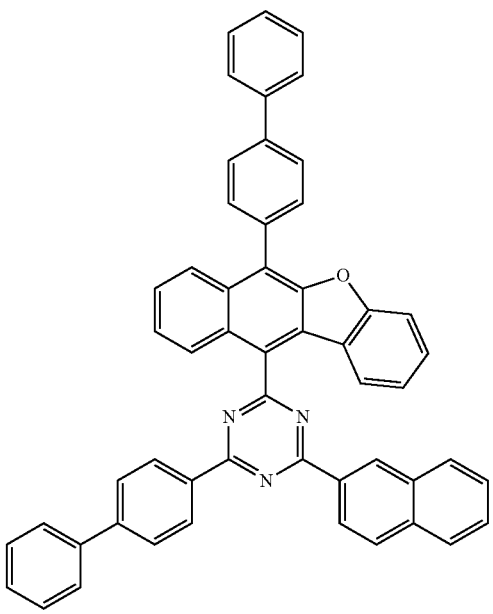

C-83
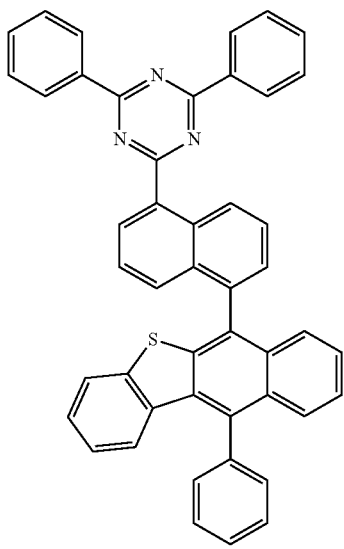
C-84
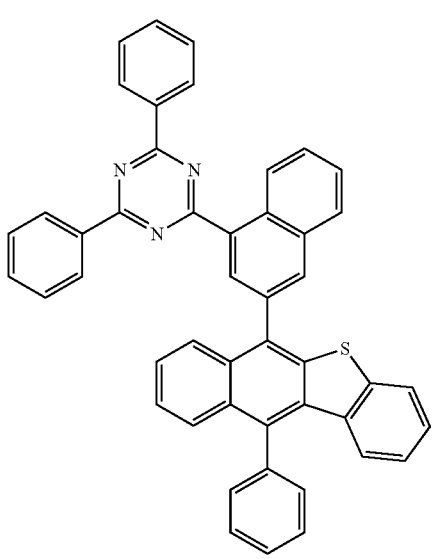
C-85
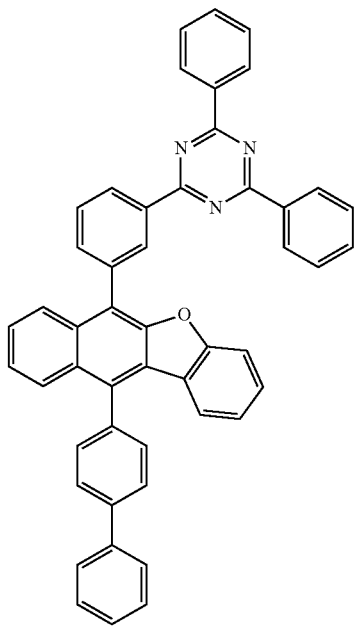
C-86
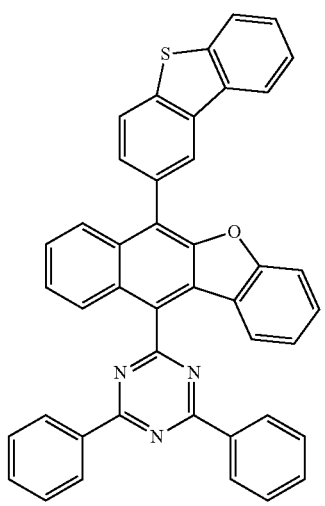

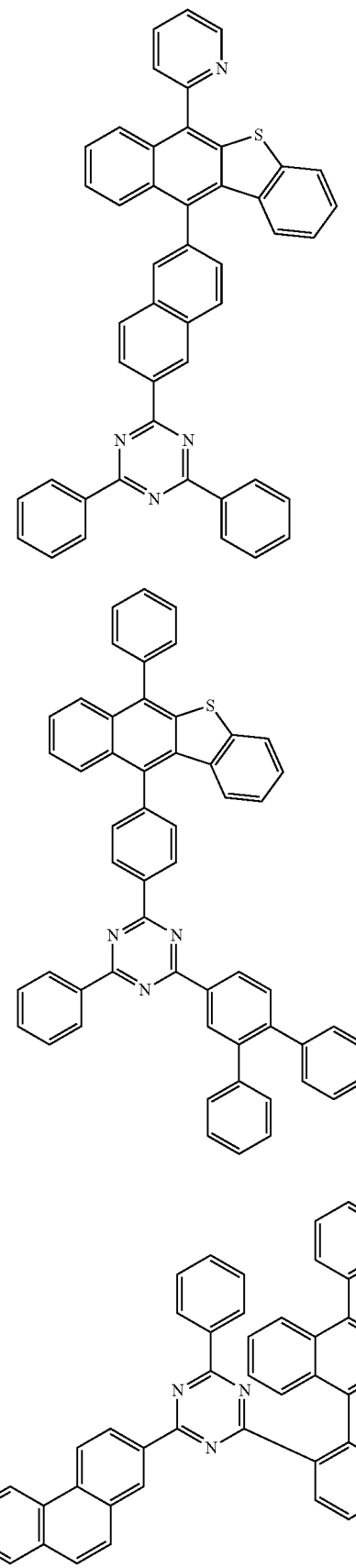
C-87
C-88
C-89
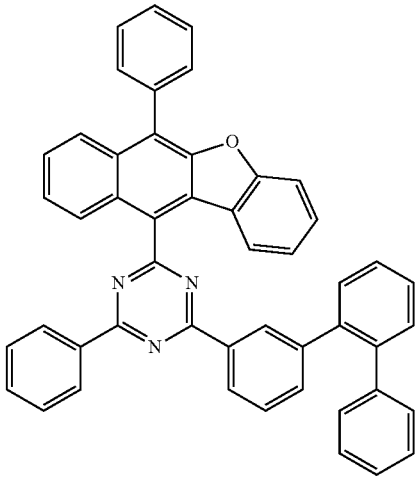
C-90
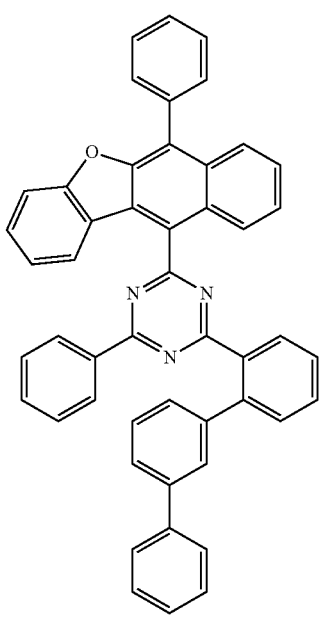
C-91
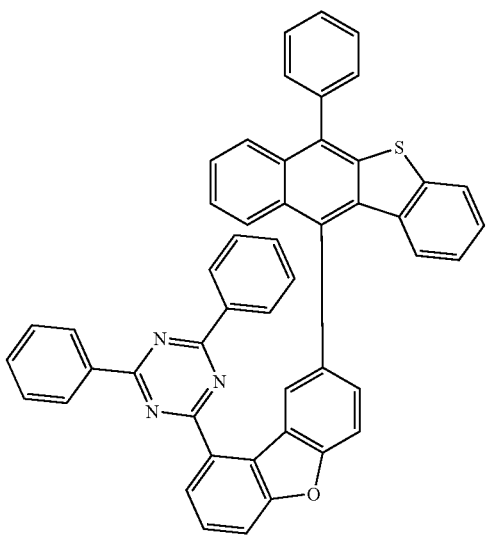
C-92

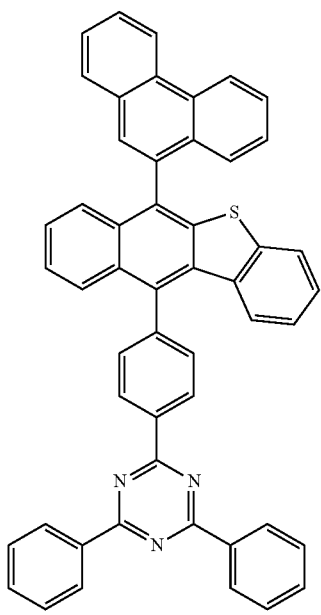
C-93
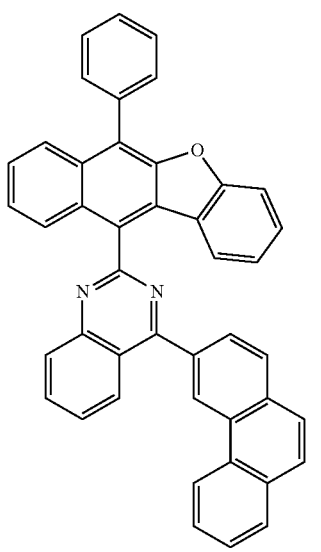
C-94
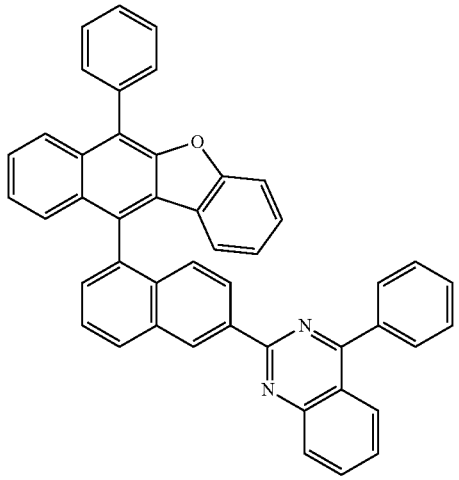
C-95
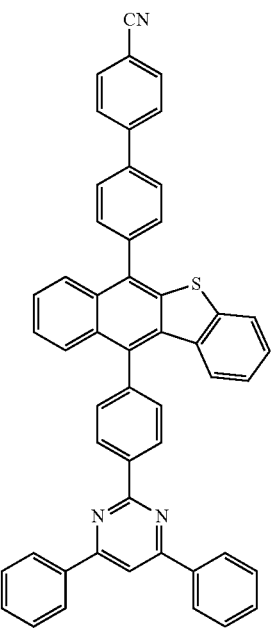
C-96
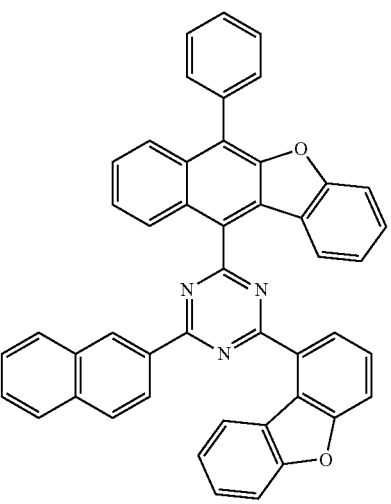
C-97

C-98
C-99
C-100
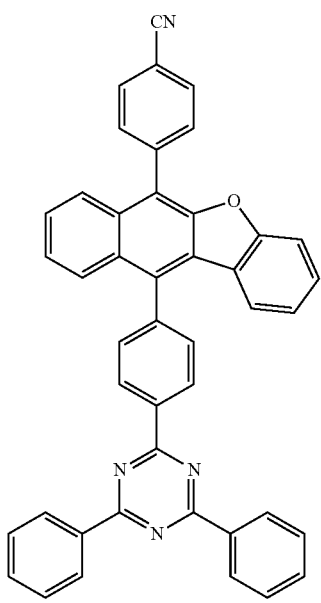
C-101
C-102
C-103
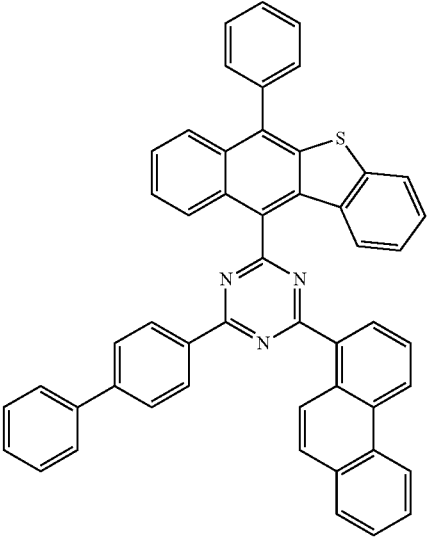

C-104
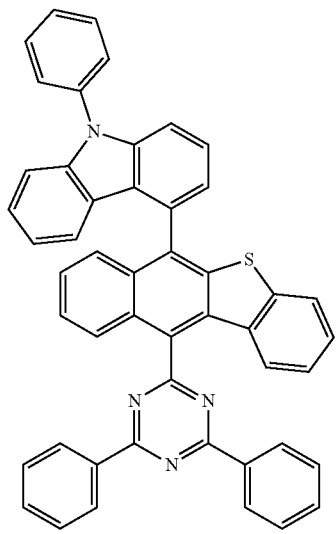
C-105
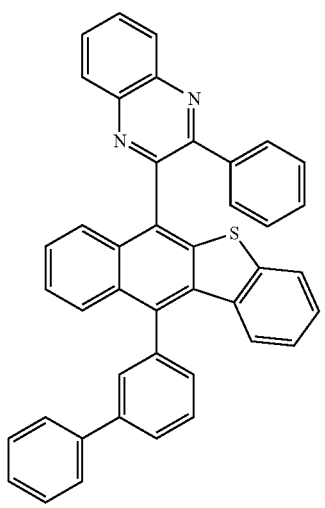
C-106
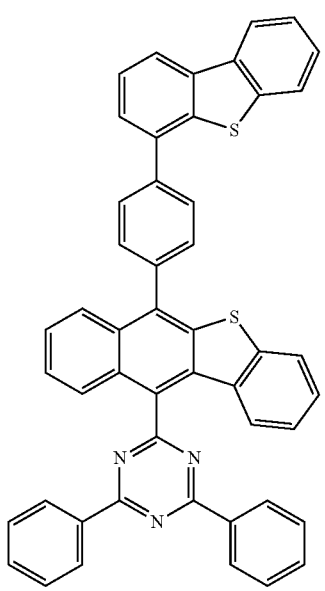
C-107
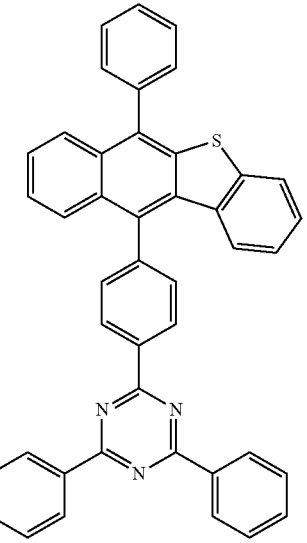
C-108
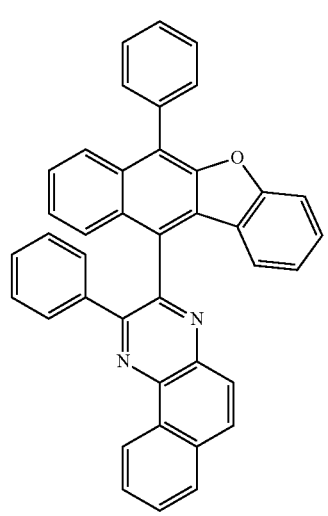
C-109
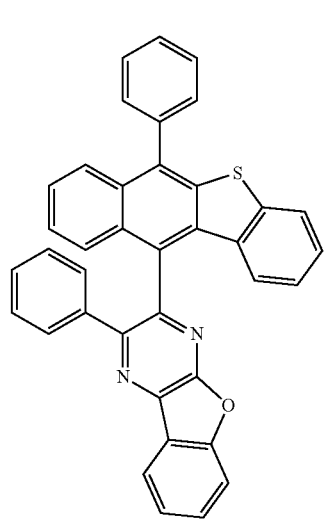

C-110
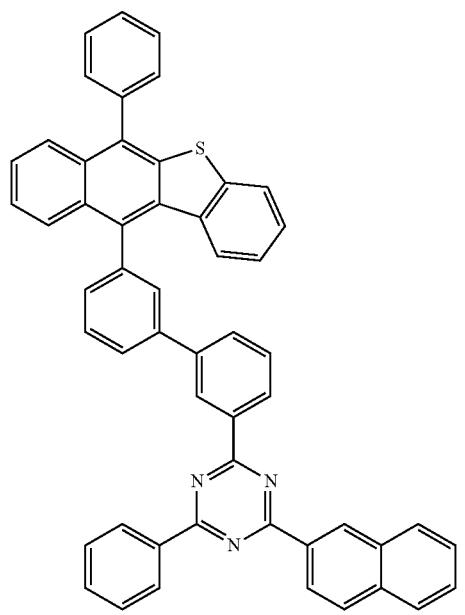
C-111
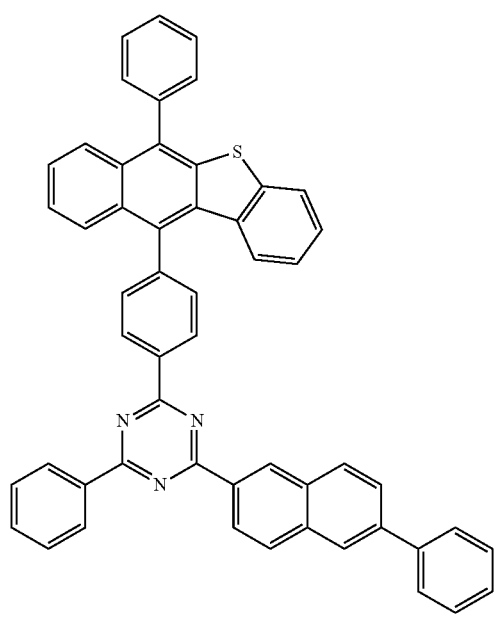
C-112
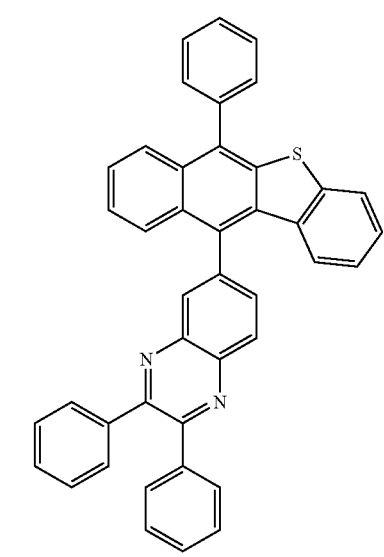
C-113
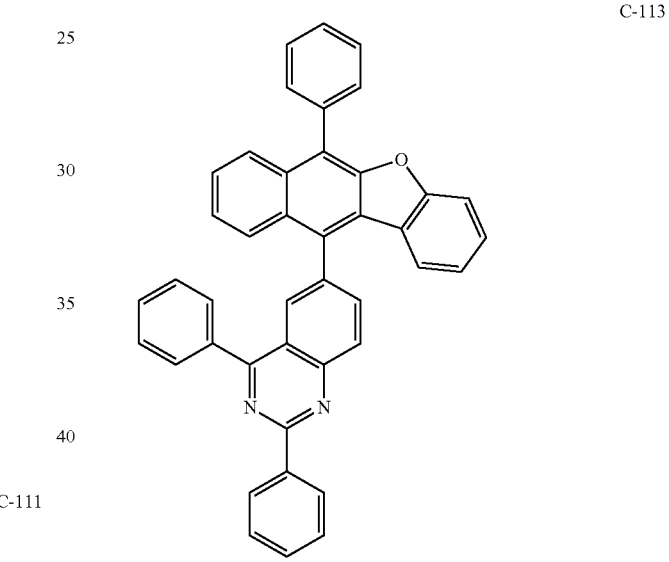
C-114
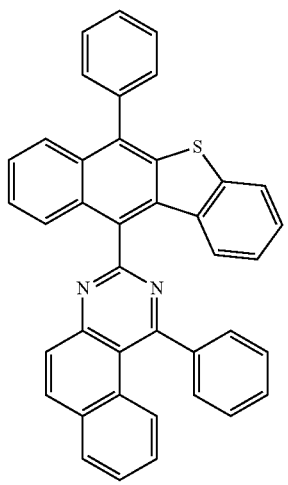

C-115
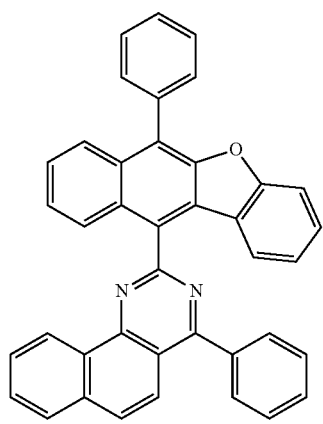
C-116
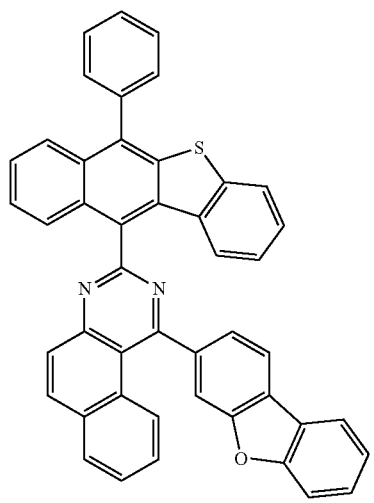
C-117
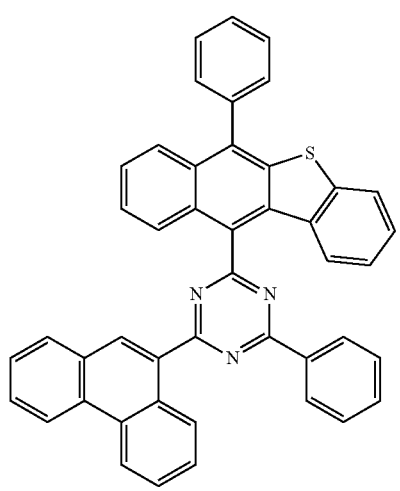
C-118
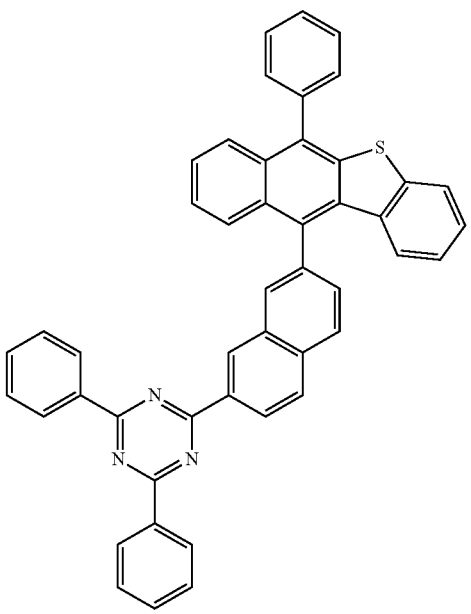
C-119
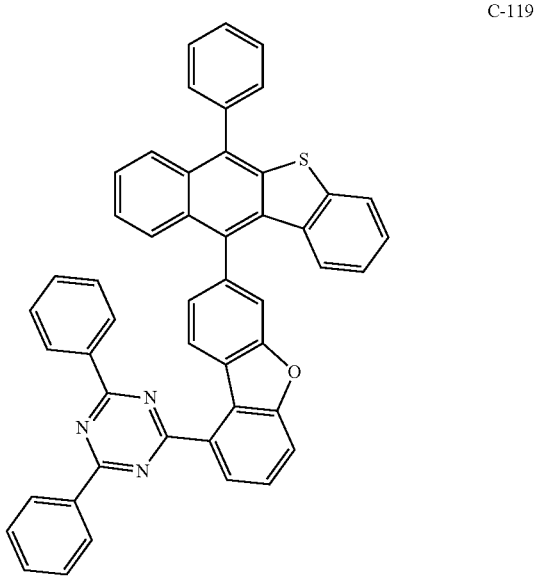

C-120
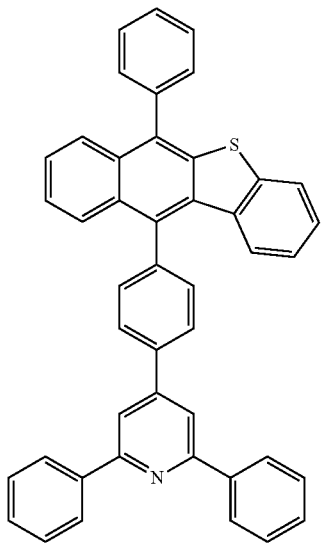
C-121
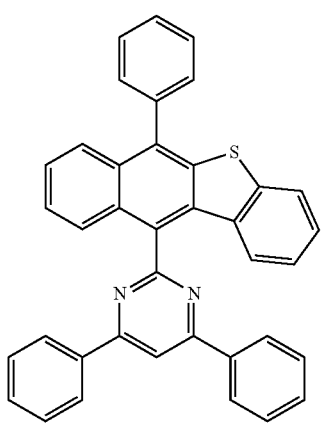
C-122
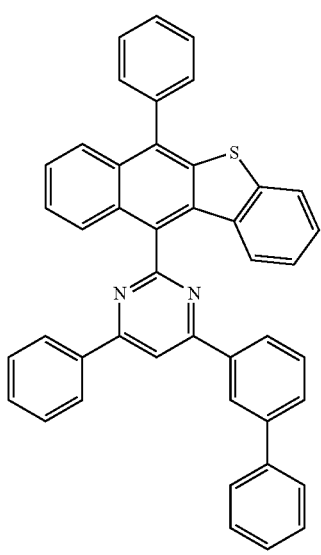
C-123
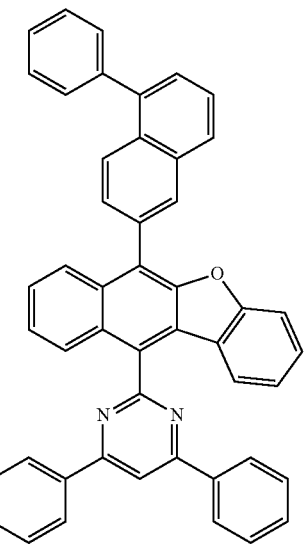
C-124
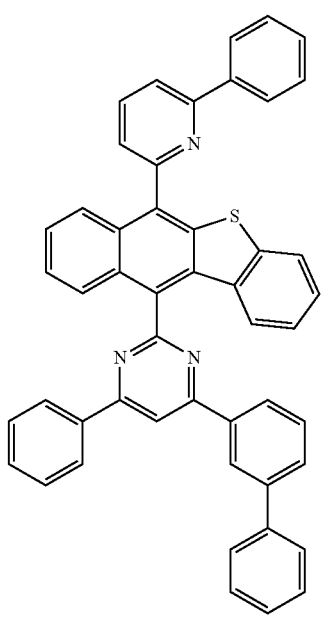
C-125
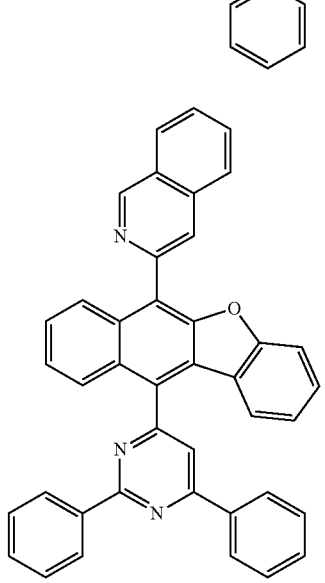

143

-continued

C-126

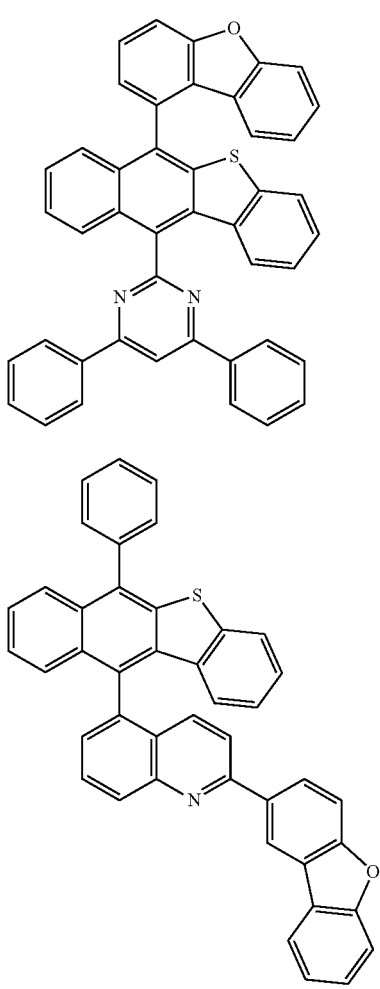

C-127

The combination of at least one of compounds H1-1 to H1-136 and at least one of compounds C-1 to C-127 may be used in an organic electroluminescent device.

The compound of formula 1 according to the present disclosure may be prepared by a synthetic method known to one skilled in the art, for example, by referring to Korean Patent Appln. 2017-0022865 (published on Mar. 2, 2017), Korean Patent Appln. Laid-Open No. 2017-0051198 (published on May 11, 2017), Korean Patent Appln. Laid-Open No. 2018-0094572 (published on Aug. 24, 2018), etc., but is not limited thereto.

The compound of formula 2 according to the present disclosure may be prepared by a synthetic method known to one skilled in the art, for example, by referring to the following reaction schemes 1 to 3, but is not limited thereto.

[Reaction Scheme 1]

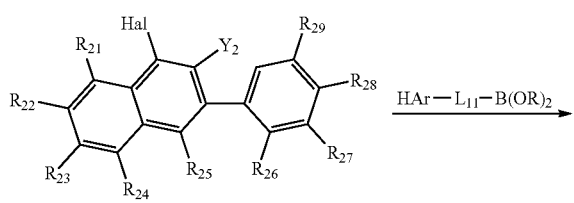

144

-continued

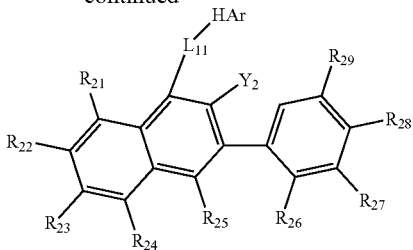

[Reaction Scheme 2]

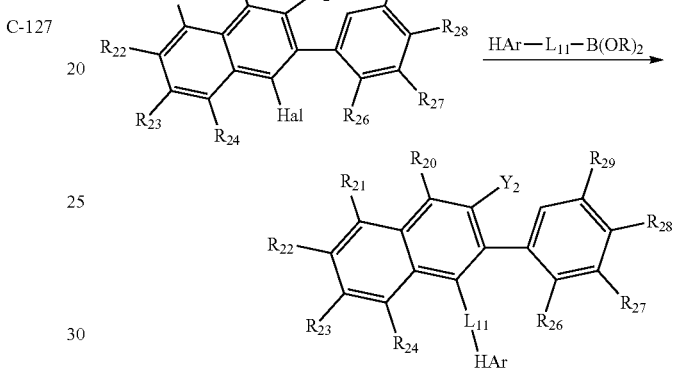

[Reaction Scheme 3]

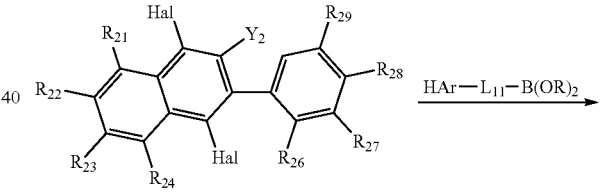

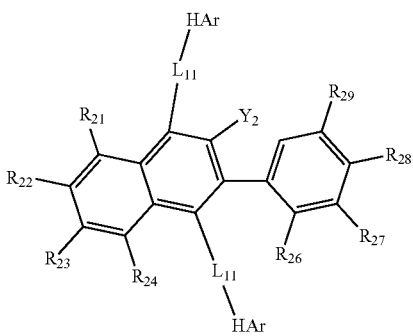

In reaction schemes 1 to 3, $Y_2$, $R_{20}$ to $R_{29}$, $L_{11}$, HAr, and e are as defined in formula 2, and Hal is a halogen atom.

Although illustrative synthesis examples of the compounds represented by formula 2 are described above, one skilled in the art will be able to readily understand that all of them are based on a Buchwald-Hartwig cross-coupling reaction, an N-arylation reaction, H-mont-mediated etherification reaction, a Miyaura borylation reaction, a Suzuki cross-coupling reaction, an intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, a Phosphine-mediated reductive cyclization reaction, etc., and the reactions above proceed even when substituents, which are defined in formula 2 but are not specified in the specific synthesis examples, are bonded.

The organic electroluminescent device of the present disclosure comprises an anode, a cathode, and at least one organic layer between the anode and the cathode, wherein the organic layer may comprise a plurality of organic electroluminescent materials including the compound represented by formula 1 as a first organic electroluminescent material and the compound represented by formula 2 as a second organic electroluminescent material. According to one embodiment of the present disclosure, the organic electroluminescent device of the present disclosure comprises an anode, a cathode, and at least one light-emitting layer between the anode and the cathode, wherein the light-emitting layer may comprise the compound represented by formula 1 and the compound represented by formula 2.

The light-emitting layer comprises a host(s) and a dopant, wherein the host includes a plurality of host materials, wherein the compound represented by formula 1 may be included as a first host compound of the plurality of host materials, and the compound represented by formula 2 may be included as a second host compound of the plurality of host materials. Herein, the weight ratio of the first host compound to the second host compound is from about 1:99 to about 99:1, preferably from about 10:90 to about 90:10, more preferably from about 30:70 to about 70:30, more preferably about 40:60 to about 60:40, and even more preferably about 50:50.

In the present disclosure, the light-emitting layer is a layer that emits light, which may be a single layer or a plurality of layers in which two or more layers are stacked. In the plurality of host materials of the present disclosure, the first and second host materials may be included in one layer or in different light-emitting layers, respectively. According to one embodiment of the present disclosure, the doping concentration of the dopant compound with respect to the host compound of the light-emitting layer may be less than 20 wt %.

The organic electroluminescent device according to the present disclosure may comprise at least one layer selected from a hole injection layer, a hole transport layer, a hole auxiliary layer, a light-emitting auxiliary layer, an electron transport layer, an electron injection layer, an interlayer, an electron buffer layer, a hole blocking layer, and an electron blocking layer. According to one embodiment of the present disclosure, the organic electroluminescent device according to the present disclosure may further comprise an amine-based compound as at least one of a hole injection material, a hole transport material, a hole auxiliary material, a light-emitting material, a light-emitting auxiliary material, and an electron blocking material, in addition to the plurality of host materials according to the present disclosure. In addition, according to one embodiment of the present disclosure, the organic electroluminescent device according to the present disclosure may further comprise an azine-based compound as at least one of an electron transport material, an electron injection material, an electron buffer material, and a hole blocking material, in addition to the plurality of host materials according to the present disclosure.

The plurality of host materials according to the present disclosure may be used as light-emitting materials for a white organic light-emitting device. The white organic light-emitting device has been suggested in various structures such as a side-by-side structure or a stacking structure depending on the arrangement of R (Red), G (Green) or YG (Yellowish Green), and B (Blue) light-emitting parts, or a color conversion material (CCM) method, etc. In addition, the plurality of host materials according to the present disclosure may also be used in the organic electroluminescent device comprising a QD (Quantum Dot).

A hole injection layer, a hole transport layer, an electron blocking layer, or a combination thereof may be used between an anode and a light-emitting layer. The hole injection layer may be multilayers in order to lower the hole injection barrier (or hole injection voltage) from the anode to the hole transport layer or the electron blocking layer, wherein two compounds may be simultaneously used in each of the multilayers. In addition, the hole injection layer may be doped with a p-dopant. The electron blocking layer may be placed between the hole transport layer (or hole injection layer) and the light-emitting layer, and may block overflow of electrons from the light-emitting layer and confine the excitons in the light-emitting layer to prevent light leakage. The hole transport layer or the electron blocking layer may be multilayers, wherein a plurality of compounds may be used in each of the multilayers.

An electron buffer layer, a hole blocking layer, an electron transport layer, an electron injection layer, or a combination thereof may be used between a light-emitting layer and a cathode. The electron buffer layer may be multilayers in order to control electron injection and improve interfacial properties between the light-emitting layer and the electron injection layer, wherein two compounds may be simultaneously used in each of the multilayers. The hole blocking layer or the electron transport layer may also be multilayers, wherein a plurality of compounds may be used in each of the multilayers. In addition, the electron injection layer may be doped with an n-dopant.

The dopants that can be comprised in the organic electroluminescent device of the present disclosure may be at least one phosphorescent or fluorescent dopant, preferably a phosphorescent dopant. The phosphorescent dopant materials applied to the organic electroluminescent device according to the present disclosure are not particularly limited, but may be selected from metallated complex compounds of iridium (Ir), osmium (Os), copper (Cu), and platinum (Pt), may be preferably selected from ortho-metallated complex compounds of iridium (Ir), osmium (Os), copper (Cu), and platinum (Pt), and may be more preferably an ortho-metallated iridium complex compound.

The dopant comprised in the organic electroluminescent device of the present disclosure may be a compound represented by the following formula 101, but is not limited thereto.

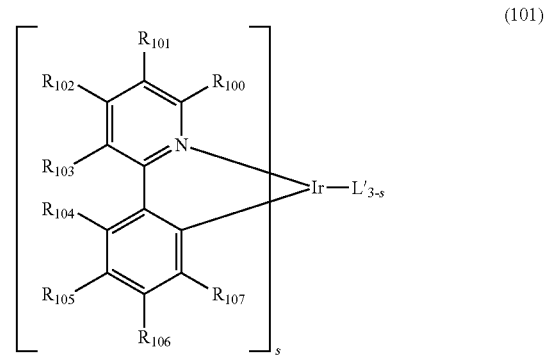

(101)

In formula 101,
L' is selected from the following structures 1 to 3:

[Structure 1]

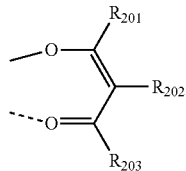

[Structure 2]

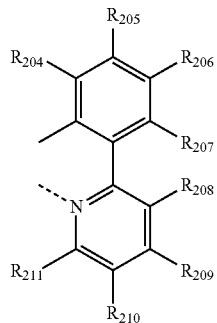

[Structure 3]

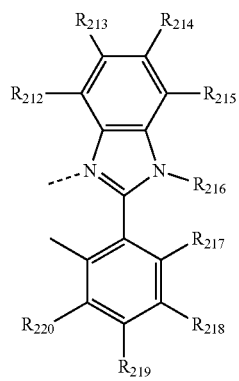

$R_{100}$ to $R_{103}$, each independently, represent hydrogen, deuterium, a halogen, a (C1-C30)alkyl unsubstituted or substituted with deuterium(s) and/or a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30) alkoxy; or may be linked to an adjacent substituent to form a ring(s), e.g., a substituted or unsubstituted, quinoline, isoquinoline, benzofuropyridine, benzothienopyridine, indenopyridine, benzofuroquinoline, benzothienoquinoline, or indenoquinoline ring, together with pyridine;

$R_{104}$ to $R_{107}$, each independently, represent hydrogen, deuterium, a halogen, a (C1-C30)alkyl unsubstituted or substituted with deuterium(s) and/or a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to an adjacent substituent to form a ring, e.g., a substituted or unsubstituted, naphthalene, fluorene, dibenzothiophene, dibenzofuran, indenopyridine, benzofuropyridine, or benzothienopyridine ring, together with benzene;

$R_{201}$ to $R_{220}$, each independently, represent hydrogen, deuterium, a halogen, a (C1-C30)alkyl unsubstituted or substituted with deuterium(s) and/or a halogen(s), a substituted or unsubstituted (C3-C30)cycloalkyl, or a substituted or unsubstituted (C6-C30)aryl; or may be linked to an adjacent substituent to form a ring; and s represents an integer of 1 to 3.

The specific examples of the dopant compound are as follows, but are not limited thereto.

D-1

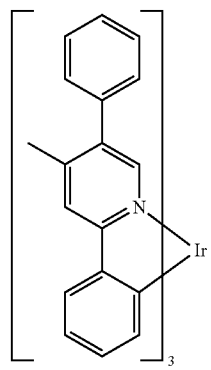

D-2

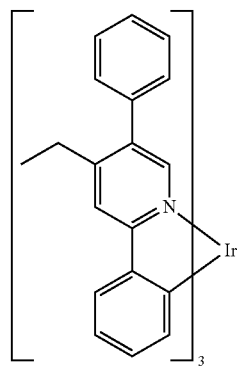

D-3

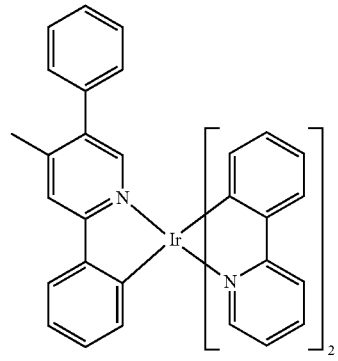

D-4

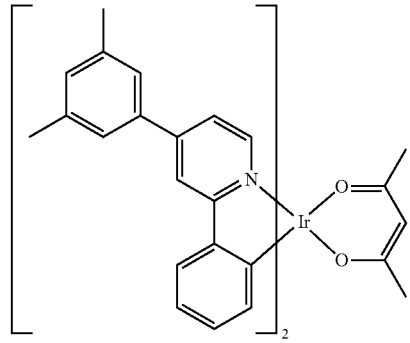

-continued
D-5
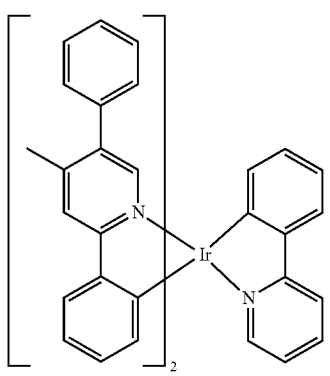
D-6
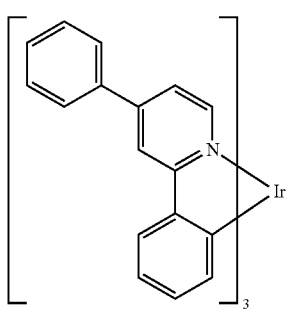
D-7
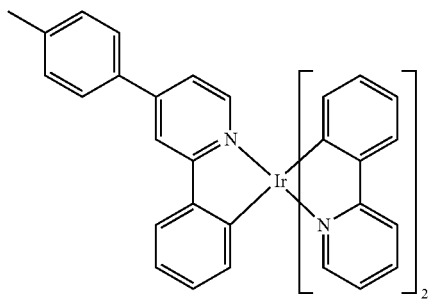
D-8
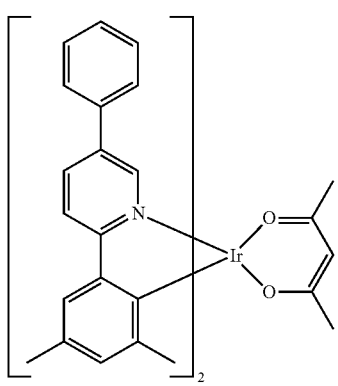
-continued
D-9
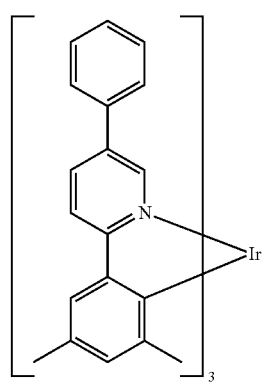
D-10
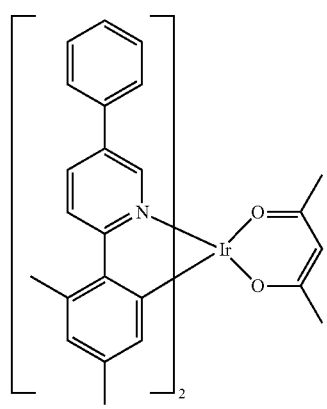
D-11
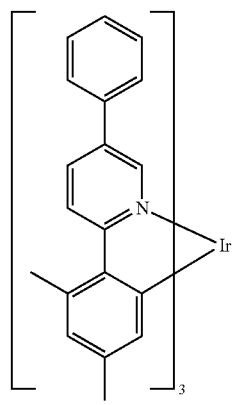
D-12
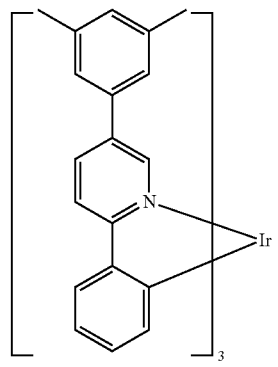

D-13
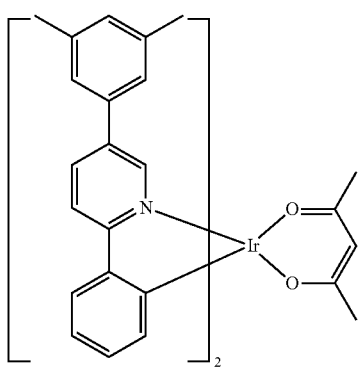
D-14
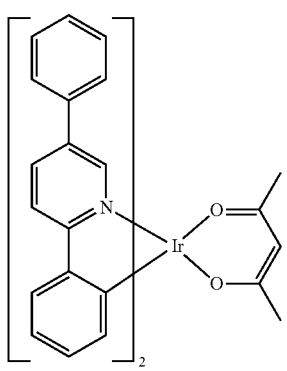
D-15
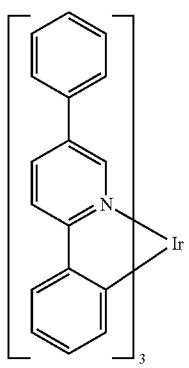
D-16
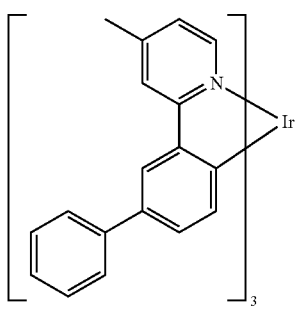
D-17
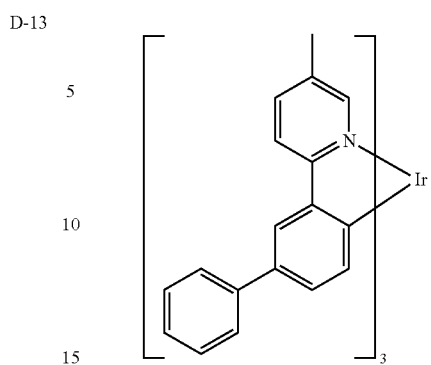
D-18
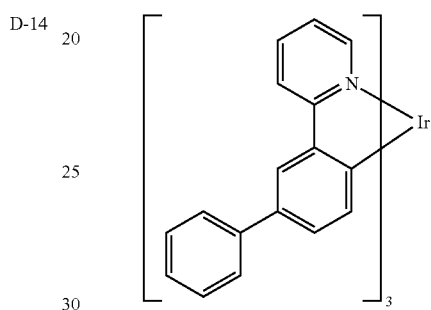
D-19
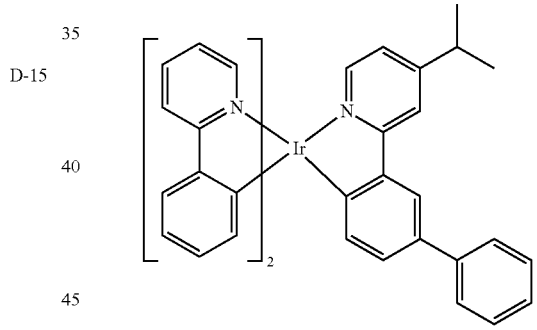
D-20
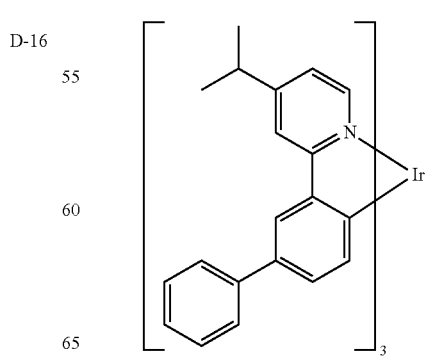

-continued
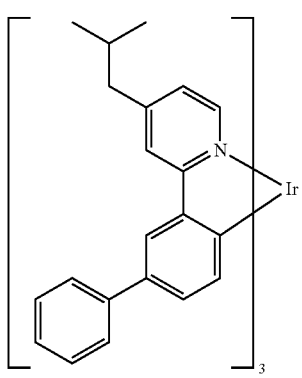
D-21
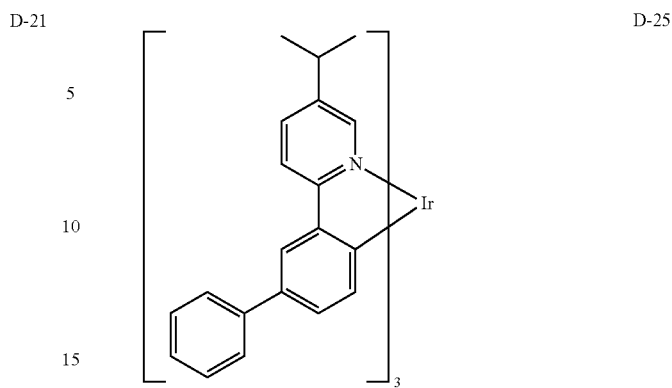
D-25
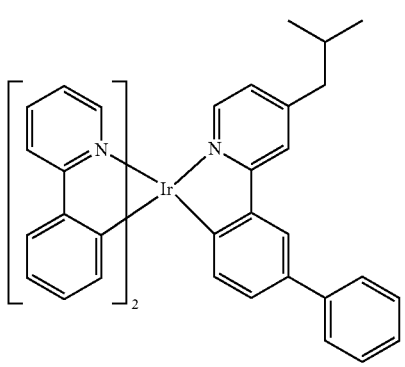
D-22
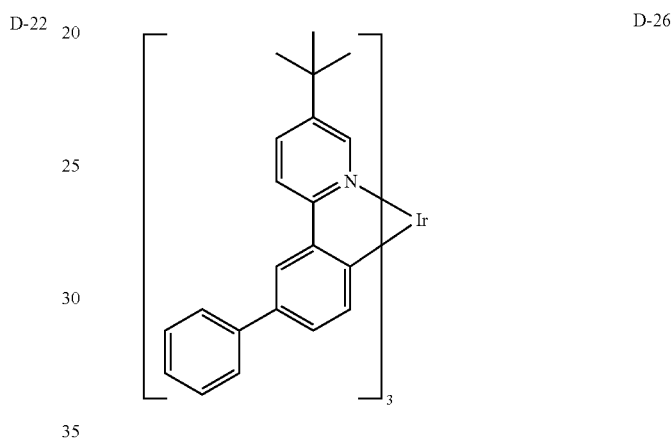
D-26
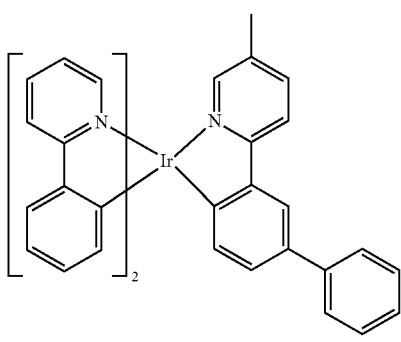
D-23
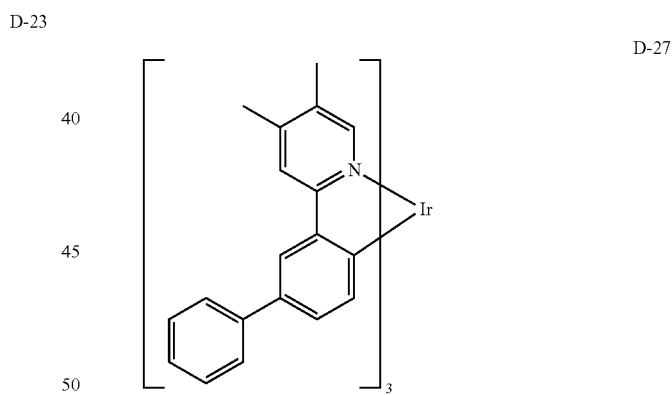
D-27
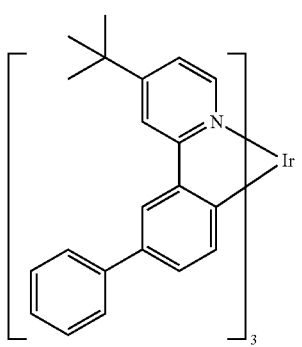
D-24
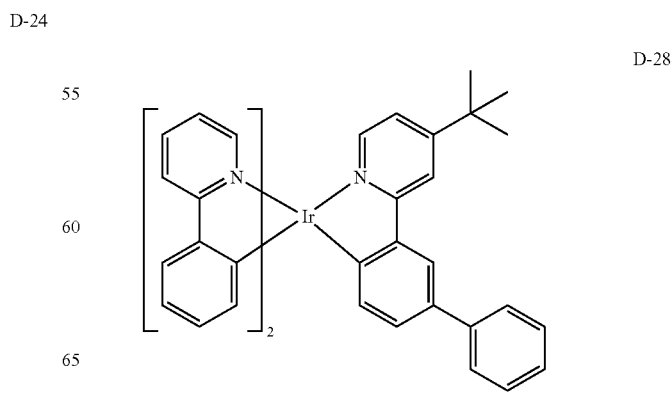
D-28

D-29 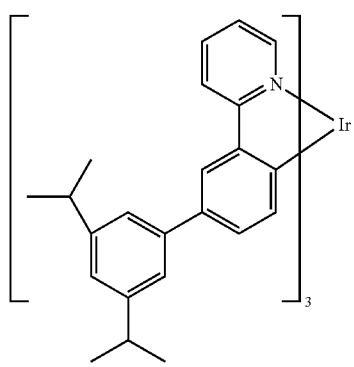
D-30 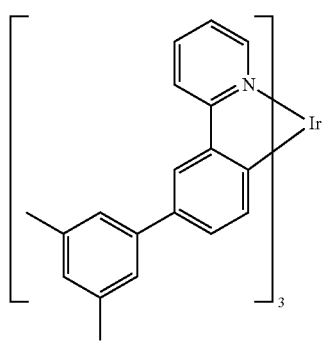
D-31 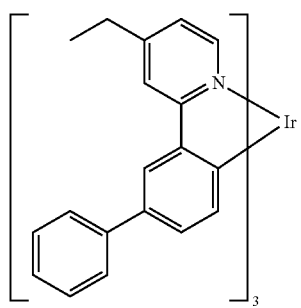
D-32 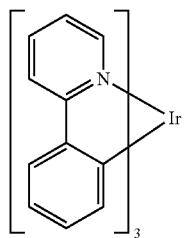
D-33 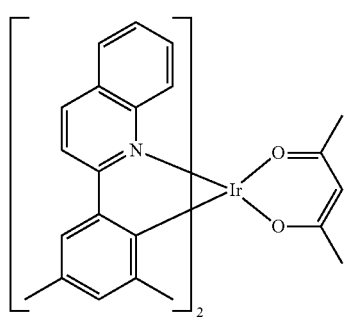
D-34 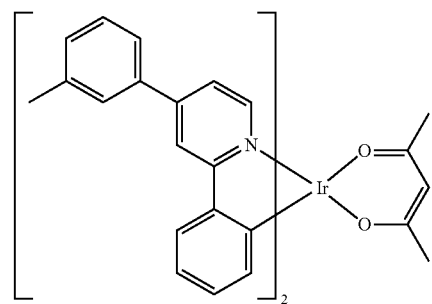
D-35 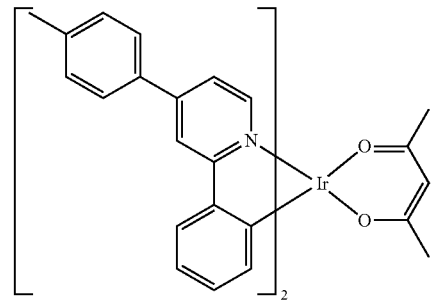
D-36 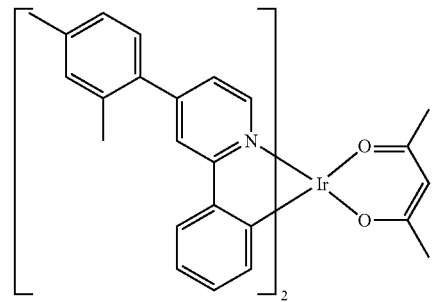
D-37 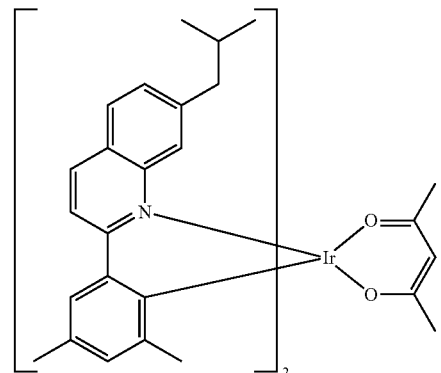
D-38 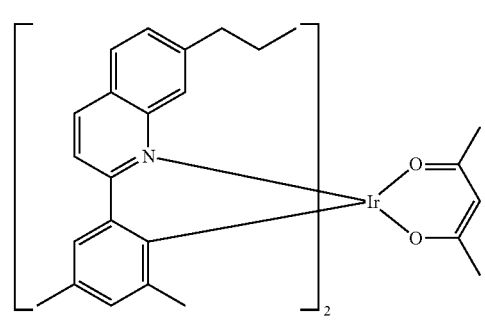

D-39
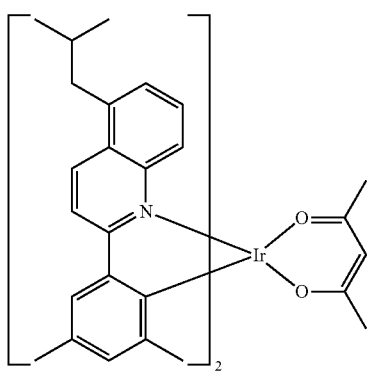
D-40
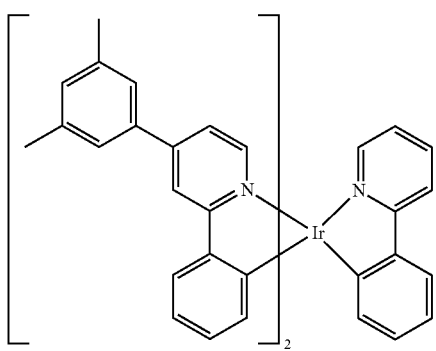
D-41
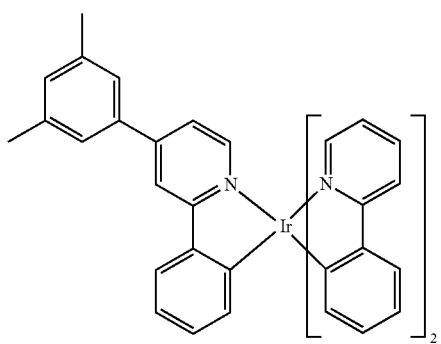
D-42
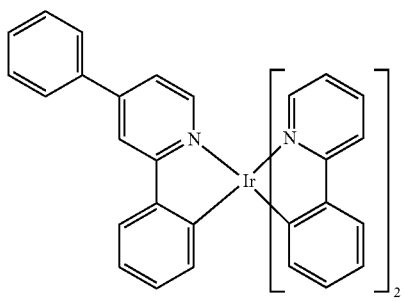
D-43
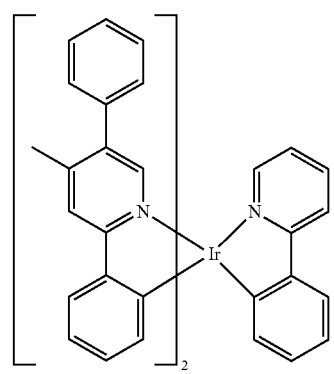
D-44
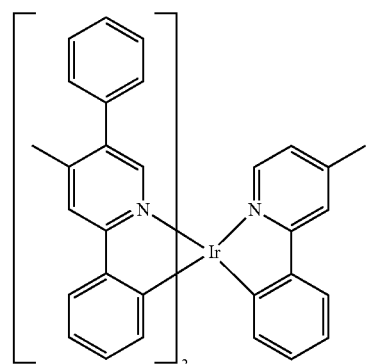
D-45
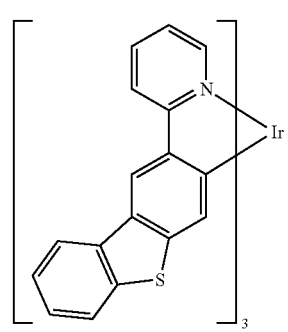
D-46
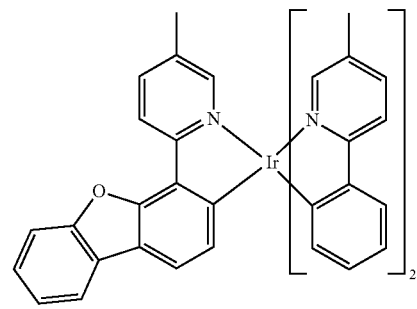

-continued
D-47
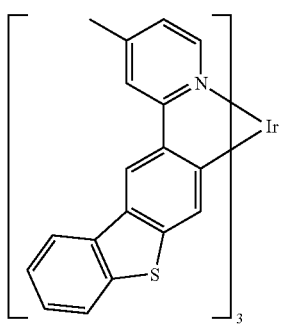
D-48
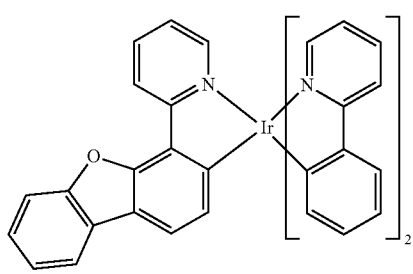
D-49
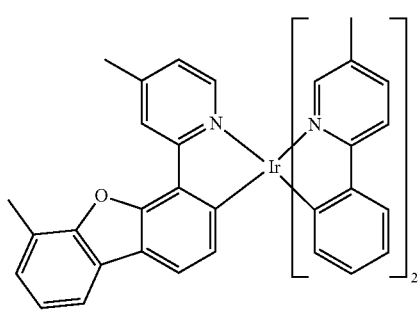
D-50
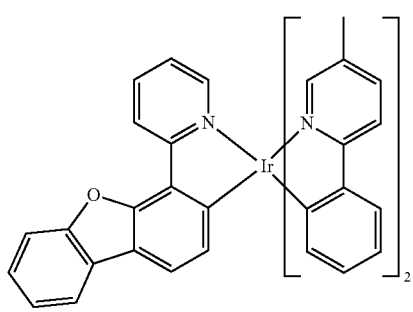
D-51
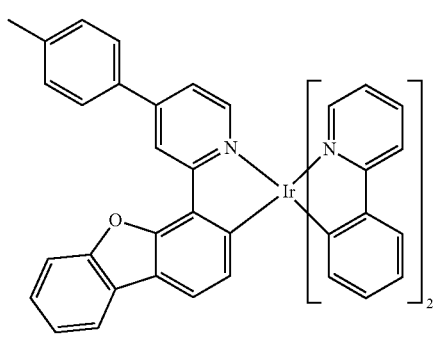
-continued
D-52
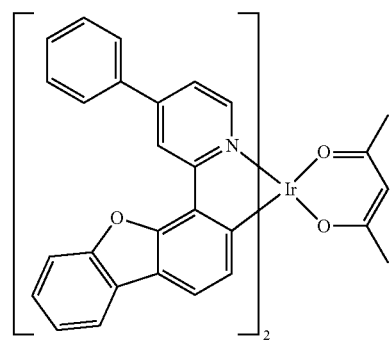
D-53
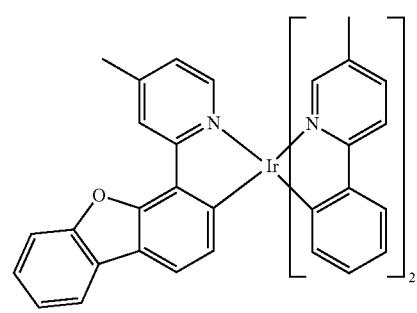
D-54
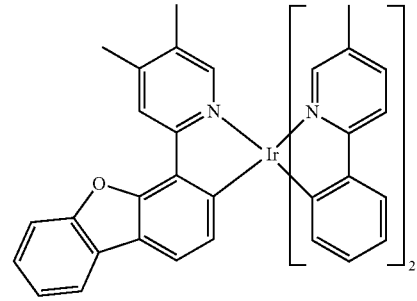
D-55
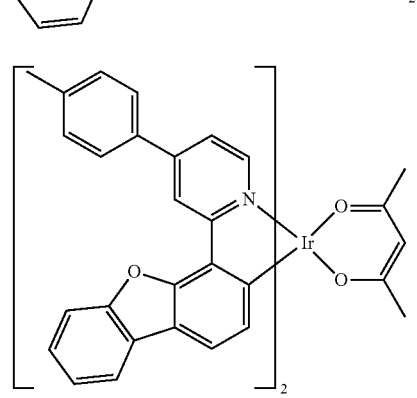
D-56
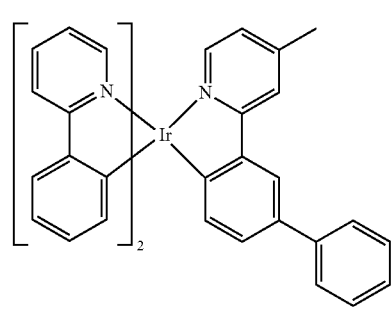

D-57
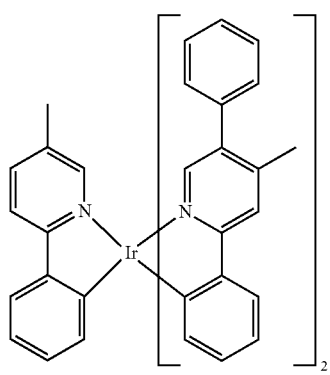
D-58
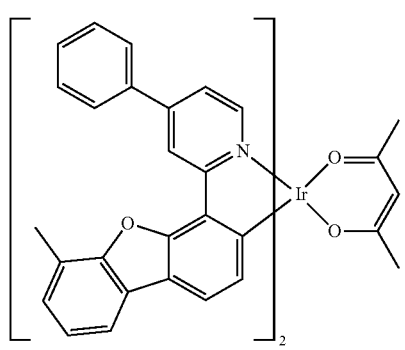
D-59
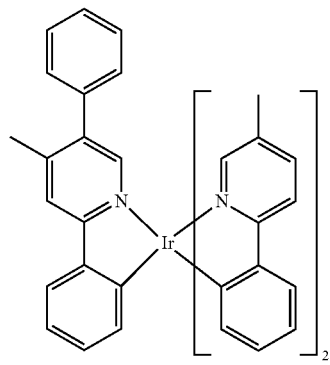
D-60
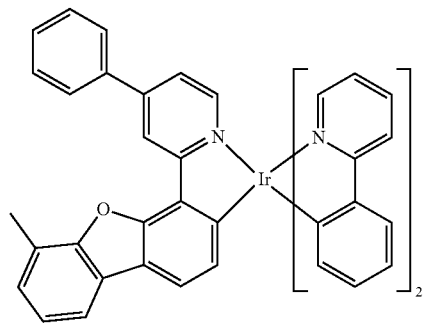
D-61
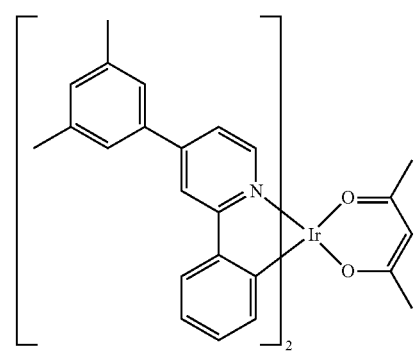
D-62
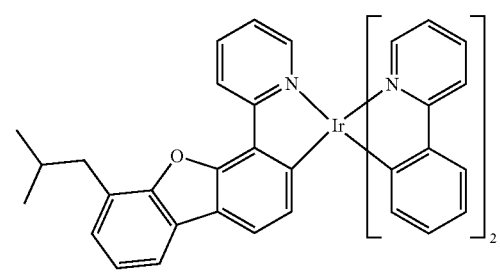
D-63
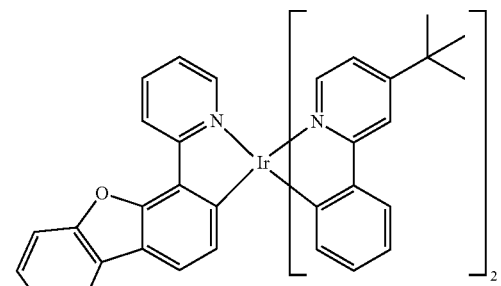
D-64
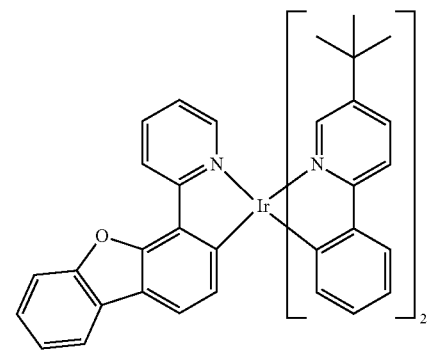

D-65
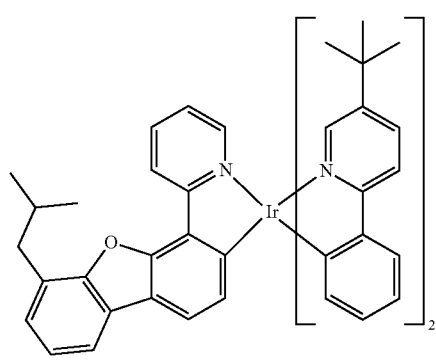
D-66
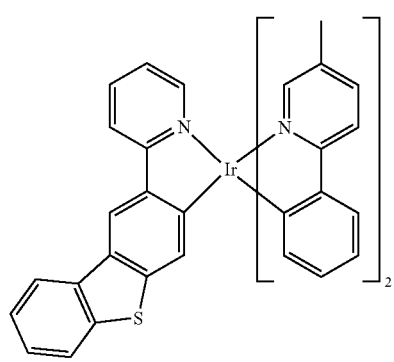
D-67
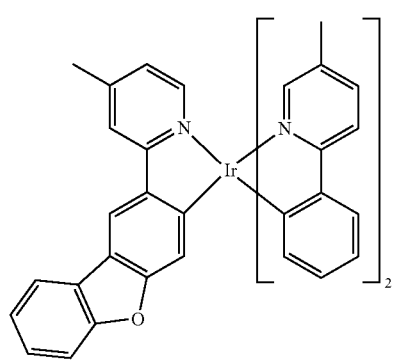
D-68
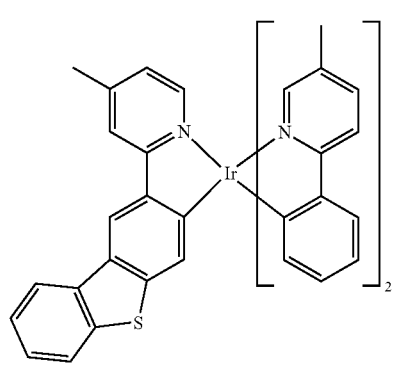
D-69
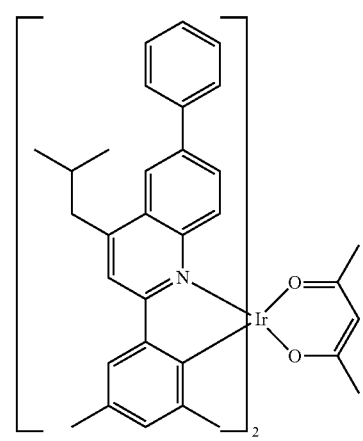
D-70
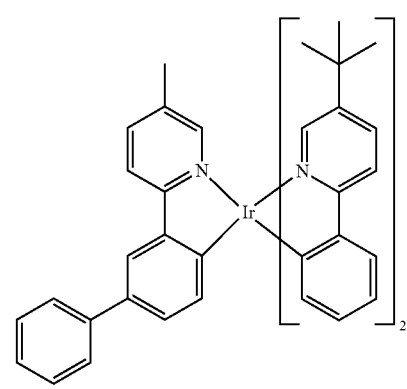
D-71
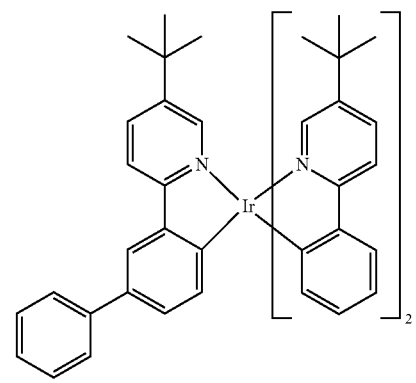
D-72
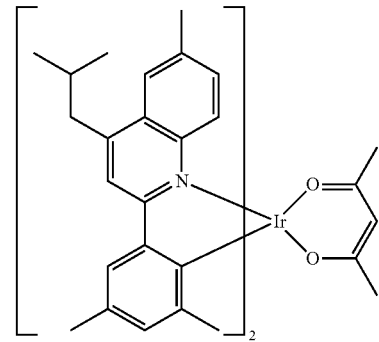

D-73
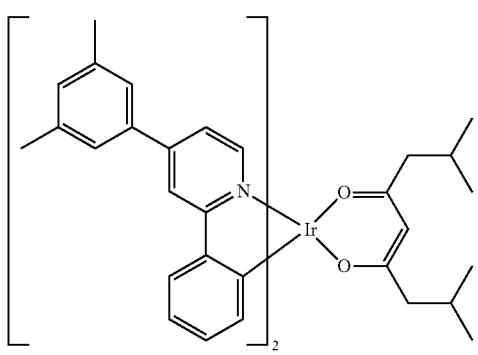
D-77
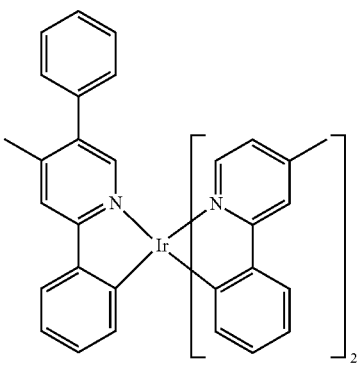
D-74
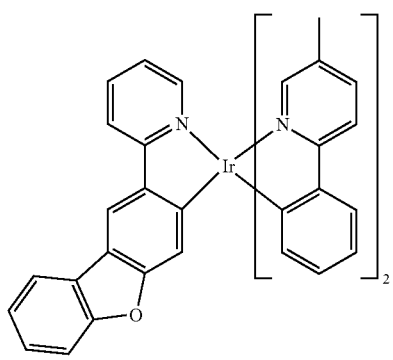
D-78
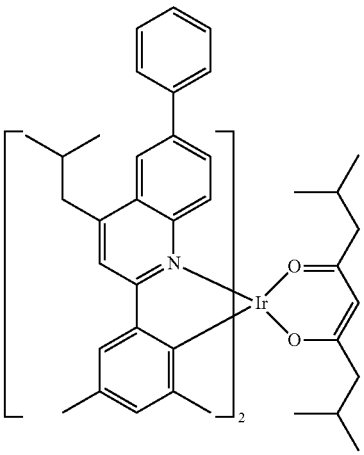
D-75
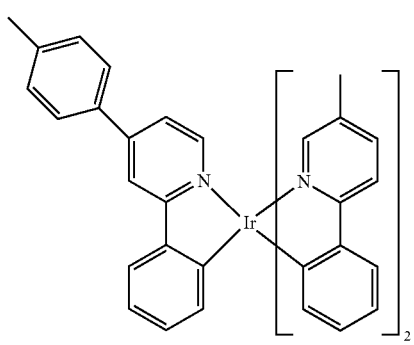
D-79
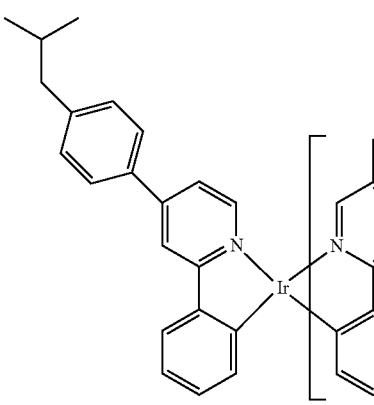
D-76
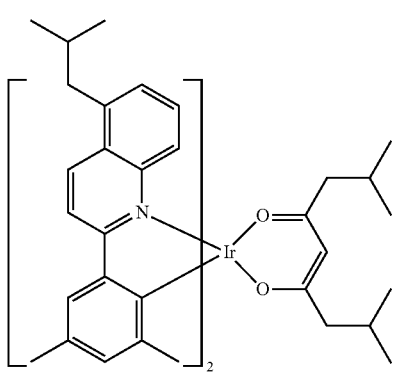
D-80
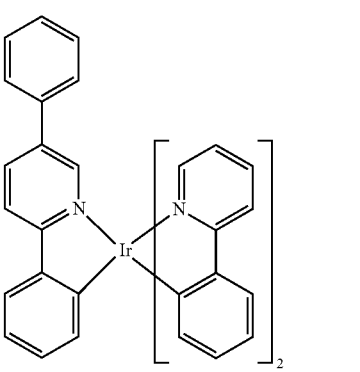

D-81
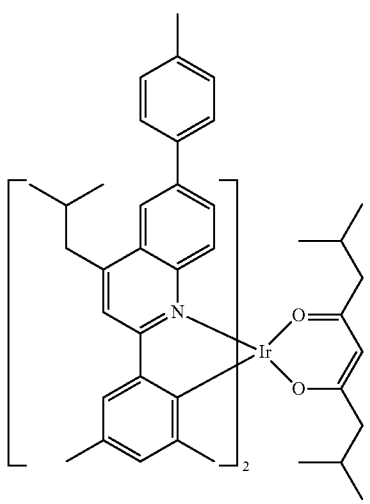
D-82
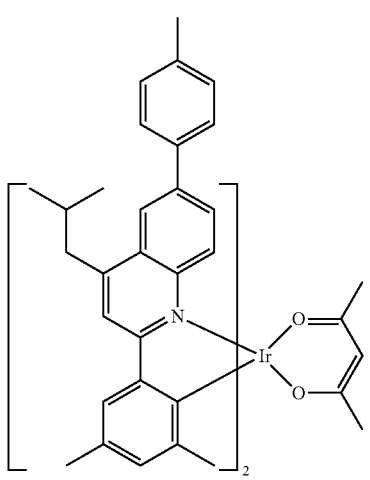
D-83
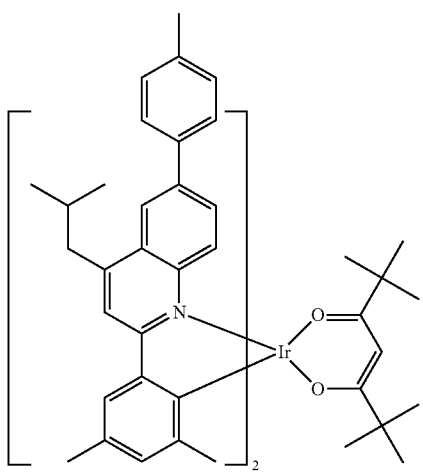
D-84
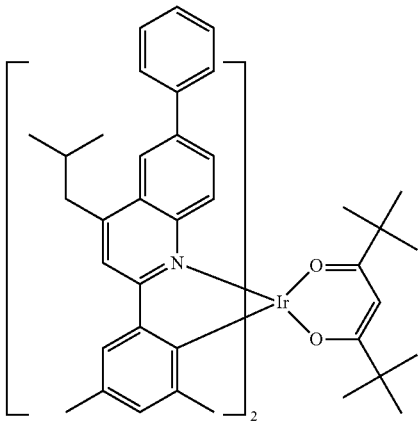
D-85
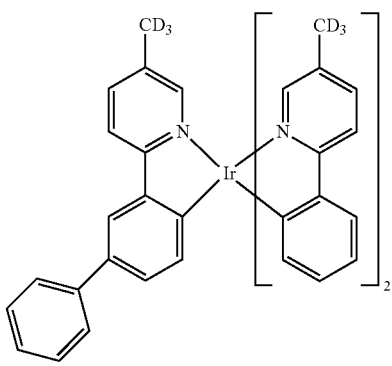
D-86
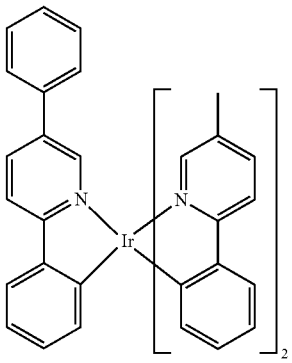
D-87
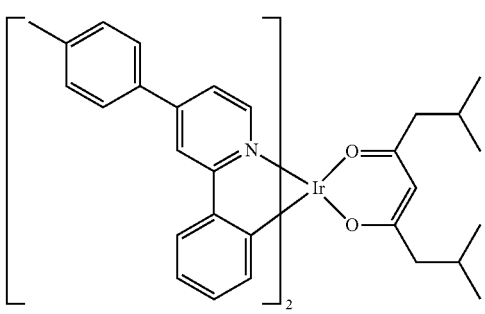

-continued
D-88
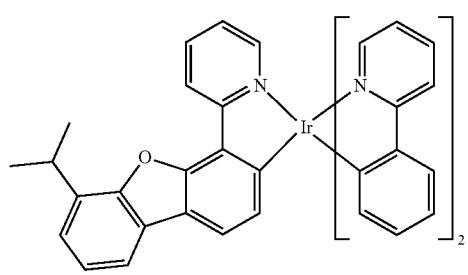
D-89
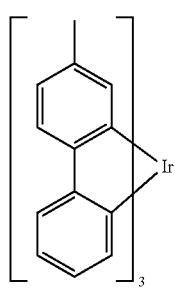
D-90
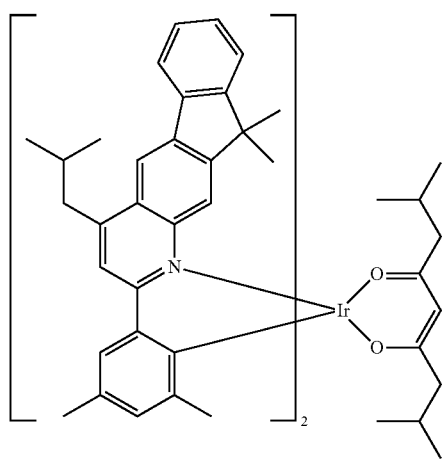
D-91
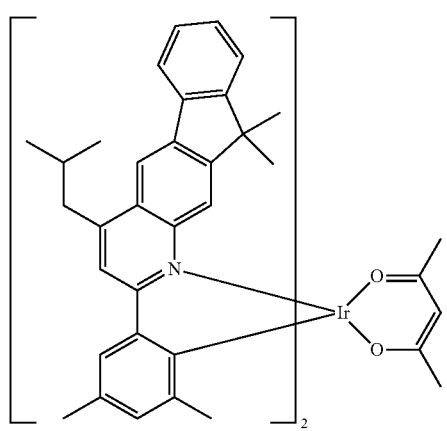
-continued
D-92
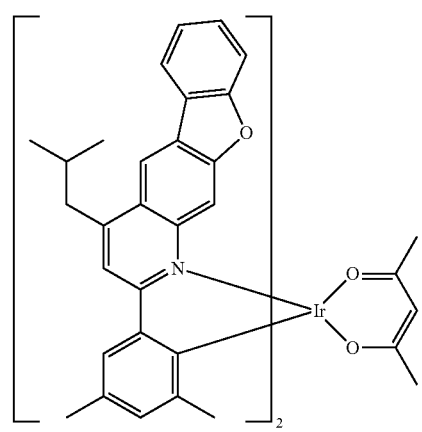
D-93
D-94
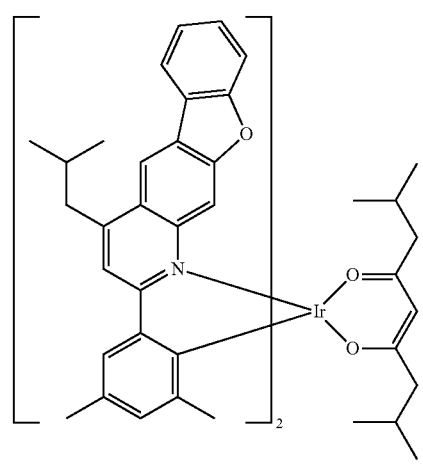

-continued
D-95
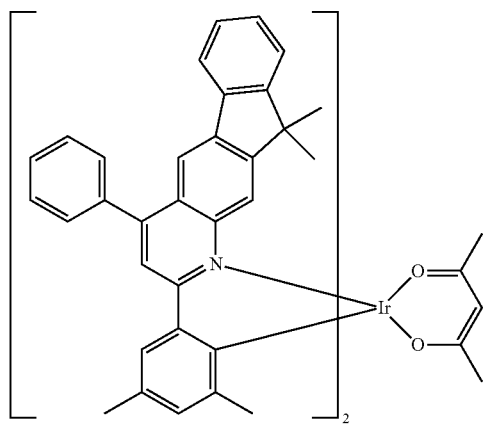
D-96
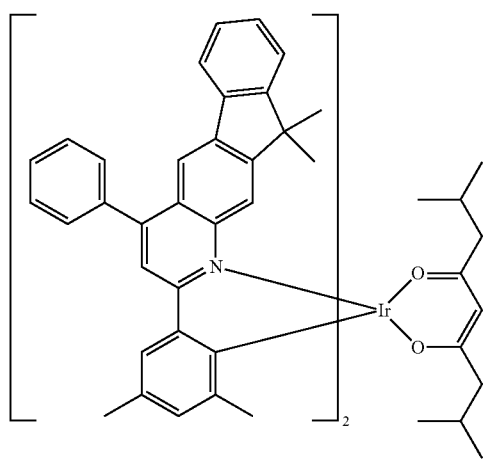
D-97
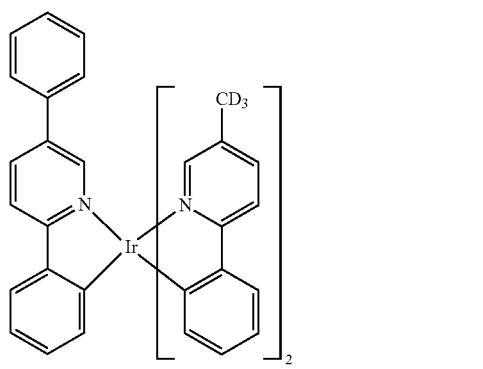
D-98
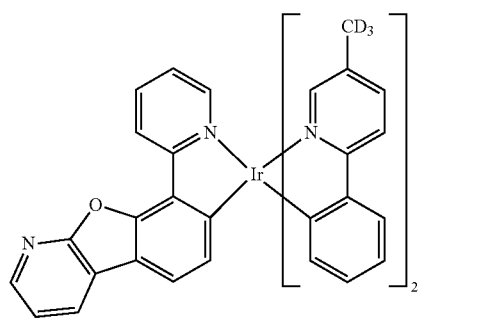
-continued
D-99
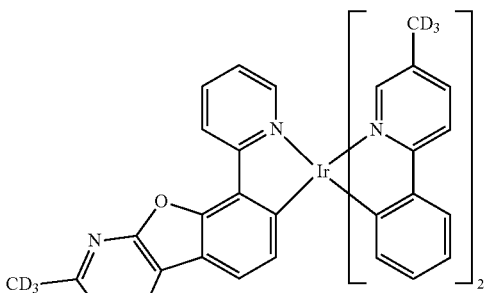
D-100
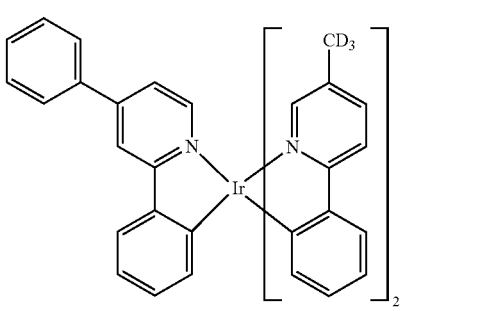
D-101
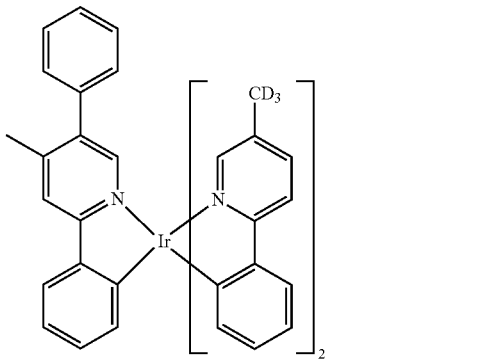
D-102
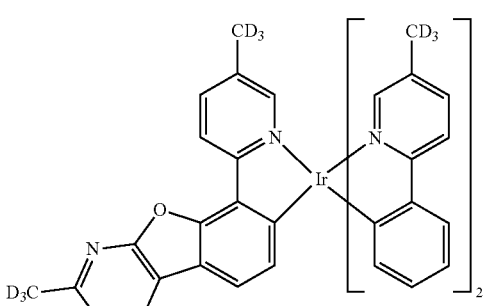

D-103
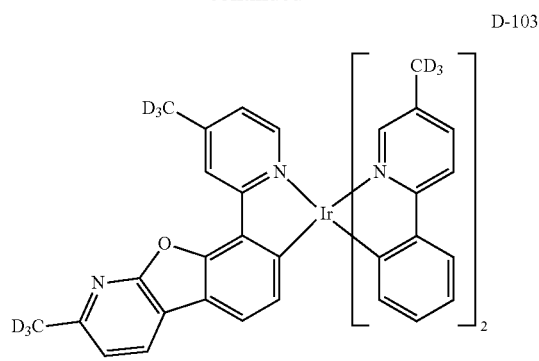
D-104
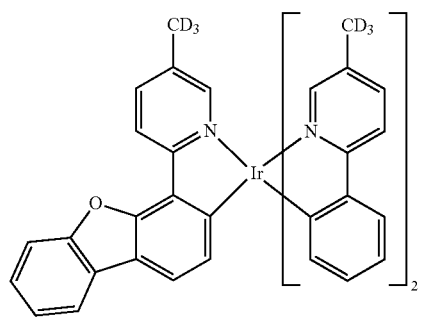
D-105
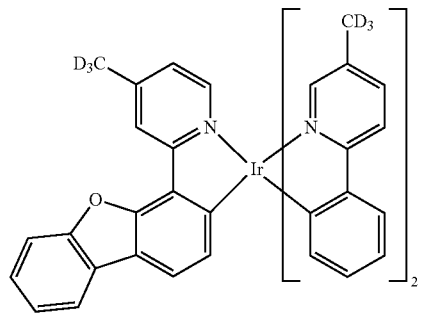
D-106
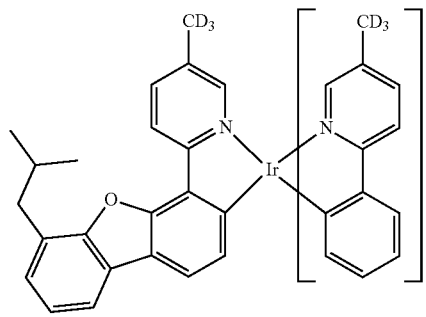
D-107
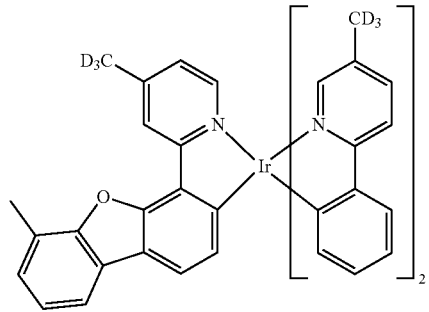
D-108
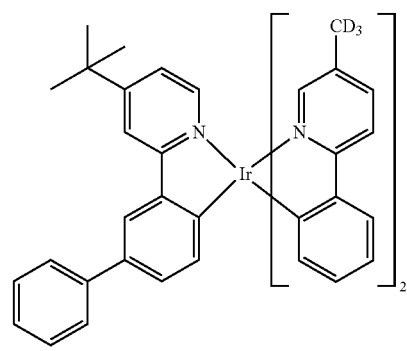
D-109
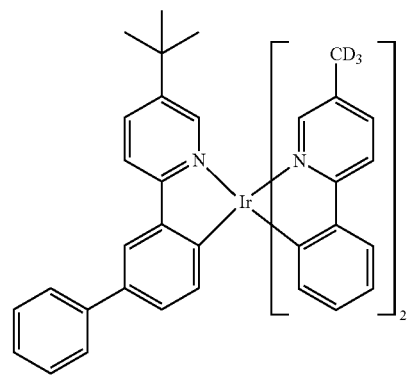
D-110
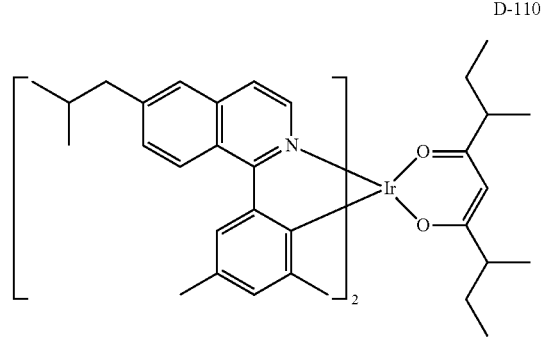
D-111
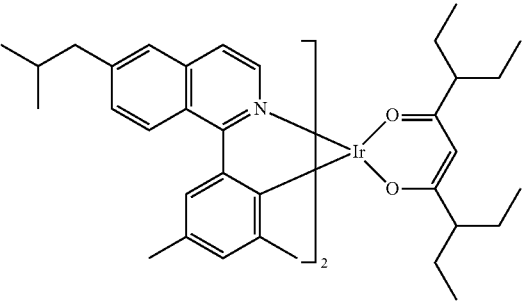

D-112
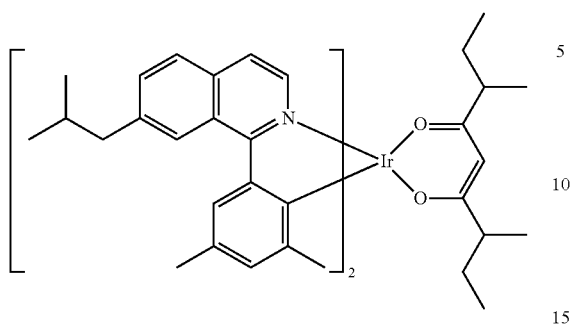
D-116
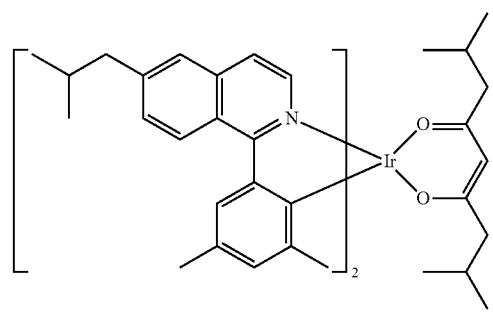
D-113
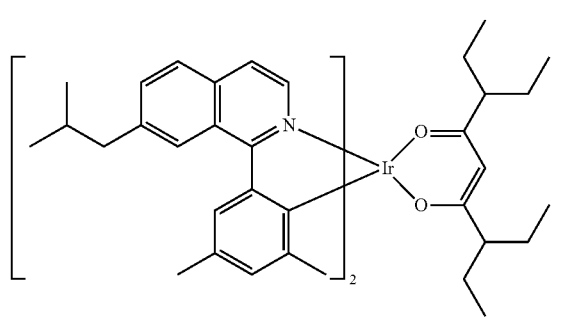
D-117
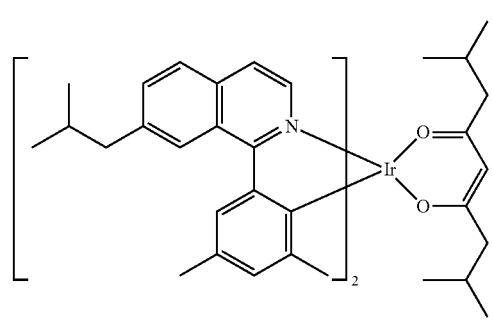
D-114
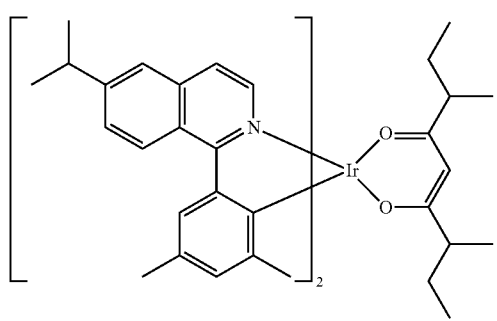
D-118
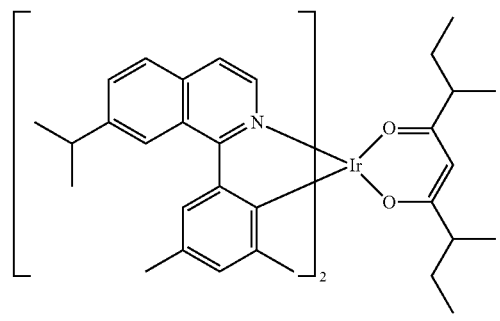
D-115
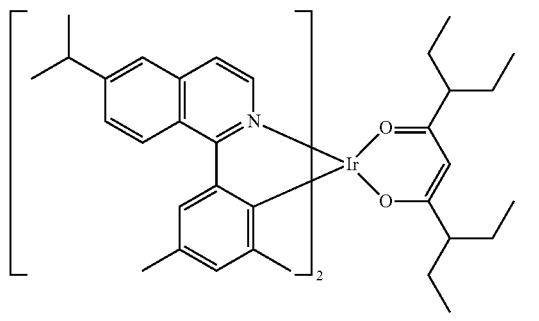
D-119
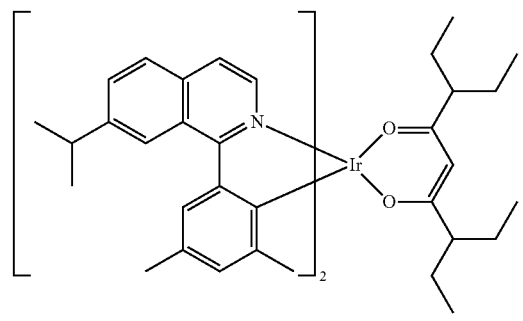

D-120 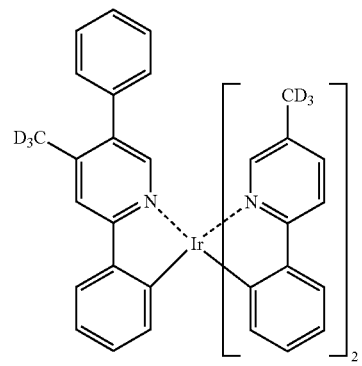
D-121 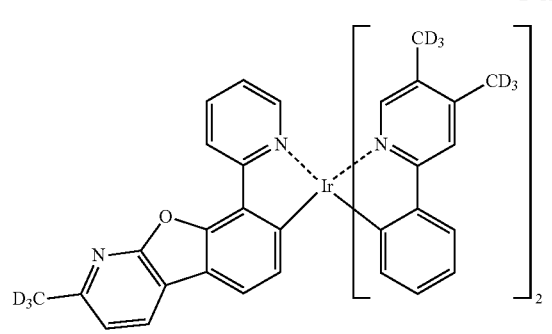
D-122 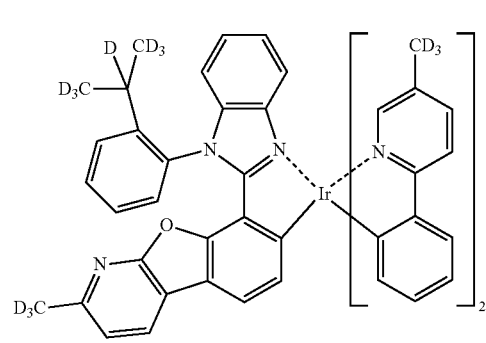
D-123 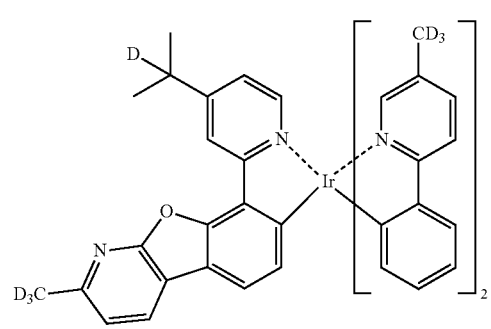
D-124 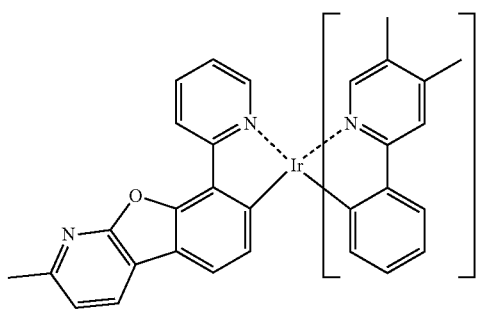
D-125 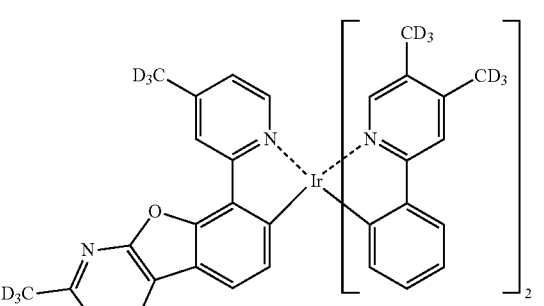
D-126 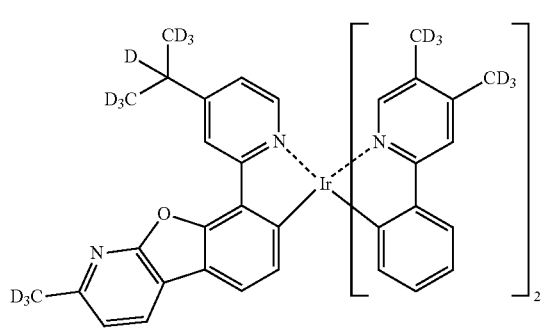
D-127 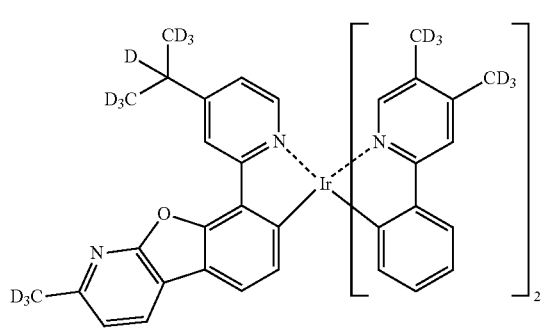
D-128 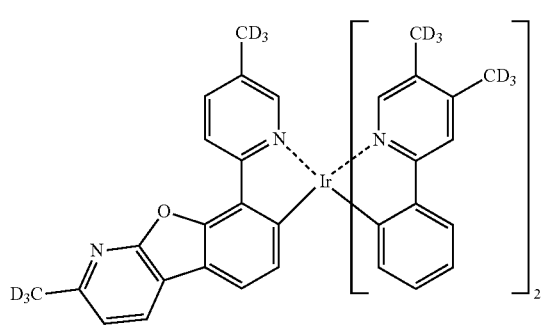

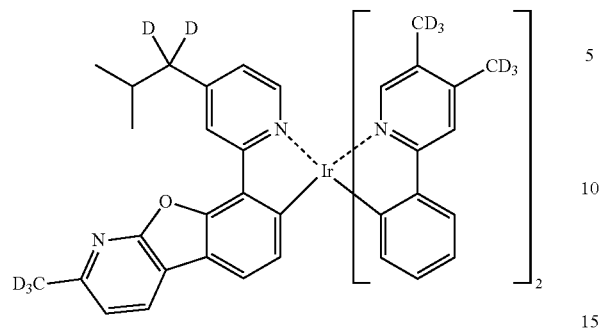
D-129
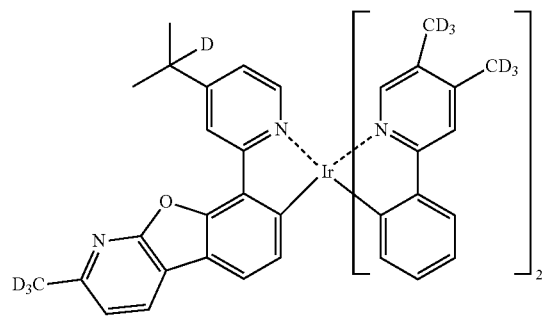
D-133
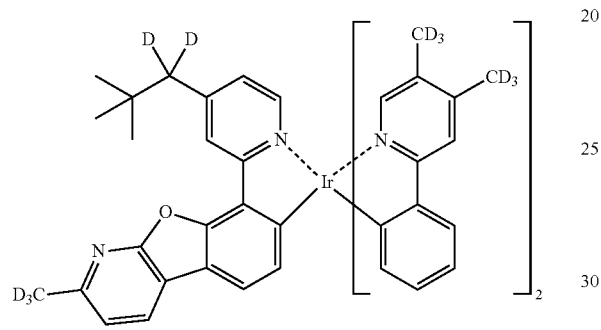
D-130
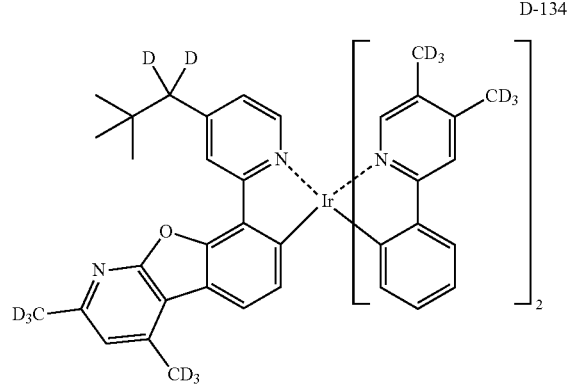
D-134
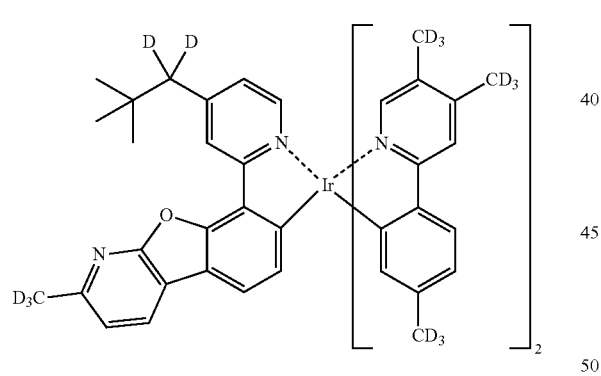
D-131
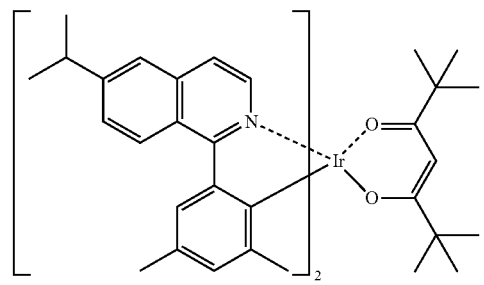
D-135
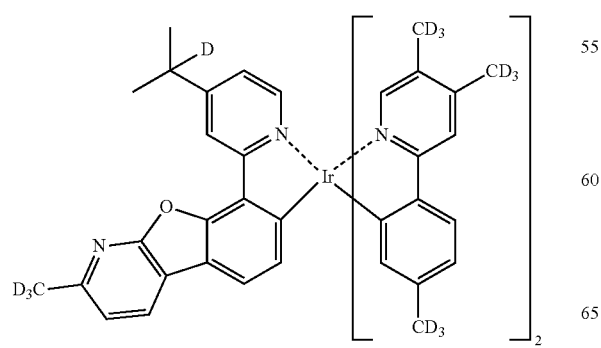
D-132
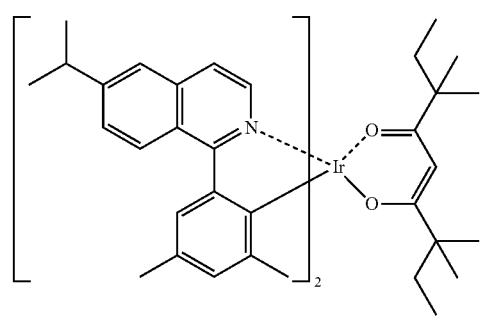
D-136

D-137
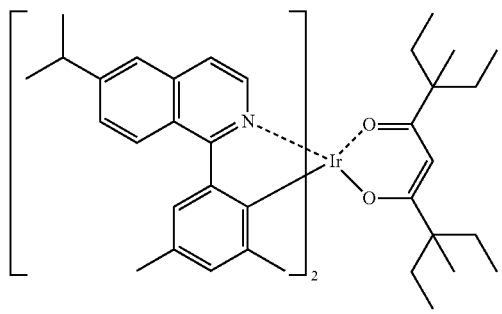
D-141
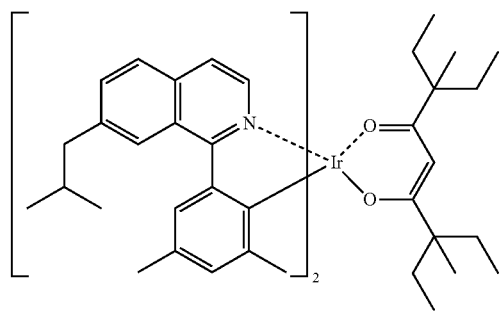
D-138
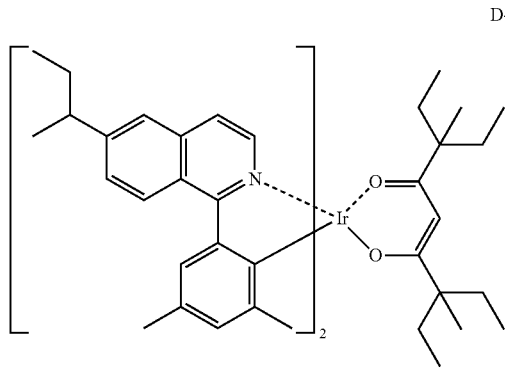
D-142
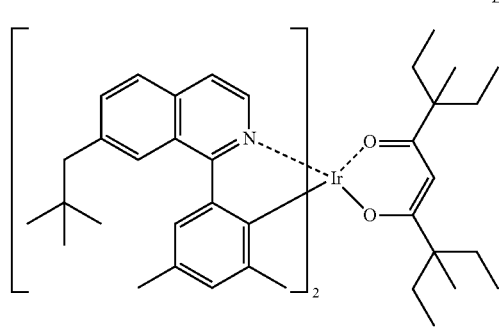
D-139
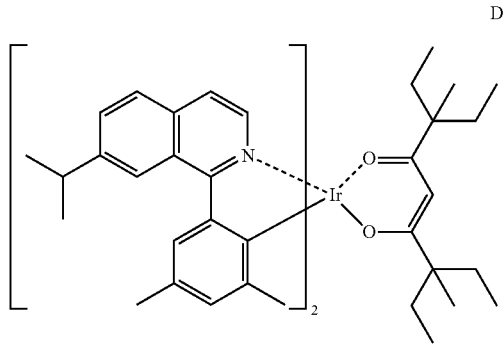
D-143
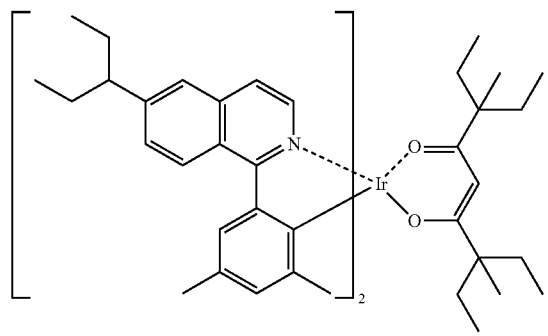
D-140
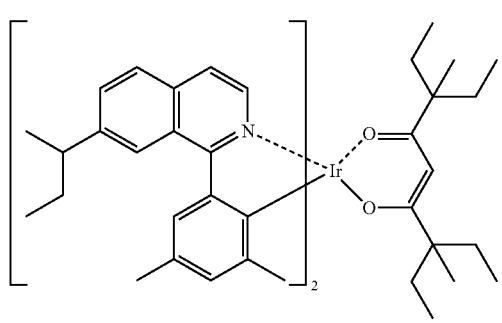
D-144
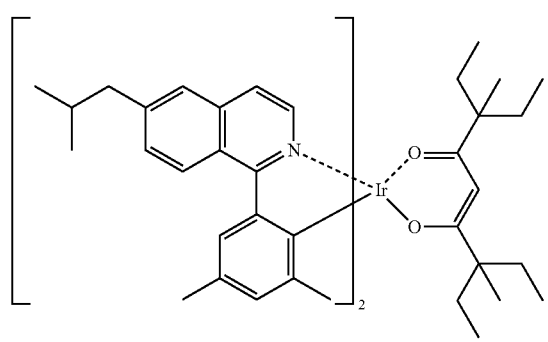

D-145
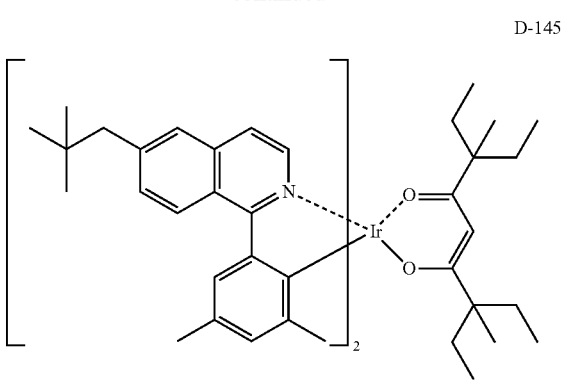

D-146
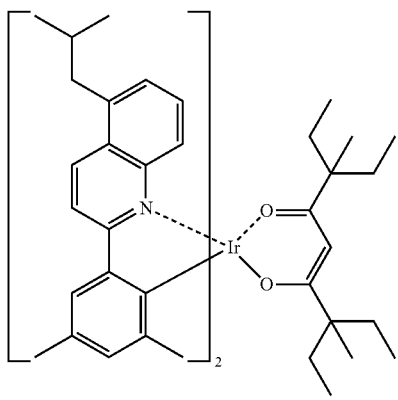

D-147
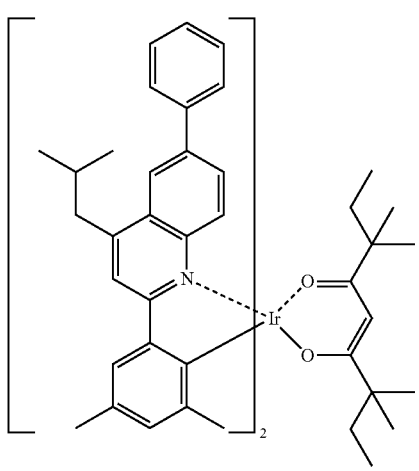

D-148
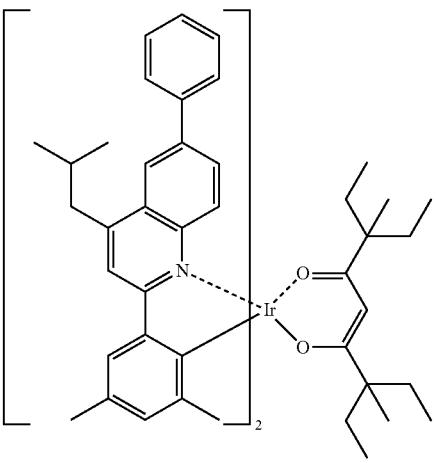

D-149
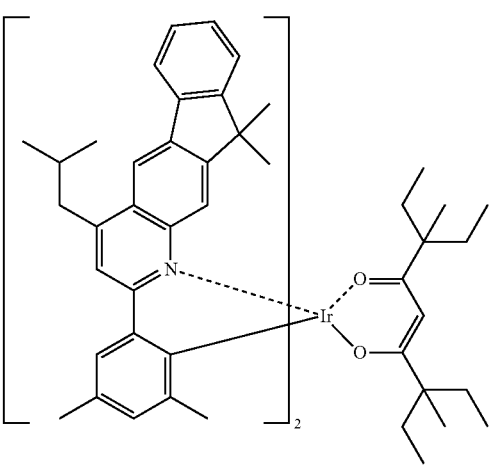

Each layer of the organic electroluminescent device of the present disclosure may be formed by any one of methods of dry film-forming methods such as vacuum evaporation, sputtering, plasma, ion plating, etc., or wet film-forming methods such as ink jet printing, nozzle printing, slot coating, spin coating, dip coating, flow coating, etc.

When using a wet film-forming method, a thin film can be formed by dissolving or diffusing the materials forming each layer into any suitable solvent such as ethanol, chloroform, tetrahydrofuran, dioxane, etc. The solvent is not specifically limited as long as the material forming each layer is soluble or dispersible in the solvents, which do not cause any problems in forming a film.

In addition, the first and the second host compounds according to the present disclosure may be film-formed by the aforementioned listed methods, commonly by co-evaporation or mixture-evaporation process. The co-evaporation is a mixed deposition method in which two or more materials are placed in a respective individual crucible source and a current is applied to both cells at the same time to evaporate the materials. The mixture-evaporation is a mixed deposition method in which two or more materials are mixed in one crucible source before evaporation, and a current is applied to the cell to evaporate the materials. In addition, when the first and second host compounds are present in the same layer or in different layers in an organic electroluminescent device, the two host compounds may be film-formed individually, respectively. For example, the second host compound may be evaporated after the first host compound is evaporated.

The present disclosure may provide a display system by using the organic electroluminescent compound represented by formula 2' or formula 2", or by using a plurality of host materials comprising the compound represented by formula 1 and the compound represented by formula 2. That is, it is possible to produce a display system or a lighting system by using the organic electroluminescent compound represented by formula 2' or formula 2", or by using a plurality of host materials of the present disclosure. Specifically, it is possible to produce a display system, e.g., a display system for a white organic light-emitting device, smartphones, tablets, notebooks, PCs, TVs, or cars, or a lighting system, e.g., an outdoor or indoor lighting system.

Hereinafter, the preparation method of the compound of the present disclosure, and the properties thereof, and the properties of the organic electroluminescent device comprising a plurality of host materials according to the present disclosure will be explained in detail with reference to the representative compounds of the present disclosure. The following examples only describe the properties of the organic electroluminescent device comprising the compound or the plurality of host materials according to the present disclosure, but the present disclosure is not limited to the following examples.

Example 1: Preparation of Compound H1-27

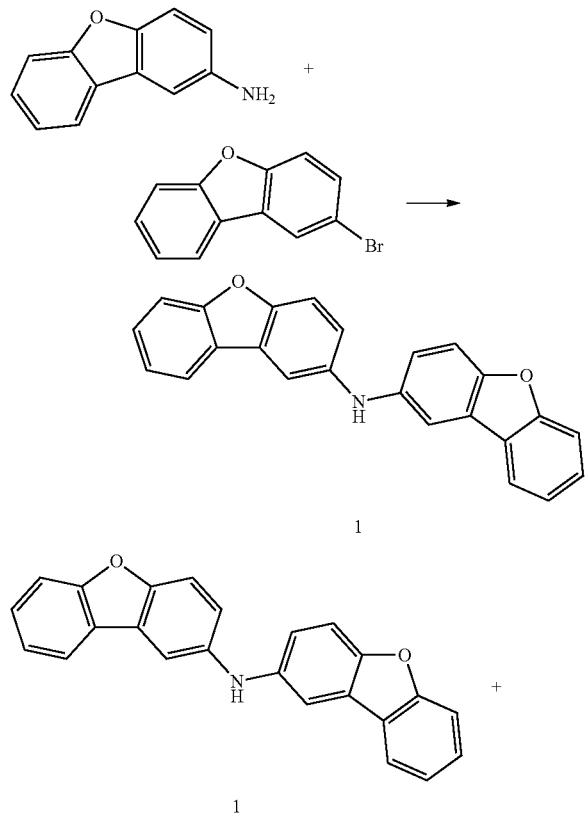

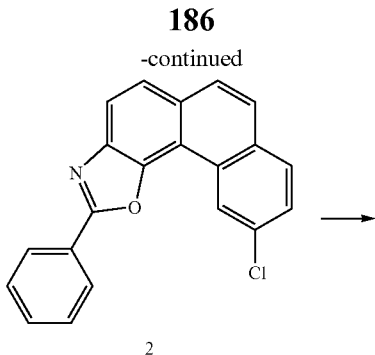

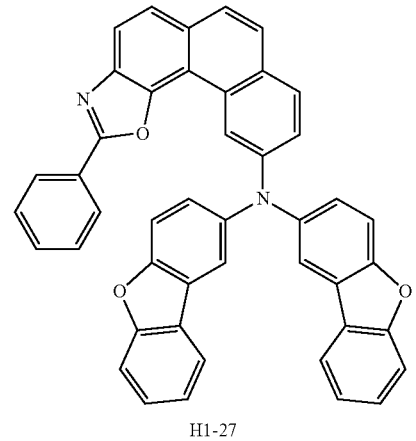

Synthesis of Compound 1

Dibenzofuran-2-amine (20 g, 144.7 mmol), 2-bromo dibenzofuran (23.8 g, 96.47 mmol), Pd(OAc)$_2$ (1.1 g, 4.82 mmol), 2-dicyclohexylphosphino-2',6'-dimethoxybiphenyl (S-Phos) (3.9 g, 9.65 mmol), NaOt-Bu (13.9 g, 144.7 mmol), and 485 mL of o-xylene were added to a flask and stirred at 160° C. for 3 hours. After the reaction was completed, the mixture was cooled to room temperature. The organic layer was extracted with ethyl acetate, and residual moisture was removed using magnesium sulfate. The residue was dried, and separated by column chromatography to obtain compound 1 (4.9 g, yield: 10%).

Synthesis of Compound H1-27

Compound 1 (4.9 g, 12.76 mmol), compound 2 (4.2 g, 14.0 mmol), Pd(dba$_3$)$_2$ (0.584 g, 0.638 mmol), S-Phos (0.523 g, 1.276 mmol), NaOt-Bu (1.8 g, 19.14 mmol), and 65 mL of o-xylene were added to a flask and stirred at 160° C. for 2 hours. After the reaction was completed, the mixture was cooled to room temperature. The organic layer was extracted with ethyl acetate, and residual moisture was removed using magnesium sulfate. The residue was dried, and separated by column chromatography to obtain compound H1-27 (5.6 g, yield: 68.3%).

| Compound | MW | M.P. |
| --- | --- | --- |
| H1-27 | 642.19 | 237° C. |

Example 2: Preparation of Compound H1-46

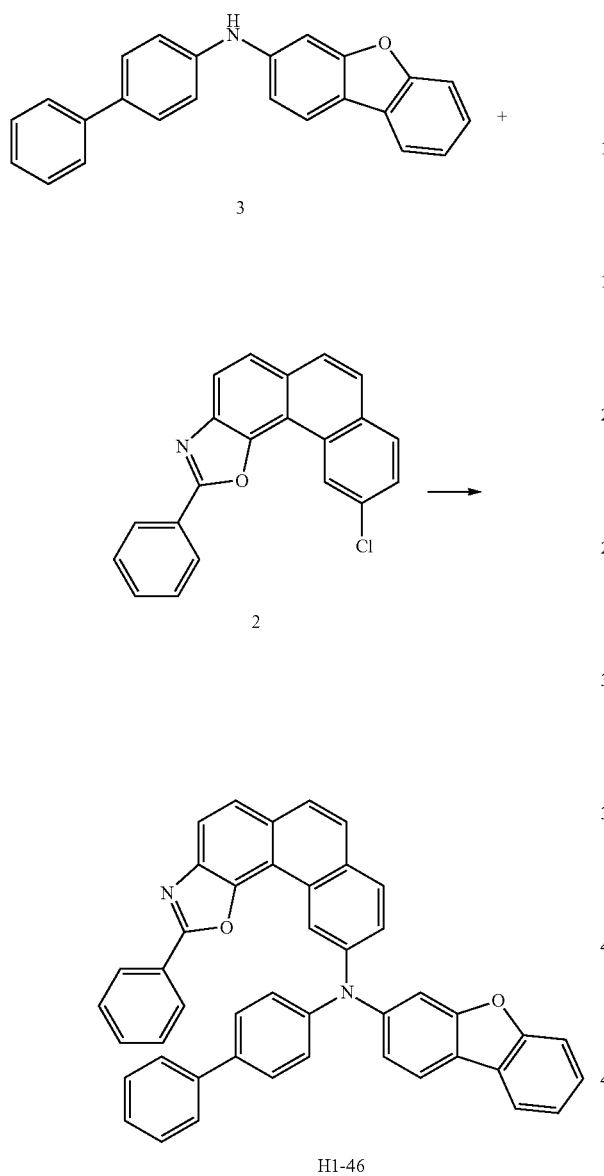

H1-46

Compound 3 (25 g, 74.48 mmol), compound 2 (42.58 g, 81.93 mmol), Pd(OAc)$_2$ (0.16 g, 7.5 mmol), P(t-Bu)$_3$ (0.28 g, 7.5 mmol), NaOt-Bu (14.31 g, 150 mmol), and 284.09 mL of o-xylene were added to a flask and stirred at 160° C. for 2 hours. After the reaction was completed, the mixture was cooled to room temperature. The organic layer was extracted with ethyl acetate, and residual moisture was removed using magnesium sulfate. The residue was dried, and separated by column chromatography to obtain compound H1-46 (23.4 g, yield: 50%).

| Compound | MW | M.P. |
| --- | --- | --- |
| H1-46 | 628.22 | 256.5° C. |

Example 3: Preparation of Compound H1-43

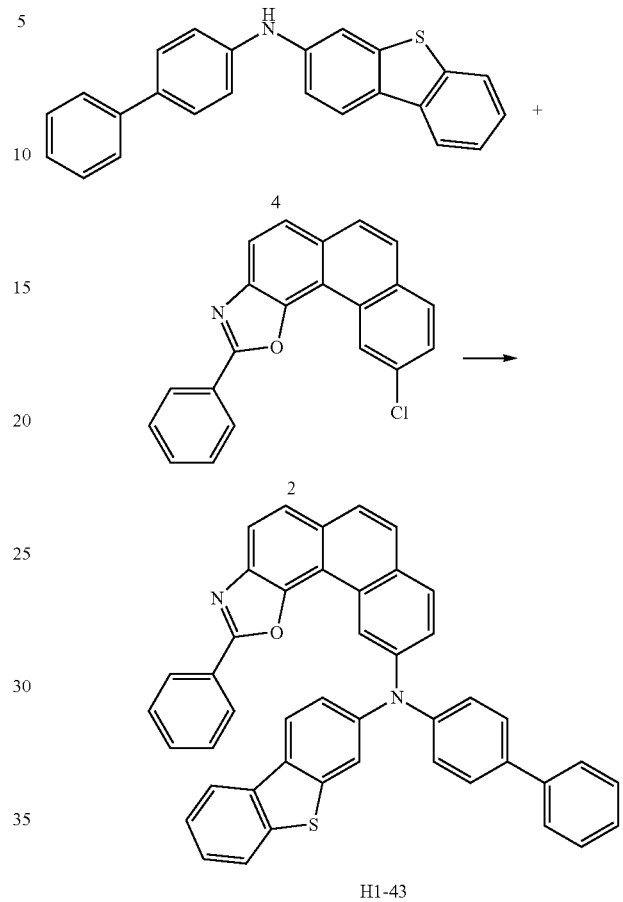

H1-43

Compound 4 (20 g, 56.96 mmol), compound 2 (18.8 g, 57.13 mmol), Pd(OAc)$_2$ (0.13 g, 5.7 mmol), P(t-Bu)$_3$ (0.22 g, 5.7 mmol), NaOt-Bu (11 g, 113.92 mmol), and 227.27 mL of o-xylene were added to a flask and stirred at 160° C. for 2 hours. After the reaction was completed, the mixture was cooled to room temperature. The organic layer was extracted with ethyl acetate, and residual moisture was removed using magnesium sulfate. The residue was dried, and separated by column chromatography to obtain compound H1-43 (12.5 g, yield: 34%)

| Compound | MW | M.P. |
| --- | --- | --- |
| H1-43 | 644.19 | 249° C. |

Example 4: Preparation of Compound H1-123

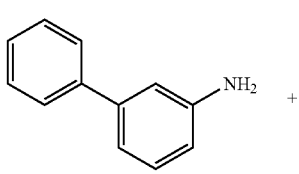

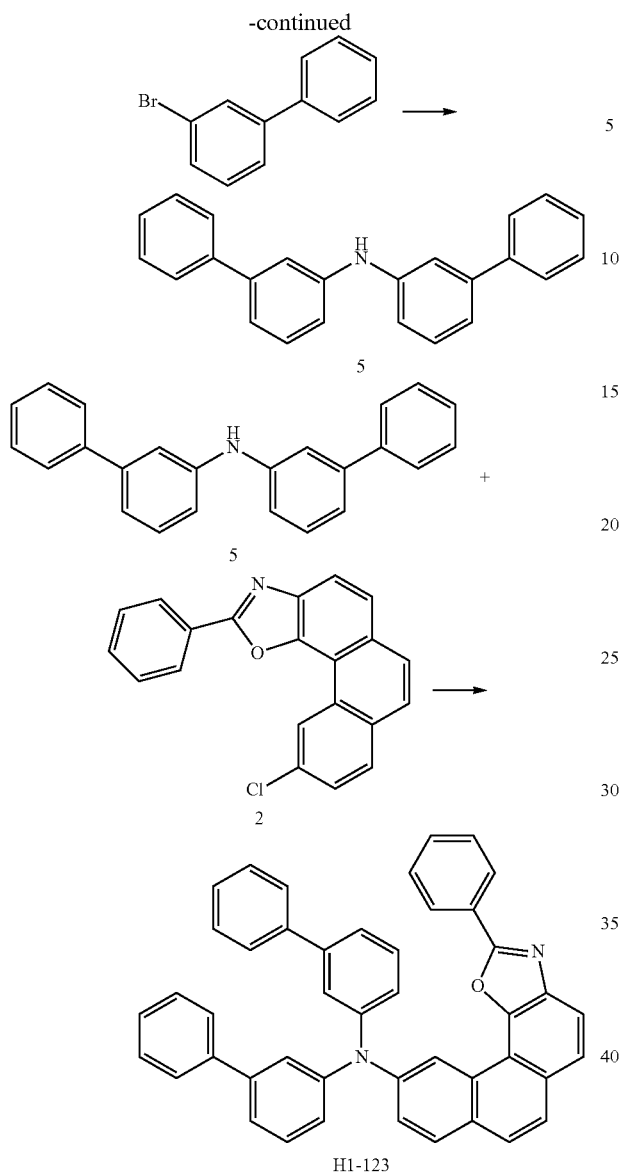

| Compound | MW | M.P. |
|---|---|---|
| H1-123 | 614.24 | 210° C. |

Example 5: Preparation of Compound H1-136

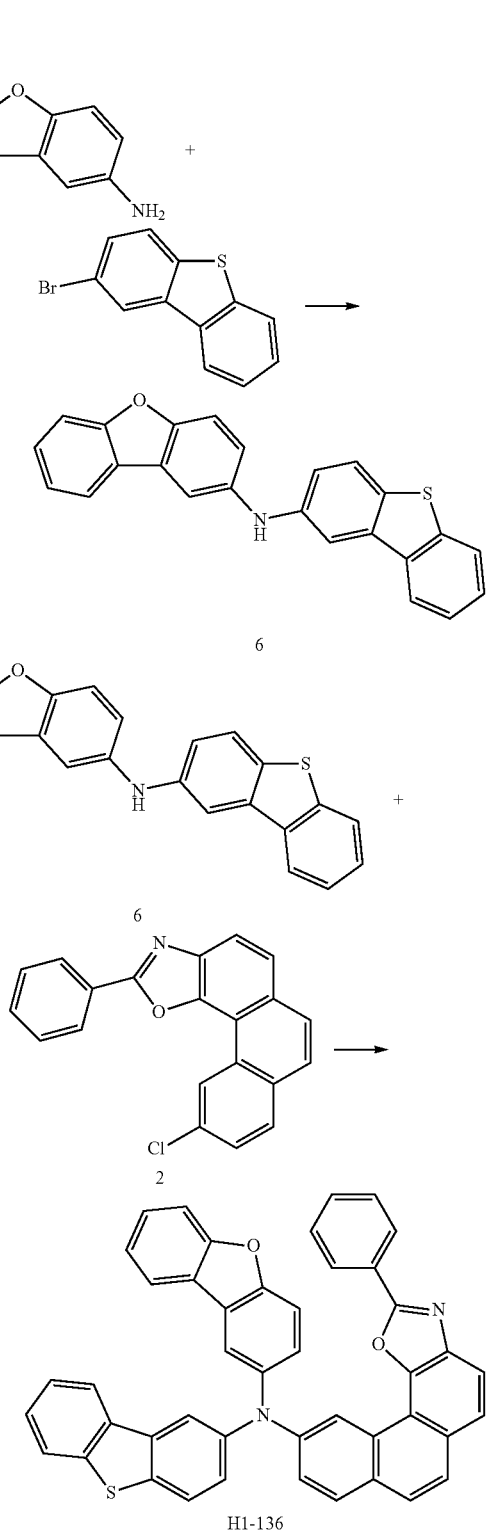

Synthesis of Compound 5

3-aminobiphenyl (54 g, 319 mmol), 3-bromobiphenyl (70 g, 301 mmol), Pd(OAc)$_2$ (0.33 g, 1.47 mmol), tricyclohexylphosphine (0.84 g, 2.8 mmol), NaOt-Bu (57 g, 593 mmol), and 280 mL of toluene were added to a flask and stirred at 95° C. for 8 hours. After the reaction was completed, the mixture was cooled to room temperature. The organic layer was extracted with ethyl acetate, and residual moisture was removed using magnesium sulfate. The residue was dried, and separated by column chromatography to obtain compound 5 (60.23 g, yield: 85%).

Synthesis of Compound H1-123

Compound 5 (60.23 g, 187.5 mmol), compound 2 (60 g, 182.33 mmol), Pd(OAc)$_2$ (0.41 g, 1.83 mmol), S-Phos (1.74 g, 4.23 mmol), NaOt-Bu (26.23 g, 272 mmol), and 300 mL of xylene were added to a flask and stirred at 110° C. for 10 hours. After the reaction was completed, the mixture was cooled to room temperature. The organic layer was extracted with ethyl acetate, and residual moisture was removed using magnesium sulfate. The residue was dried, and separated by column chromatography to obtain compound H1-123 (36.9 g, yield: 33%).

Synthesis of Compound 6

Dibenzofuran-2-amine (29.24 g, 159.7 mmol), 2-bromodibenzothiophene (40 g, 152.7 mmol), Pd(OAc)₂ (0.17 g, 0.75 mmol), tricyclohexylphosphine (0.43 g, 1.45 mmol), NaOt-Bu (29.22 g, 304 mmol), and 250 mL of toluene were added to a flask and stirred at 95° C. for 8 hours. After the reaction was completed, the mixture was cooled to room temperature. The organic layer was extracted with ethyl acetate, and residual moisture was removed using magnesium sulfate. The residue was dried, and separated by column chromatography to obtain compound 6 (17.12 g, yield: 86%).

Synthesis of Compound H1-136

Compound 6 (17.12 g, 46.89 mmol), compound 2 (15 g, 45.58 mmol), Pd(OAc)₂ (0.05 g, 0.22 mmol), S-Phos (0.22 g, 0.535 mmol), NaOt-Bu (6.56 g, 68.2 mmol), and 75 mL of xylene were added to a flask and stirred at 110° C. for 10 hours. After the reaction was completed, the mixture was cooled to room temperature. The organic layer was extracted with ethyl acetate, and residual moisture was removed using magnesium sulfate. The residue was dried, and separated by column chromatography to obtain compound H1-136 (10.2 g, yield: 34%).

| Compound | MW | M.P. |
|---|---|---|
| H1-136 | 658.17 | 254° C. |

Example 6: Preparation of Compound H1-85

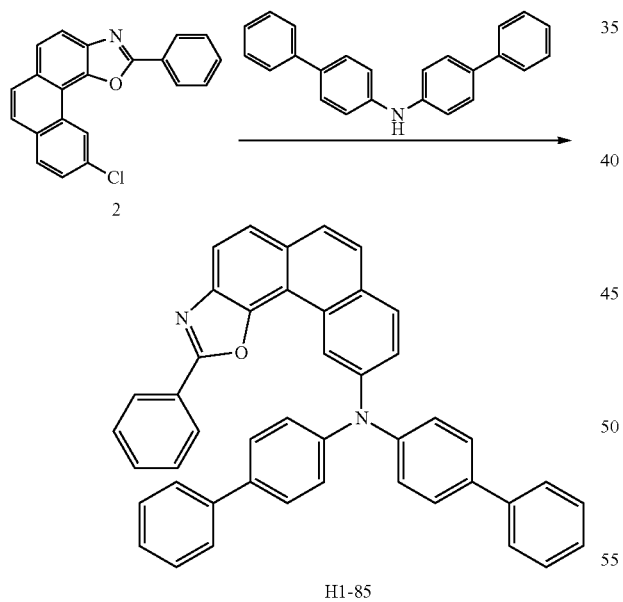

H1-85

Compound 2 (5.0 g, 15.2 mmol), di([1,1'-biphenyl]-4-yl)amine (4.9 g, 15.2 mmol), Pd(OAc)₂ (0.2 g, 0.8 mmol), P(t-Bu)₃ (0.8 mL, 1.5 mmol), NaOt-Bu (2.9 g, 30.4 mmol), and 76 mL of xylene were added to a flask and stirred at 160° C. for 5 hours. After the reaction was completed, the mixture was cooled to room temperature. The precipitated solid was washed with distilled water and methanol, and separated by column chromatography to obtain compound H1-85 (5.5 g, yield: 59%).

Example 7: Preparation of Compound H1-51

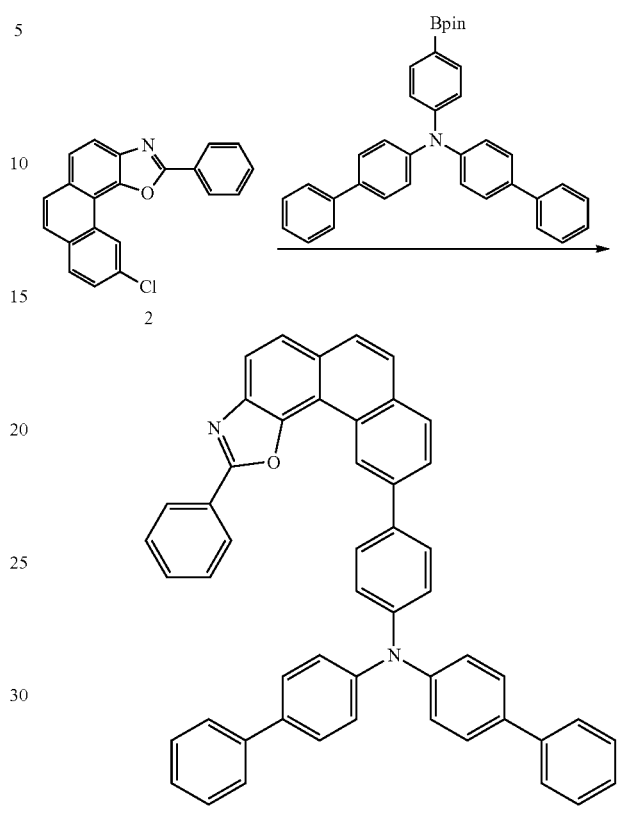

H1-51

Compound 2 (4 g, 12 mmol), bis(biphenyl-4-yl)[4-(4,4,5,5-tetramethyl-[1,3,2]-dioxaborolane-2-yl)phenyl]amine (6.8 g, 13 mmol), Pd(OAc)₂ (0.3 g, 1 mmol), S-Phos (0.9 g, 2 mmol), Cs₂CO₃ (11.5 g, 35 mmol), 60 mL of o-xylene, 15 mL of EtOH, and 15 mL of distilled water were added to a flask and stirred under reflux at 150° C. for 3 hours. After the reaction was completed, the mixture was cooled to room temperature and washed with distilled water. The organic layer was extracted with ethyl acetate, and residual moisture was removed using magnesium sulfate The residue was dried, and separated by column chromatography to obtain compound H1-51 (2.2 g, yield: 27%).

Example 8: Preparation of Compound H1-68

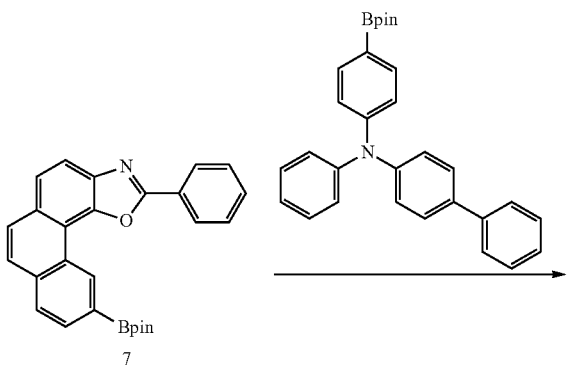

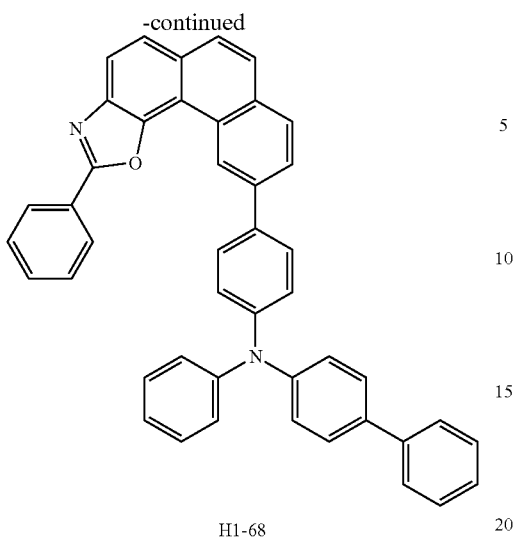

H1-68

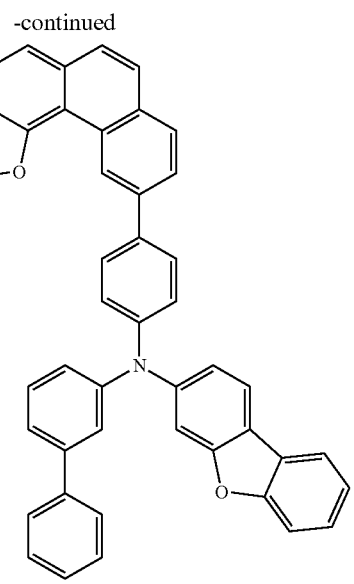

H1-15

Compound 7 (4.8 g, 11.34 mmol), N-(4-bromophenyl)-N-phenyl-[1,1'-biphenyl]-4-amine (5 g, 12.47 mmol), Pd(PPh$_3$)$_4$ (0.4 g, 0.34 mmol), Na$_2$CO$_3$ (3.0 g, 28.35 mmol), 57 mL of toluene, 14 mL of ethanol, and 14 mL of distilled water were added to a flask and stirred at 120° C. for 4 hours. After the reaction was completed, the mixture was added dropwise to methanol and the resulting solid was filtered. The resulting solid was purified by column chromatography to obtain compound H1-68 (1.4 g, yield: 20.0%).

Example 9: Preparation of Compound H1-15

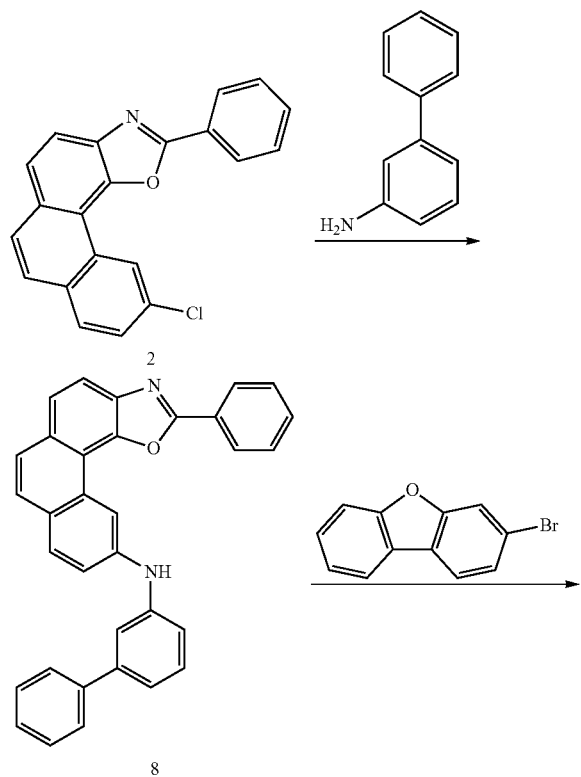

Synthesis of Compound 8

Compound 2 (10.0 g, 30.3 mmol), [1,1'-biphenyl]-3-amine (6.7 g, 39.4 mmol), Pd(OAc)$_2$ (0.34 g, 1.5 mmol), P(t-Bu)$_3$ (1.5 mL, 3.03 mmol), NaOt-Bu (5.8 g, 60.6 mmol), and 150 mL of xylene were added to a flask and stirred at 160° C. for 6 hours. After the reaction was completed, the mixture was washed with distilled water. The organic layer was extracted with ethyl acetate and dried using magnesium sulfate. The solvent was removed using a rotary evaporator. The residue was separated by column chromatography to obtain compound 8 (10.8 g, yield: 36%).

Synthesis of Compound H1-15

Compound 8 (5.0 g, 10.8 mmol), 3-bromodibenzofuran (3.2 g, 12.9 mmol), Pd$_2$(dba)$_3$ (0.5 g, 0.54 mmol), S-Phos (0.45 g, 1.08 mmol), NaOt-Bu (2.0 g, 21.6 mmol), and 60 mL of o-xylene were added to a flask and stirred at 160° C. for 6 hours. After the reaction was completed, the mixture was cooled to room temperature. The organic layer was extracted with ethyl acetate, and residual moisture was removed using magnesium sulfate. The residue was dried, and separated by column chromatography to obtain compound H1-15 (1.45 g, yield: 21%).

| Compound | MW | M.P. |
| --- | --- | --- |
| H1-15 | 628.73 | 205° C. |

Example 10: Preparation of Compound C-2

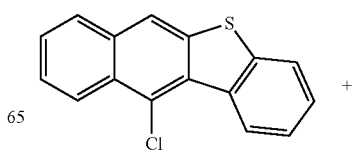

-continued

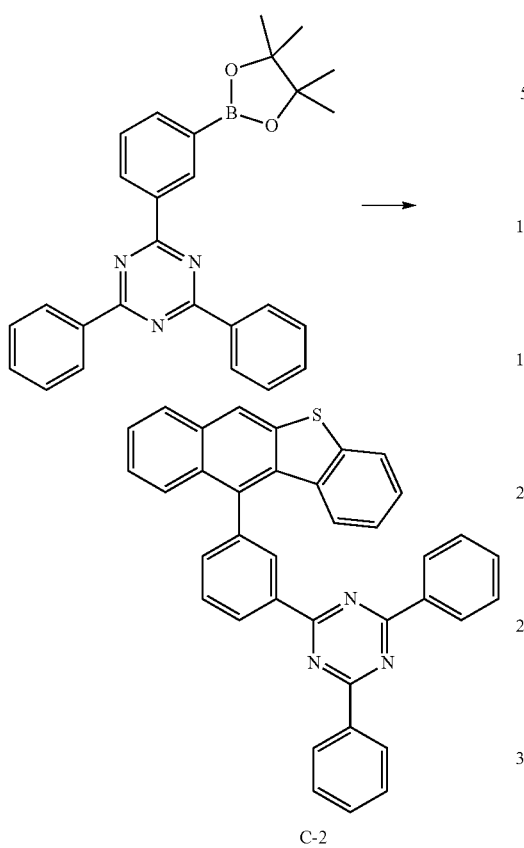

C-2

11-chlorobenzo[b]naphtho[2,3-d]thiophene (3.6 g, 13.4 mmol), 2,4-diphenyl-6-(3-(4,4,5,5-tetramethyl-1,3,2-dioxaborolan-2-yl)phenyl)-1,3,5-triazine (6.4 g, 14.77 mmol), Pd₂(dba)₃ (613 mg, 0.67 mmol), 2-dicyclohexylphosphino-2',6'-dimethoxybiphenyl (S-Phos) (550 mg, 1.34 mmol), K₃PO₄ (7.1 g, 33.5 mmol), and 70 mL of o-xylene were added to a flask and stirred under reflux for 4 hours. After the reaction was completed, the mixture was cooled to room temperature and filtered through silica gel. The organic layer was distilled under reduced pressure and recrystallized with o-xylene to obtain compound C-2 (3.0 g, yield: 41.3%).

| Compound | MW | M.P. |
|---|---|---|
| C-2 | 541.2 | 301° C. |

Example 11: Preparation of Compound C-57

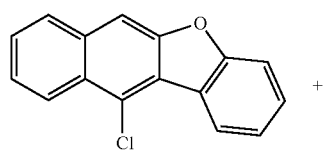

+

-continued

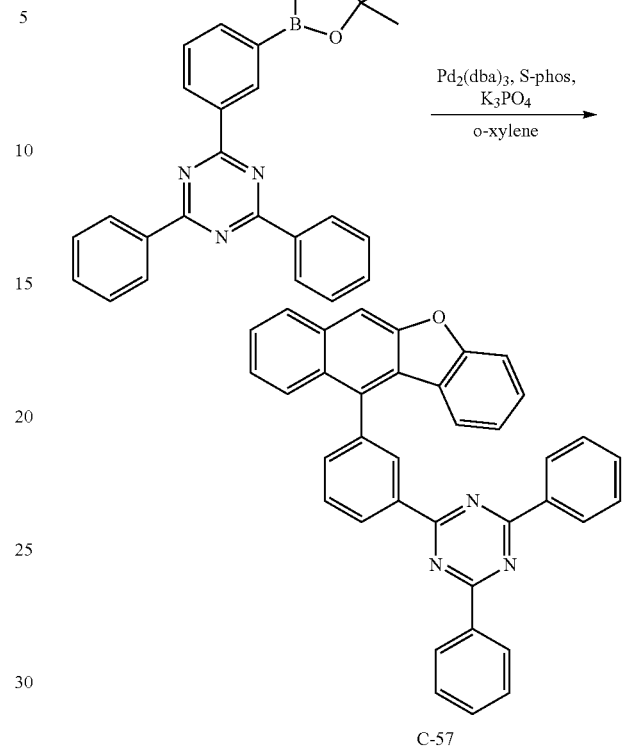

C-57

11-chlorobenzo[b]naphtho[2,3-d]furan (1.4 g, 5.5 mmol), 2,4-diphenyl-6-(3-(4,4,5,5-tetramethyl-1,3,2-dioxaborolan-2-yl)phenyl)-1,3,5-triazine (2.7 g, 6.1 mmol), Pd₂(dba)₃ (252 mg, 0.275 mmol), S-Phos (225 mg, 0.55 mmol), K₃PO₄ (2.9 g, 13.75 mmol), and 30 mL of o-xylene were added to a flask and stirred under reflux for 4 hours. After the reaction was completed, the mixture was cooled to room temperature and filtered through silica gel. The organic layer was distilled under reduced pressure and recrystallized with o-xylene to obtain compound C-57 (0.9 g, yield: 30%).

| Compound | MW | M.P. |
|---|---|---|
| C-57 | 525.61 | 265.5° C. |

Device Examples 1 and 2: Producing a Red Light-Emitting OLED Deposited with a Compound According to the Present Disclosure as a Host An OLED according to the present disclosure was produced. First of all, a transparent electrode indium tin oxide (ITO) thin film (10 Ω/sq) on a glass substrate for an OLED (GEOMATEC CO., LTD., Japan) was subjected to an ultrasonic washing with acetone, and isopropyl alcohol, sequentially, and then was stored in isopropyl alcohol before use. The ITO substrate was mounted on a substrate holder of a vacuum vapor deposition apparatus. Compound HI-1 of Table 3 was introduced into a cell of the vacuum vapor deposition apparatus, and compound HT-1 of Table 3 was introduced into another cell. The two materials were evaporated at different rates to deposit a hole injection layer with a thickness of 10 nm by doping compound HI-1 in an amount of 3 wt % based to the total amount of compound HI-1 and compound HT-1. Subsequently, compound HT-1 was deposited as a first hole transport layer with a thickness of 80 nm on the hole injection layer. Subsequently, compound HT-2 was introduced into another cell of the vacuum vapor deposition apparatus and was evaporated by applying an electric current to the cell, thereby depositing a second hole transport layer with a thickness of 60 nm on the first hole transport layer. After forming the hole injection layer and the hole transport layers, a light-emitting layer was deposited thereon as follows: A compound of Table 1 below was introduced into a cell of the vacuum vapor deposition apparatus as a host and compound D-39 was introduced into another cell as a dopant, followed by doping a dopant in an amount of 3 wt % based on the total amount of the host and dopant to deposit a light-emitting layer having a thickness of 40 nm on the second hole transport layer. Subsequently, compound ETL-1: compound EIL-1 were evaporated at a rate of 1:1 to deposit an electron transport layer having a thickness of 35 nm on the light-emitting layer. After depositing compound EIL-1 as an electron injection layer having a thickness of 2 nm on the electron transport layer, an Al cathode having a thickness of 80 nm was deposited by another vacuum vapor deposition apparatus on the electron injection layer to produce an OLED.

Comparative Example 1: Producing a Red Light-Emitting OLED Deposited with a Conventional Compound as a Host An OLED was produced in the same manner as in Device Examples 1 and 2, except that compound A of Table 3 below was used as a host of a light-emitting layer.

The driving voltage, luminous efficiency, power efficiency, and light-emitting color based on a luminance of 1,000 nit of the organic electroluminescent device of Device Examples 1 and 2 and Comparative Example 1 prepared as described above are shown in Table 1 below.

TABLE 1

|  | Host | Driving Voltage (V) | Luminous Efficiency (cd/A) | Power Efficiency (lm/W) | Light-Emitting Color |
|---|---|---|---|---|---|
| Device Example 1 | C-2 | 3.3 | 30.8 | 29.3 | Red |
| Device Example 2 | C-57 | 3.7 | 30.4 | 25.6 | Red |
| Comparative Example 1 | A | 5.0 | 30.8 | 19.5 | Red |

Table 1 shows that the organic electroluminescent device comprising the organic electroluminescent compound according to the present disclosure as a host exhibits equivalent luminous efficiency to Comparative Example 1, while providing excellent driving voltage and power efficiency properties compared to Comparative Example 1. The organic electroluminescent device including a host material according to the present disclosure may also have advantages in lifespan characteristics.

LUMO energy level, HOMO energy level, and triplet energy of parent structures of the organic electroluminescent compound represented by formula 2' and the organic electroluminescent compound represented by formula 2" according to the present disclosure were respectively measured and shown in Table 1-1 below.

TABLE 1-1

|  | LUMO (eV) | HOMO (eV) | Triplet (eV) |
|---|---|---|---|
|  | −1.404 | −5.531 | 2.426 |
|  | −1.432 | −5.434 | 2.365 |
|  | −1.423 | −5.399 | 2.349 |
|  | −1.460 | −5.316 | 2.309 |
|  | −1.408 | −5.327 | 2.324 |
|  | −1.451 | −5.349 | 2.320 |

TABLE 1-1-continued

| Structure | LUMO (eV) | HOMO (eV) | Triplet (eV) |
|---|---|---|---|
| [naphthobenzofuran with m-biphenyl substituent] | −1.431 | −5.409 | 2.352 |
| [naphthobenzofuran with phenyl substituent] | −1.376 | −5.444 | 2.396 |
| [naphthobenzothiophene with phenyl-naphthyl substituent] | −1.411 | −5.361 | 2.338 |
| [naphthobenzothiophene with biphenyl substituent] | −1.396 | −5.347 | 2.339 |
| [naphthobenzofuran linked via phenylene to dibenzofuran] | −1.463 | −5.481 | 2.386 |

*The structure was optimized by applying the background sets of B3LYP and 6-31G(d), which are hybrid DFT (hybrid density functional theory), with Gaussian 16 of Gaussian's quantum chemistry calculation program, and TD-DFT (time dependent DFT) was used to calculate the triplet state.

Table 1-1 above shows that the parent structure of the organic electroluminescent compound represented by formula 2″ according to the present disclosure (introducing a substituent into $R_{20}$ or $R_{25}$) has a similar energy level to the parent structure of compounds C-2 and C-57, which correspond to the organic electroluminescent compound represented by formula 2′ used in Device Examples 1 and 2. Accordingly, it is expected that an organic electroluminescent device using the organic electroluminescent compound represented by formula 2″ as a host material will also have a similar device properties to Device Examples 1 and 2.

Device Examples 3 to 5: Producing a Red Light-Emitting OLED Deposited with a Plurality of Host Materials According to the Present Disclosure as a Host An OLED was produced in the same manner as in Device Examples 1 and 2, except that a first host compound and a second host compound shown in Table 2 below were added respectively to two cells of the vacuum vapor deposition apparatus as hosts, and compound D-39 was introduced into another cell as a dopant, and then the two host materials were evaporated at a rate of 1:1 and the dopant was evaporated at a different rate at the same time, thereby doping a dopant in an amount of 3 wt % based on the total amount of the host and dopant to deposit a light-emitting layer.

The driving voltage, luminous efficiency, and light-emitting color based on a luminance of 1,000 nit of the organic electroluminescent device of Device Examples 3 to 5 prepared as described above are shown in Table 2 below.

TABLE 2

| | First Host | Second Host | Driving Voltage (V) | Luminous Efficiency (cd/A) | Light-Emitting Color |
|---|---|---|---|---|---|
| Device Example 3 | H1-45 | C-2 | 3.1 | 34.1 | Red |
| Device Example 4 | H1-15 | C-2 | 3.2 | 35.4 | Red |
| Device Example 5 | H1-15 | C-57 | 3.2 | 36.5 | Red |

It was previously confirmed in Device Examples 1 and 2 that an OLED having excellent luminous efficiency, driving voltage, and power efficiency properties was provided when the organic electroluminescent compound represented by formula 2' or formula 2" of the present disclosure was used as a single host. In addition, Table 2 shows that the organic electroluminescent device comprising a plurality of host materials according to the present disclosure as a host provides improved driving voltage, luminous efficiency and/or power efficiency properties compared to the organic electroluminescent device comprising an organic electroluminescent compound represented by formula 2' or formula 2" of the present disclosure as a single host. The organic electroluminescent device comprising a plurality of host materials according to the present disclosure may also have an advantage in lifespan properties.

Without being limited by theory, the light-emitting layer was made into an electron-dominant system by using the compound of formula 2 according to the present disclosure as a second host, and the compound of formula 1 according to the present disclosure, which is an amine-based compound, was used as a first host to provide sufficient excitons by providing a large number of holes. In addition, without being limited by theory, it was possible to lower HOMO barrier between a hole transport layer and a light-emitting layer due to high HOMO energy level of a first host. As a result, low driving voltage, high power efficiency, and long lifespan properties can be obtained.

The compounds used in Device Examples 1 to 5 and Comparative Example 1 are shown in Table 3 below.

TABLE 3

| Hole Injection Layer/ Hole Transport Layer | |
|---|---|
| 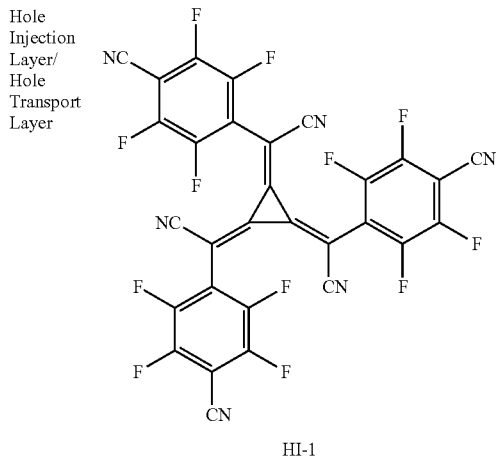 HI-1 | |
| 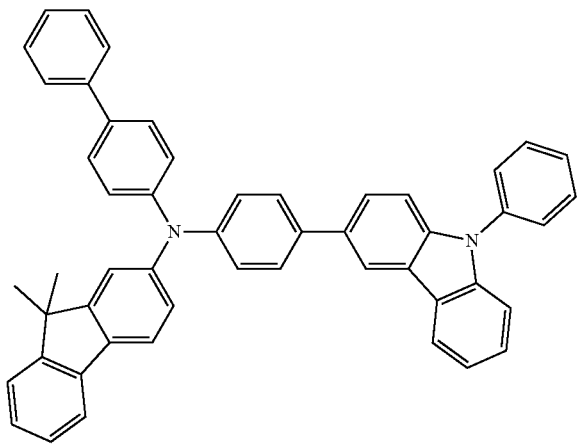 HT-1 | |

TABLE 3-continued
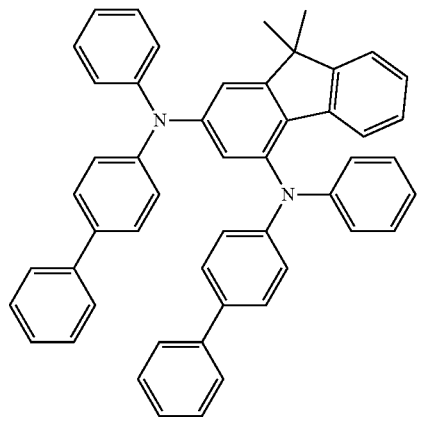
HT-2
Light-
Emitting
Layer
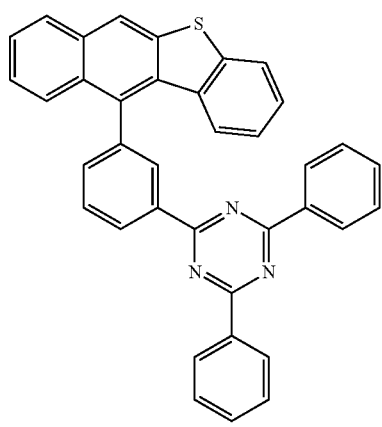
C-2
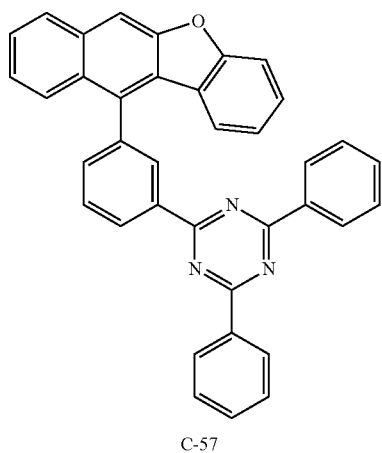
C-57

TABLE 3-continued
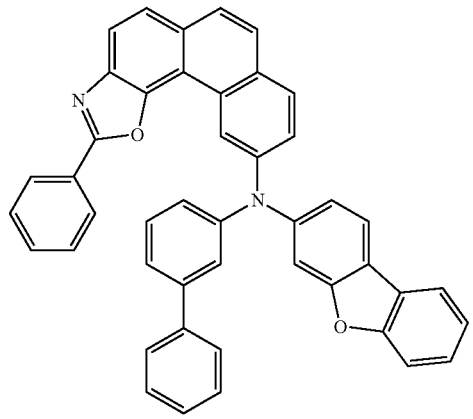
H1-15
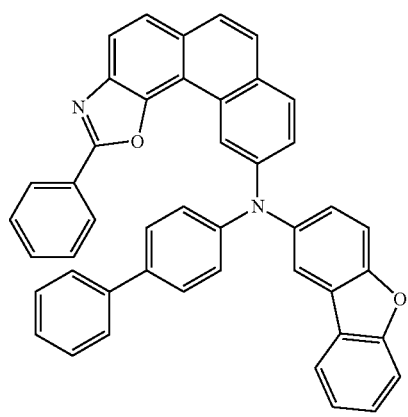
H1-45
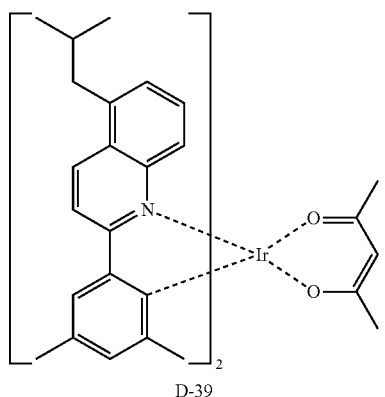
D-39

TABLE 3-continued

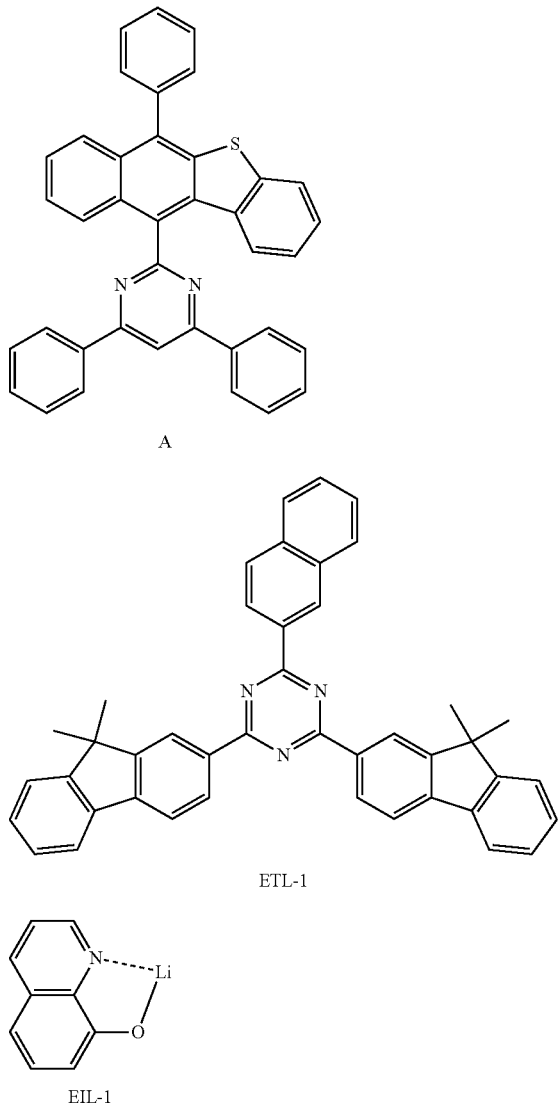

Electron Transport Layer/ Electron Injection Layer

Device Example 6: Producing a Blue Light-Emitting OILED Deposited with a Compound According to the Present Disclosure as an Electron Transport Layer An OLED according to the present disclosure was produced. First of all, a transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropyl alcohol before use. The ITO substrate was mounted on a substrate holder of the vacuum vapor deposition apparatus. Compound HI-1 of Table 5 was introduced into a cell of the vacuum vapor deposition apparatus as a first hole injection compound, and compound HT-1 of Table 5 was introduced into another cell. The two materials were evaporated at different rates to deposit a hole injection layer with a thickness of 10 nm by doping compound HI-1 in an amount of 3 wt % based to the total amount of compound HI-1 and compound HT-1. Subsequently, compound HT-1 was deposited as a first hole transport layer with a thickness of 80 nm on the hole injection layer. Subsequently, compound HT-3 was introduced into another cell of the vacuum vapor deposition apparatus and was evaporated by applying an electric current to the cell, thereby depositing a second hole transport layer with a thickness of 5 nm on the first hole transport layer. After forming the hole injection layer and the hole transport layers, a light-emitting layer was deposited thereon as follows: Compound BH of Table 5 was introduced into one cell of the vacuum vapor deposition apparatus as a host, and compound BD was introduced into another cell as a dopant. The two host materials were evaporated at a rate of 1:1 and the dopant was evaporated at a different rate at the same time, thereby doping a dopant in an amount of 3 wt % based on the total amount of the host and dopant to deposit a light-emitting layer having a thickness of 20 nm on the hole transport layer. Subsequently, compound BF was deposited as an electron buffer layer with a thickness of 5 nm on the light-emitting layer. Subsequently, compound C-2: compound of EIL-1 were evaporated in a weight ratio of 50:50 to deposit an electron transport layer having a thickness of 30 nm on the light-emitting layer. After depositing compound EIL-1 as an electron injection layer having a thickness of 2 nm on the electron transport layer, an Al cathode having a thickness of 80 nm was deposited by another vacuum vapor deposition apparatus on the electron injection layer to produce an OLED. Each compound of materials was purified by vacuum sublimation under $10^6$ torr before use.

Comparative Example 2: Producing a Blue Light-Emitting OLED Deposited with a Conventional Compound as an Electron Transport Layer An OLED was produced in the same manner as in Device Example 6, except that compound A of Table 5 instead of compound C-2 was used as an electron transport layer.

The driving voltage, luminous efficiency, light-emitting color, and external quantum efficiency based on a luminance of 1,000 nit of the OLEDs produced in Device Example 6 and Comparative Example 2 prepared as described above are shown in Table 4 below.

TABLE 4

| | Electron Transport Layer | Driving Voltage (V) | Luminous Efficiency (cd/A) | Light-Emitting Color | External Quantum Efficiency (EQE) |
|---|---|---|---|---|---|
| Device Example 6 | C-2: EIL-1 | 3.7 | 6.3 | Blue | 8.6 |
| Comparative Example 2 | A: EIL-1 | 4.6 | 5.4 | Blue | 7.8 |

Table 4 shows that the organic electroluminescent device comprising a compound according to the present disclosure as an electron transport layer provides excellent driving voltage, luminous efficiency and/or external quantum efficiency properties compared to the organic electroluminescent device of Comparative Example 2 comprising a conventional compound as an electron transport layer.

The compounds used in Device Example 6 and Comparative Example 2 are shown in Table 5 below.

TABLE 5

| Hole Injection Layer/ Hole Transport Layer | |
|---|---|
| 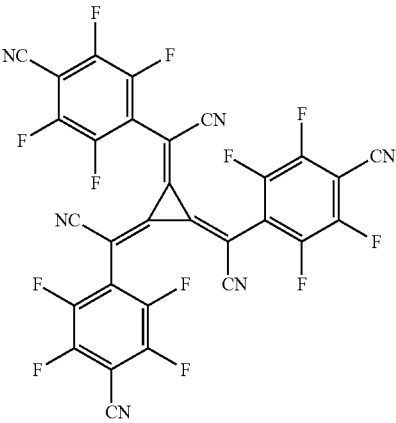 | |

HI-1

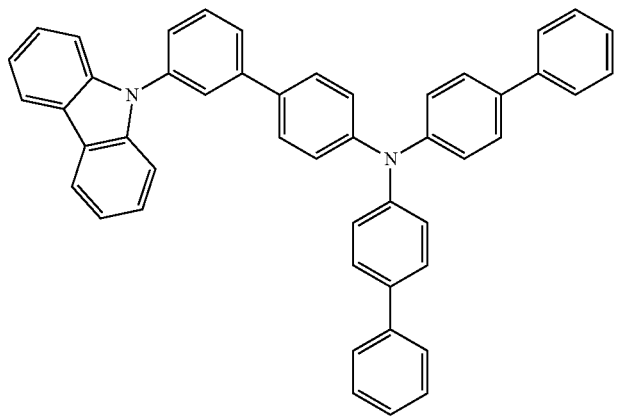

HT-1

TABLE 5-continued
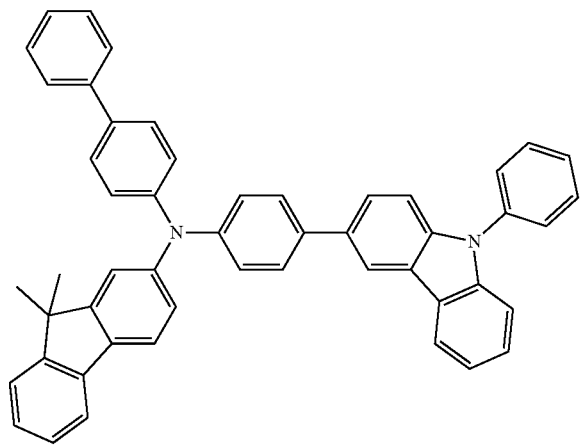
HT-3
Light-
Emitting
Layer
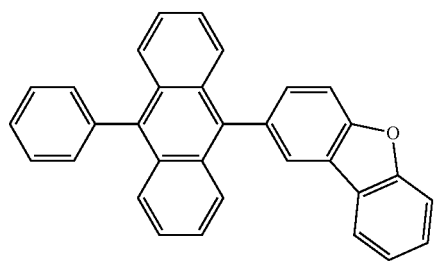
BH
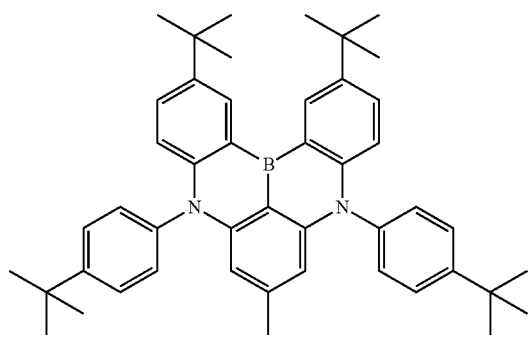
BD
Electron
Buffer
Layer
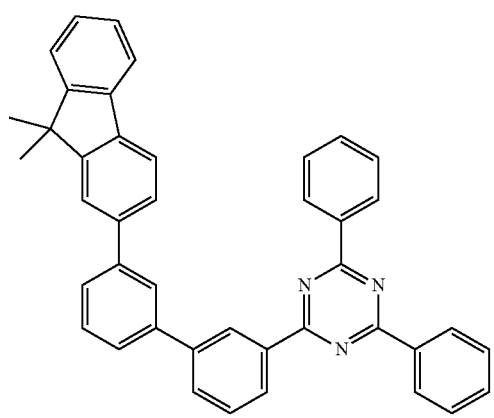
BF TABLE 5-continued
Electron Transport Layer/ Electron Injection Layer
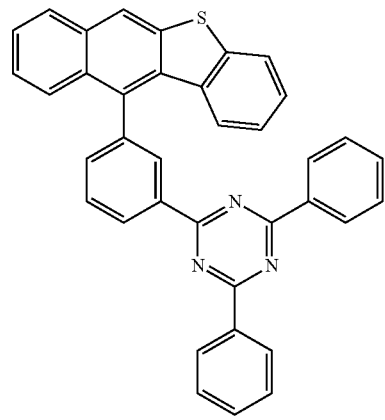
C-2
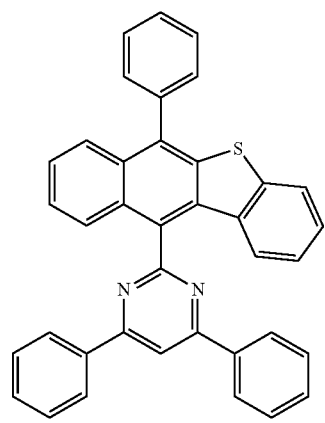
A
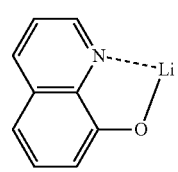
EIL-1

The invention claimed is:

1. A plurality of host materials comprising at least one first host compound and at least one second host compound, wherein the first host compound is represented by the following formula 1, and the second host compound is represented by the following formula 2:

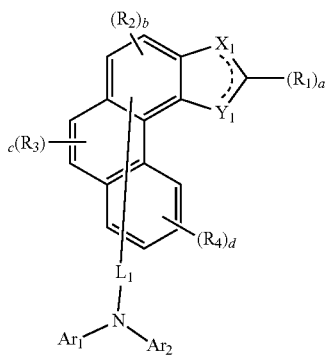

(1)

wherein $X_1$ and $Y_1$ each independently represent —N═, —$NR_5$—, —O—, or —S—, with the proviso that any one of $X_1$ and $Y_1$ represents —N═, and the other one of $X_1$ and $Y_1$ represents —$NR_5$—, —O—, or —S—;

$R_1$ represents a substituted or unsubstituted (C6-C30)aryl, or a substituted or unsubstituted (3- to 30-membered) heteroaryl;

$L_1$ represents a single bond, a substituted or unsubstituted (C6-C30)arylene, or a substituted or unsubstituted (3- to 30-membered)heteroarylene;

$Ar_1$ and $Ar_2$ each independently represent a substituted or unsubstituted (C6-C30)aryl, or a substituted or unsubstituted (3- to 30-membered)heteroaryl;

$R_2$ to $R_5$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring(s) and a (C6-C30)aromatic ring(s), or -$L_3$-N($Ar_3$) ($Ar_4$); or may be linked to an adjacent substituent to form a ring;

a represents 1, b and c each independently represent 1 or 2, and d represents an integer of 1 to 4, where if b to d are an integer of 2 or more, each of $R_2$ to each of $R_4$ may be the same as or different from each other;

(2)

wherein

HAr each independently represents a substituted or unsubstituted nitrogen-containing (3- to 20-membered) heteroaryl;

$L_{11}$ each independently represents a single bond, a substituted or unsubstituted (C6-C30)arylene, or a substituted or unsubstituted (3- to 30-membered)heteroarylene;

$Ar_{11}$ each independently represents any one of the following formulas 3 to 5:

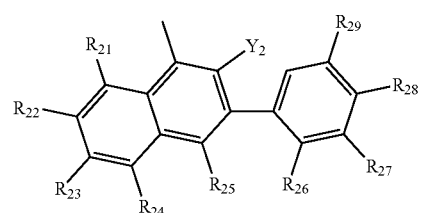

(3)

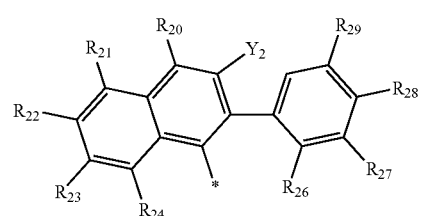

(4)

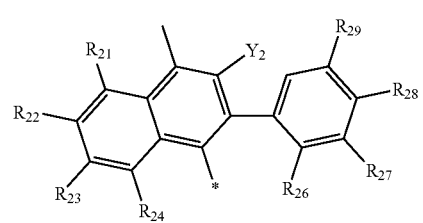

(5)

wherein $Y_2$ represents O or S;

$R_{20}$ to $R_{29}$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of a (C3-C30)aliphatic ring(s) and a (C6-C30)aromatic ring(s), or -$L_3$-N($Ar_3$) ($Ar_4$);

e represents 1 or 2, where if e is 2, each of ($L_{11}$-HAr) may be the same as or different from each other;

* represents a site linked to $L_{11}$;

in formulas 1 and 3 to 5, $L_3$ each independently represents a single bond, a substituted or unsubstituted (C6-C30)arylene, or a substituted or unsubstituted (3- to 30-membered)heteroarylene; and $Ar_3$ and $Ar_4$ each independently represent hydrogen, a substituted or unsubstituted (C1-C30)alkyl, a substituted or unsubstituted (C2-C30)alkenyl, a substituted or unsubstituted fused ring of a (C3-C30)aliphatic ring(s) and a (C6-C30)aromatic ring(s), a substituted or unsubstituted (C6-C30)aryl, or a substituted or unsubstituted (3- to 30-membered)heteroaryl.

2. The plurality of host materials according to claim 1, wherein the substituents of the substituted alkyl, the substituted alkenyl, the substituted aryl, the substituted arylene, the substituted heteroaryl, the substituted heteroarylene, the substituted nitrogen-containing heteroaryl, the substituted cycloalkyl, the substituted alkoxy, the substituted trialkylsilyl, the substituted dialkylarylsilyl, the substituted alkyldiarylsilyl, the substituted triarylsilyl, and the substituted fused ring of an aliphatic ring(s) and an aromatic ring(s) each independently are at least one selected from the group consisting of deuterium; a halogen; a cyano; a carboxyl; a nitro; a hydroxyl; a phosphine oxide; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with at least one of a (C1-C30)alkyl(s) and a (C6-C30)aryl(s); a (C6-C30)aryl unsubstituted or substituted with at least one of deuterium, a cyano(s), a (C1-C30)alkyl(s), a (C3-C30)cycloalkyl(s), a tri(C1-C30)alkylsilyl(s), a (C6-C30)aryl(s), and a (3- to 30-membered)heteroaryl(s); tri(C1-C30)alkylsilyl; a tri(C6-C30)arylsilyl; a di(C1-C30)alkyl(C6-C30)arylsilyl; a (C1-C30)alkyldi(C6-C30)arylsilyl; a fused ring of a (C3-C30)aliphatic ring(s) and a (C6-C30)aromatic ring(s); an amino; a mono- or di-(C1-C30)alkylamino; a mono- or di-(C2-C30)alkenylamino; a (C1-C30)alkyl(C2-C30)alkenylamino; a mono- or di-(C6-C30)arylamino(s); a (C1-C30)alkyl(C6-C30)arylamino; a mono- or di-(3- to 30-membered)heteroarylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30)arylcarbonyl; a (C6-C30)arylphosphine; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

3. The plurality of host materials according to claim 1, wherein formula 1 is represented by at least one of the following formulas 1-1 to 1-4:

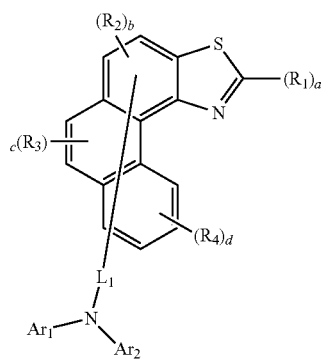

(1-1)

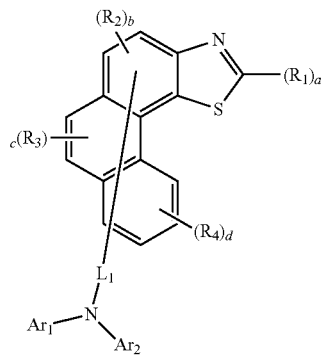

(1-2)

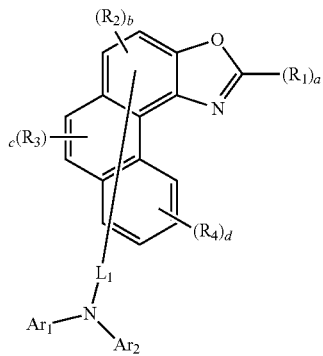

(1-3)

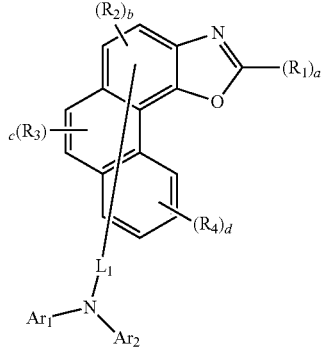

(1-4)

wherein $R_1$ to $R_4$, $Ar_1$, $Ar_2$, $L_1$, and a to d are as defined in claim 1.

4. The plurality of host materials according to claim 1, wherein $R_1$, $Ar_1$, and $Ar_2$ of formula 1 each independently represent a substituted or unsubstituted phenyl, a substituted or unsubstituted naphthyl, a substituted or unsubstituted biphenyl, a substituted or unsubstituted terphenyl, a substituted or unsubstituted phenanthrenyl, a substituted or unsubstituted fluorenyl, a substituted or unsubstituted benzofluorenyl, a substituted or unsubstituted triphenylenyl, a substituted or unsubstituted spirobifluorenyl, a substituted or unsubstituted pyridyl, a substituted or unsubstituted triazinyl, a substituted or unsubstituted pyrimidinyl, a substituted or unsubstituted quinolyl, a substituted or unsubstituted quinazolinyl, a substituted or unsubstituted quinoxalinyl, a substituted or unsubstituted benzoquinazolinyl, a substituted or unsubstituted benzoquinoxalinyl, a substituted or unsubstituted benzofuropyridyl, a substituted or unsubstituted benzofuropyrimidinyl, a substituted or unsubstituted carbazolyl, a substituted or unsubstituted dibenzothiophenyl, a substituted or unsubstituted benzothiophenyl, a substituted or unsubstituted dibenzofuranyl, a substituted or unsubstituted benzofuranyl, a substituted or unsubstituted naphthyridinyl, a substituted or unsubstituted benzonaphthofuranyl, or a substituted or unsubstituted benzonaphthothiophenyl.

5. The plurality of host materials according to claim 1, wherein HAr of formula 2 each independently represents a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted carbazolyl, a substituted or unsubstituted triazolyl, a substituted or unsubstituted pyrazolyl, a substituted or unsubstituted naphthyridinyl, a substituted or unsubstituted triazanaphthyl, a substituted or unsubstituted benzofuropyrimidinyl, or a substituted or unsubstituted benzothienopyrimidinyl.

6. The plurality of host materials according to claim 1, wherein the compound represented by formula 1 is at least one selected from the following compounds:

H1-1
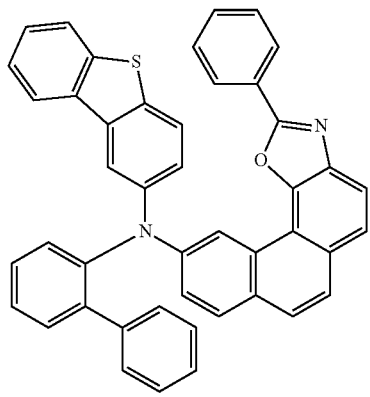

H1-2
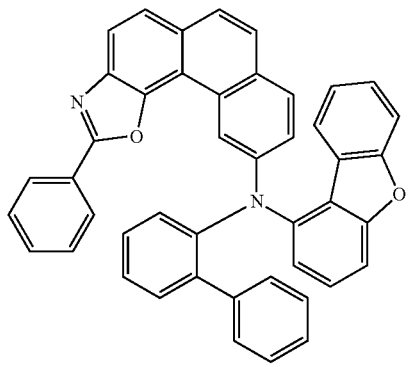

H1-3
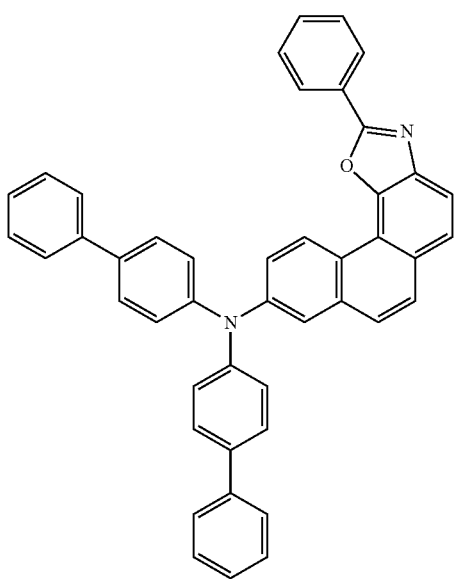

H1-4
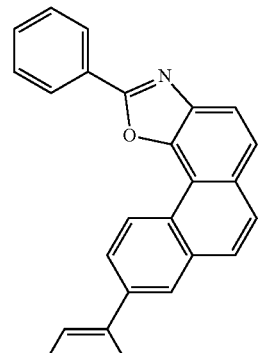

H1-5
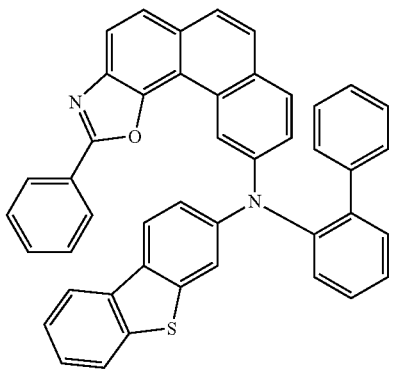

H1-6
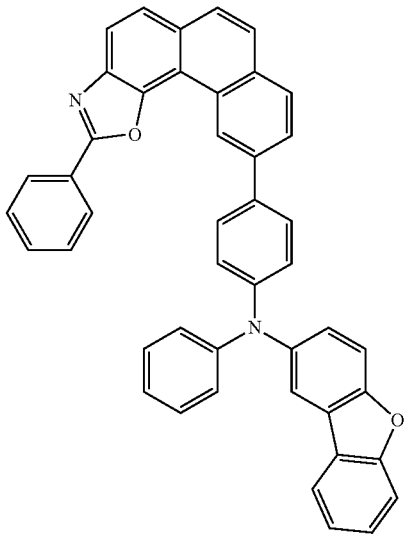

H1-7
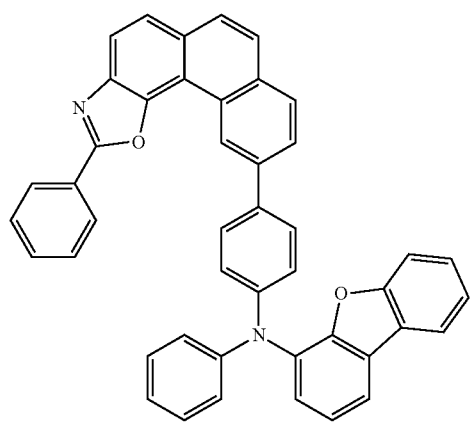
H1-8
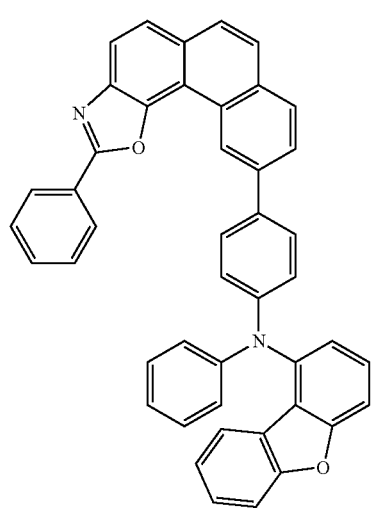
H1-9
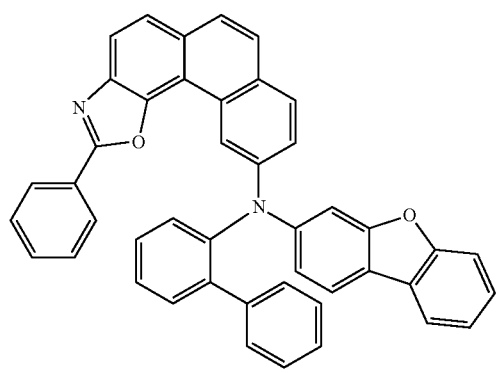
H1-10
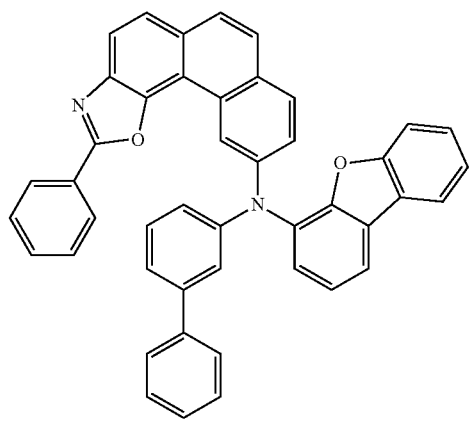
H1-11
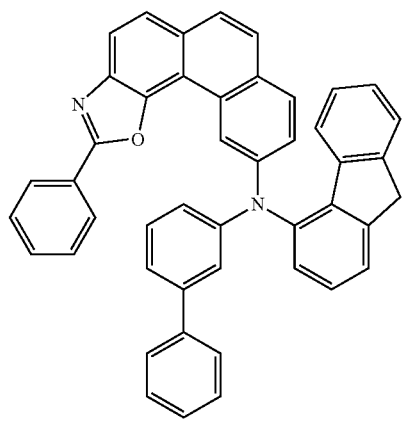
H1-12
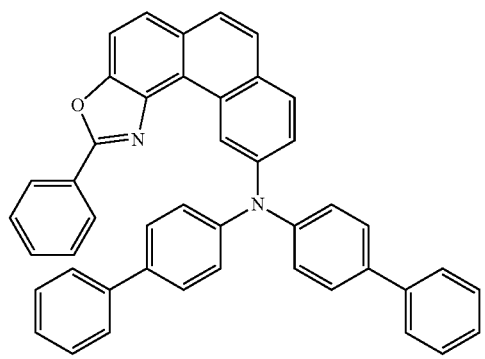
H1-13
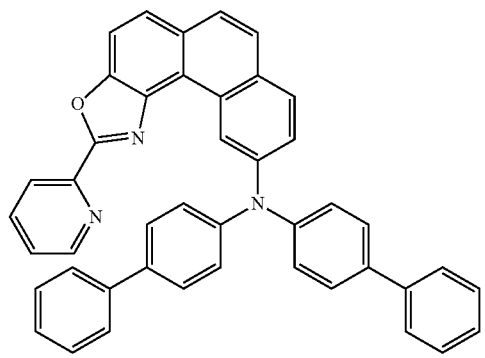

H1-14
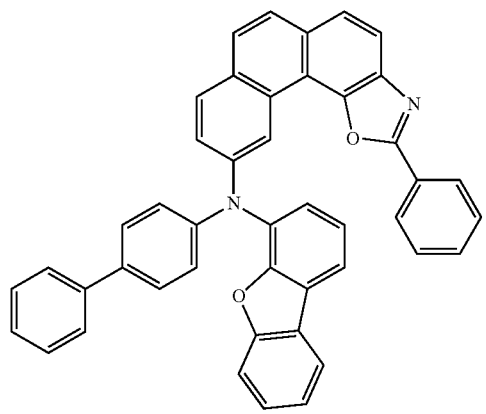
H1-15
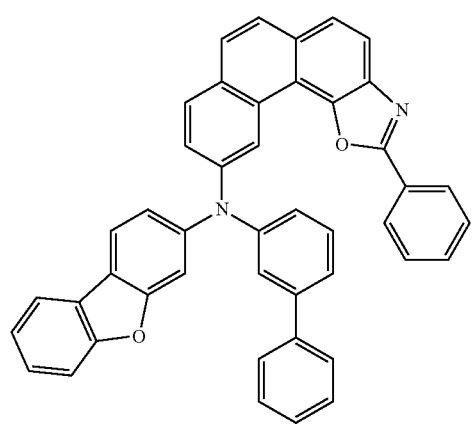
H1-16
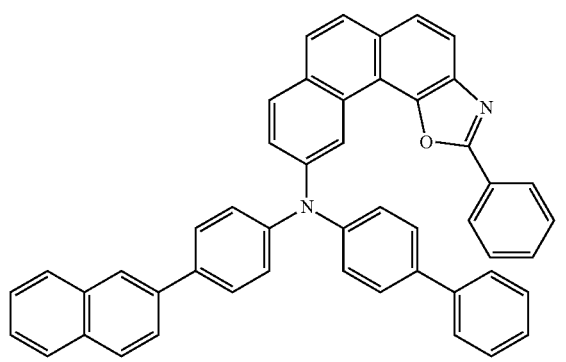
H1-17
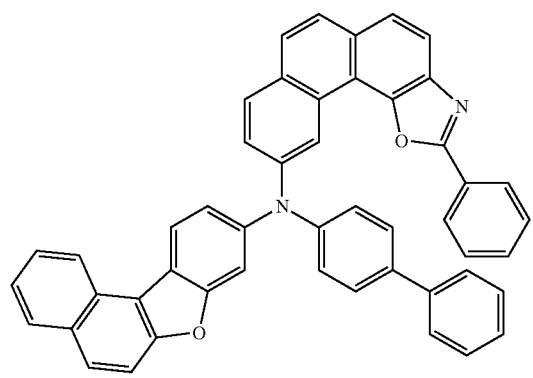
H1-18
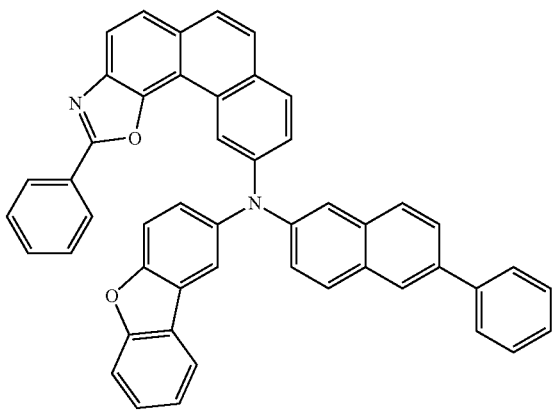
H1-19
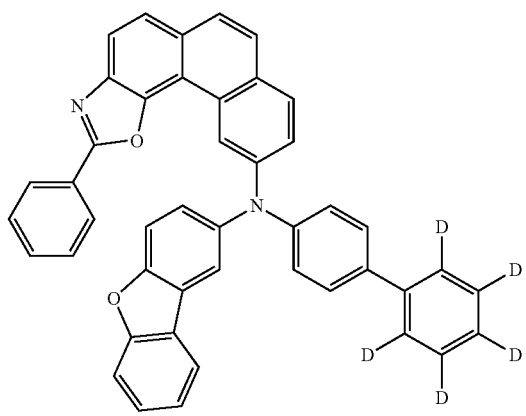
H1-20
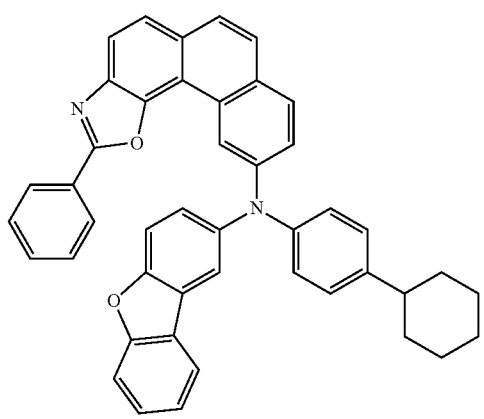

-continued
H1-21
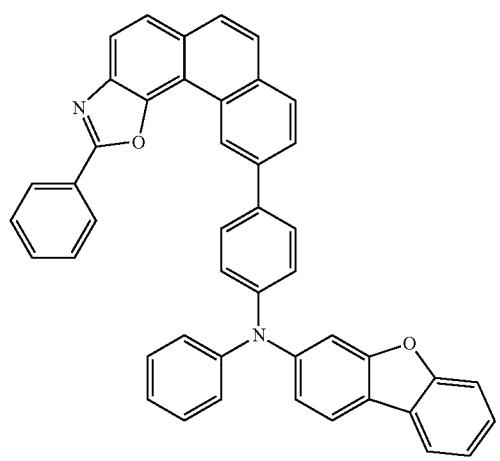
H1-22
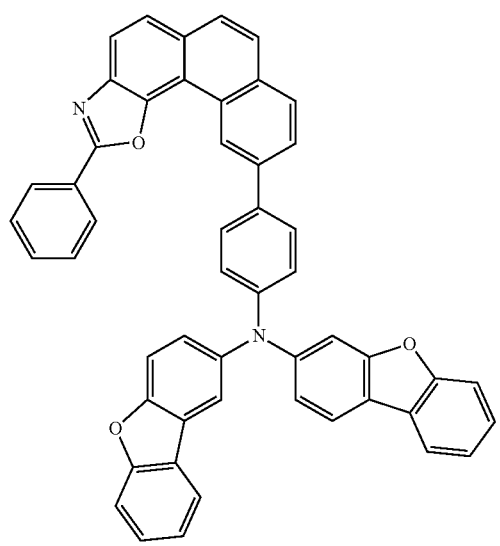
H1-23
-continued
H1-24
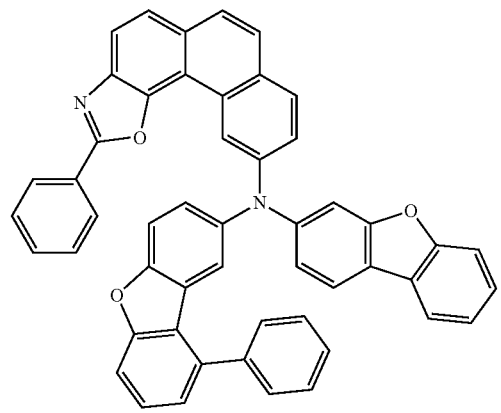
H1-25
H1-26
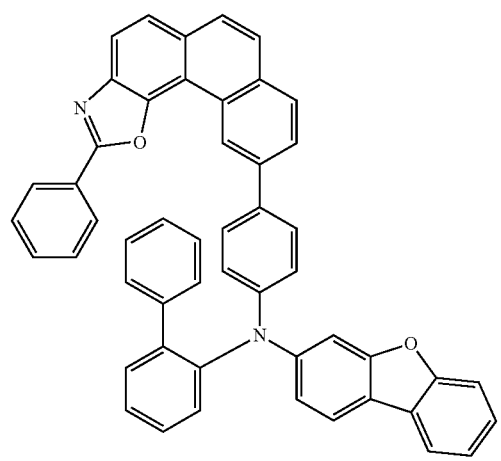

H1-27
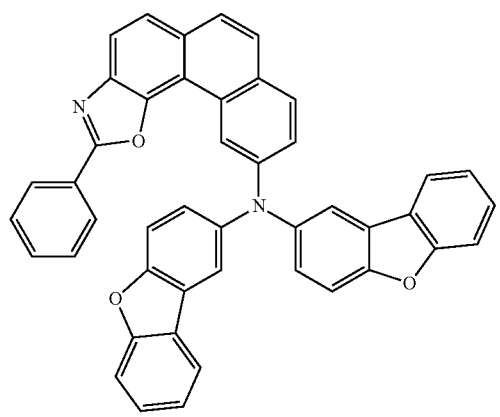
H1-30
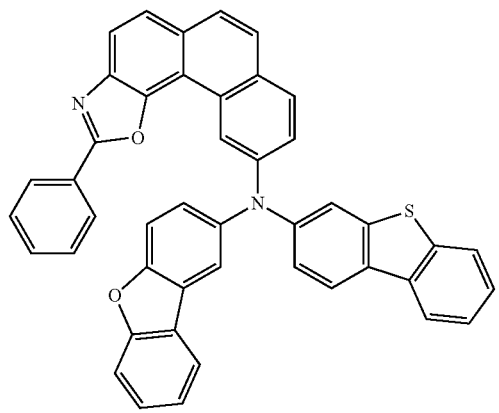
H1-28
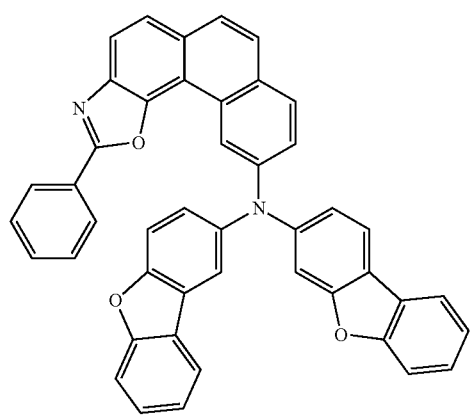
H1-31
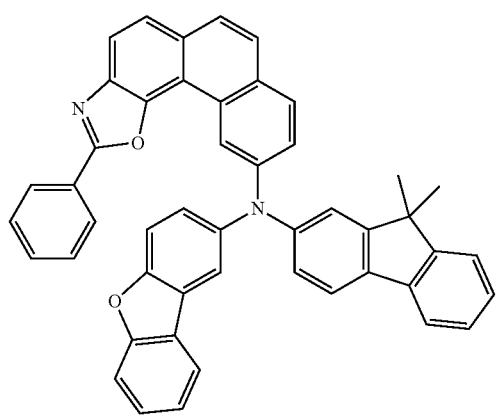
H1-29
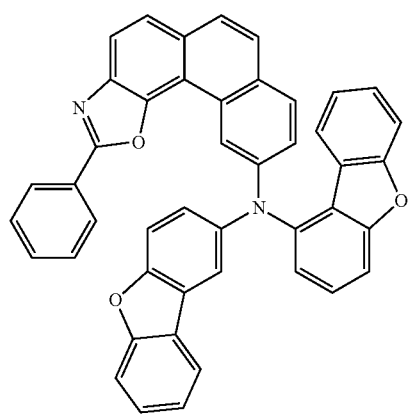
H1-32
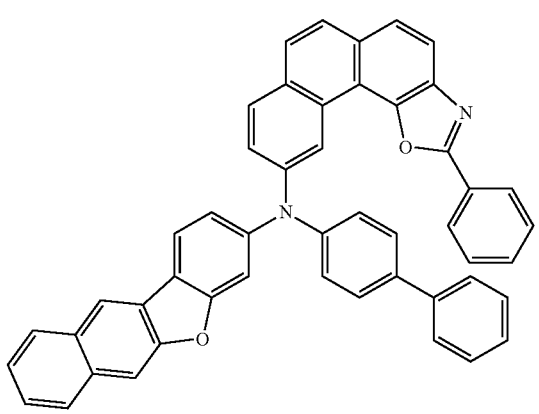

-continued
H1-33
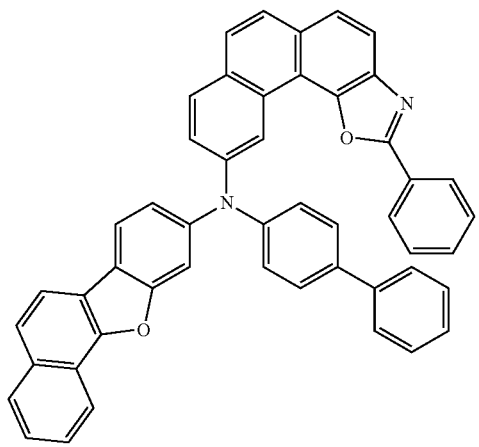
H1-34
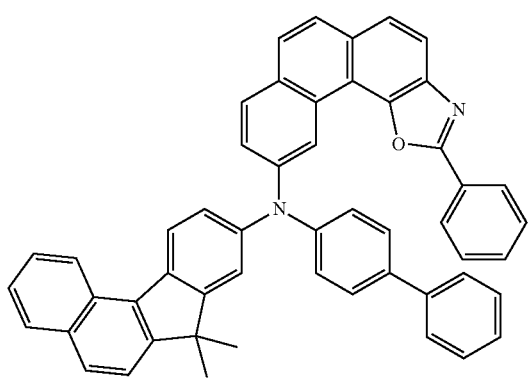
H1-35
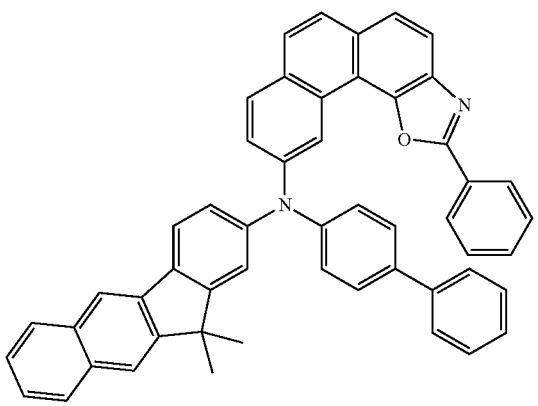
H1-36
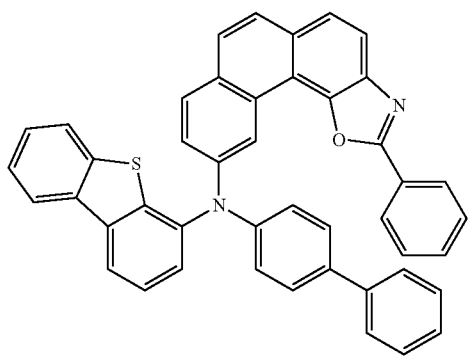
-continued
H1-37
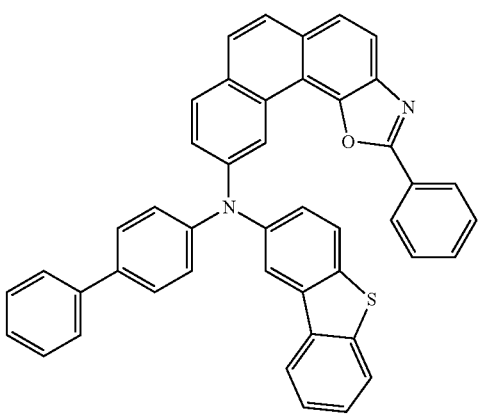
H1-38
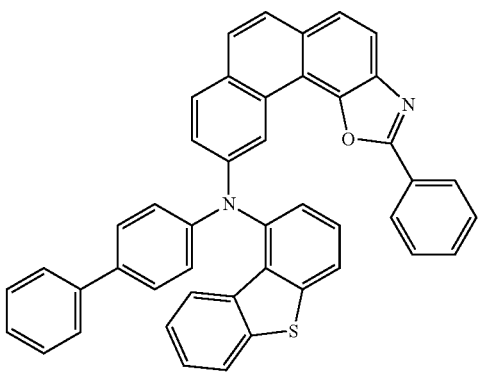
H1-39
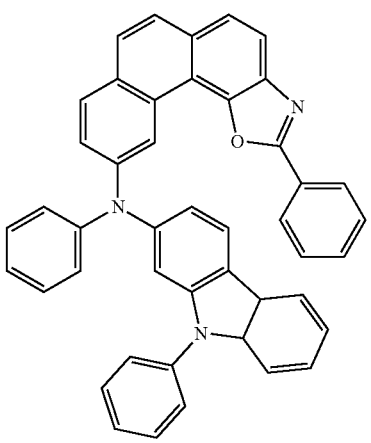

H1-40
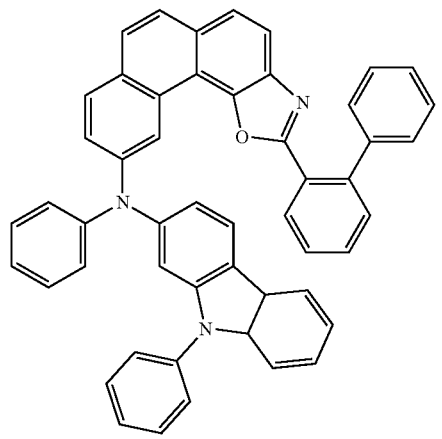
H1-41
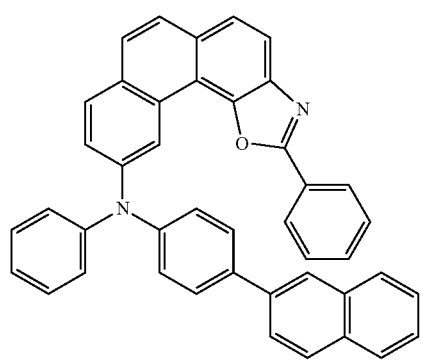
H1-42
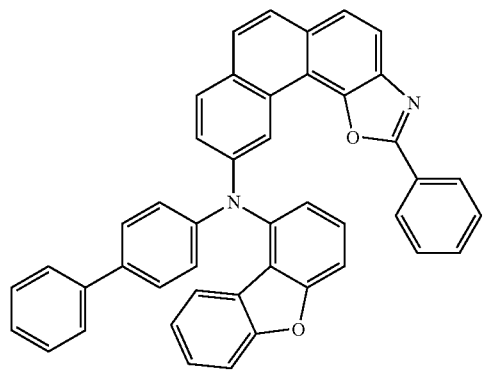
H1-43
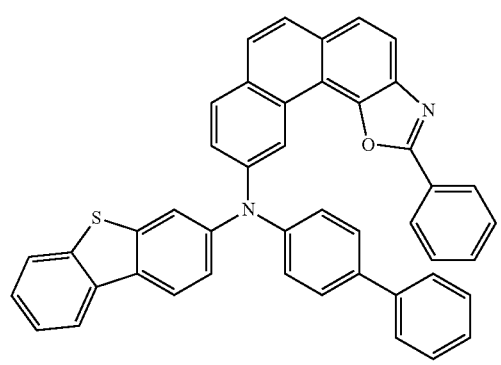
H1-44
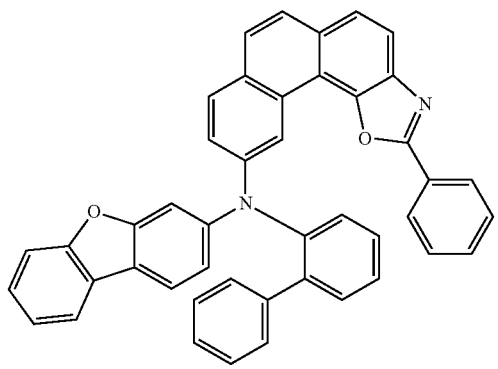
H1-45
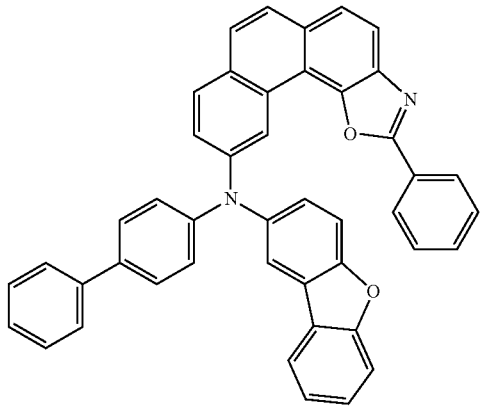
H1-46
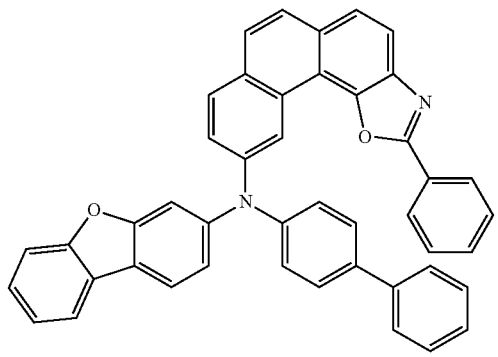
H1-47
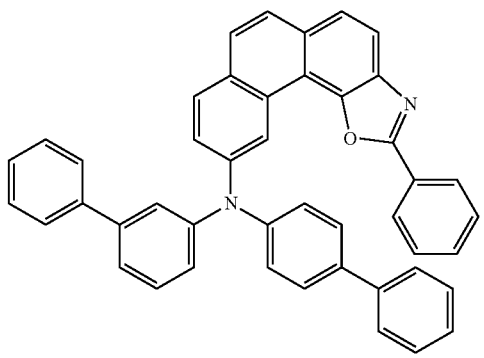

233
-continued
H1-48
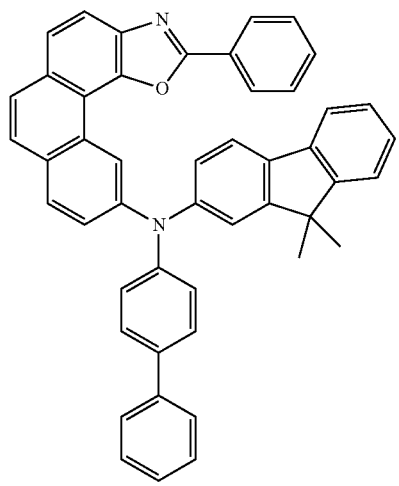
H1-49
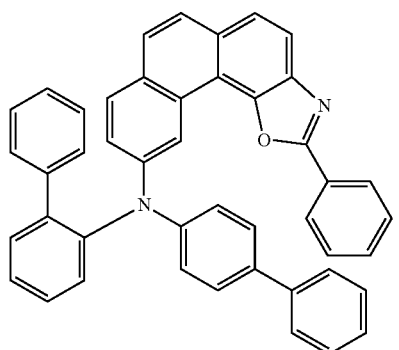
H1-50
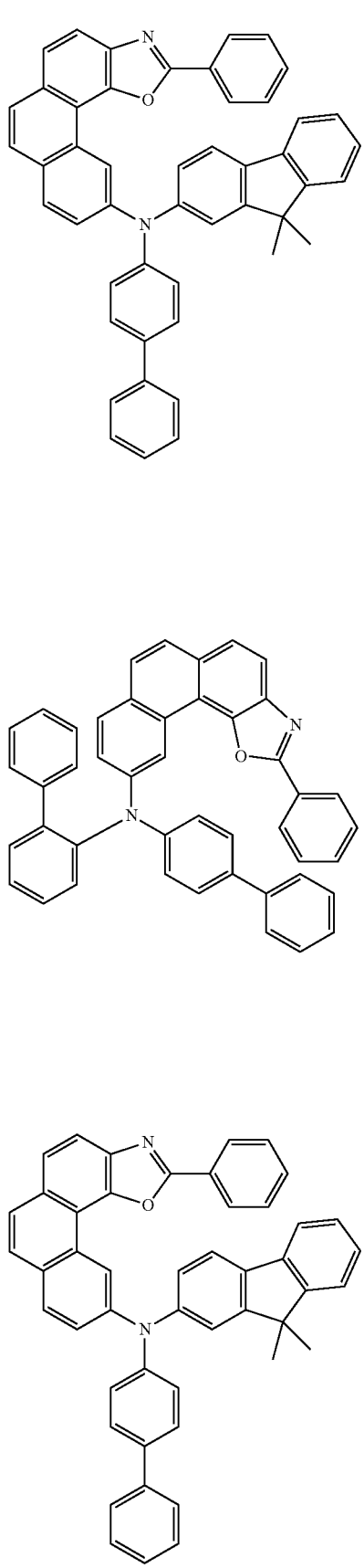
234
-continued
H1-51
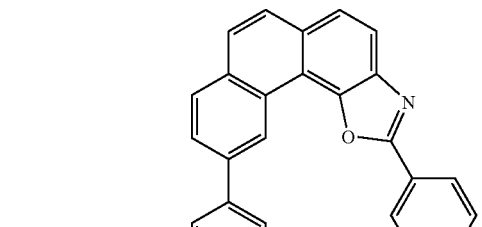
H1-52
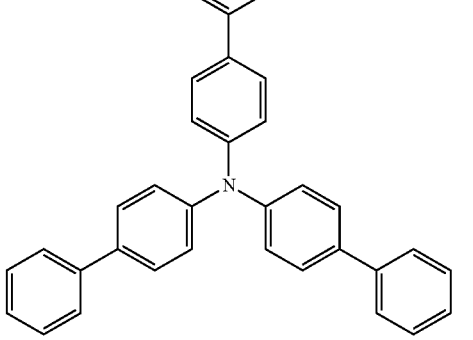
H1-53
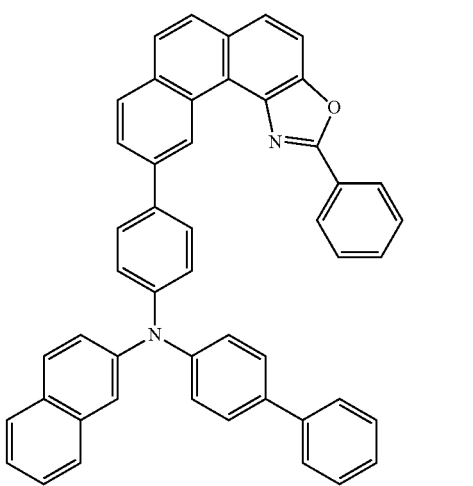

H1-54
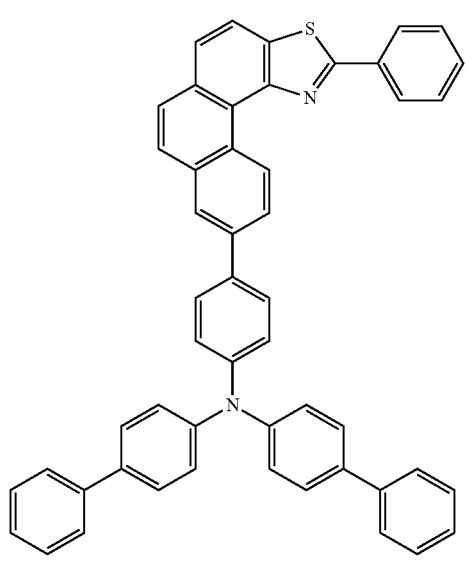
H1-55
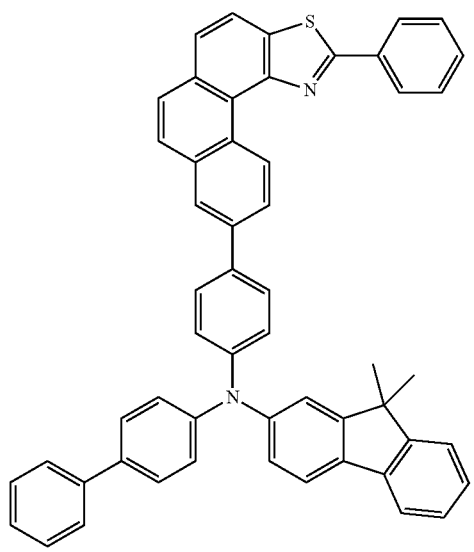
H1-56
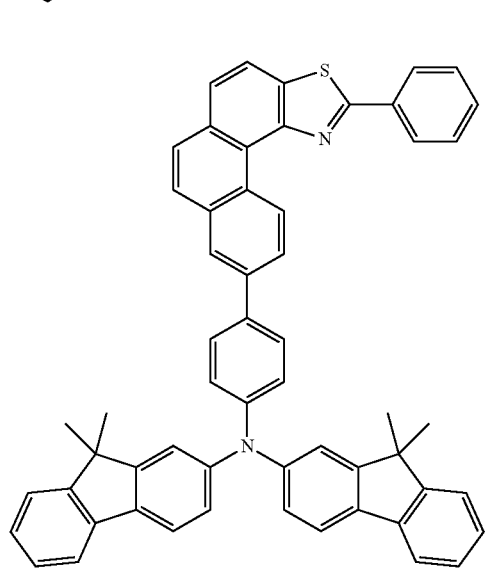
H1-57
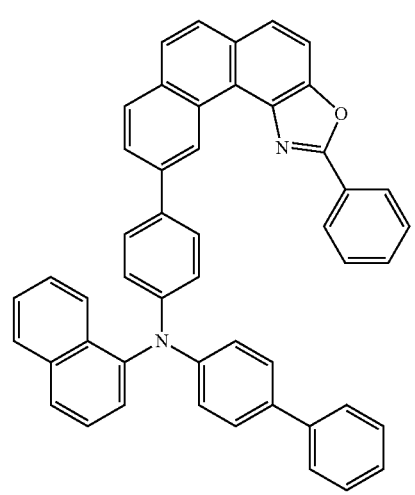
H1-58
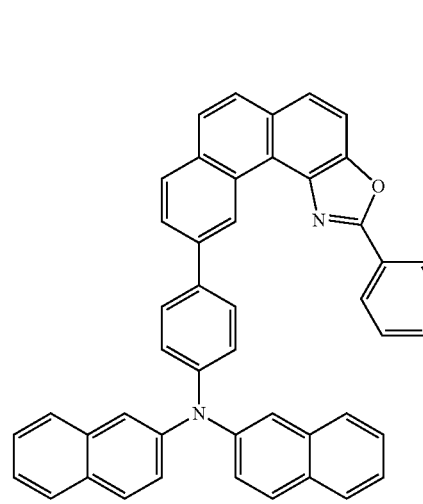
H1-59
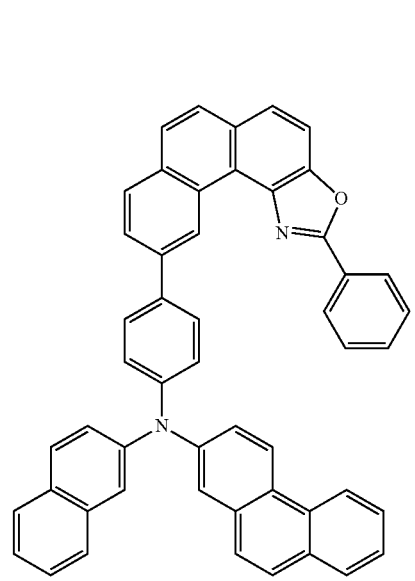

-continued
H1-60
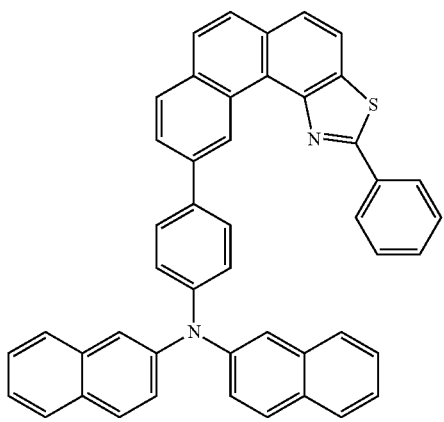
H1-61
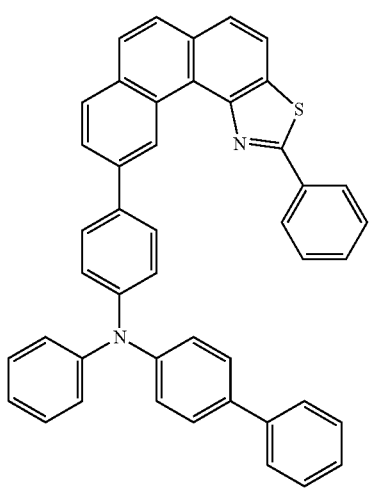
H1-62
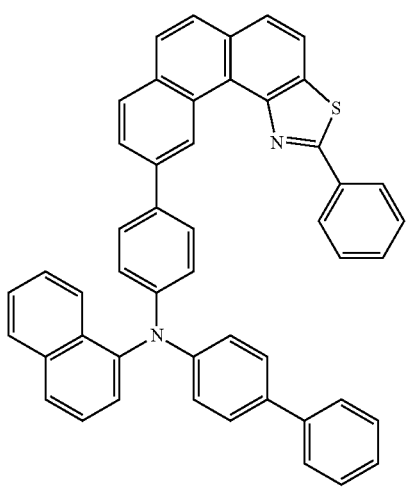
-continued
H1-63
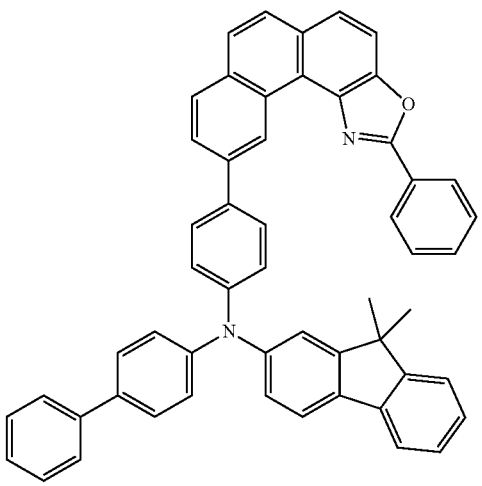
H1-64
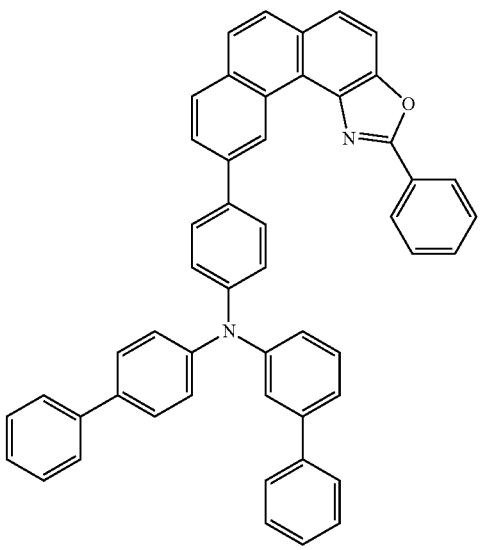
H1-65
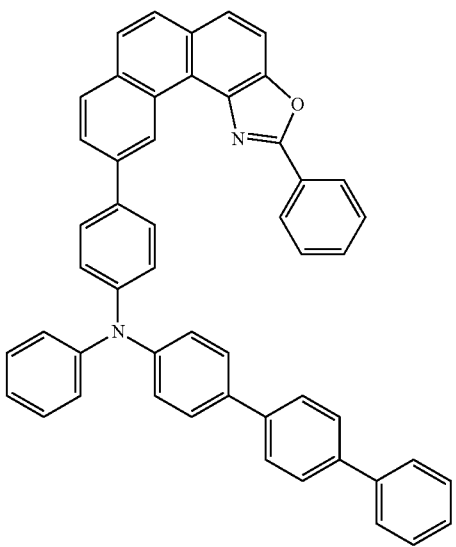

H1-66
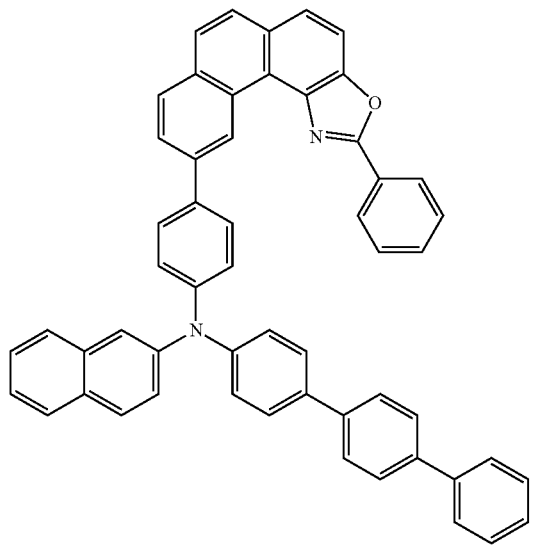
H1-67
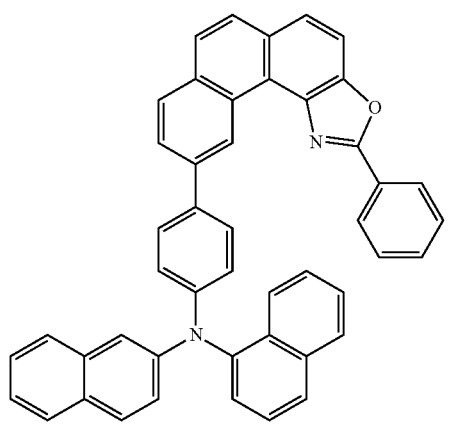
H1-68
H1-69
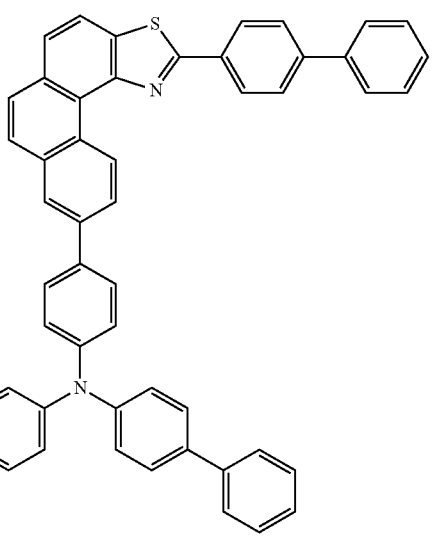
H1-70
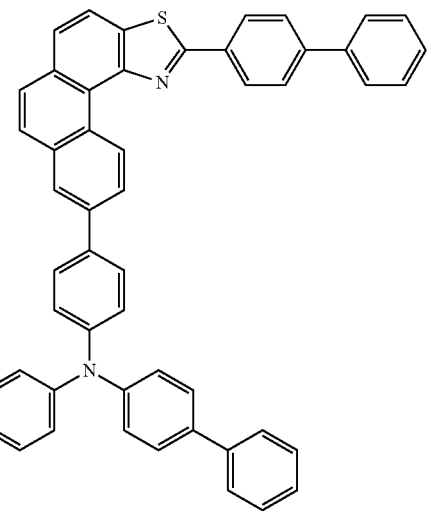
H1-71
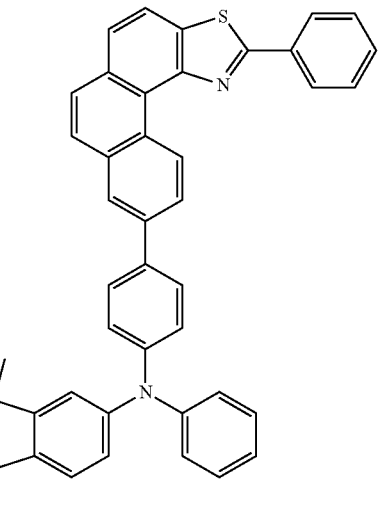

H1-72
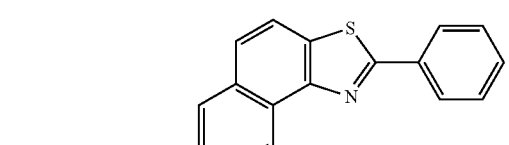
H1-73
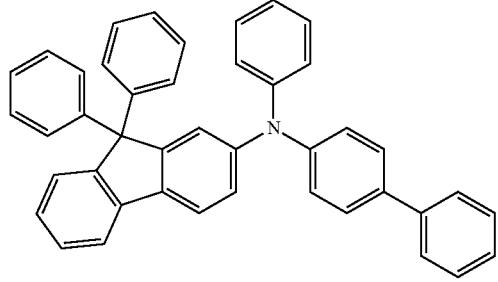
H1-74
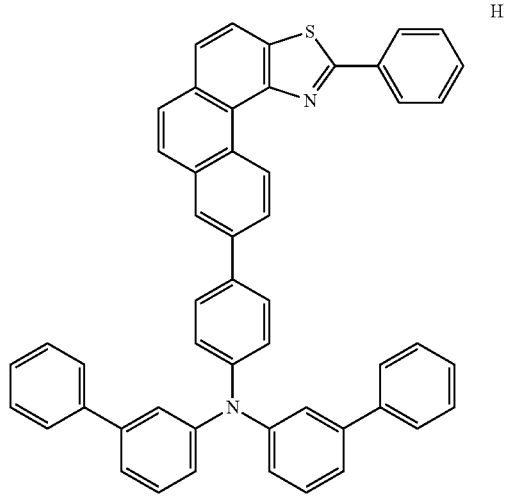
H1-75
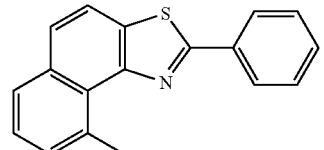
H1-76
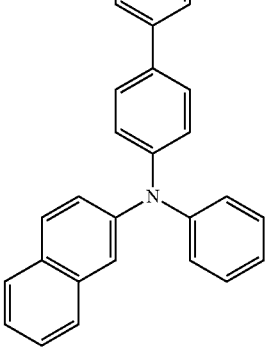
H1-77
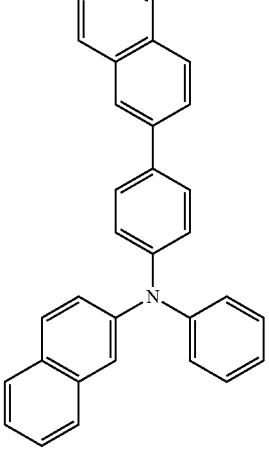

H1-78
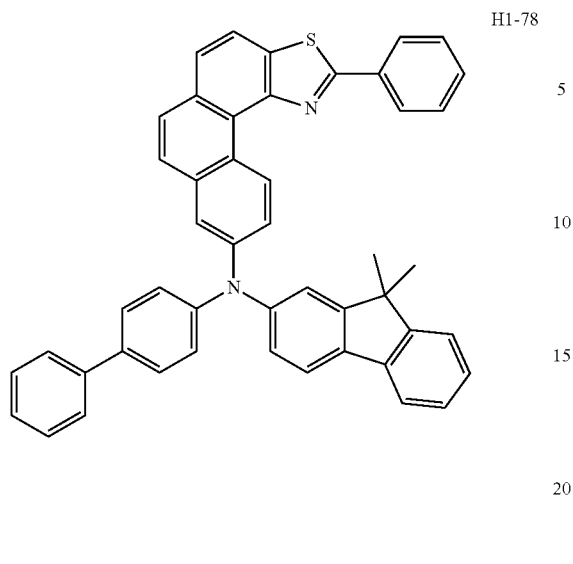
H1-79
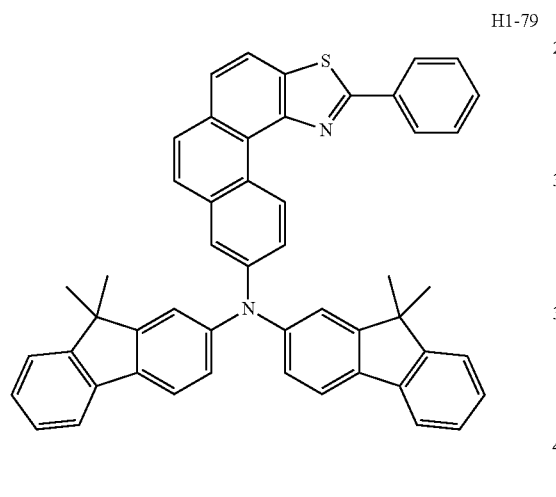
H1-80
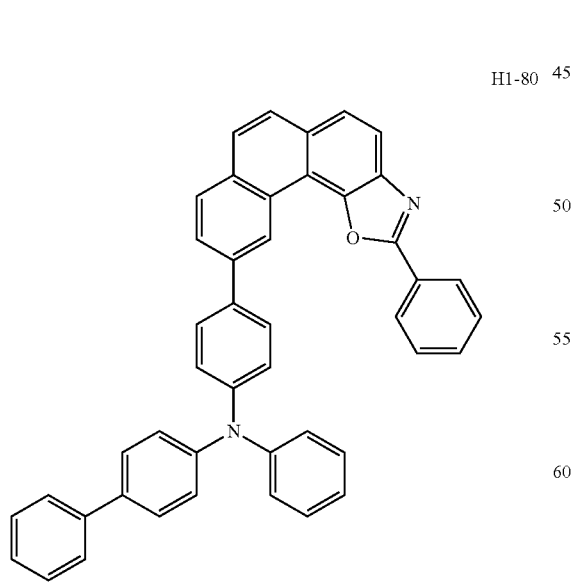
H1-81
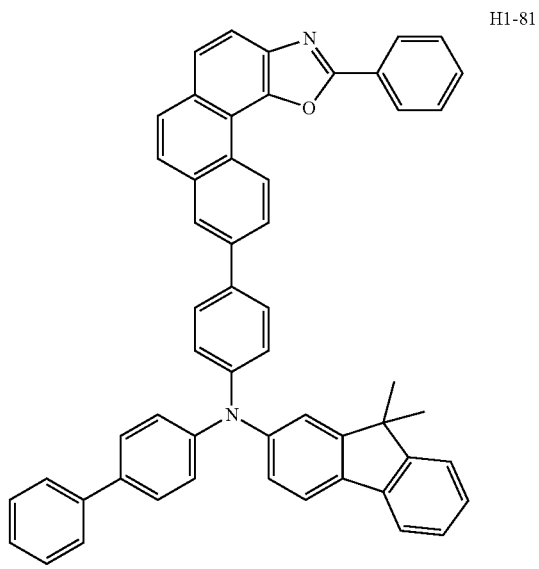
H1-82
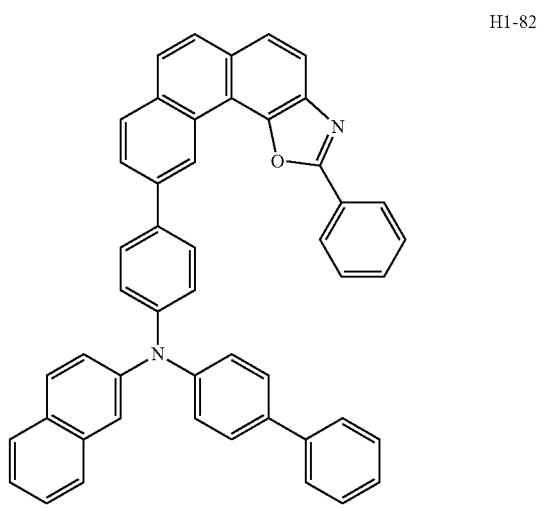
H1-83
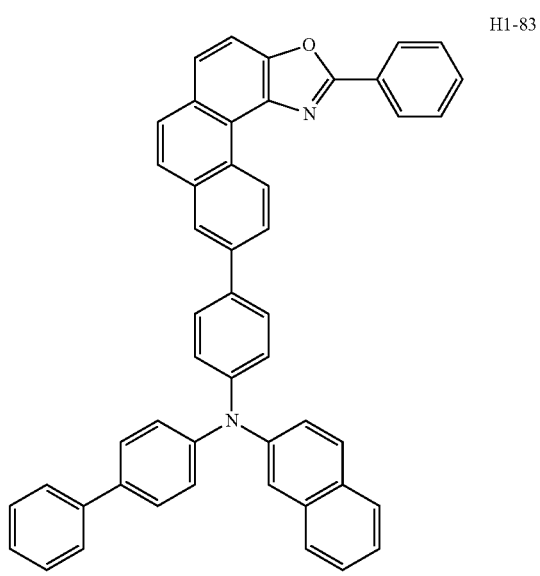

H1-84
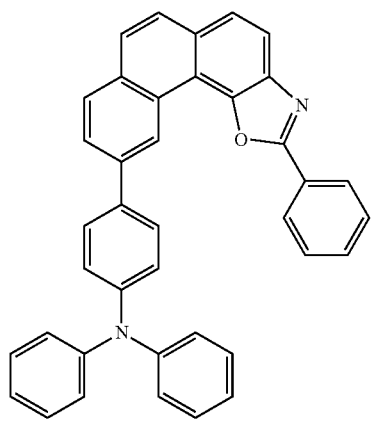
H1-87
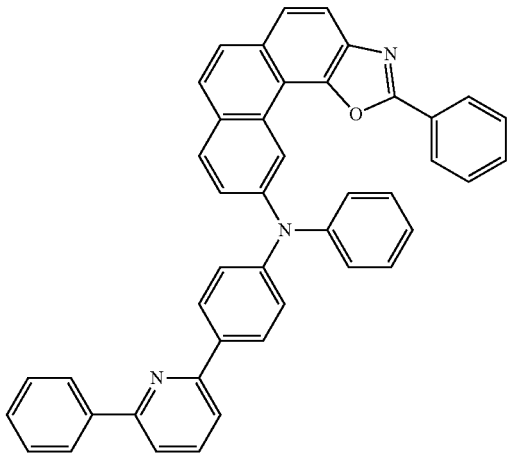
H1-85
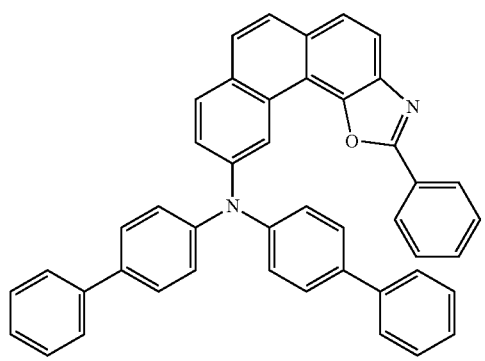
H1-88
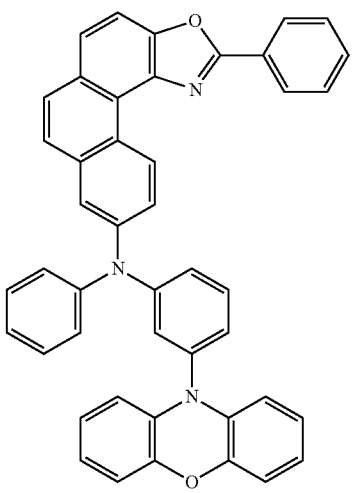
H1-86
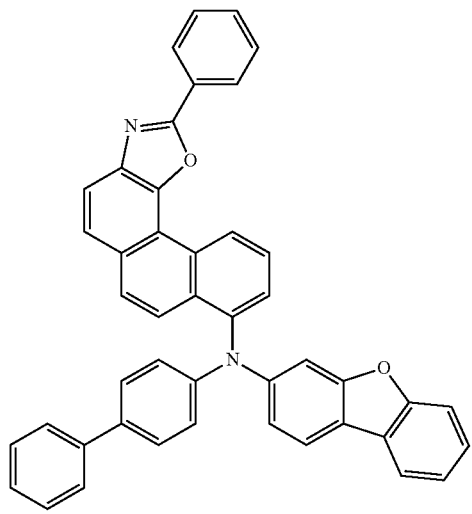
H1-89

H1-90
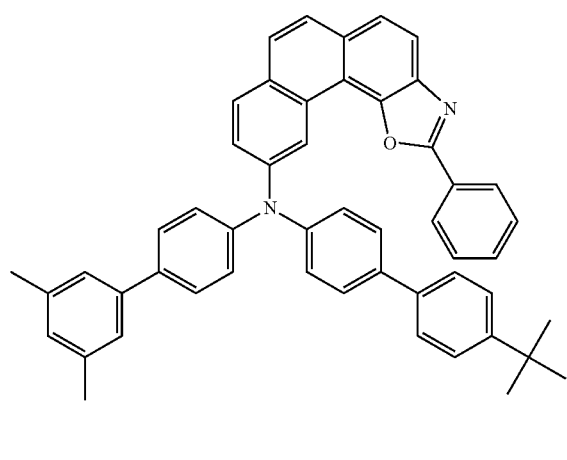
H1-91
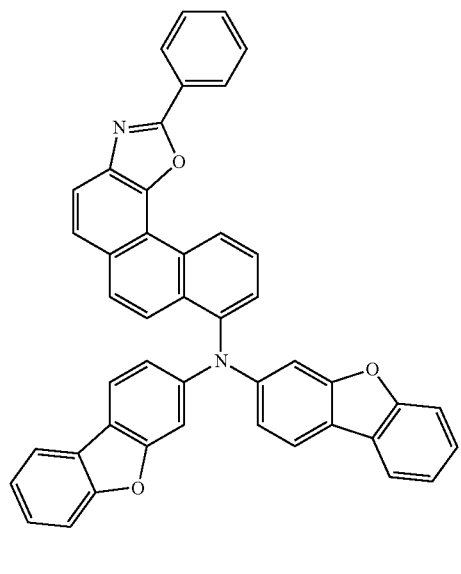
H1-92
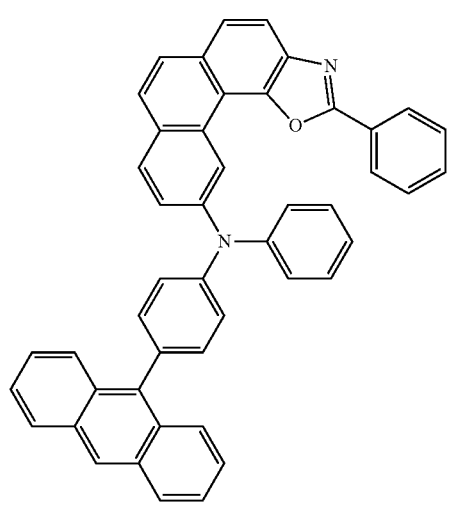
H1-93
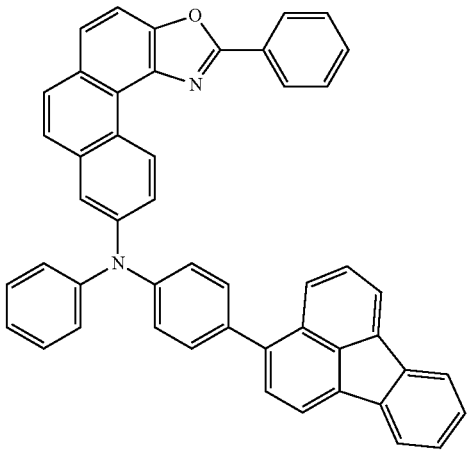
H1-94
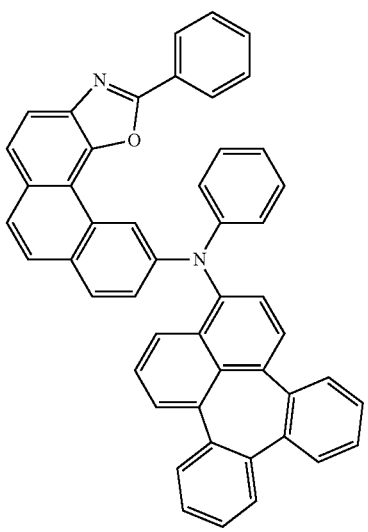
H1-95
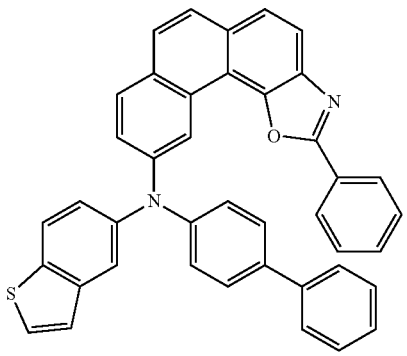

H1-96 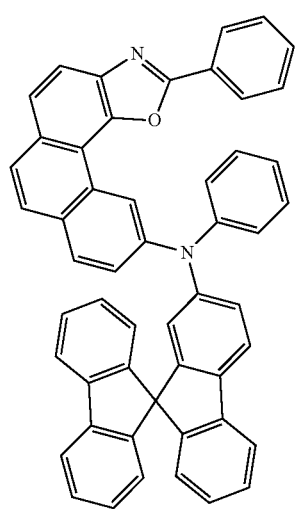
H1-99 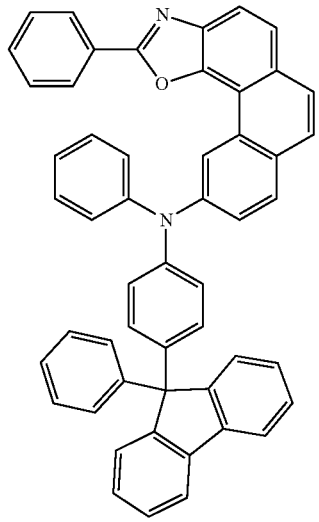
H1-97 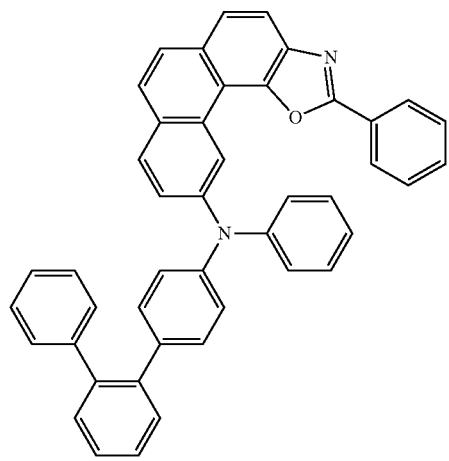
H1-100 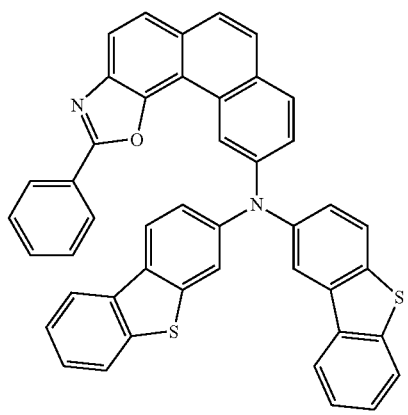
H1-98 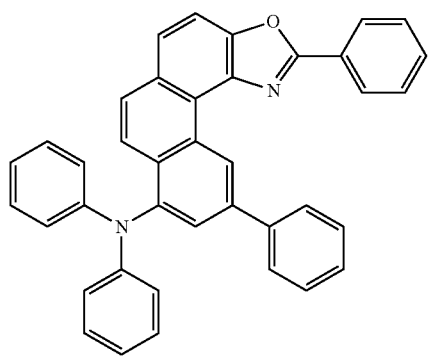
H1-101

H1-102
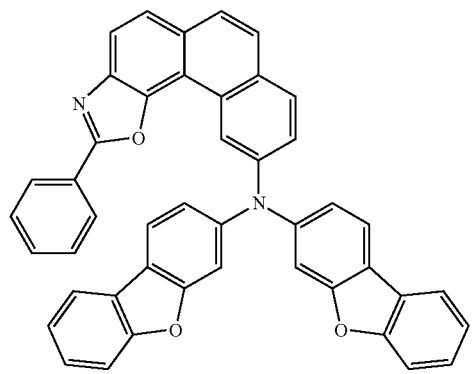
H1-103
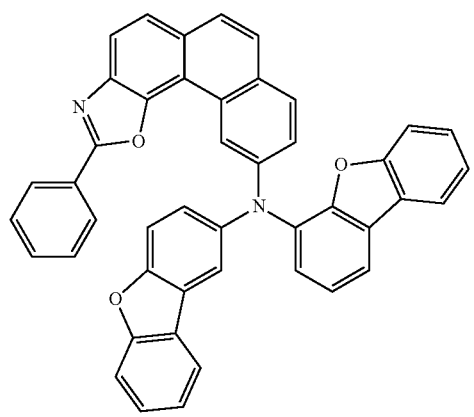
H1-104
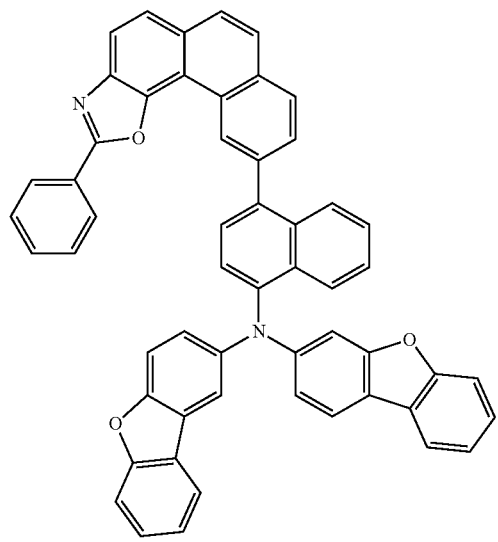
H1-105
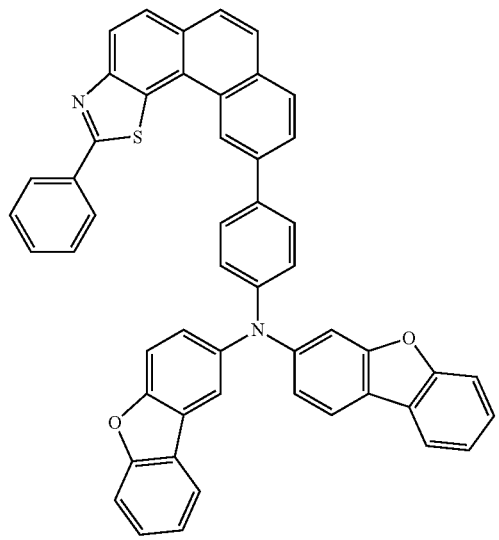
H1-106
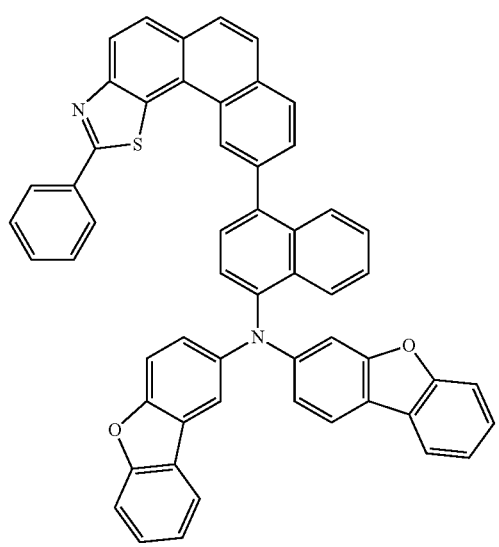
H1-107
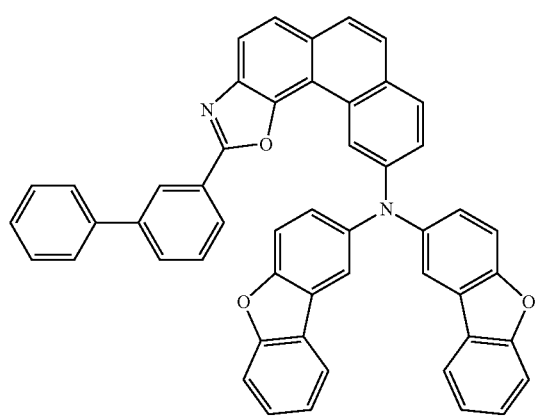

H1-108
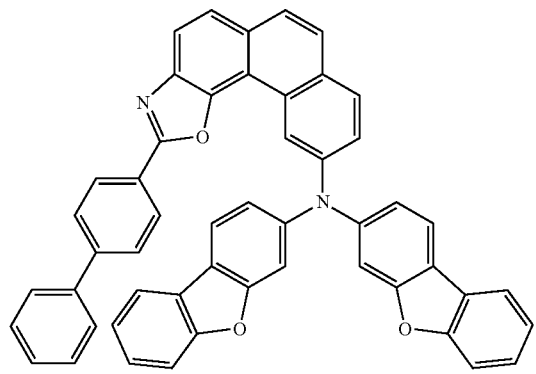
H1-111
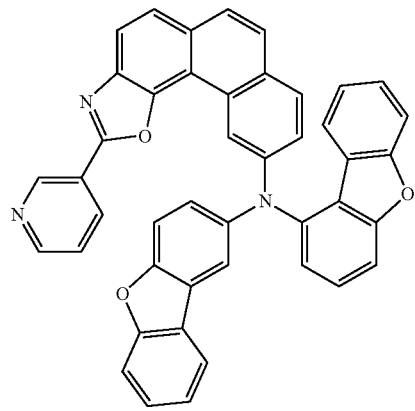
H1-109
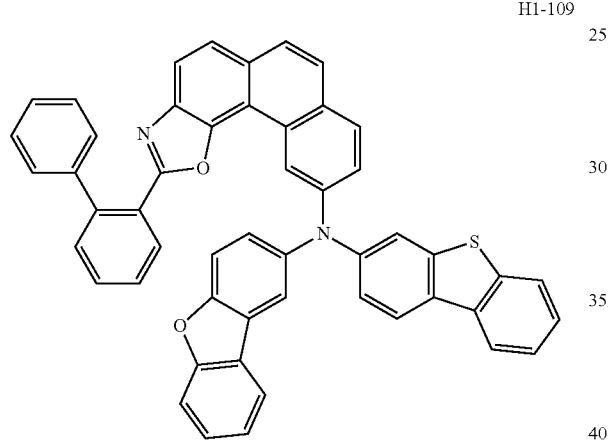
H1-112
H1-110
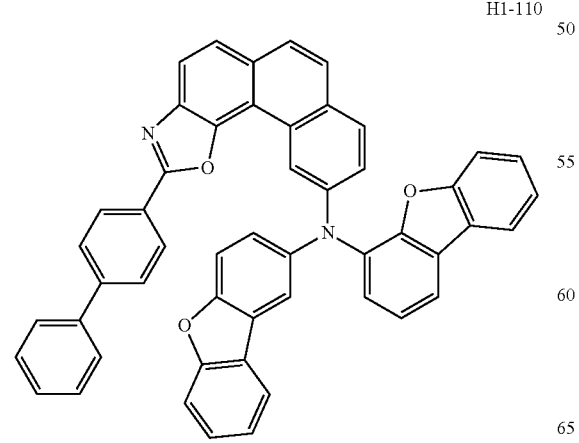
H1-113
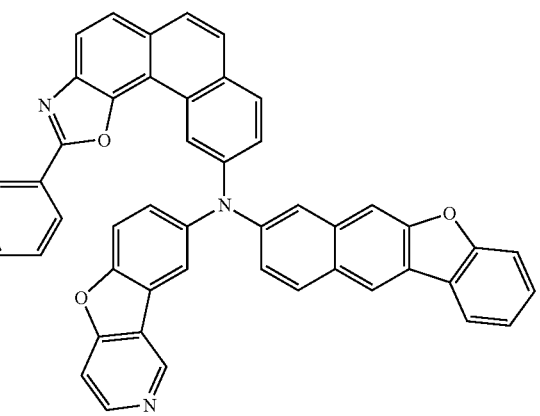

H1-114
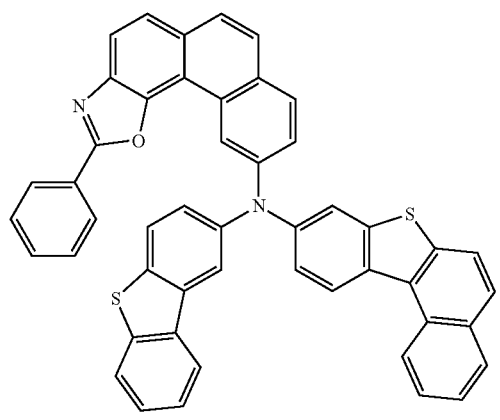
H1-115
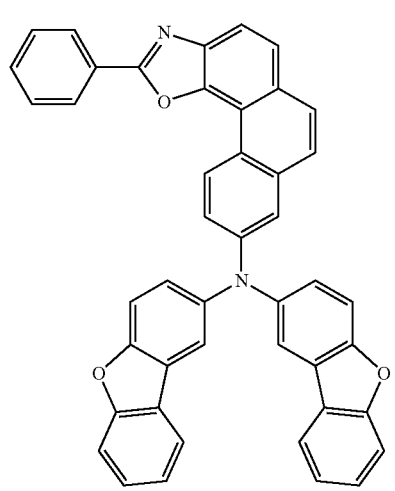
H1-116
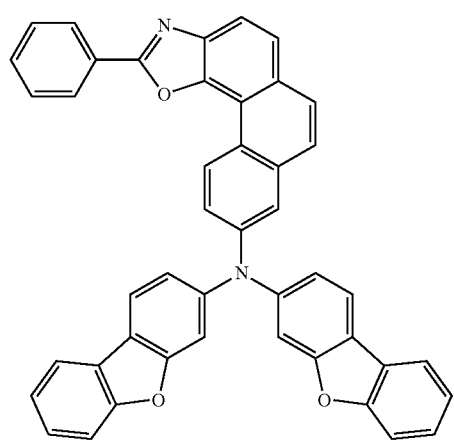
H1-117
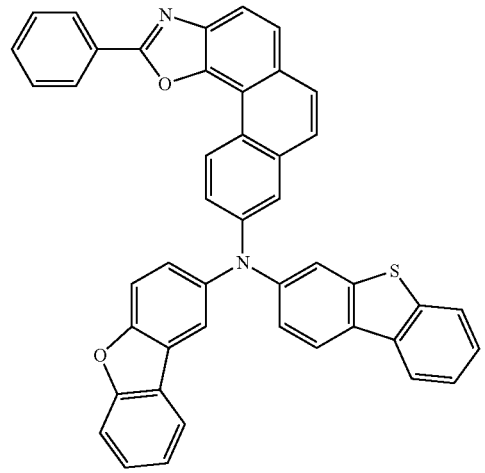
H1-118
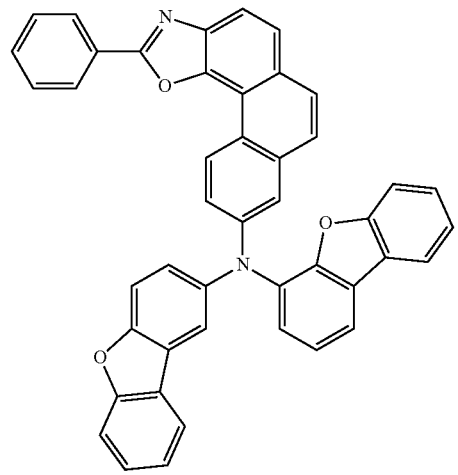
H1-119
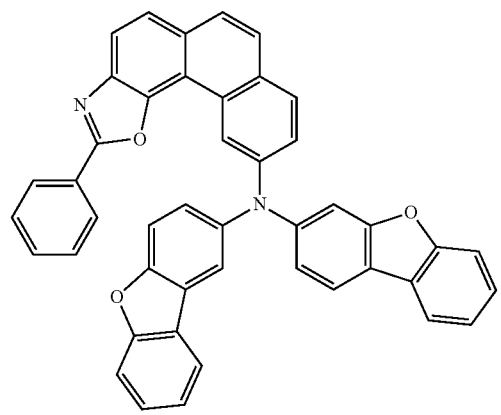

H1-120
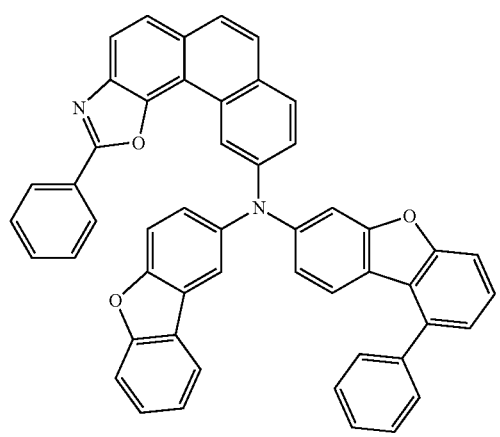
H1-123
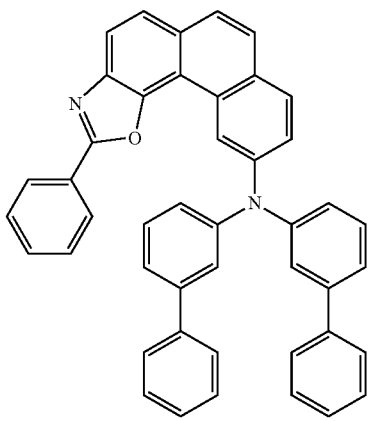
H1-121
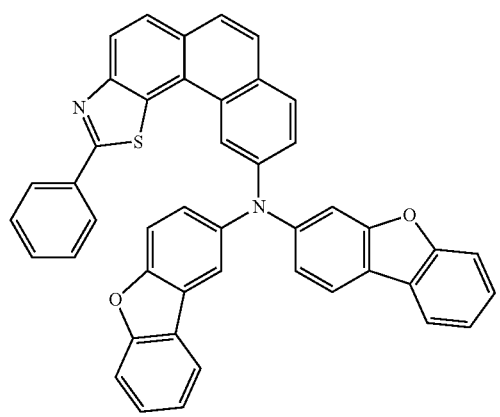
H1-124
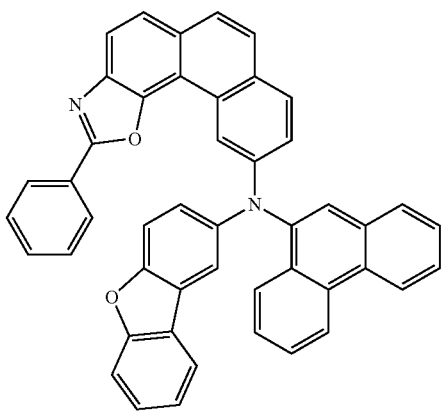
H1-122
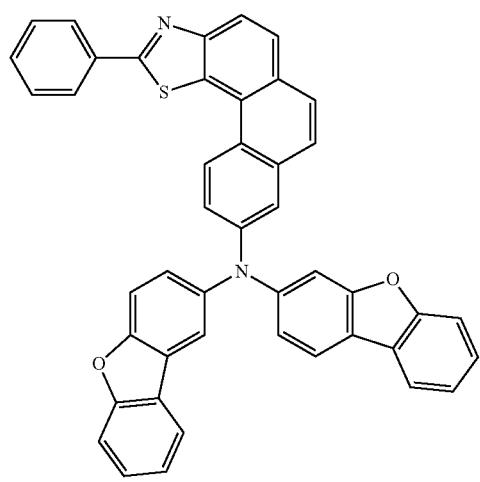
H1-125
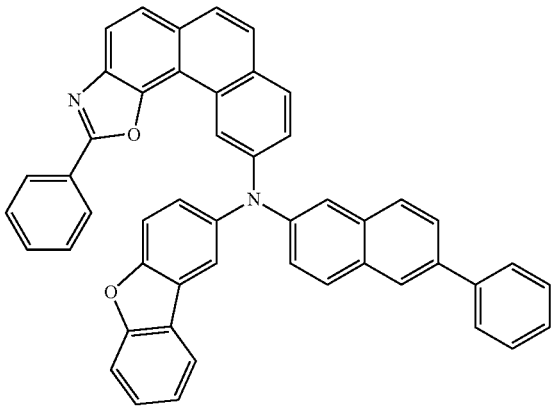

H1-126
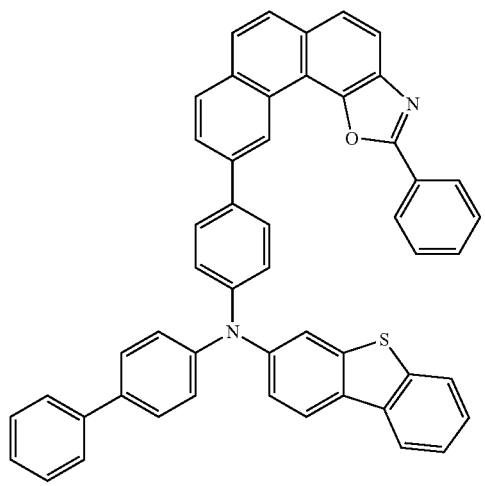
H1-127
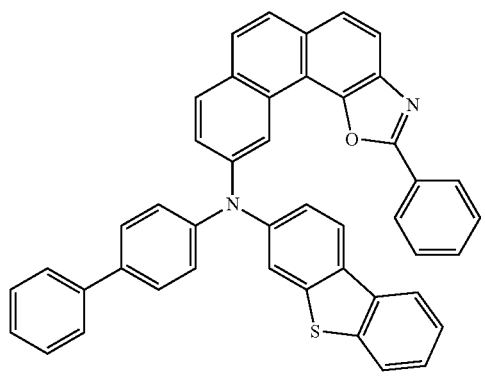
H1-128
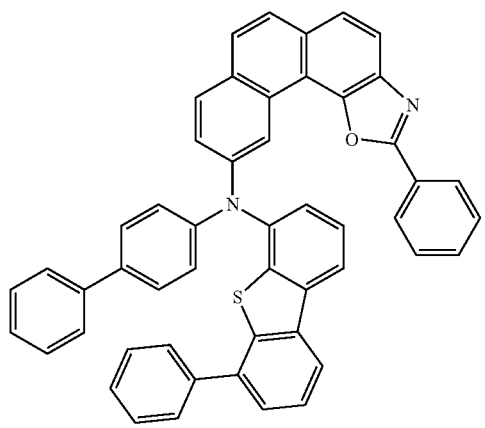
H1-129
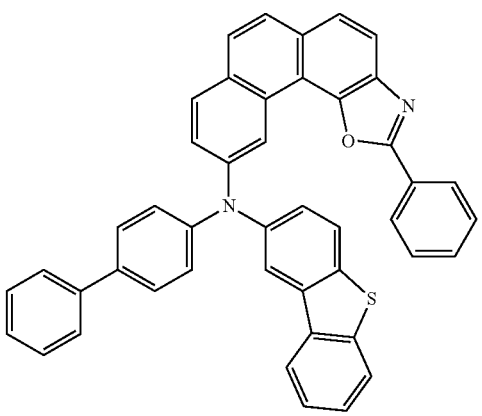
H1-130
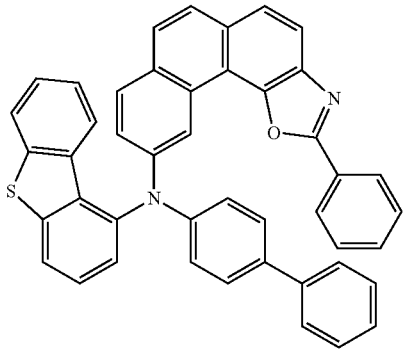
H1-131
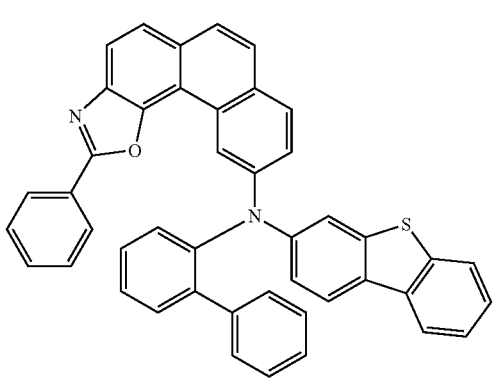

H1-132
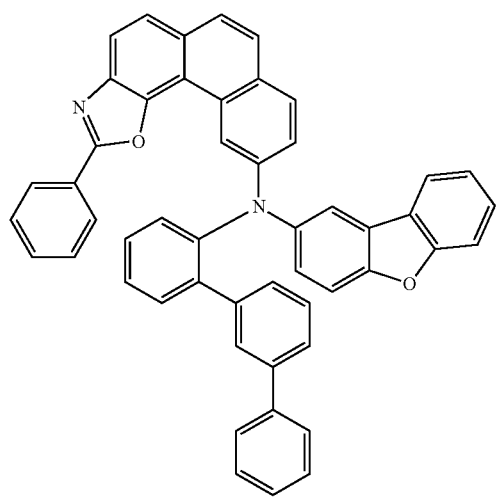
H1-135
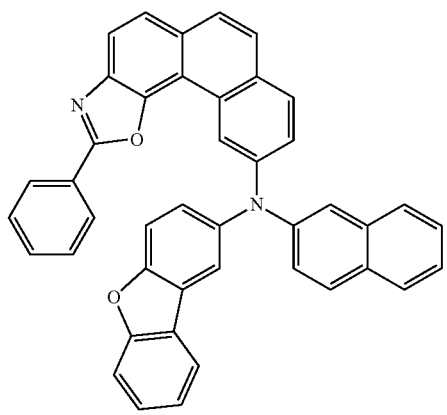
and
H1-133
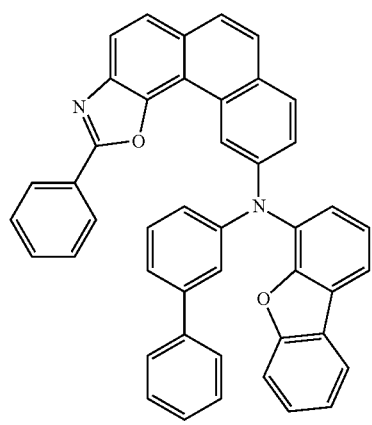
H1-136
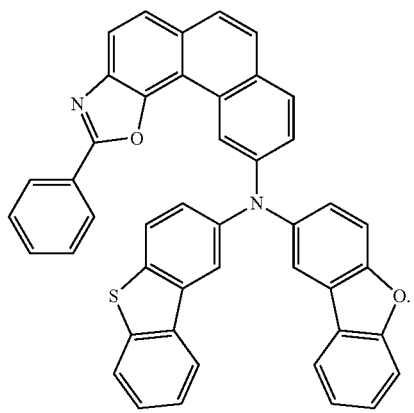
7. The plurality of host materials according to claim 1, wherein the compound represented by formula 2 is at least one selected from the following compounds:
H1-134
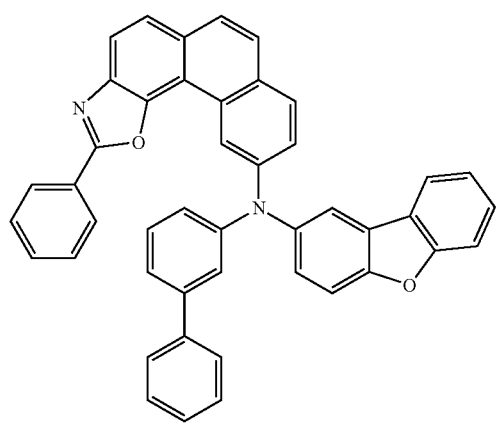
C-1
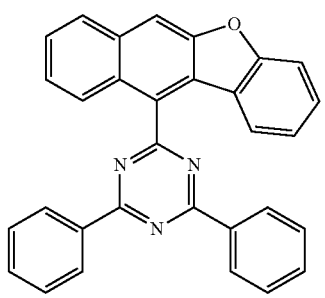

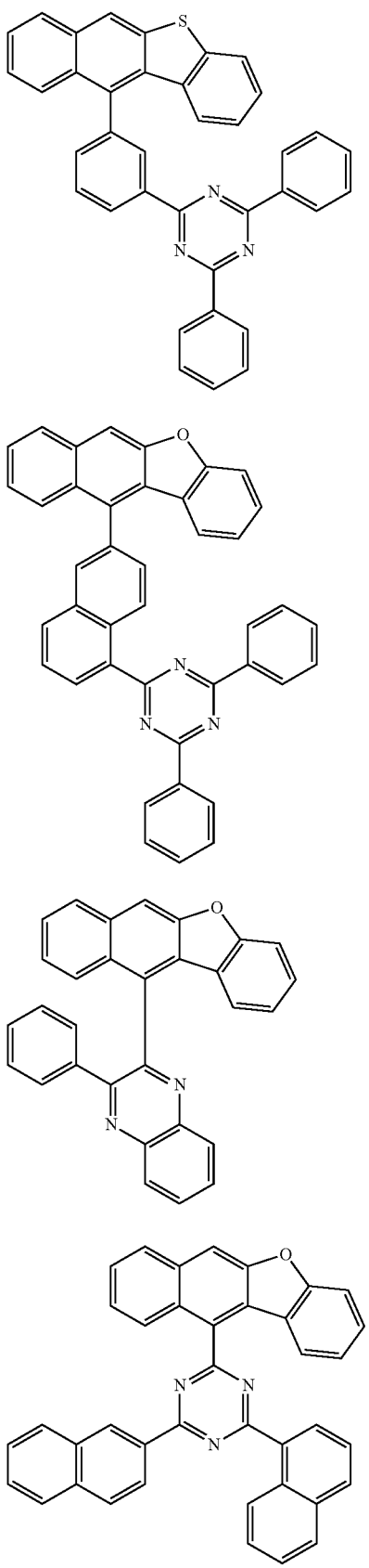
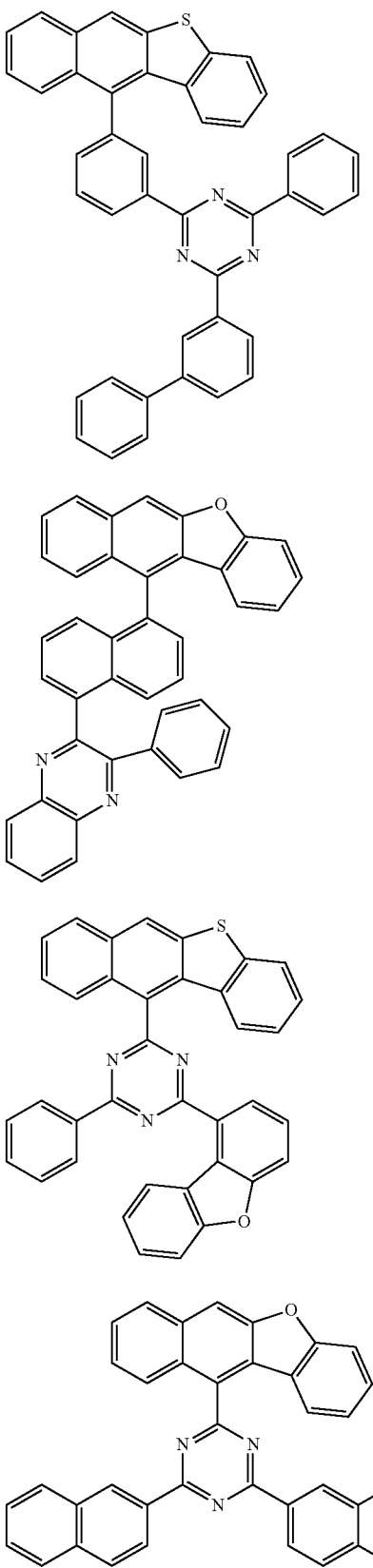

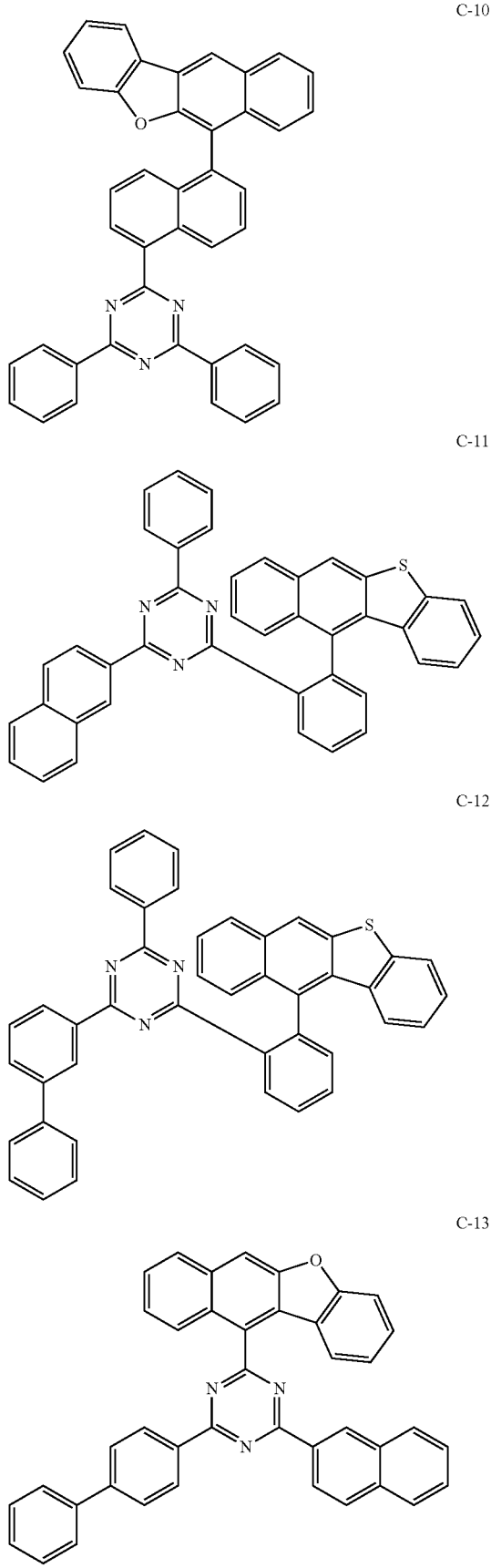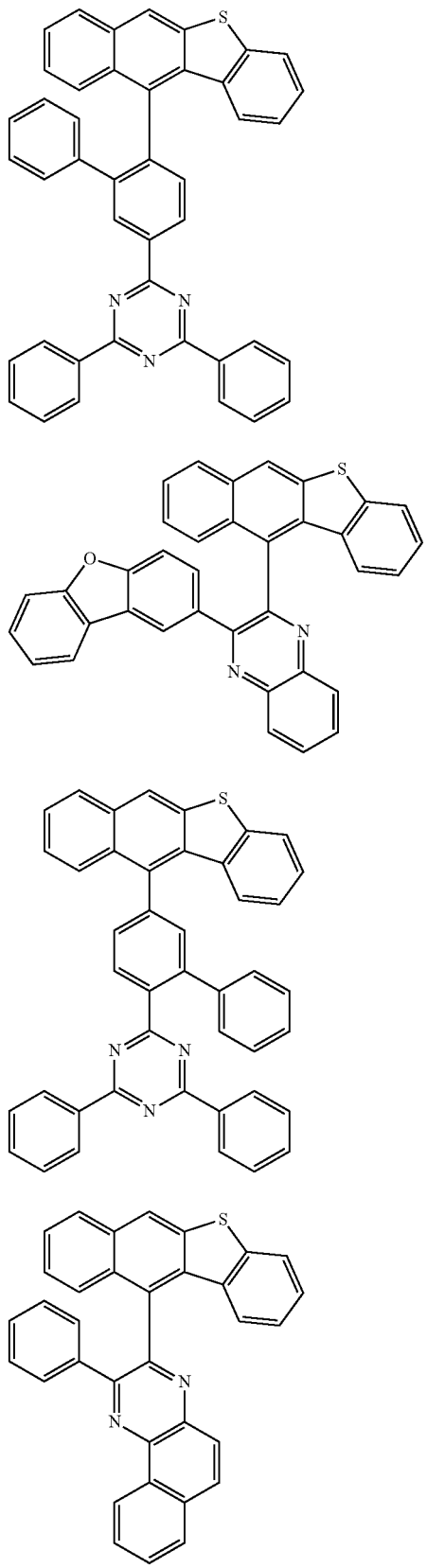

-continued
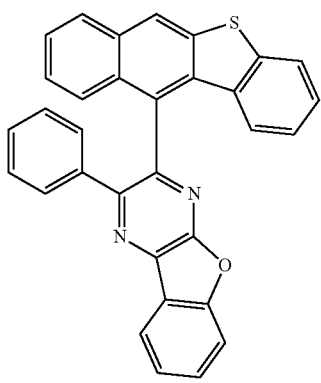
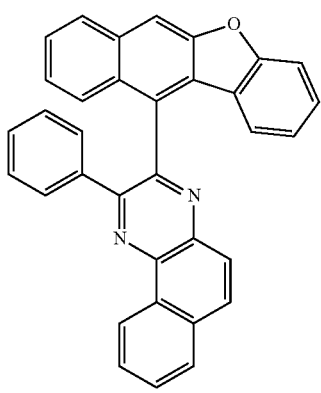
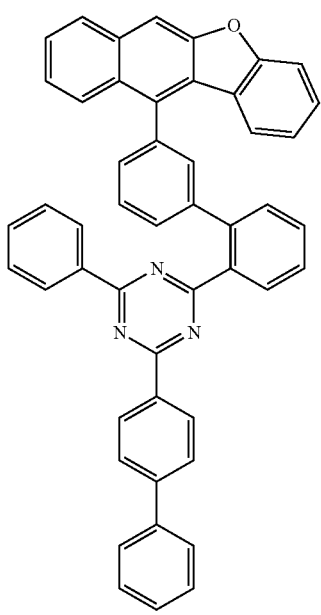
-continued
C-18
C-19
C-20
C-21
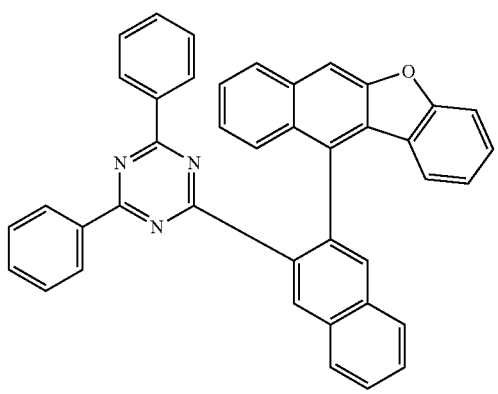
C-22
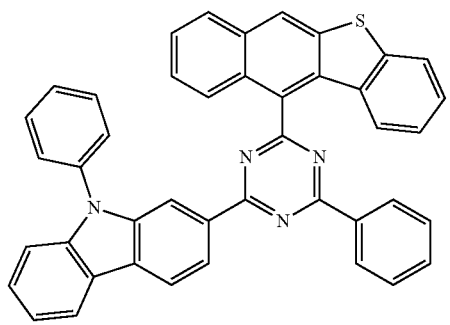
C-23
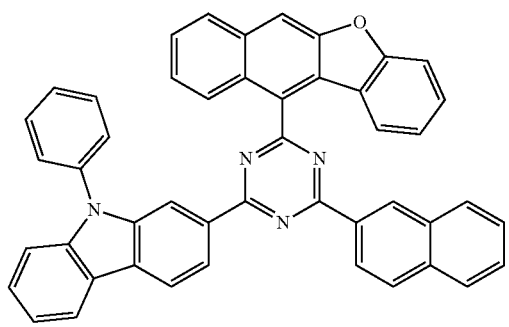
C-24
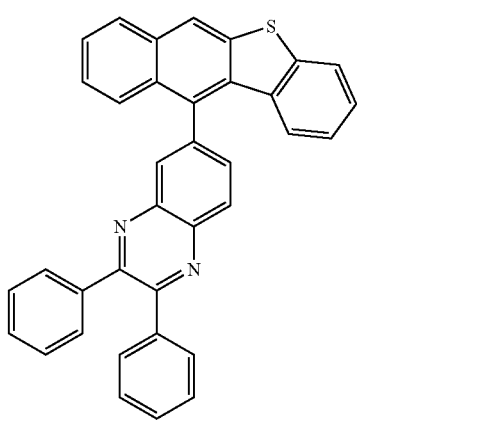

C-25 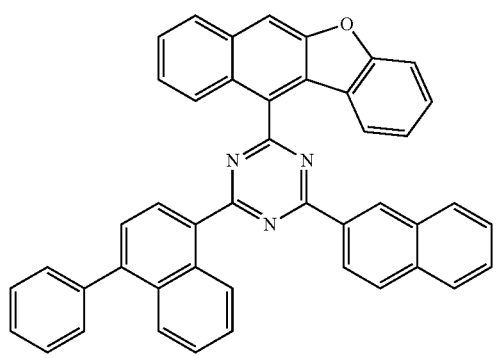
C-26 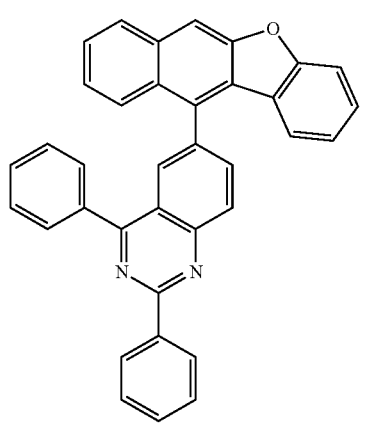
C-27 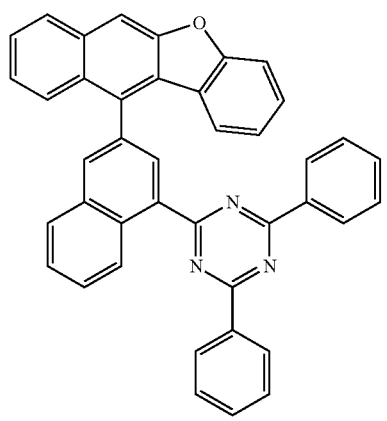
C-28 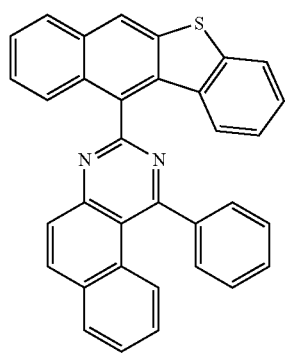
C-29 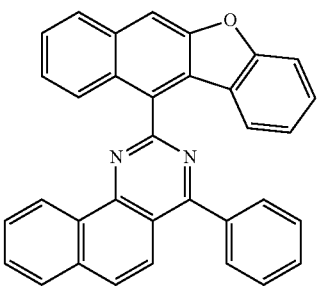
C-30 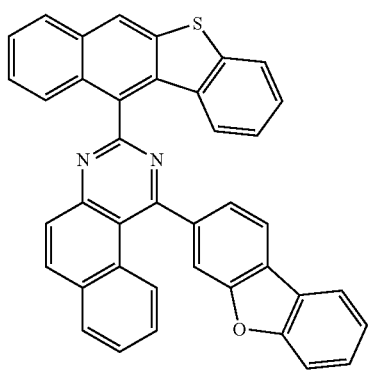
C-31 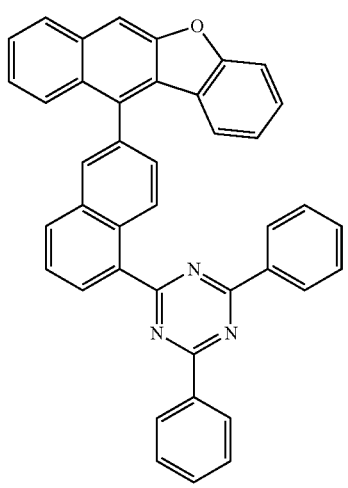
C-32 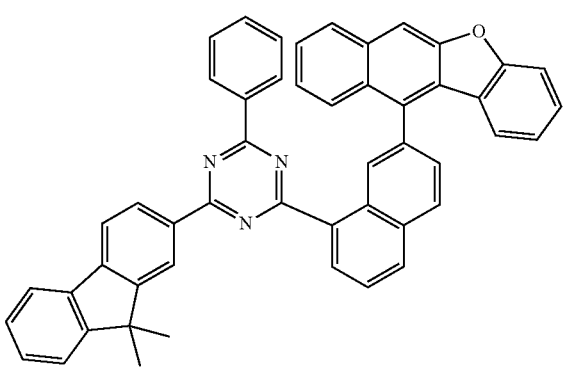

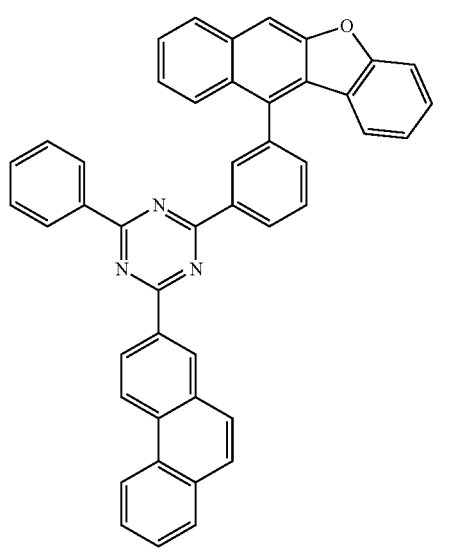
C-33
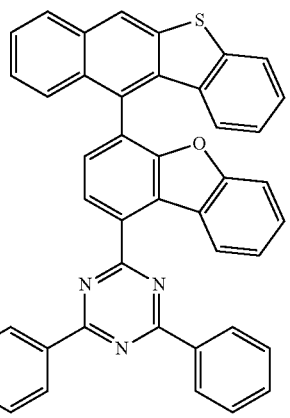
C-36
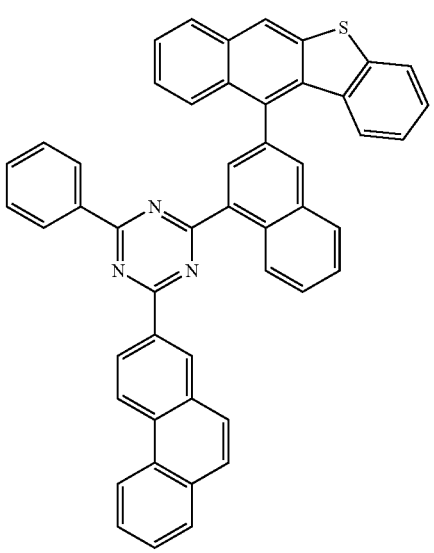
C-37
C-34
C-35
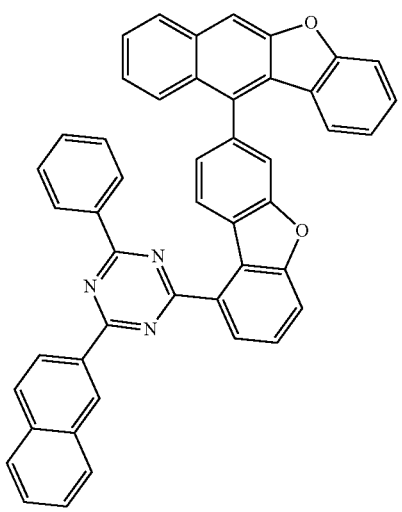
C-38

C-39
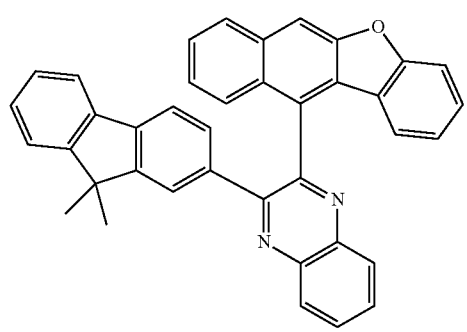
C-40
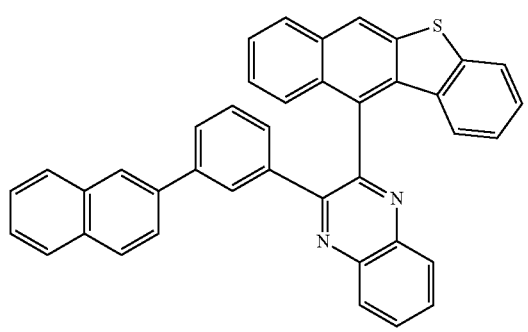
C-41
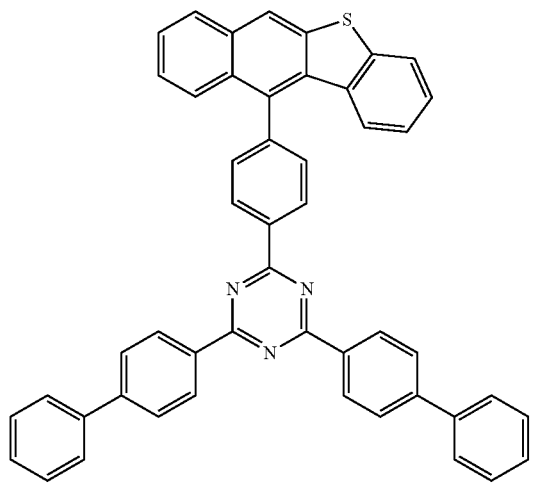
C-42
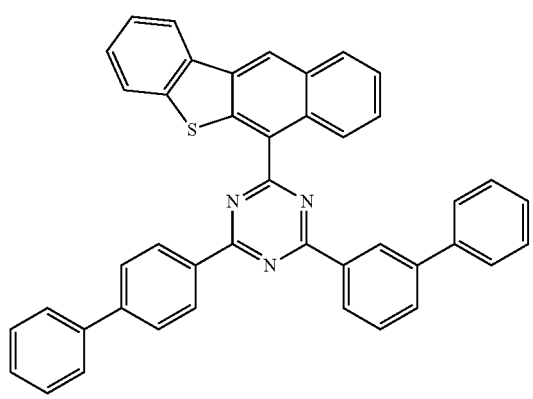
C-43
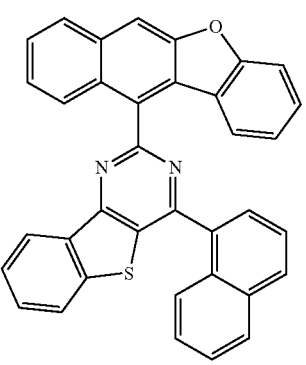
C-44
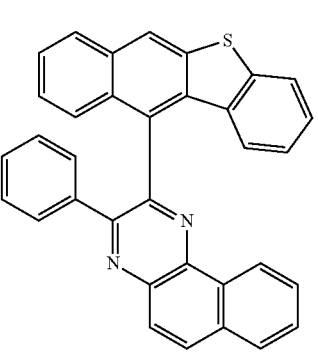
C-45
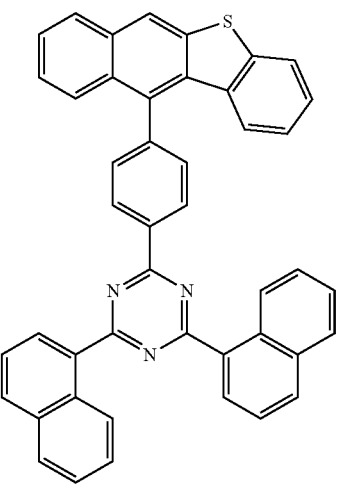
C-46
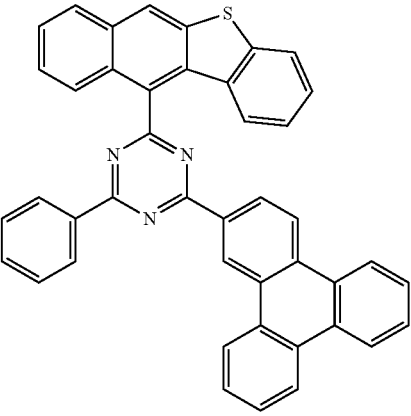

C-47
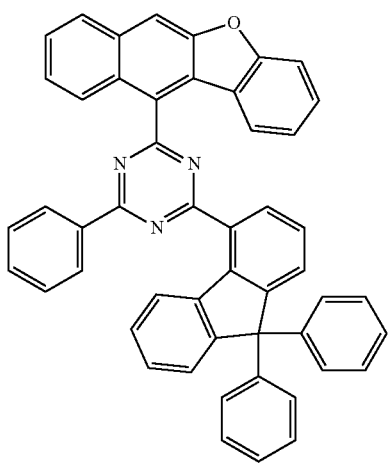
C-48
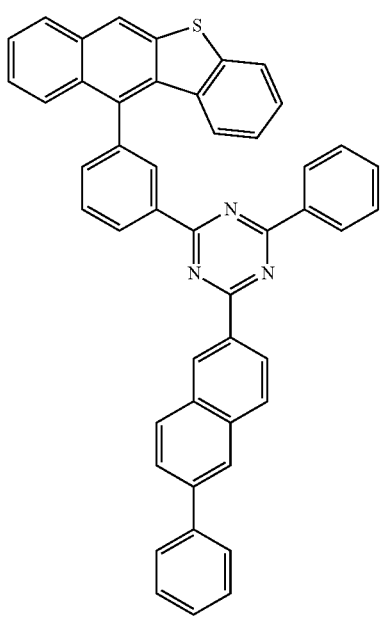
C-49
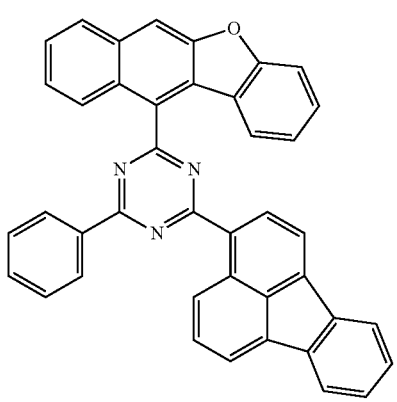
C-50
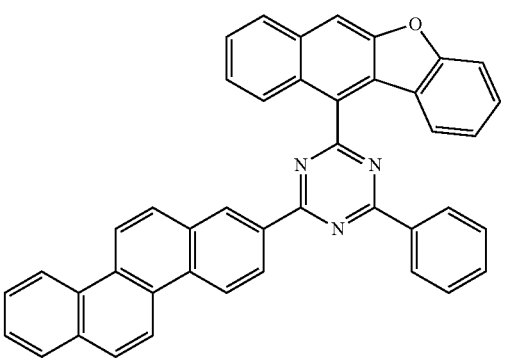
C-51
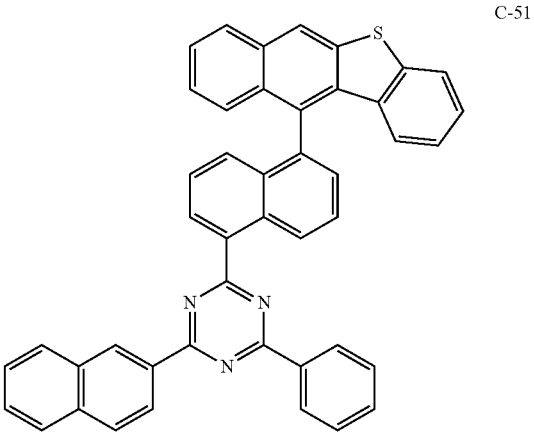
C-52
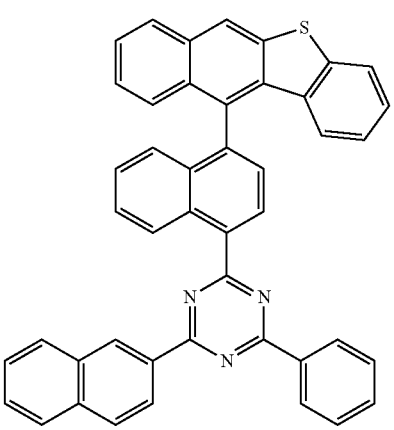

C-53
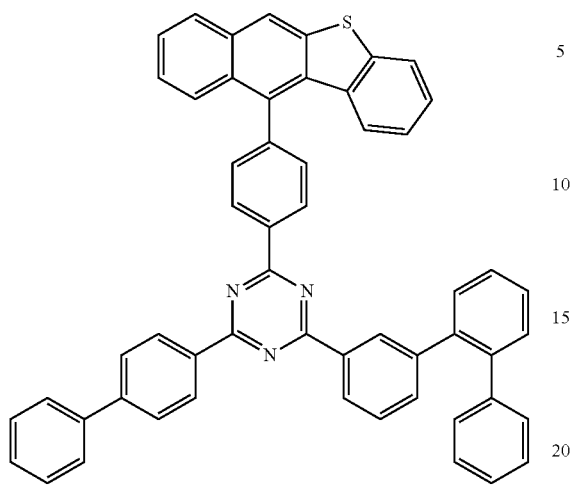
C-54
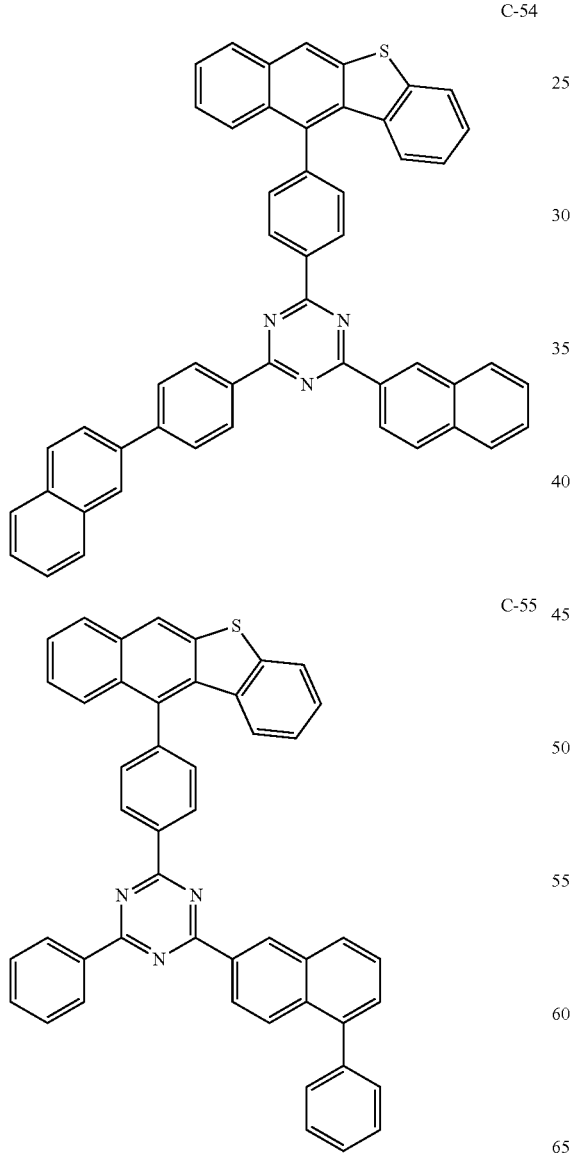
C-55
C-56
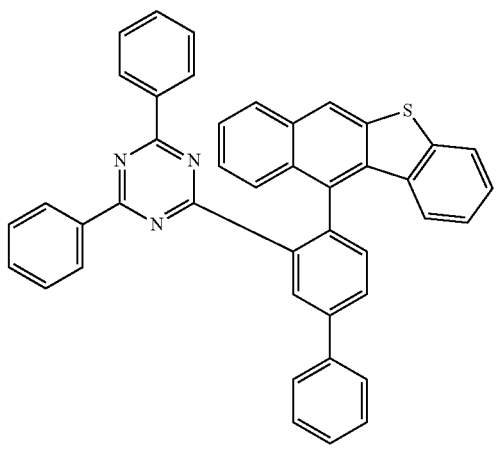
C-57
C-58
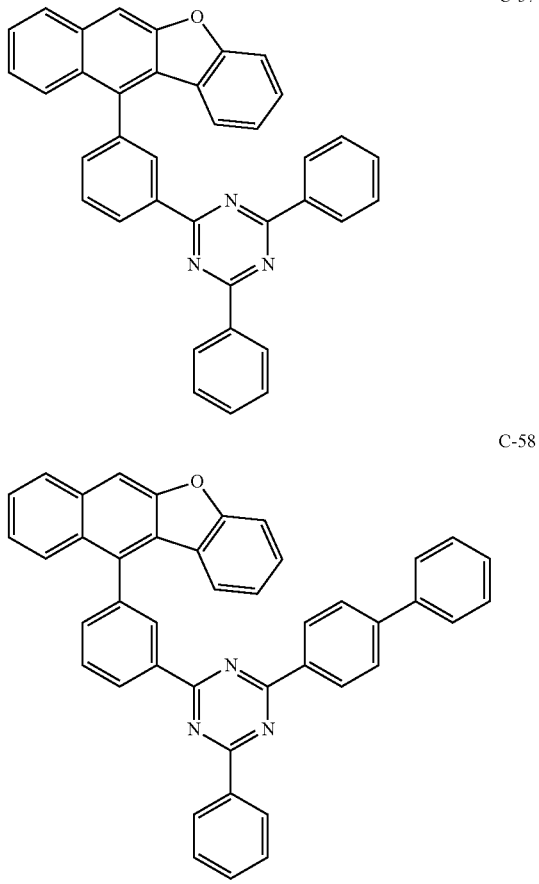
C-59
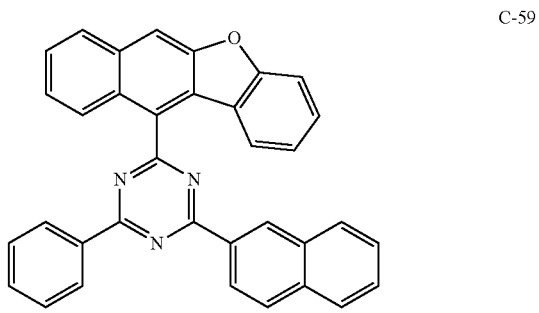

C-60
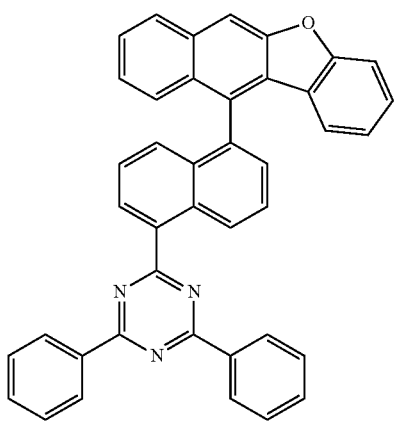
C-61
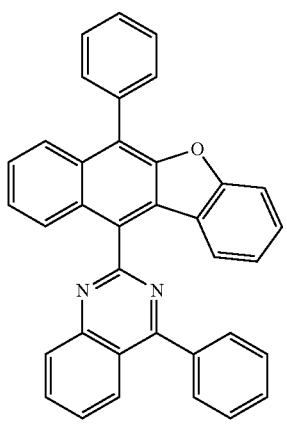
C-62
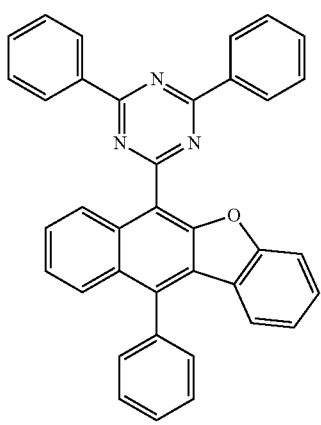
C-63
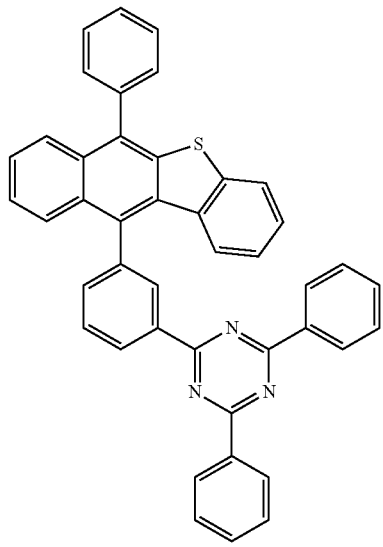
C-64
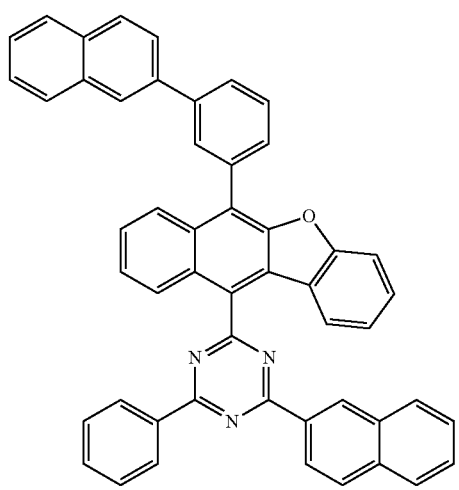
C-65
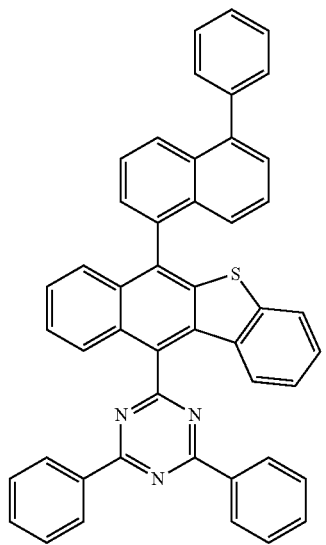

C-66
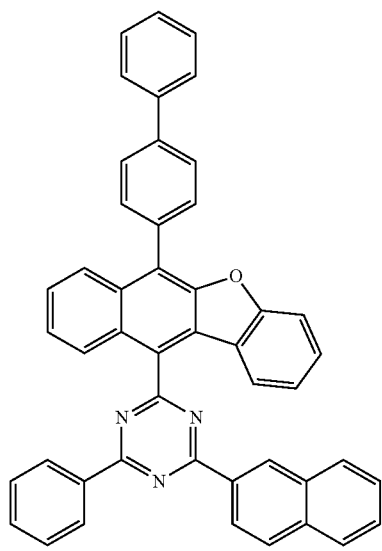
C-67
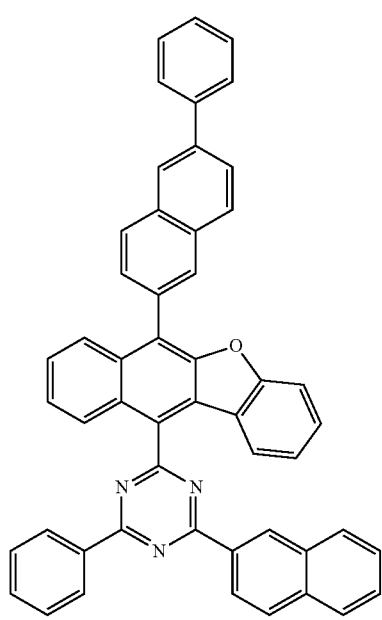
C-68
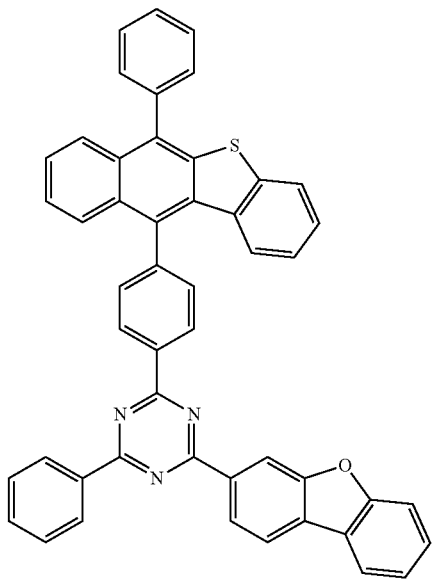
C-69
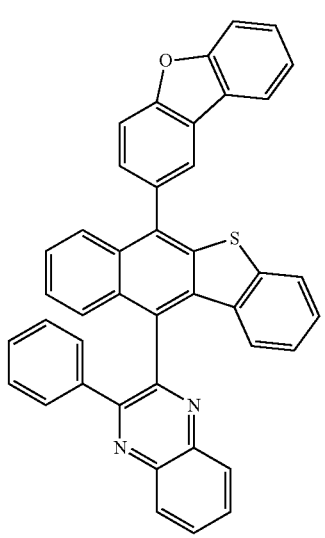

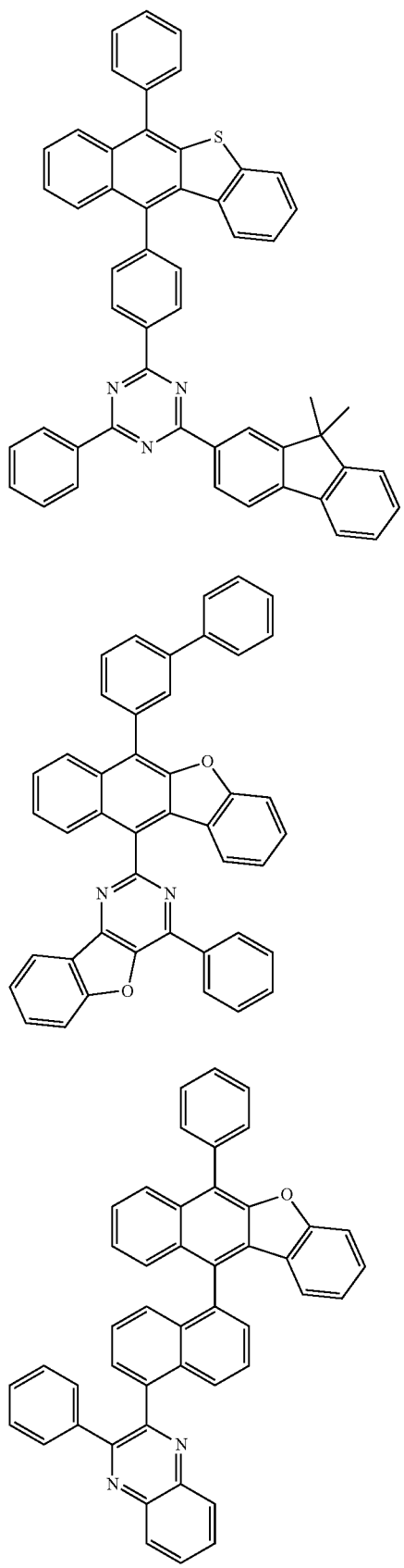
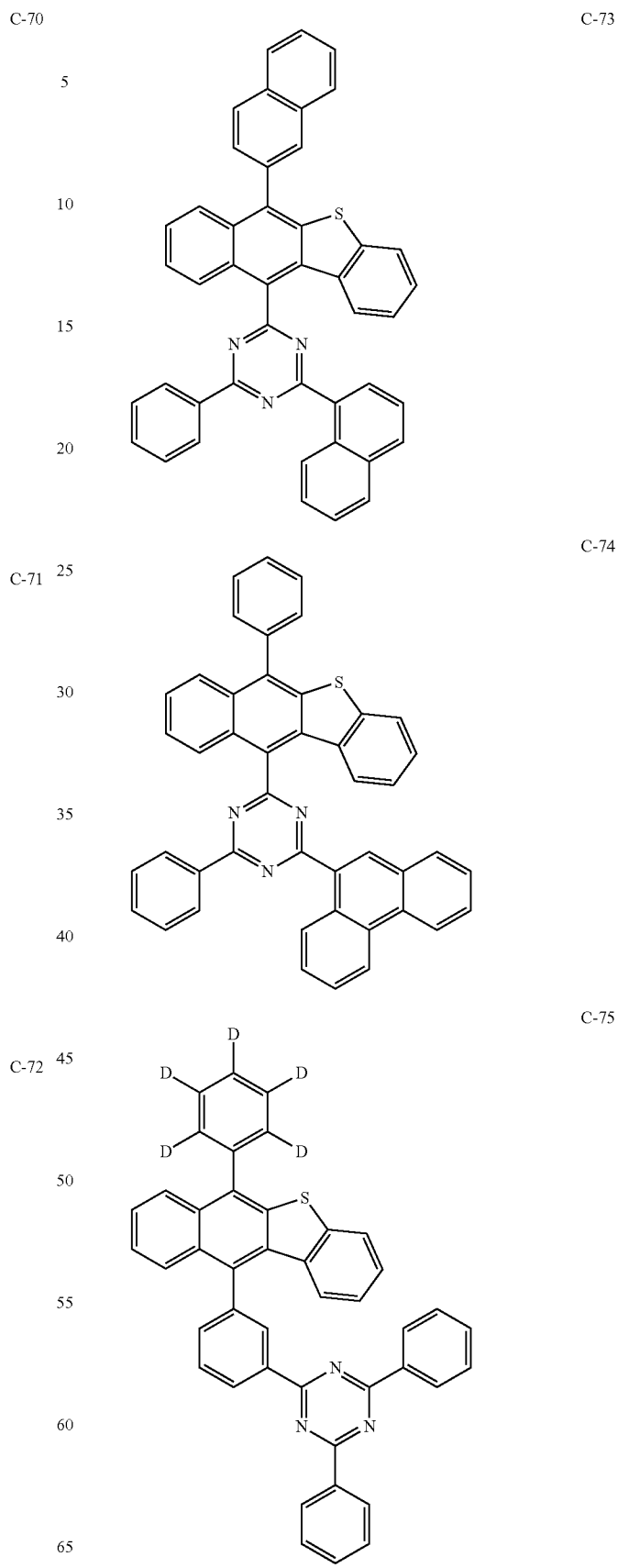

C-76
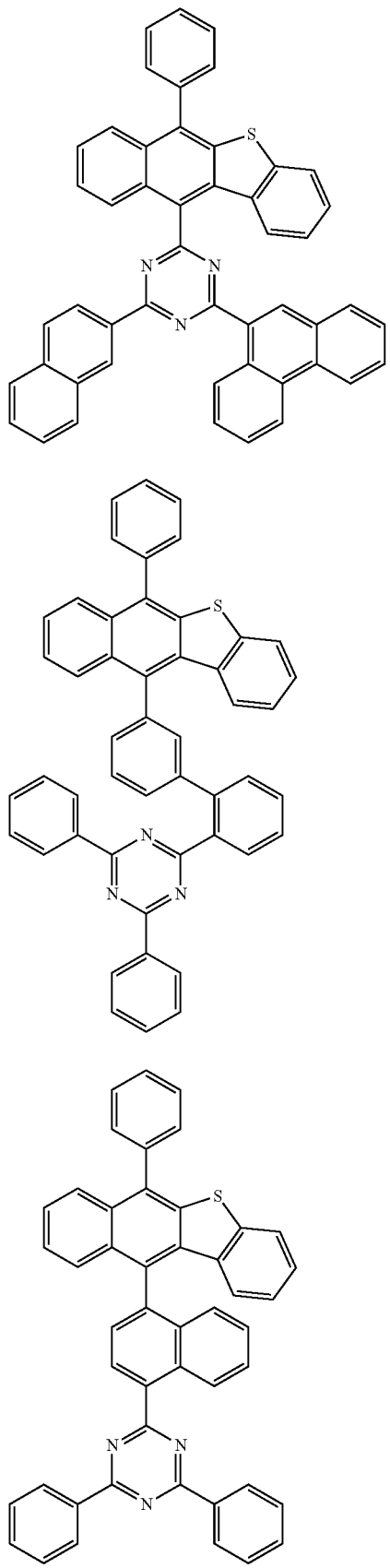
C-77
C-78
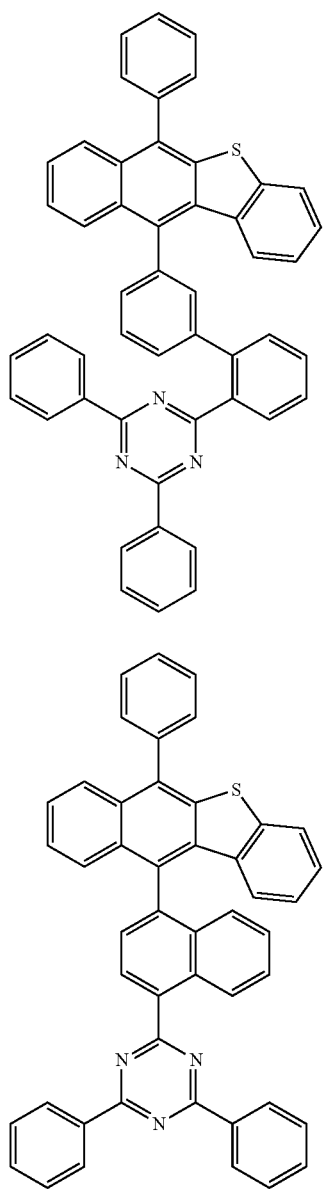
C-79
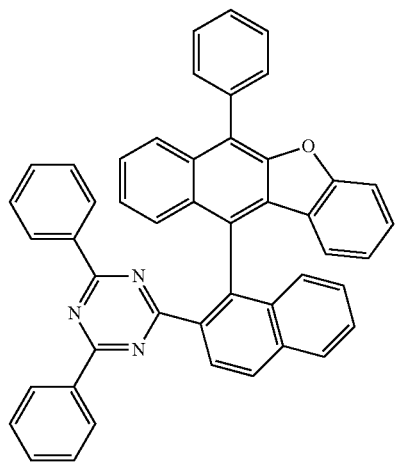
C-80
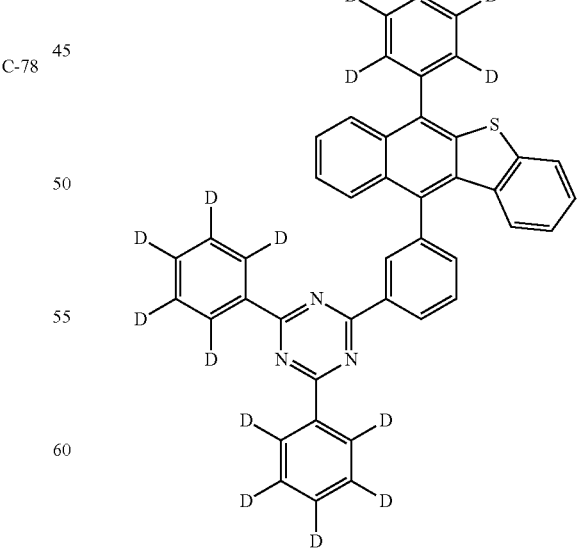

C-81
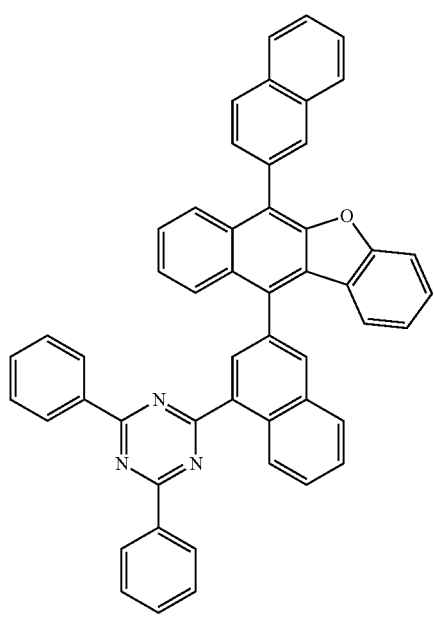
C-83
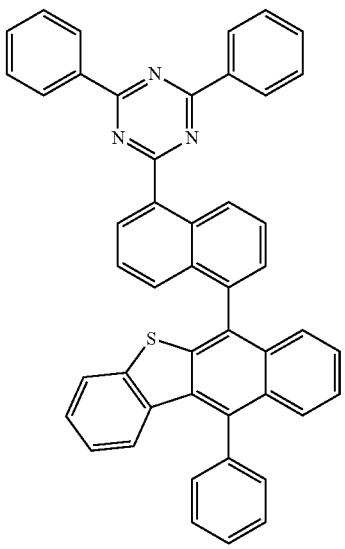
C-82
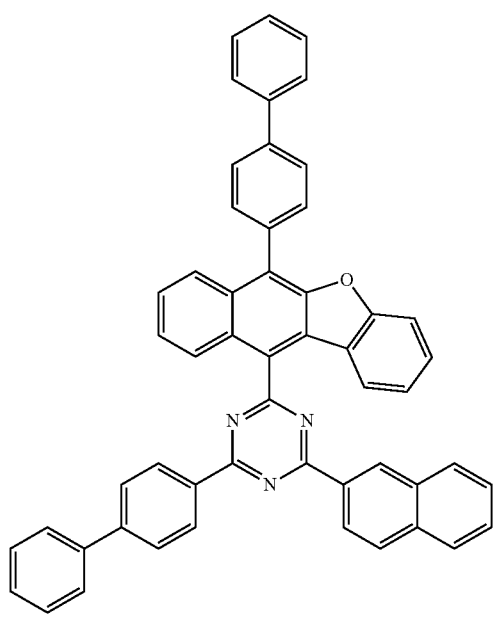
C-84
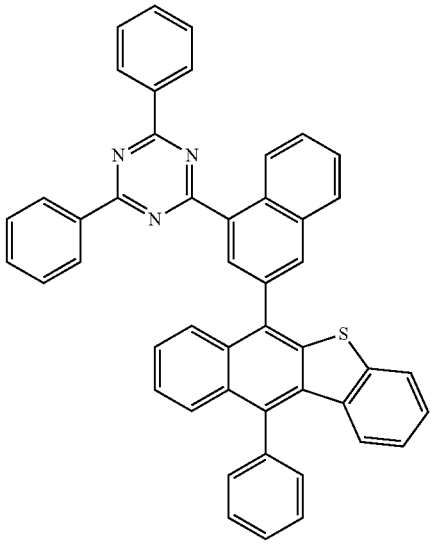

C-85
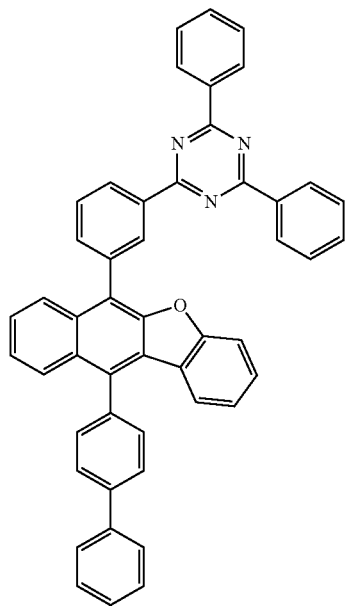
C-86
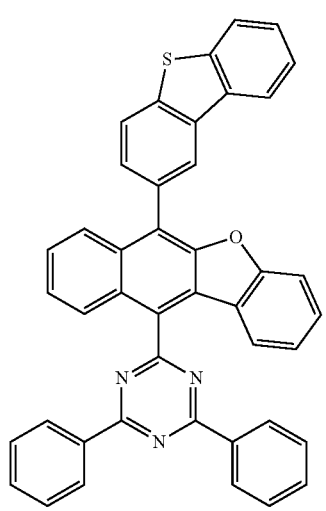
C-87
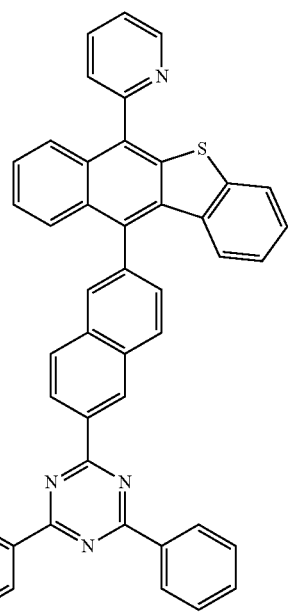
C-88
C-89
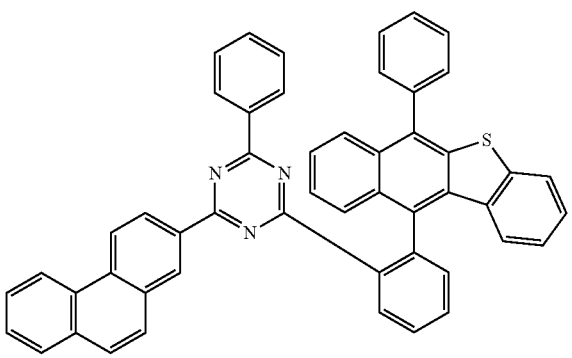

C-90
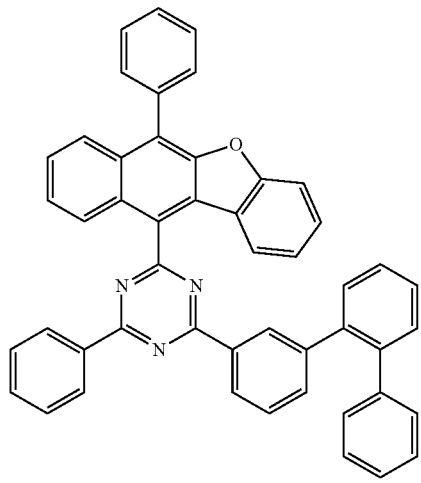
C-91
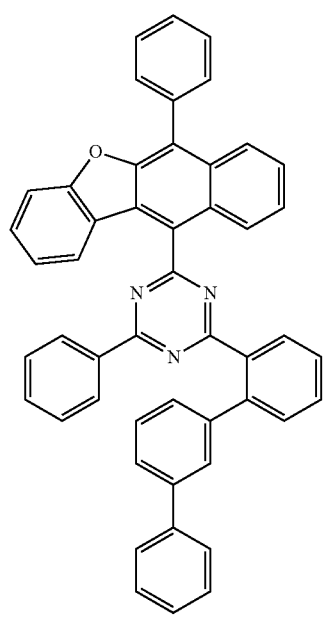
C-92
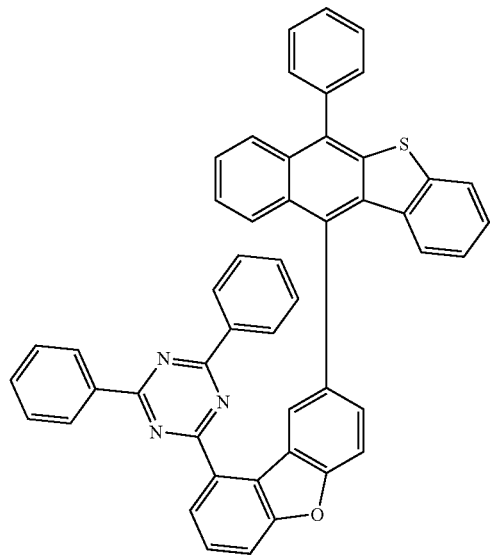
C-93
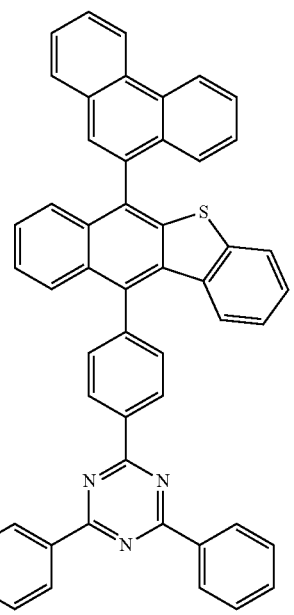
C-94
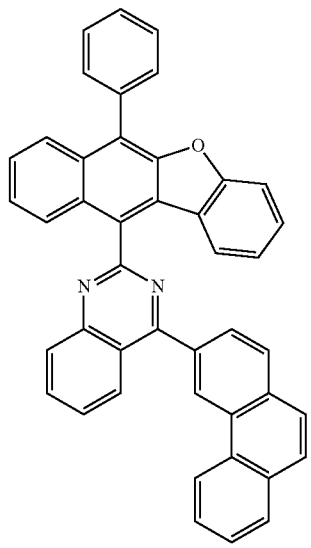
C-95
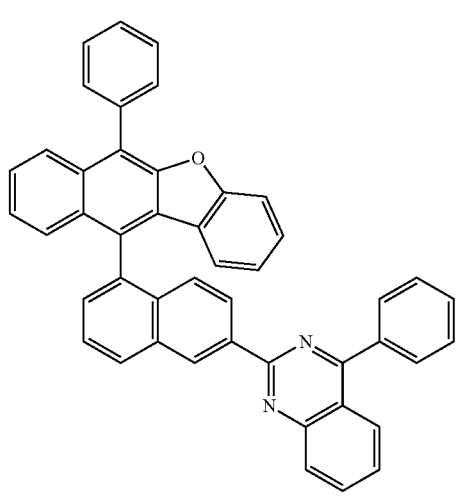

C-96
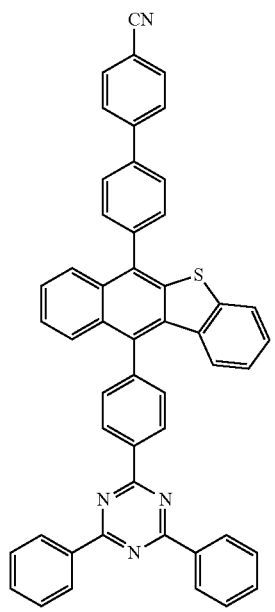
C-97
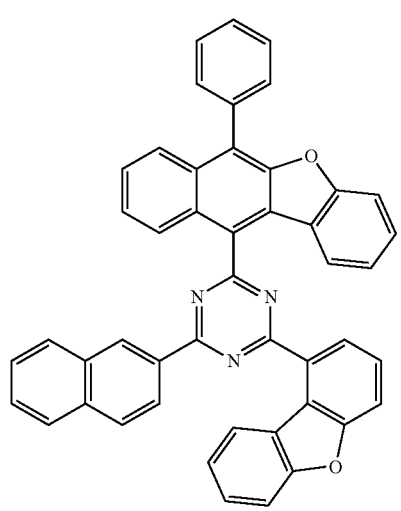
C-98
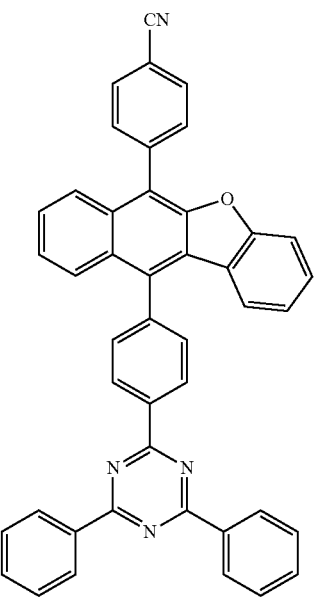
C-99
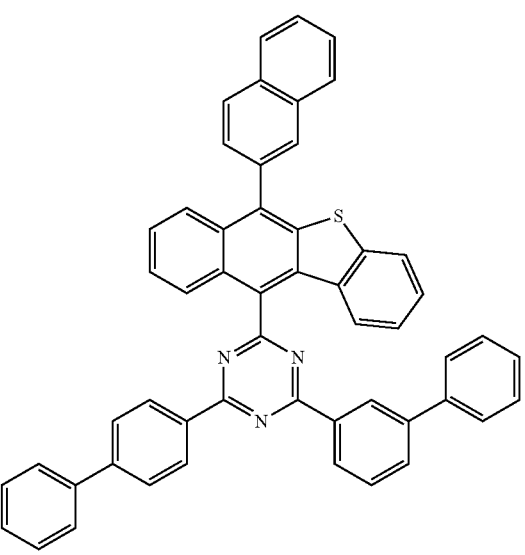
C-100

C-101
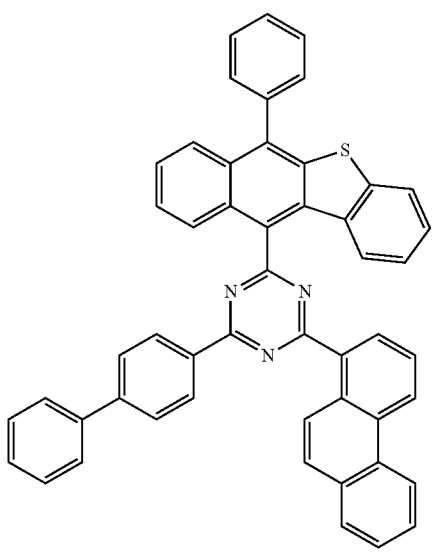
C-102
C-103
C-104
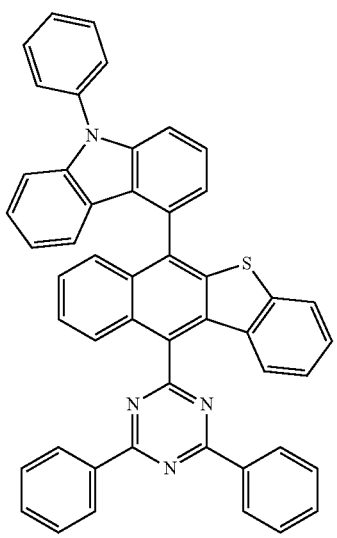
C-105
C-106
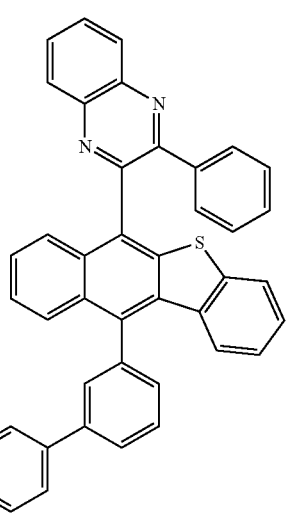
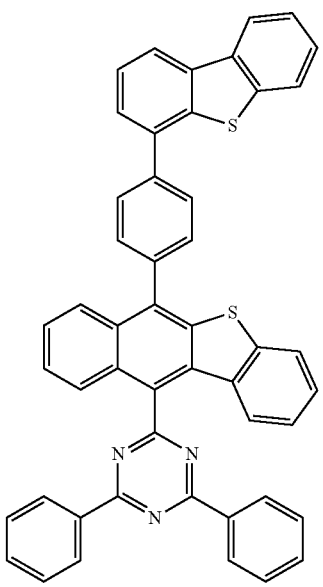

C-107
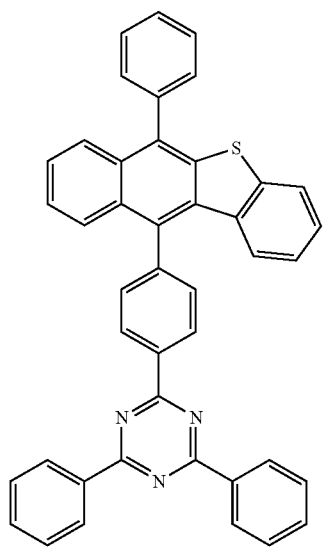
C-108
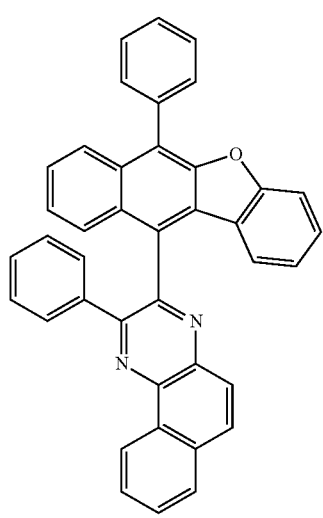
C-109
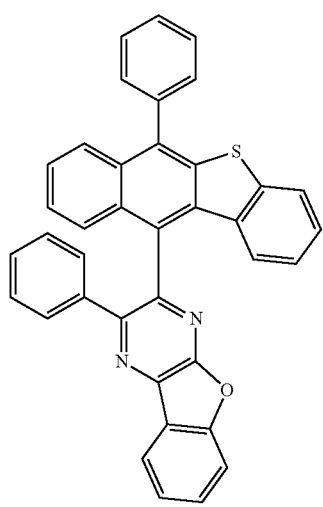
C-110
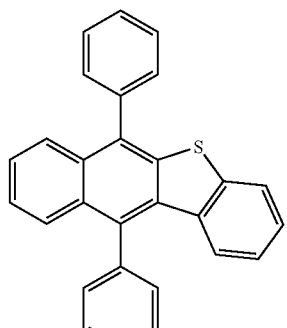
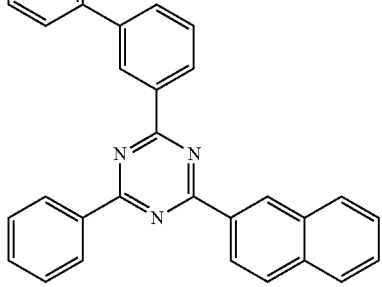
C-111
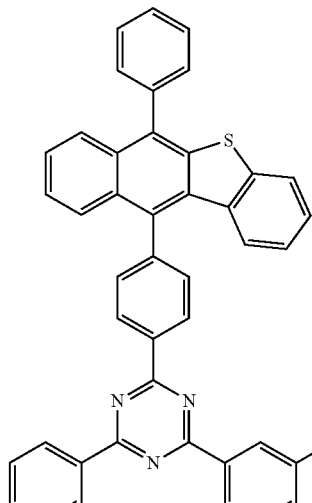

C-112
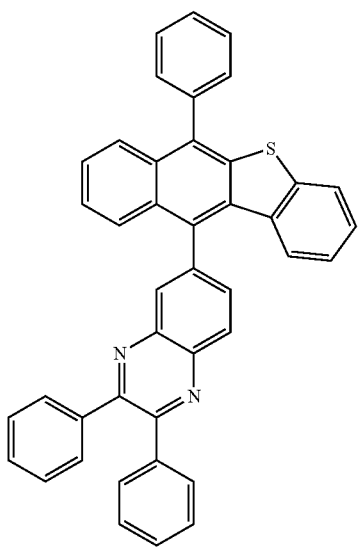
C-113
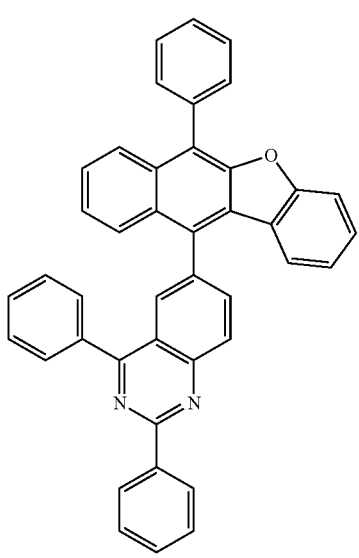
C-114
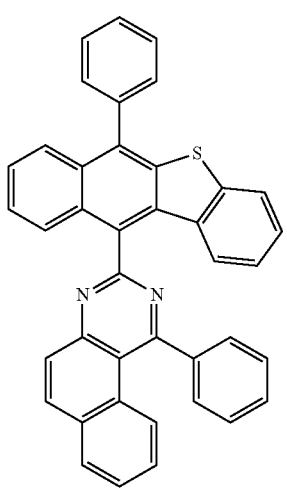
C-115
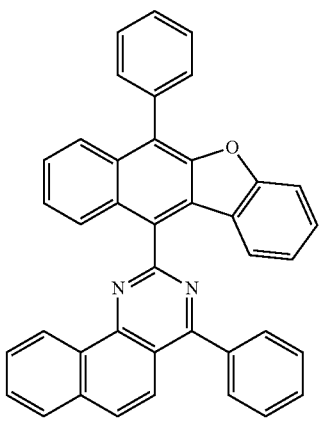
C-116
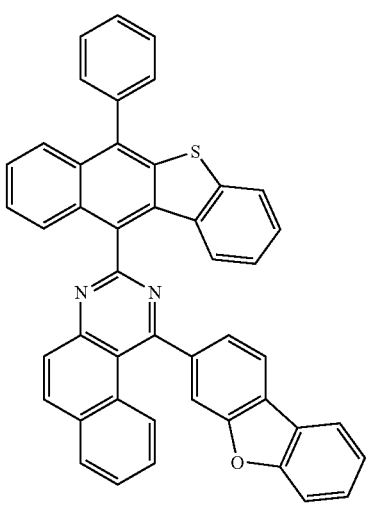
C-117
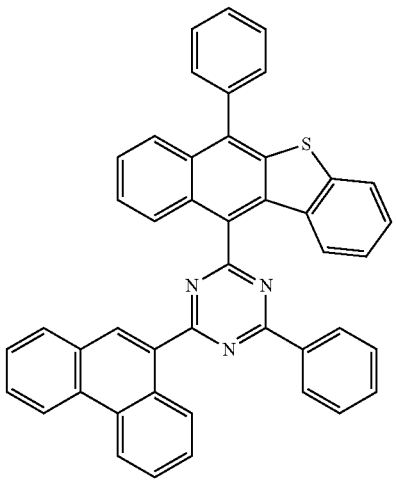

C-118
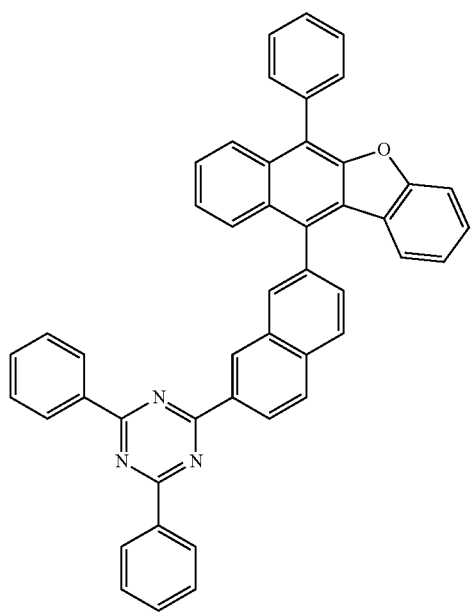
C-119
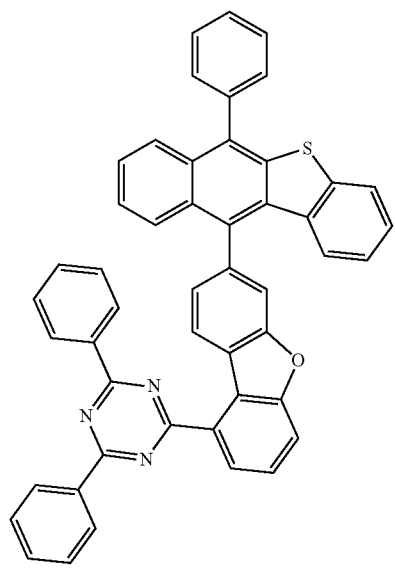
C-120
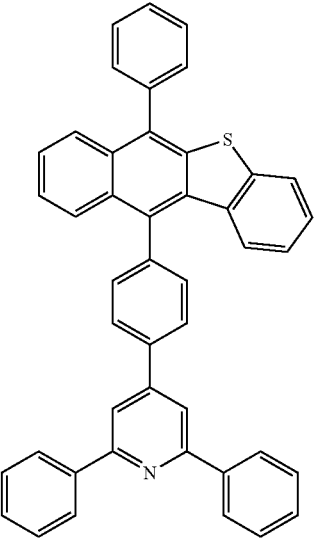
C-121
The structure shows a phenyl-substituted naphtho-benzofuran linked to a 4,6-diphenylpyrimidine.
C-122
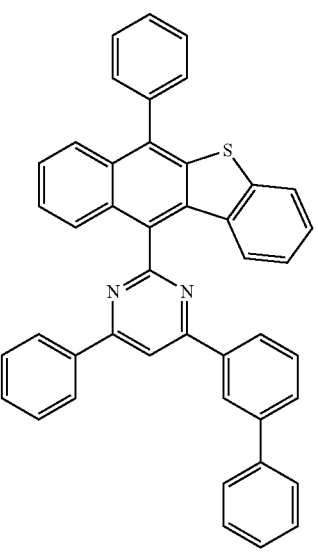

C-123
C-124
C-125
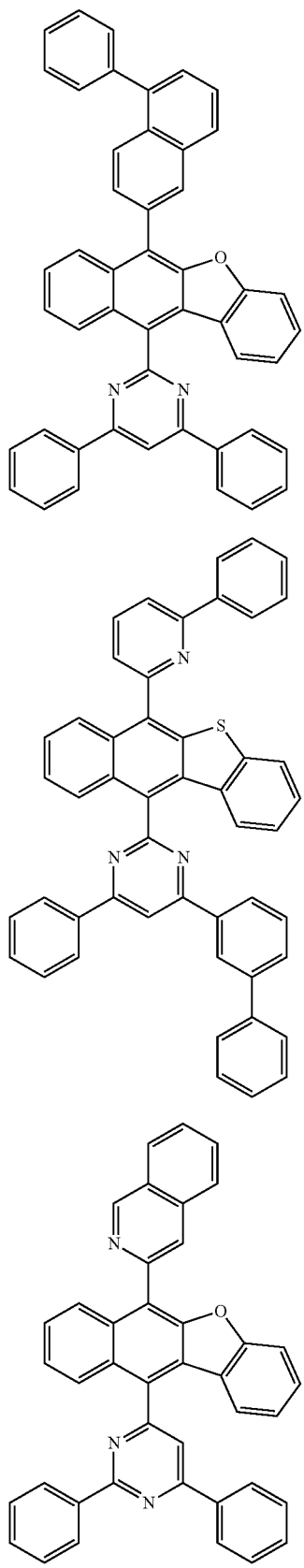
C-126
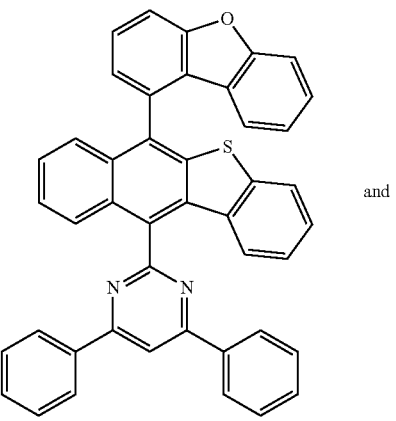
and
C-127
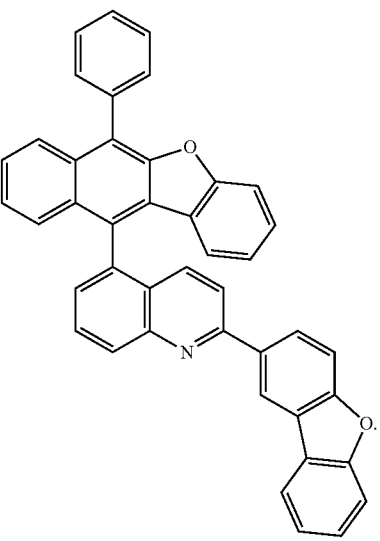
8. An organic electroluminescent device comprising an anode; a cathode; and at least one light-emitting layer between the anode and the cathode, wherein the at least one light-emitting layer comprises the plurality of host materials according to claim 1.
* * * * *